US011440909B2

(12) United States Patent
Yang et al.

(10) Patent No.: US 11,440,909 B2
(45) Date of Patent: Sep. 13, 2022

(54) 10H-PHENOTHIAZINE FERROPTOSIS INHIBITOR AS WELL AS THE PREPARATIVE METHOD AND THE USE THEREOF

(71) Applicant: CHENGDU HENGHAO INVESTMENT CO. LIMITED, Sichuan (CN)

(72) Inventors: Shengyong Yang, Sichuan (CN); Linli Li, Sichuan (CN)

(73) Assignee: CHENGDU HENGHAO INVESTMENT CO. LIMITED, Sichuan (CN)

( * ) Notice: Subject to any disclaimer, the term of this patent is extended or adjusted under 35 U.S.C. 154(b) by 0 days.

(21) Appl. No.: 17/078,802

(22) Filed: Oct. 23, 2020

(65) Prior Publication Data

US 2021/0040079 A1 Feb. 11, 2021

Related U.S. Application Data

(63) Continuation-in-part of application No. PCT/CN2019/079421, filed on Mar. 25, 2019.

(30) Foreign Application Priority Data

Apr. 27, 2018 (CN) ......................... 201810393712.2
Feb. 19, 2019 (CN) ......................... 201910122341.9
Feb. 19, 2019 (CN) ......................... 201910124457.6

(51) Int. Cl.
*C07D 417/12* (2006.01)
*C07D 279/20* (2006.01)
*C07D 471/08* (2006.01)

(52) U.S. Cl.
CPC ......... *C07D 417/12* (2013.01); *C07D 279/20* (2013.01); *C07D 471/08* (2013.01)

(58) Field of Classification Search
CPC .. C07D 417/12; C07D 417/14; C07D 279/20; A61P 9/10
USPC .......................................... 544/35; 514/224.8
See application file for complete search history.

(56) References Cited

U.S. PATENT DOCUMENTS 4,915,873 A * 4/1990 Abruscato ................ C07C 7/20 252/402

FOREIGN PATENT DOCUMENTS

| | | | | | |
|---|---|---|---|---|---|
| CN | 1131944 | A | | 9/1996 | |
| CN | 107496401 | A | | 12/2017 | |
| CS | 231000 | B1 | * | 4/1983 | ............... C08K 5/46 |
| JP | 57115435 | | * | 7/1982 | ............... C08K 5/46 |

OTHER PUBLICATIONS

Xie, Yangchun et al.; "Identification of Baicalein as a Ferroptosis Inhibitor by Natural Product Library Screening" Biochemical and Biophysical Research Communications; vol. 473, Mar. 30, 2016, pp. 775-780.
Zilka, O. et al.; . "On the Mechanism of Cytoprotection by Ferrostatin-1 and Liproxstatin-1 and the Role of Lipid Peroxidation in Ferroptotic Cell Death"; ACS Central Science, vol. 3, 07, Mar. 7, 2017, pp. 232-243.
Skouta, R. et al.; "Ferrostatins Inhibit Oxidative Lipid Damage and Cell Death in Diverse Disease Models"; J. Am. Chem. Soc., vol. 136, Mar. 4, 2014, pp. 4551-4556.
Hofmans, S. et al.; . Novel Ferroptosis Inhibitors with Improved Potency and ADME Properties; J. Med. Chem., vol. 59, Dec. 22, 2015, pp. 2041-2053.
Registry. "169317-49-1"; Oct. 27, 1995, p. 2, L1.
Jiang, Yina et al.; "Mechanism of Ferroptosis and Its Role in Neurological Diseases"; Chinese Pharmacological Bulletin), vol. 34, No. (2), Feb. 28, 2018, pp. 166-170.

* cited by examiner

*Primary Examiner* — Jeffrey H Murray
(74) *Attorney, Agent, or Firm* — Novick, Kim & Lee, PLLC; Allen Xue

(57) ABSTRACT

10H-phenothiazine derivatives capable of inhibiting ferroptosis has structural formula (I). The derivatives, pharmaceutically acceptable salts thereof, crystal forms thereof, or solvates thereof exhibit inhibitory effect on ferroptosis, and therapeutic effect on a rat model of focal cerebral ischemia and thus can be used as a main active ingredient in the preparation of ferroptosis inhibitors. The compounds and the inhibitors prepared by the compounds have good medicinal potential and are expected to be used as drug candidates for the treatment of stroke.

I

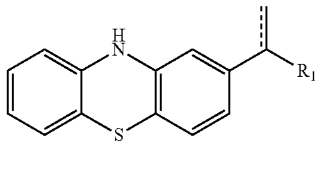

20 Claims, 1 Drawing Sheet

10H-PHENOTHIAZINE FERROPTOSIS INHIBITOR AS WELL AS THE PREPARATIVE METHOD AND THE USE THEREOF

TECHNICAL FIELD

The present invention relates to the technical field of chemically synthetic drugs, in particular to a 10H-phenothiazine ferroptosis inhibitor as well as the preparative method and the use thereof.

BACKGROUND ART

Cell ferroptosis is a new mode of cell death caused by iron-dependent oxidative damage that has only been discovered in recent years, and it is different from the traditional death modes of apoptosis, necrosis and autophagy, whose typical features are the increase of reactive oxygen free radicals in cytoplasm and lipid, the shrinkage of mitochondria, and the density increase of the mitochondrial bilayer membrane. Since this mode of cell death depends on the presence of iron, Dixon et al. named it "Ferroptosis" in 2012.

Cell ferroptosis is closely related to the occurrence and development of neurodegeneration, tissue ischemia-reperfusion injury, stroke, cardiovascular diseases, renal failure, and diabetic complications, and ferroptosis inhibitors are considered to be potential drugs for treatment of these diseases.

At present, most of the small molecule inhibitors of ferroptosis are antioxidants or iron chelating agents. Here, we mainly introduce three kinds of compounds with specific anti-ferroptosis activity:

Ferrostatin: the first generation of Ferrostatin is called Ferrostatin-1, which inhibits the formation of iron ions induced by Erastin- and RSL3 in HT1080 cells. The activity of Ferrostain-1 mainly depends on aromatic amines, which specifically inhibit the accumulation of ROS caused by lipid oxidation.

Compared with Ferrostatin-1, the second generation (called SRS11-92) and the third generation of Ferrostatins (called SRS16-86) have better plasma stability and metabolic stability, and can significantly prevent the damage of tissues in vivo (such as acute kidney injury and ischemia-reperfusion injury).

Liproxstatin-1: Liproxstatin-1 can prevent ROS accumulation and cell death in GPX4–/– cells. In addition, Liproxstatin-1 inhibits ferroptosis induced by FINs (such as Erastin, RSL3, and BSO). In inducible GPX4–/– mice, intraperitoneal administration of Liproxstatin-1 (10 mg/kg) can increase the survival rate of the animals against kidney injury. Liproxstatin-1 can also protect mice from liver injury caused by ischemia-reperfusion.

Zileuton: Zileuton is an active specific inhibitor of oral 5-LOX, but not an inhibitor of 12/15-LOX.

Zileuton inhibits the production of ROS in cytosol and provides significant protection against the increase of iron ions induced by glutamate and ergosporin in HT22 cells (mouse hippocampal cell line).

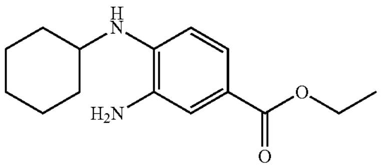

Ferrostain-1

-continued

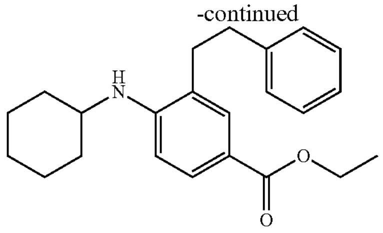

SRS11-92

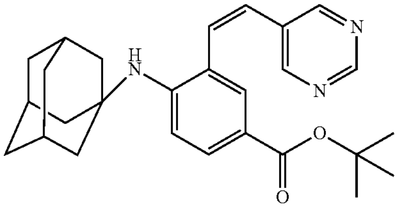

SRS16-86

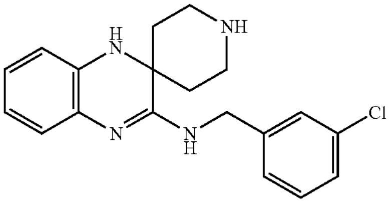

Liproxstatin-1

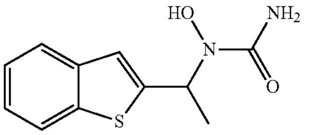

Zileuton

The above-mentioned ferroptosis inhibitors have strong targeted activity, but the activity is not high, and there is no application for stroke genes. Therefore, how to prepare a ferroptosis inhibitor with high activity, which can be used as a drug for treatment of stroke, is a problem that urgently needs to be solved.

CONTENT OF THE INVENTION

In order to solve above problems, the present invention provides the compound of formula I, or a pharmaceutically acceptable salt, or crystal, or solvate thereof:

I

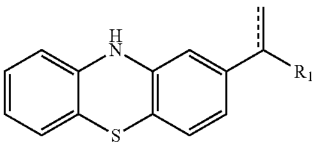

Wherein,

When the dotted line is a bond, $R_1$ is selected from 3-10 membered saturated cycloalkyl, 3-10 membered unsaturated cycloalkyl, 3-10 membered saturated heterocyclic group, and 3-10 membered unsaturated heterocyclic group, all of which are substituted by m $R_2$;

m is an integer of 0-5;

$R_2$ is selected from the group consisting of substituted or unsubstituted $C_1$-$C_8$ alkyl, substituted or unsubstituted $C_1$-$C_8$ alkoxy, substituted or unsubstituted 3-10 membered saturated cycloalkyl, substituted or unsubstituted 3-10 membered saturated heterocyclic group, substituted or unsubstituted 3-10 membered unsaturated cycloalkyl, carbazolyl, amino, hydroxyl, nitro, cyano, halogen, —C(O)$OR_{51}$, —N(H)C(O)$R_{51}$, —C(O)$R_{51}$, —S(O)(O)$R_{51}$, —C(O)N(H)$R_{51}$; $R_{51}$ is selected from the group consisting of H, $C_1$-$C_8$ alkyl, amino, substituted or unsubstituted 3-10 membered unsaturated cycloalkyl, substituted or unsubstituted 3-10 membered saturated heterocyclic group, —$NR_{52}R_{53}$;

$R_{52}$ and $R_{53}$ are each independently selected from H, substituted or unsubstituted 5-10 membered saturated heterocyclic group, substituted or unsubstituted $C_1$-$C_8$ alkyl, substituted or unsubstituted 3-8 membered saturated cycloalkyl;

The substituent of the alkyl is halogen, substituted or unsubstituted 4-10 membered saturated heterocyclic group;

The substituent of the alkoxyl is halogen, 3-10 membered unsaturated cycloalkyl;

The substituent of the saturated cycloalkyl is $C_1$-$C_8$ alkyl;

The substituent of the unsaturated cycloalkyl is $C_1$-$C_8$ alkyl;

The substituent of the saturated heterocyclic group is $C_1$-$C_8$ alkyl;

The heteroatom of the unsaturated heterocyclic group is N, O, and S, and the number of heteroatoms is 1 or 2;

The heteroatom of the saturated heterocyclic group is N, O, and S, and the number of heteroatoms is 1 or 2;

When the dotted line is none, $R_1$ is selected from the group consisting of 3-10 membered unsaturated cycloalkyl, benzo(3-8 membered saturated)heterocyclic group, benzo(3-8 membered unsaturated) heterocyclic group, naphthyl, anthryl, 3-10 membered unsaturated heterocyclic group, 3-10 membered saturated cycloalkyl, all of which are substituted by n $R_3$ and —S(O)(O)$R_1$';

n is an integer of 0-5;

$R_3$ is selected from the group consisting of halogen, cyano, hydroxyl, amino, nitro, substituted or unsubstituted 3-10 membered unsaturated cycloalkyl, phenoxyl, substituted or unsubstituted 3-10 membered saturated heterocyclic group, substituted or unsubstituted $C_1$-$C_8$ alkyl, substituted or unsubstituted $C_1$-$C_8$ alkoxy, —C(O)$OR_{51}$, —N(H)C(O)$R_{51}$, —$NR_{52}R_{53}$;

$R_1$' is selected from 3-10 membered saturated heterocyclic group, 3-10 membered saturated cycloalkyl, 3-10 membered unsaturated cycloalkyl, and 3-10 membered unsaturated heterocyclic group, all of which are substituted by p $R_4$;

p is an integer of 0-5;

$R_4$ is selected from the group consisting of hydroxyl, substituted or unsubstituted $C_1$-$C_8$ alkyl, —C(O)$R_{51}$, —N(H)C(O)$OR_{51}$, —S(O)(O)$R_{51}$, —C(O)$OR_{51}$, substituted or unsubstituted 3-10 membered unsaturated heterocyclic group, substituted or unsubstituted 3-10 membered saturated heterocyclic group, and substituted or unsubstituted 3-10 membered unsaturated cycloalkyl;

$R_{51}$ is selected from the group consisting of $C_1$-$C_{10}$ alkyl, amino, 3-8 membered saturated heterocyclic group, and benzo(3-8 membered saturated)heterocyclic group;

$R_{52}$ and $R_{53}$ are each independently selected from 3-10 membered unsaturated cycloalkyl, $C_1$-$C_8$ alkyl;

The substituent of the alkyl is halogen, benzo(5-10 membered saturated)heterocyclic group, substituted or unsubstituted 3-10 membered unsaturated cycloalkyl, 5-10 membered saturated heterocyclic group, hydroxyl, —N(H)C(O)$OR_{51}$, —C(O)$R_{51}$, —$NR_{52}R_{53}$;

The substituent of the alkoxyl is 3-10 membered unsaturated cycloalkyl, halogen;

The substituent of the unsaturated cycloalkyl is halogen, $C_1$-$C_6$ alkoxyl, cyano, nitro, substituted or unsubstituted $C_1$-$C_8$ alkyl;

The substituent of the saturated heterocyclic group is $C_1$-$C_8$ alkyl;

The substituent of the unsaturated heterocyclic group is $C_1$-$C_8$ alkyl;

The heteroatom of the saturated heterocyclic group is O, N, and S, and the number of heteroatoms is 1 or 2;

The heteroatom of the unsaturated heterocyclic group is N, O, and S, and the number of heteroatoms is 1 or 2.

Further,

When the dotted line is a bond, $R_1$ is selected from 3-8 membered unsaturated cycloalkyl, and 3-8 membered unsaturated heterocyclic group, all of which are substituted by m $R_2$;

m is an integer of 0-4;

$R_2$ is selected from the group consisting of substituted or unsubstituted $C_1$-$C_6$ alkyl, substituted or unsubstituted $C_1$-$C_6$ alkoxy, 3-8 membered saturated cycloalkyl, substituted or unsubstituted 3-8 membered saturated heterocyclic group, 3-8 membered unsaturated cycloalkyl, carbazolyl, amino, hydroxyl, nitro, cyano, halogen, —C(O)$OR_{51}$, —N(H)C(O)$R_{51}$, —C(O)$R_{51}$, —S(O)(O)$R_{51}$, —C(O)N(H)$R_{51}$;

$R_{51}$ is selected from the group consisting of H, $C_1$-$C_4$ alkyl, amino, substituted or unsubstituted 3-8 membered unsaturated cycloalkyl, substituted or unsubstituted 5-8 membered saturated heterocyclic group, —$NR_{52}R_{53}$;

$R_{52}$ and $R_{53}$ are each independently selected from H, substituted or unsubstituted 5-8 membered saturated heterocyclic group, substituted or unsubstituted $C_1$-$C_6$ alkyl, 3-6 membered saturated cycloalkyl;

The substituent of the alkyl is halogen, substituted or unsubstituted 5-8 membered saturated heterocyclic group;

The substituent of the alkoxyl is halogen, 3-8 membered unsaturated cycloalkyl;

The substituent of the unsaturated cycloalkyl is $C_1$-$C_4$ alkyl;

The substituent of the saturated heterocyclic group is $C_1$-$C_4$ alkyl;

The heteroatom of the unsaturated heterocyclic group is N and O, and the number of heteroatoms is 1 or 2;

The heteroatom of the saturated heterocyclic group is N and O, and the number of heteroatoms is 1 or 2; When the dotted line is none, $R_1$ is selected from the group consisting of 3-8 membered unsaturated cycloalkyl, benzo(5-8 membered saturated)heterocyclic group, benzo(5-8 membered unsaturated)heterocyclic group, naphthyl, anthryl, 3-8 membered unsaturated heterocyclic group, 3-8 membered saturated cycloalkyl, all of which are substituted by n $R_3$, and —S(O)(O)$R_1$';

n is an integer of 0-4;

$R_3$ is selected from the group consisting of halogen, cyano, hydroxyl, amino, nitro, 3-8 membered unsaturated cycloalkyl, phenoxyl, substituted 5-8 membered saturated heterocyclic group, substituted or unsubstituted $C_1$-$C_6$ alkyl, substituted or unsubstituted $C_1$-$C_6$ alkoxy, —C(O)$OR_{51}$, —N(H)C(O)$R_{51}$, —$NR_{52}R_{53}$;

$R_1$' is selected from 3-8 membered saturated heterocyclic group substituted by p $R_4$;

p is an integer of 0-4;

$R_4$ is selected from the group consisting of hydroxyl, substituted or unsubstituted $C_1$-$C_6$ alkyl, —C(O)$R_{51}$, —N(H)C(O)O$R_{51}$, —S(O)(O)$R_{51}$, —C(O)O$R_{51}$, 3-8 membered unsaturated heterocyclic group, 3-8 membered saturated heterocyclic group, and substituted or unsubstituted 3-8 membered unsaturated cycloalkyl;

$R_{51}$ is selected from the group consisting of $C_1$-$C_8$ alkyl, amino, 5-8 membered saturated heterocyclic group, and benzo(5-8 membered saturated)heterocyclic group;

$R_{52}$ and $R_{53}$ are each independently selected from 3-8 membered unsaturated cycloalkyl, $C_1$-$C_4$ alkyl;

The substituent of the alkyl is halogen, benzo(5-8 membered saturated)heterocyclic group, substituted or unsubstituted 3-8 membered unsaturated cycloalkyl, 5-10 membered saturated heterocyclic group, hydroxyl, —N(H)C(O)O$R_{51}$, —C(O)$R_{51}$, —N$R_{52}R_{53}$;

The substituent of the alkoxyl is 3-8 membered unsaturated cycloalkyl, halogen;

The substituent of the unsaturated cycloalkyl is halogen, $C_1$-$C_4$ alkoxyl, cyano, nitro, substituted or unsubstituted $C_1$-$C_4$ alkyl;

The substituent of the saturated heterocyclic group is $C_1$-$C_4$ alkyl;

The heteroatom of the saturated heterocyclic group is O, N, and S, and the number of heteroatoms is 1 or 2;

The heteroatom of the unsaturated heterocyclic group is N and O, and the number of heteroatoms is 1 or 2.

Further, said compound has a structure of formula II

II

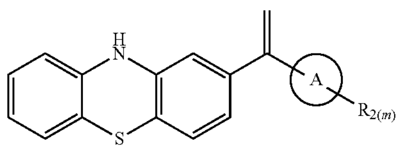

Wherein, ring A is selected from aryl or heteroaryl substituted by m $R_2$; the heteroatom of said heteroaryl is N, and the number of heteroatoms is 1 or 2.

m is an integer of 0-4;

$R_2$ is selected from the group consisting of H, substituted or unsubstituted $C_1$-$C_4$ alkyl, substituted or unsubstituted $C_1$-$C_3$ alkoxy, 6-8 membered saturated cycloalkyl, substituted or unsubstituted 6-7 membered saturated heterocyclic group, carbazolyl, amino, hydroxyl, nitro, aryl, cyano, halogen, —C(O)O$R_{51}$, —N(H)C(O)$R_{51}$, —C(O)$R_{51}$, —S(O)(O)$R_{51}$, —C(O)N(H)$R_{51}$;

$R_{51}$ is selected from the group consisting of H, $C_1$-$C_2$ alkyl, amino, substituted or unsubstituted aryl, substituted or unsubstituted 5-6 membered saturated heterocyclic group, —N$R_{52}R_{53}$;

$R_{52}$ and $R_{53}$ are each independently selected from H, substituted or unsubstituted 6-8 membered saturated heterocyclic group, substituted or unsubstituted $C_1$-$C_4$ alkyl, 4-5 membered saturated cycloalkyl;

The substituent of the alkyl is halogen, substituted or unsubstituted 6-8 membered saturated heterocyclic group;

The substituent of the alkoxyl is halogen, aryl;

The substituent of the aryl is substituted $C_1$-$C_3$ alkyl;

The substituent of the saturated heterocyclic group is $C_1$-$C_3$ alkyl; the heteroatom of said heterocyclic group is N and O, and the number of heteroatoms is 1 or 2.

Or, said compound has a structure of formula III:

III

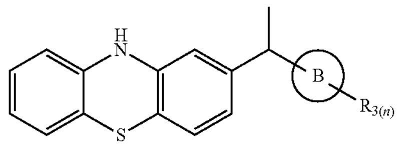

Wherein, ring Bis selected from the group consisting of aryl benzo(5-6 membered saturated)heterocyclic group, benzo(5 membered unsaturated)heterocyclic group, naphthyl, anthryl, 6-8 membered unsaturated heterocyclic group or 6-8 membered saturated cycloalkyl, all of which are substituted by n $R_3$;

n is an integer of 0-3;

$R_3$ is selected from the group consisting of H, halogen, cyano, hydroxyl, amino, nitro, aryl, phenoxy, substituted 6-8 membered saturated heterocyclic group, substituted or unsubstituted $C_1$-$C_4$ alkyl, substituted or unsubstituted $C_1$-$C_3$ alkoxy, —C(O)O$R_{51}$, —N(H)C(O)$R_{51}$, —N$R_{52}R_{53}$;

$R_{51}$ is selected from $C_1$-$C_4$ alkyl;

$R_{52}$ and $R_{53}$ are each independently selected from aryl;

The substituent of the alkyl is halogen;

The substituent of the alkoxyl is aryl, halogen;

The substituent of the saturated heterocyclic group is $C_1$-$C_2$ alkyl;

The heteroatom of the saturated heterocyclic group is N and O, and the number of heteroatoms is 1 or 2;

The heteroatom of the unsaturated heterocyclic group is N and O, and the number of heteroatoms is 1 or 2;

Or, said compound has a structure of formula IV:

IV

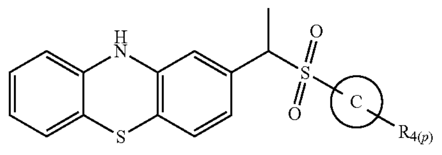

Wherein, ring C is a 5-8 membered saturated heterocyclic group substituted by p $R_4$;

p is an integer of 0-4;

$R_4$ is selected from the group consisting of H, hydroxyl, substituted or unsubstituted $C_1$-$C_4$ alkyl, —C(O)$R_{51}$, —N(H)C(O)O$R_{51}$, —S(O)(O)$R_{51}$, —C(O)O$R_{51}$, 6-8 membered unsaturated heterocyclic group, 6-8 membered saturated heterocyclic group, substituted or unsubstituted aryl;

$R_{51}$ is selected from $C_1$-$C_4$ alkyl, amino, 5 membered saturated heterocyclic group, benzo(6 membered saturated) heterocyclic group;

The substituent of the alkyl is halogen, benzo(5 membered saturated)heterocyclic group, substituted or unsubstituted aryl, 6 membered saturated heterocyclic group, hydroxyl, —N(H)C(O)O$R_{51}$, —C(O)$R_{51}$, —N$R_{52}R_{53}$;

The substituent of the aryl is halogen, $C_1$alkoxyl, cyano, nitro, substituted or unsubstituted $C_1$ alkyl;

$R_{52}$ and $R_{53}$ are each independently selected from $C_1$-$C_1$ alkyl;

The heteroatom of the saturated heterocyclic group is O, N and S, and the number of heteroatoms is 1 or 2;

The heteroatom of the unsaturated heterocyclic group is N, and the number of heteroatoms is 1 or 2.

Further, said compound has a structure of formula IIA:

IIA

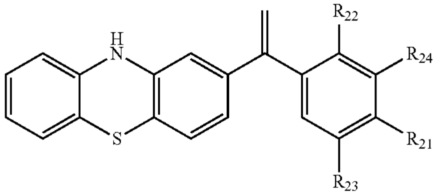

Wherein, $R_{21}$, $R_{22}$, $R_{23}$, and $R_{24}$ are each independently selected from the group consisting of H, —C(O)O$R_{51}$, substituted or unsubstituted $C_1$-$C_4$ alkyl, substituted or unsubstituted $C_1$-$C_3$ alkoxy, —N(H)C(O)$R_{51}$, 6 membered saturated cycloalkyl, —C(O)$R_{51}$, 6 membered saturated heterocyclic group, carbazolyl, amino, hydroxyl, nitro, —S(O)(O)$R_{51}$, aryl, cyano, halogen, —C(O)N(H)$R_{51}$;

$R_{51}$ is selected from the group consisting of H, $C_1$-$C_2$ alkyl, amino, substituted or unsubstituted aryl, substituted or unsubstituted 5-6 membered saturated heterocyclic group, —N$R_{52}$$R_{53}$;

$R_{52}$ and $R_{53}$ are each independently selected from H, substituted or unsubstituted 6 membered saturated heterocyclic group, substituted or unsubstituted $C_1$-$C_4$ alkyl, 4 membered cycloalkyl;

The substituent of the alkyl is halogen, substituted or unsubstituted 6 membered saturated heterocyclic group;

The substituent of the alkoxyl is halogen, aryl;

The substituent of the aryl is substituted $C_1$ alkyl;

The substituent of the saturated heterocyclic group is $C_1$ alkyl; the heteroatom of said saturated heterocyclic group is N and O, and the number of heteroatoms is 1 or 2.

Or, said compound has a structure of formula IIB:

IIB

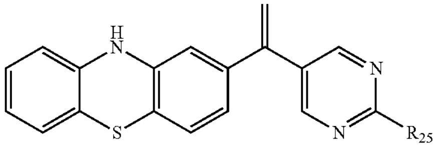

Wherein, $R_{25}$ is selected from substituted or unsubstituted 6-7 membered saturated heterocyclic group;

The substituent of the saturated heterocyclic group is $C_1$ alkyl;

The heteroatom of said heterocyclic group is N and O, and the number of heteroatoms is 2;

Or, said compound has a structure of formula IIC:

IIC

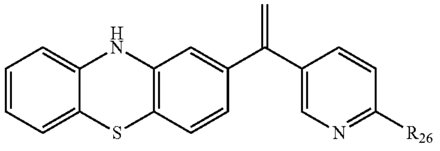

Wherein, $R_{26}$ is selected from —N(H)C(O)$R_{51}$, amino, 6 membered saturated heterocyclic group;

The heteroatom of said saturated heterocyclic group is N and O, and the number of heteroatoms is 2;

$R_{51}$ is selected from $C_1$ alkyl;

Or, said compound has a structure of formula IIIA:

IIIA

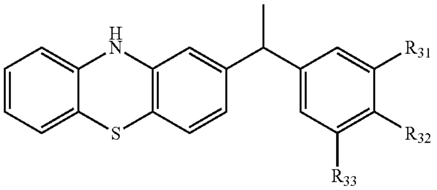

Wherein, $R_{31}$, $R_{32}$, $R_{33}$ are each independently selected from the group consisting of H, halogen, cyano, hydroxyl, amino, substituted or unsubstituted $C_1$-$C_4$ alkyl, substituted or unsubstituted $C_1$-$C_3$ alkoxy, —C(O)O$R_{51}$, —N(H)C(O)$R_{51}$, aryl, phenoxy, —N$R_{52}$$R_{53}$, substituted 6 membered saturated heterocyclic group, nitro;

$R_{51}$ is selected from $C_1$-$C_4$ alkyl;

The substituent of the alkyl is halogen;

The substituent of the alkoxyl is aryl, halogen;

The substituent of the saturated heterocyclic group is $C_1$ alkyl;

The heteroatom of the saturated heterocyclic group is N, and the number of heteroatoms is 2;

$R_{52}$ and $R_{53}$ are each independently selected from aryl;

Or, said compound has a structure of formula IIIB:

IIIB

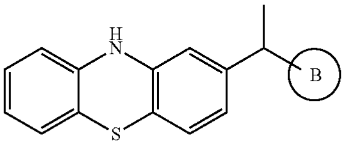

Wherein,

Ring B is selected from the group consisting of benzo(5-6 membered saturated)heterocyclic group, benzo(5 membered unsaturated)heterocyclic group, substituted or unsubstituted naphthyl, anthryl, substituted 6 membered unsaturated heterocyclic group or 6 membered saturated cycloalkyl;

The substituent of the unsaturated heterocyclic group is cyano, $C_1$ alkyl, $C_2$ alkoxyl;

The substituent of the naphthyl is $C_1$-$C_2$ alkoxyl;

The heteroatom of the saturated heterocyclic group is O, and the number of heteroatoms is 1 or 2;

The heteroatom of the unsaturated heterocyclic group is O and N, and the number of heteroatoms is 1;

Or, said compound has a structure of formula IVA:

IVA

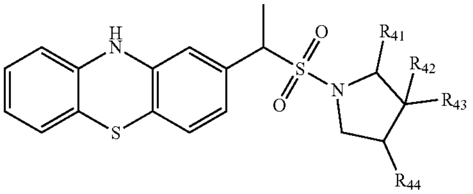

Wherein, $R_{41}$, $R_{42}$, $R_{43}$, and $R_{44}$ are each independently selected from the group consisting of H, hydroxyl, —N(H)C(O)O$R_{51}$, substituted or unsubstituted $C_1$ alkyl;

$R_{51}$ is selected from $C_4$ alkyl;

The substituent of the alkyl is —N(H)C(O)O$R_{51}$;

Or, said compound has a structure of formula IVB:

IVB

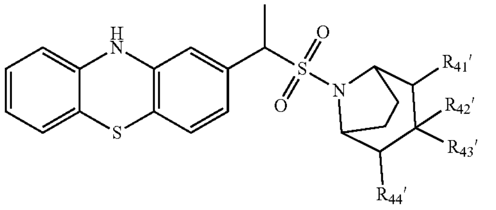

Wherein, $R_{41}'$, $R_{42}'$, $R_{43}'$, and $R_{44}'$ are each independently selected from H, hydroxyl;

Or, said compound has a structure of formula IVC:

IVC

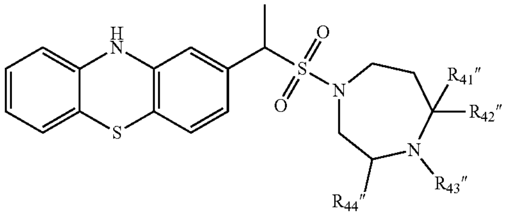

Wherein, $R_{41}''$, $R_{42}''$, $R_{43}''$, and $R_{44}''$ are each independently selected from H, $C_1$ alkyl, —C(O)$R_{51}$;

$R_{51}$ is selected from $C_1$ alkyl;

Or, said compound has a structure of formula IVD:

IVD

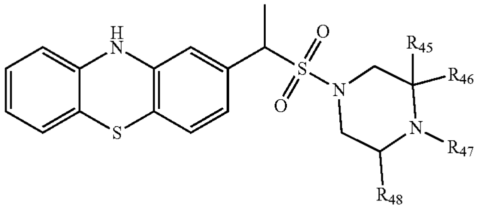

Wherein, $R_{45}$, $R_{46}$, $R_{47}$, and $R_{48}$ are each independently selected from the group consisting of H, substituted or unsubstituted $C_1$-$C_4$ alkyl, —C(O)$R_{51}$, —S(O)(O)$R_{51}$, 6 membered unsaturated heterocyclic group, —C(O)O$R_{51}$, substituted or unsubstituted aryl;

$R_{51}$ is selected from 5 membered saturated heterocyclic group, $C_1$-$C_4$ alkyl, benzo(6 membered saturated)heterocyclic group;

$R_{52}$ and $R_{53}$ are each independently selected from $C_1$ alkyl;

The substituent of the alkyl is halogen, benzo(5 membered saturated)heterocyclic group, —C(O)$R_{51}$, —N$R_{52}R_{53}$, substituted or unsubstituted aryl, 6 membered saturated heterocyclic group, hydroxyl;

The substituent of the aryl is $C_1$ alkoxyl, halogen, cyano, nitro, substituted or unsubstituted $C_1$ alkyl;

The heteroatom of the saturated heterocyclic group is O and N, and the number of heteroatoms is 1 or 2;

The heteroatom of the unsaturated heterocyclic group is N, and the number of heteroatoms is 1 or 2;

Or, said compound has a structure of formula IVE:

IVE

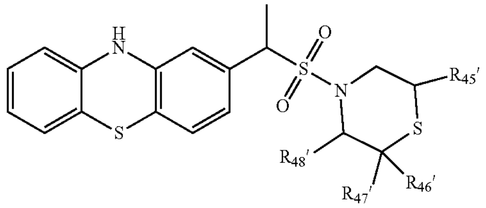

Wherein, $R_{45}'$, $R_{46}'$, $R_{47}'$, and $R_{48}'$ are each independently selected from H, $C_1$ alkyl;

Or, said compound has a structure of formula IVF:

IVF

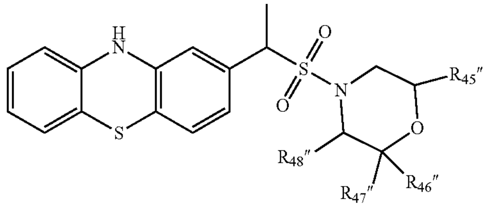

Wherein, $R_{45}''$, $R_{46}''$, $R_{47}''$, and $R_{48}''$ are each independently selected from H, $C_1$ alkyl;

Or, said compound has a structure of formula IVG:

IVG

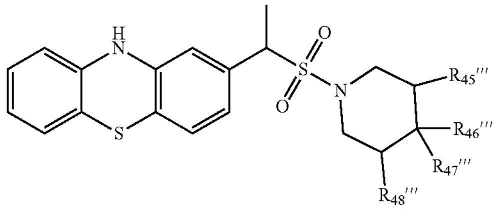

Wherein, $R_{45}'''$, $R_{46}'''$, $R_{47}'''$, and $R_{48}'''$ are each independently selected from H, hydroxyl, —C(O)O$R_{51}$, —N(H)C(O)O$R_{51}$, substituted aryl, substituted or unsubstituted $C_1$ alkyl, 6 membered saturated heterocyclic group, —C(O)$R_{51}$;

$R_{51}$ is selected from $C_2$-$C_4$ alkyl, amino;

The substituent of the aryl is halogen;

The substituent of the alkyl is —N(H)C(O)O$R_{51}$, hydroxyl;

The heteroatom of the saturated heterocyclic group is N, and the number of heteroatoms is 1.

Further, said compounds are:

A1

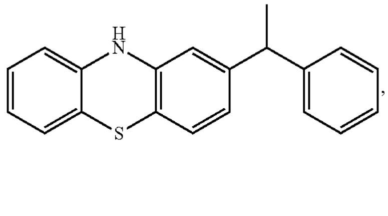,

-continued
A2
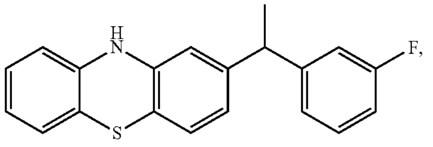
A3
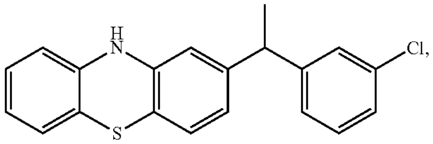
A4
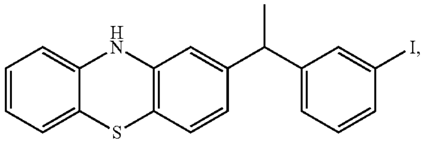
A5
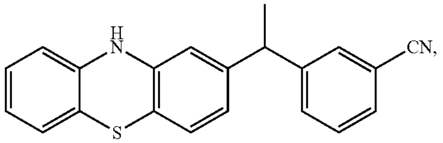
A6
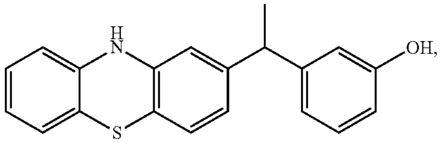
A7
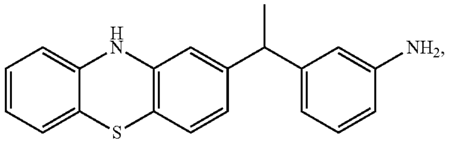
A8
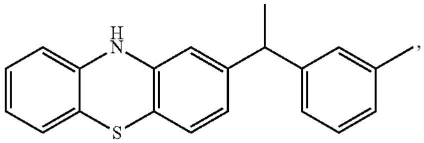
A9
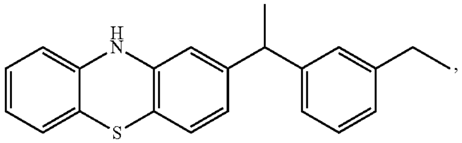
A10
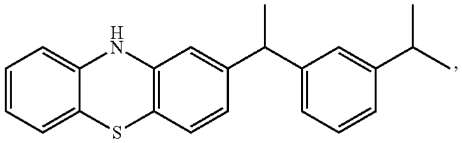
A11
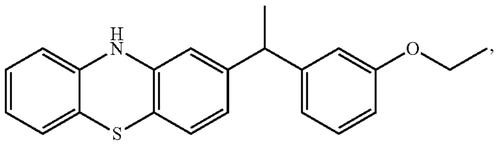
-continued
A12
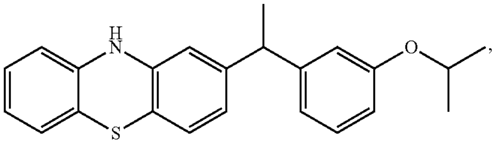
A13
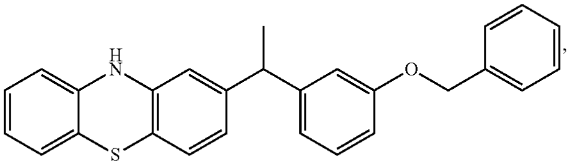
A14
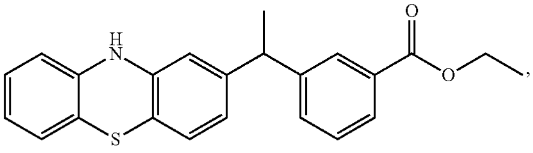
A15
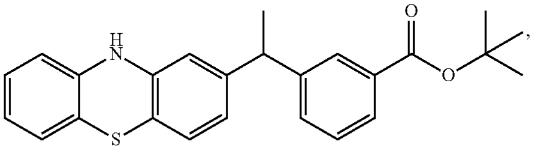
A16
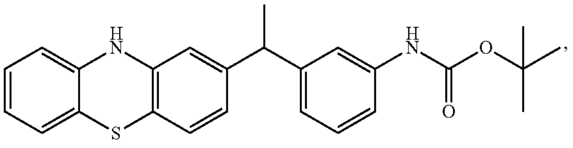
A17
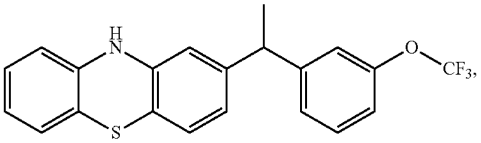
A18
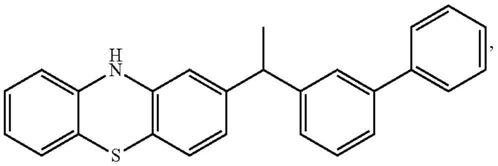
A19
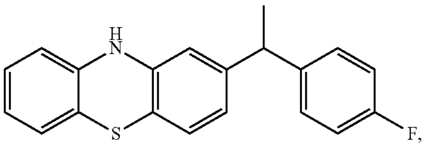
A20
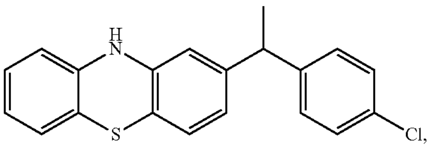

-continued
A21
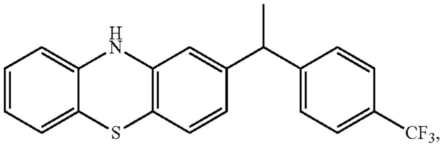
A22
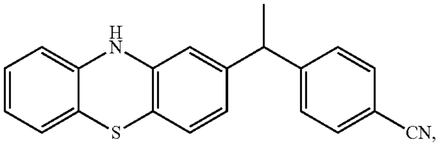
A23
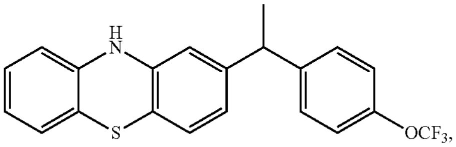
A24
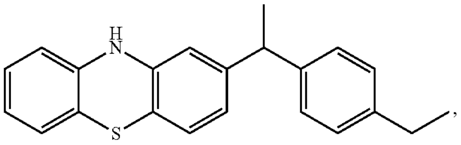
A25
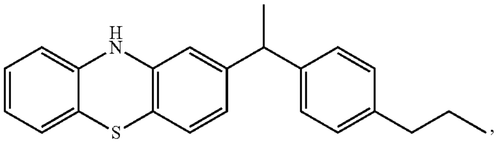
A26
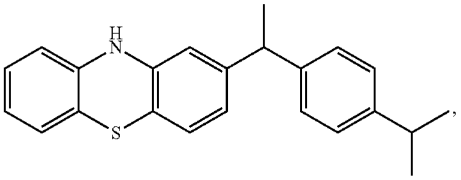
A27
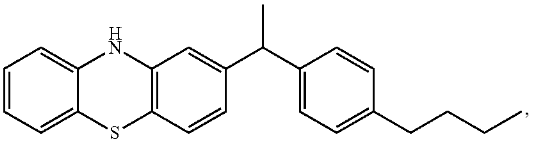
A28
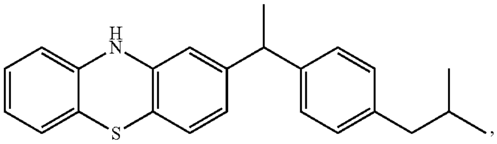
A29
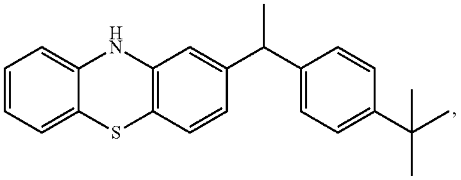
-continued
A30
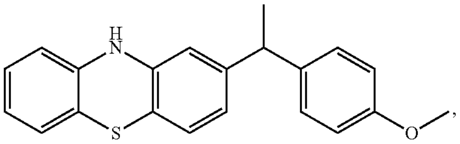
A31
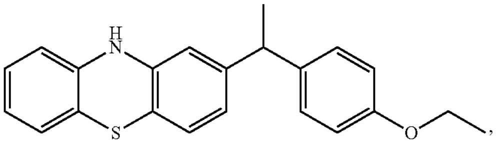
A32
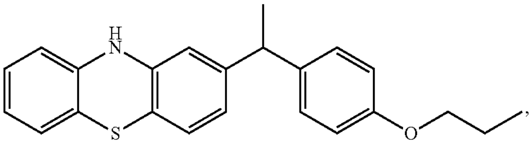
A33
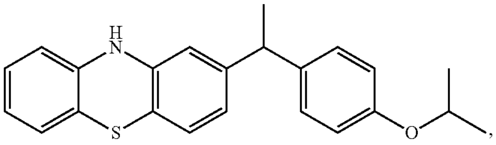
A34
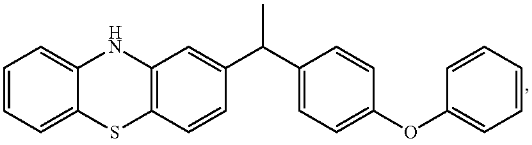
A35
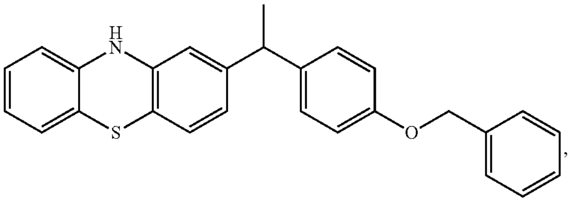
A36
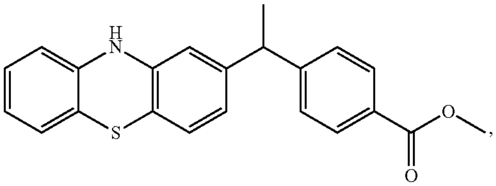
A37
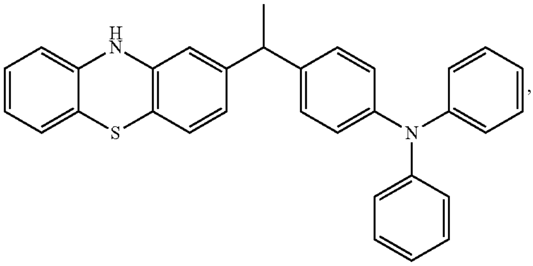

-continued
A38
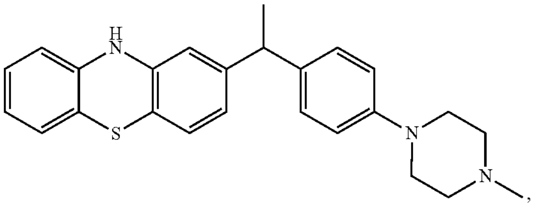
A39
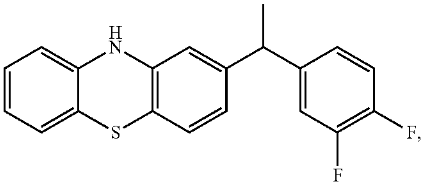
A40
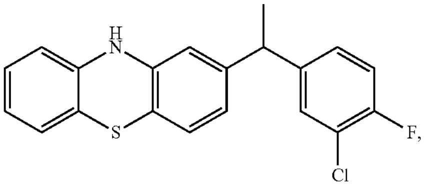
A41
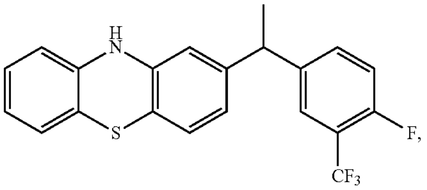
A42
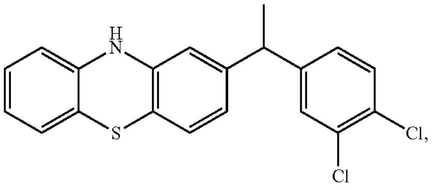
A43
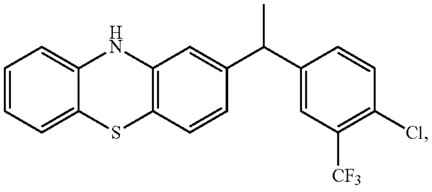
A44
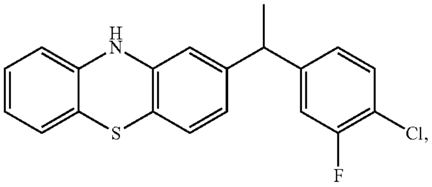
A45
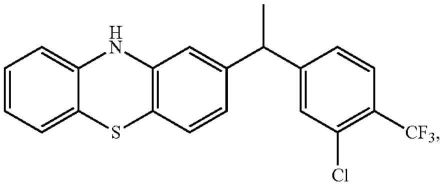
-continued
A46
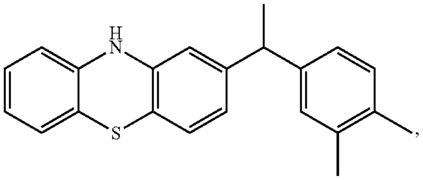
A47
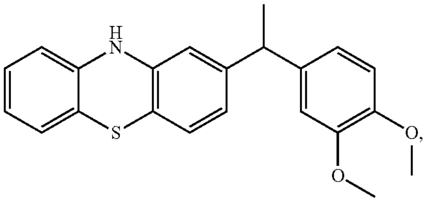
A48
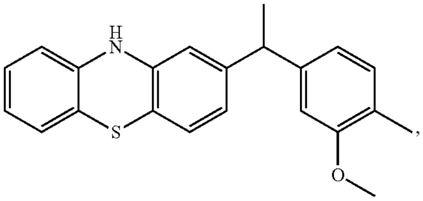
A49
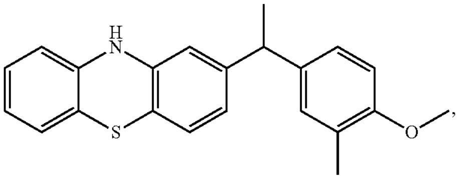
A50
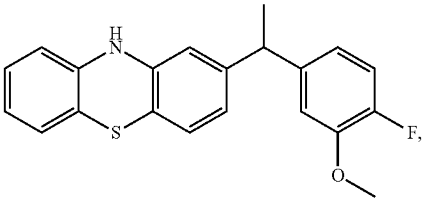
A51
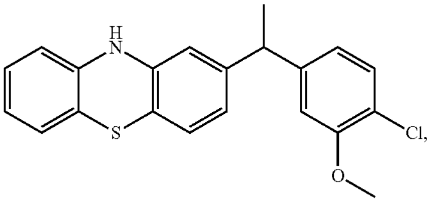
A52
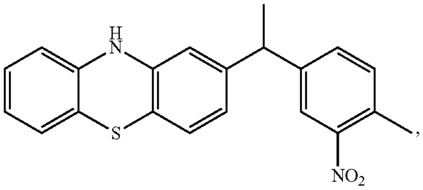
A53
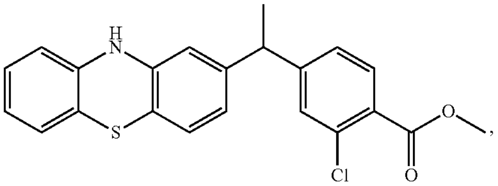

-continued
A54
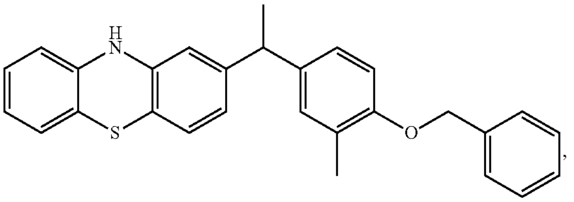
A55
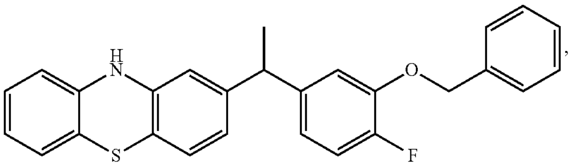
A56
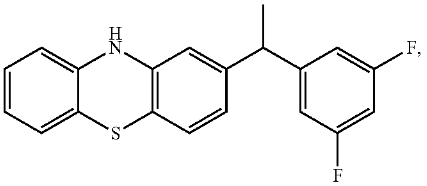
A57
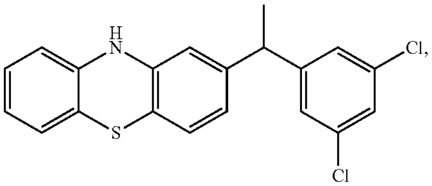
A58
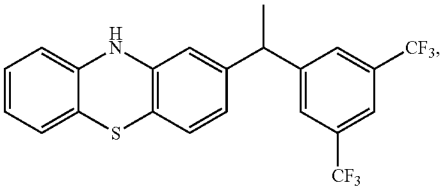
A59
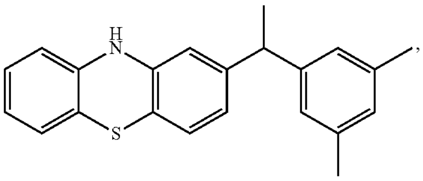
A60
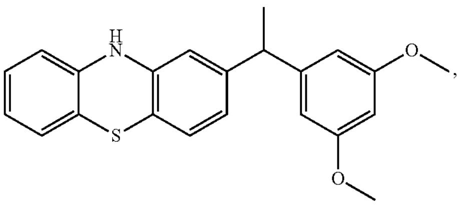
A61
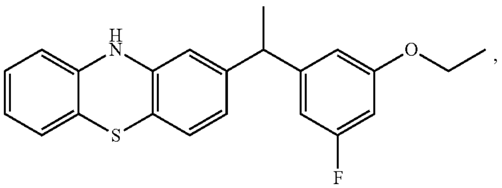
-continued
A62
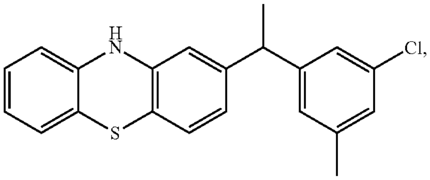
A63
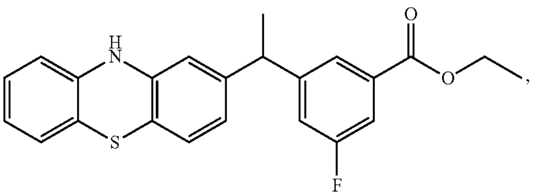
A64
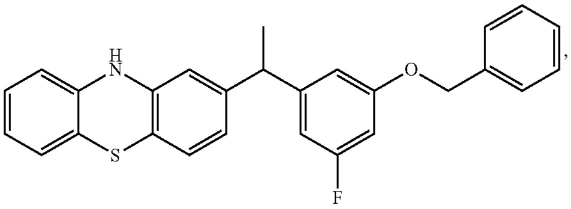
A65
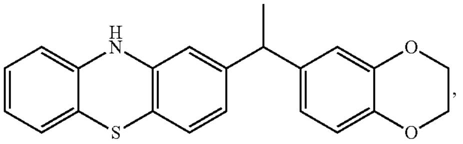
A66
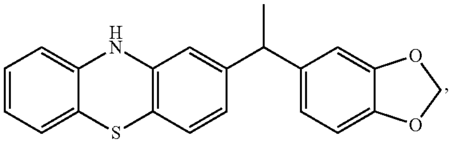
A67
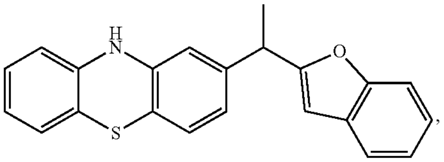
A68
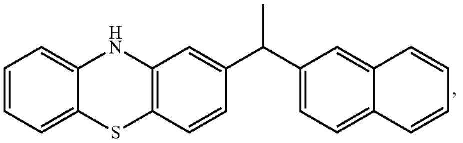
A69
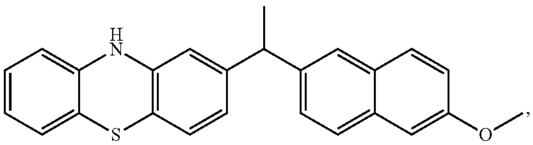
A70
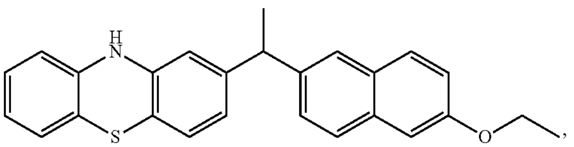

-continued
A71
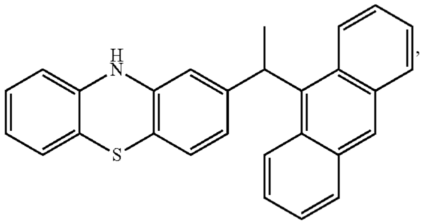
A72
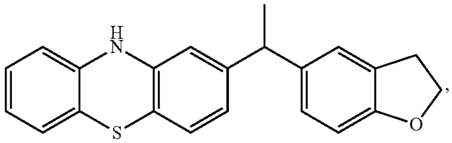
A73
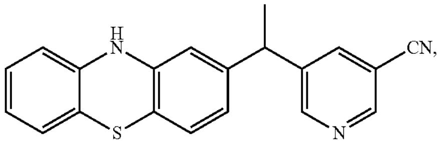
A74
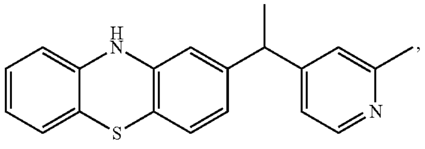
A75
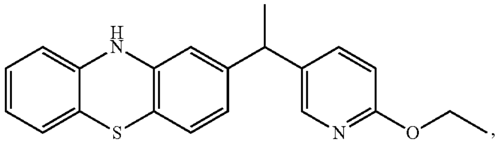
A76
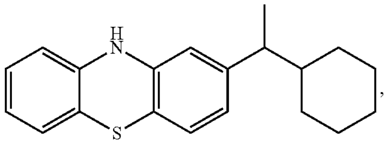
B1
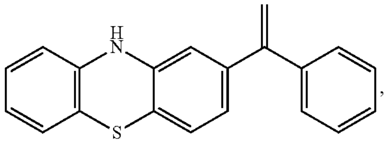
B2
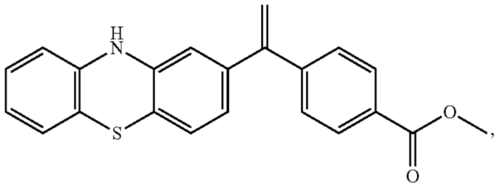
B3
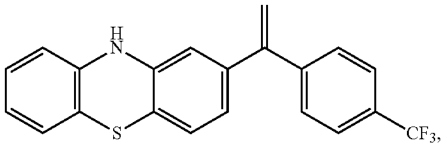
-continued
B4
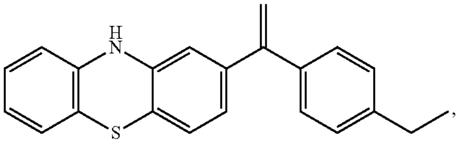
B5
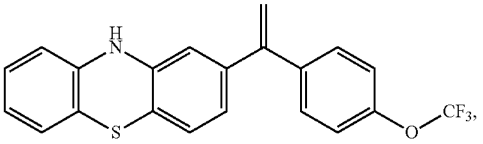
B6
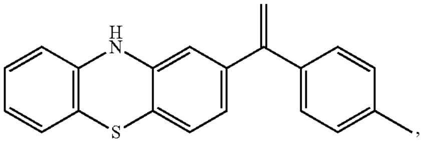
B7
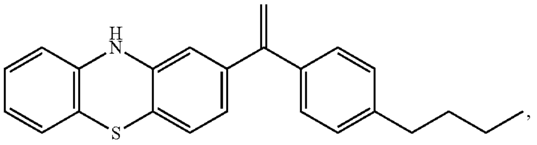
B8
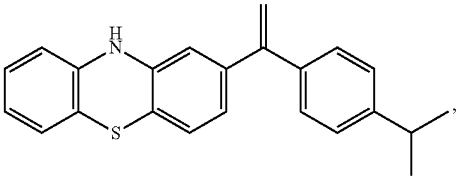
B9
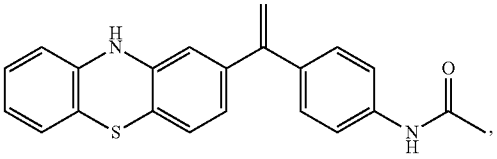
B10
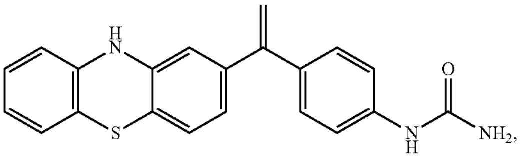
B11
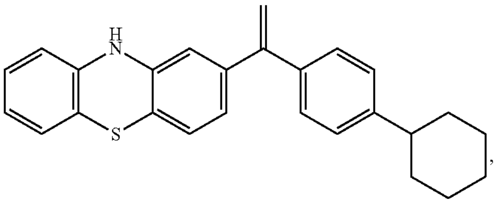
B12
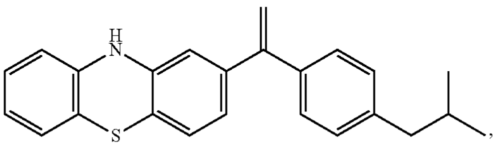

-continued
B13
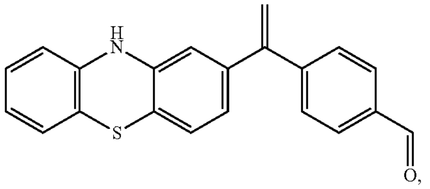
B14
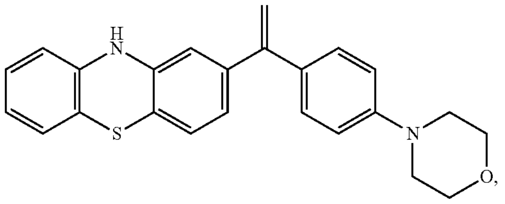
B15
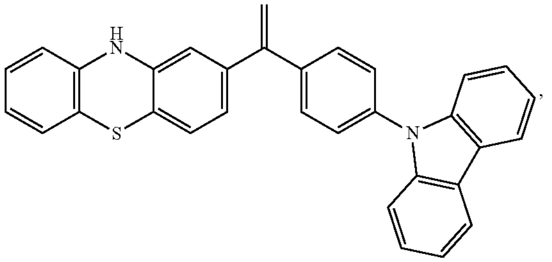
B16
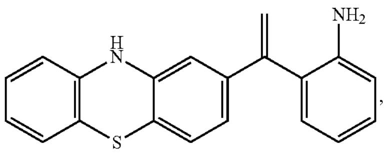
B17
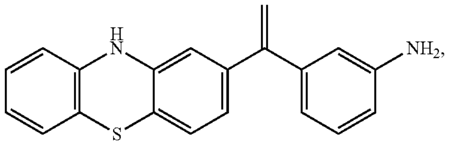
B18
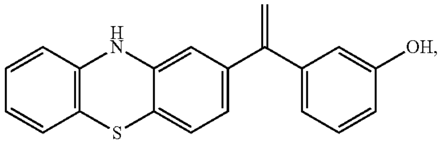
B19
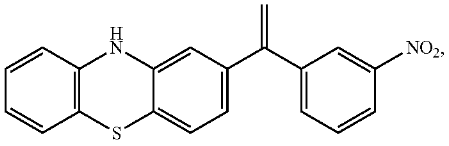
B20
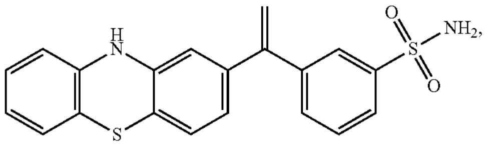
-continued
B21
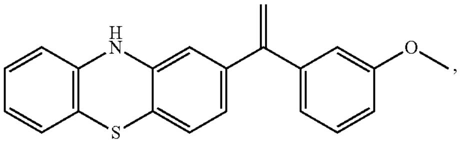
B22
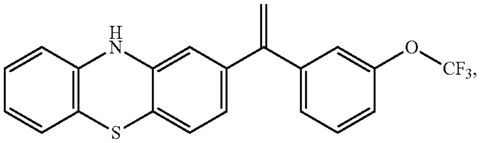
B23
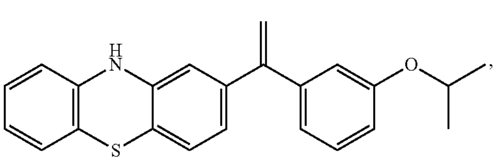
B24
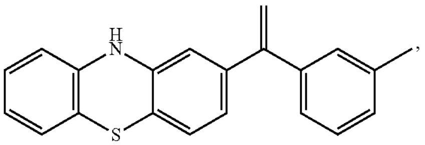
B25
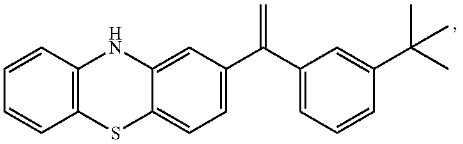
B26
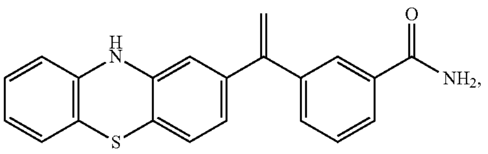
B27
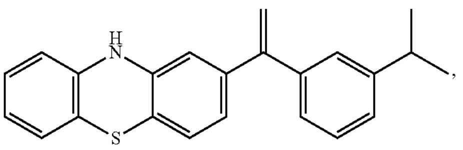
B28
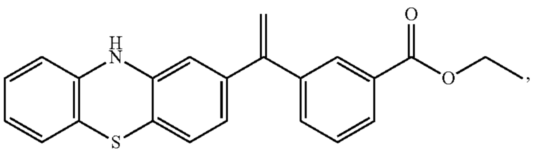
B29
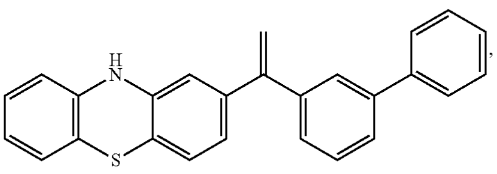

-continued
B30
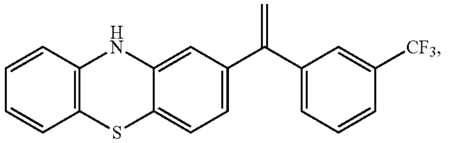
B31
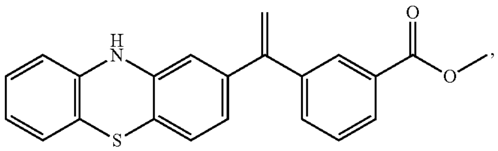
B32
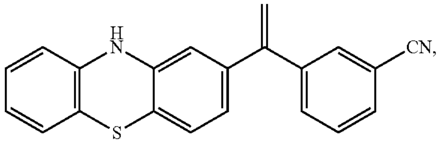
B33
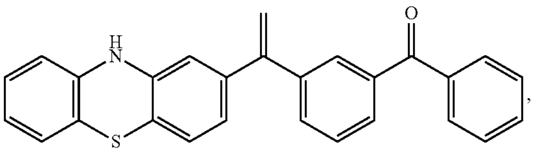
B34
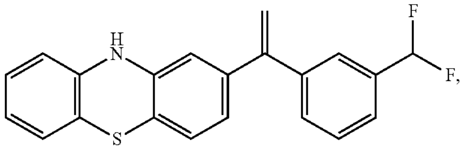
B35
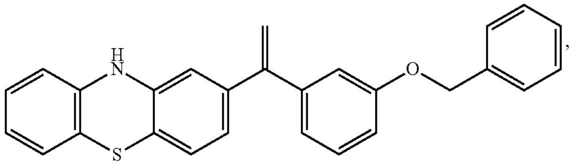
B36
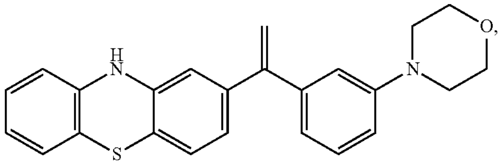
B37
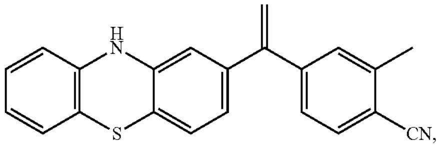
B38
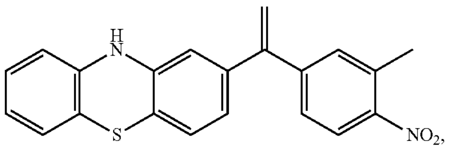
-continued
B39
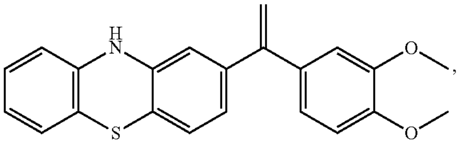
B40
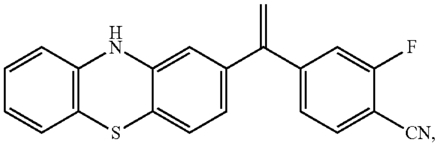
B41
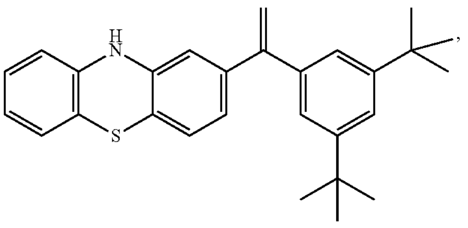
B42
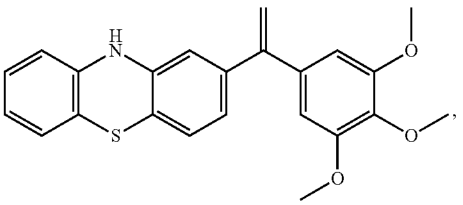
B43
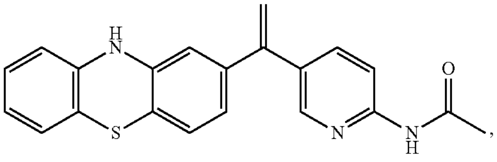
B44
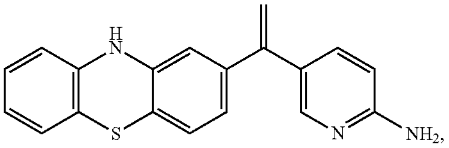
B45
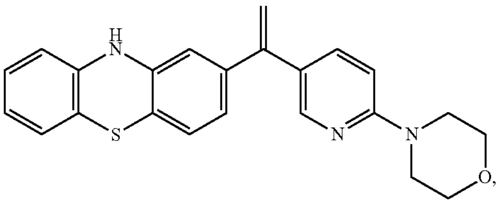
B46
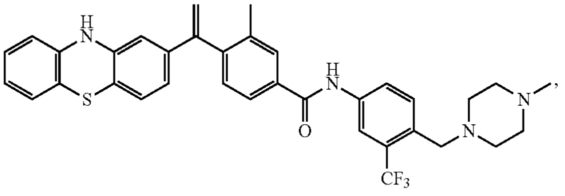

-continued
B47
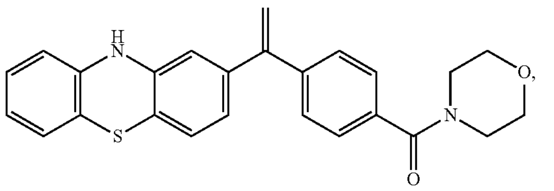
B48
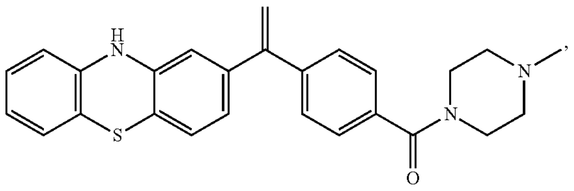
B49
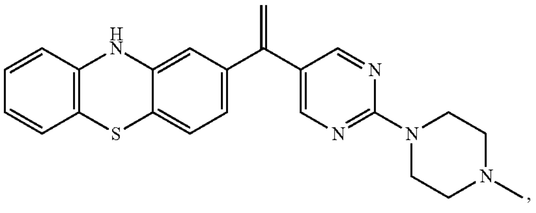
B50
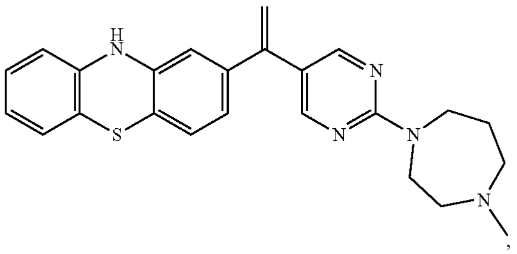
B51
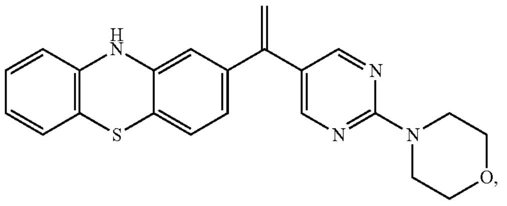
B52
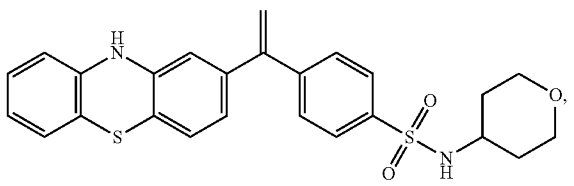
B53
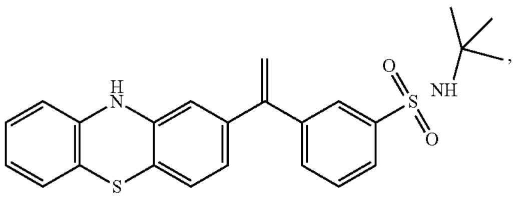
-continued
B54
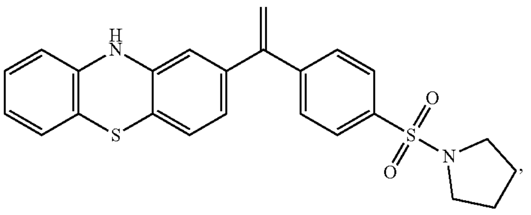
B55
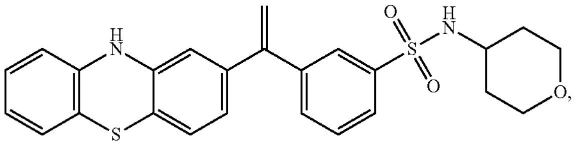
B56
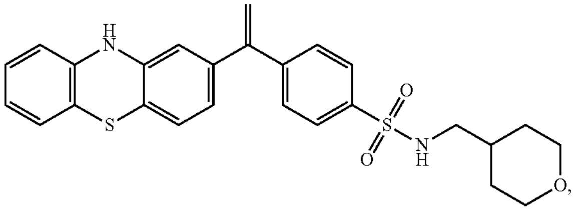
B57
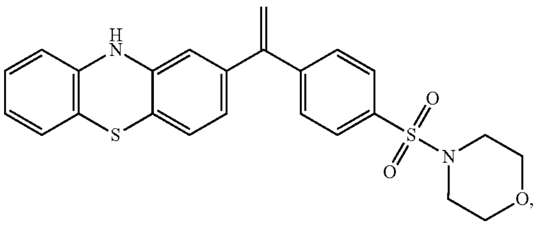
B58
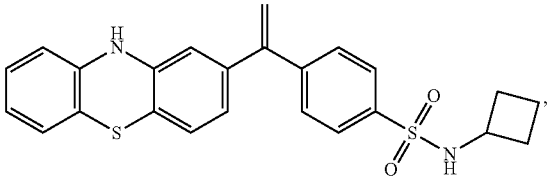
B59
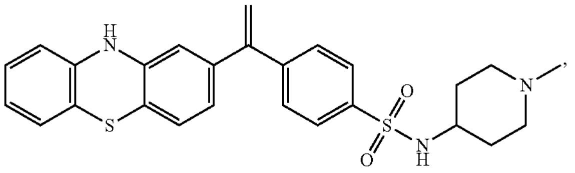
C1
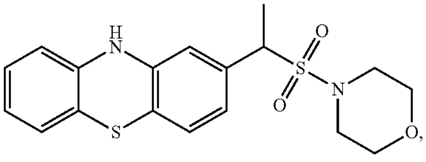

C2
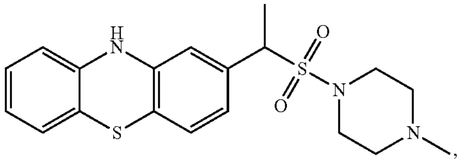
C3
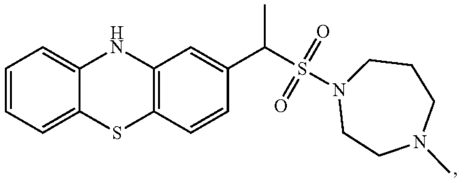
C4
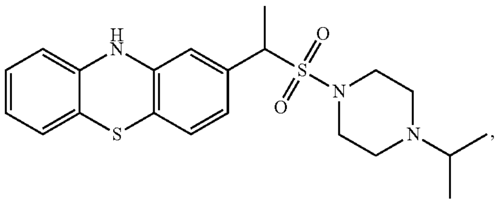
C5
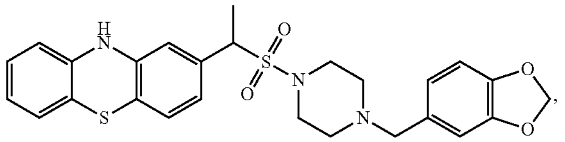
C6
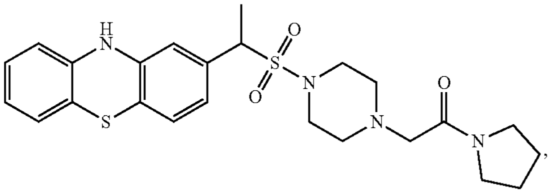
C7
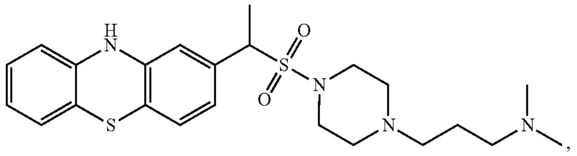
C8
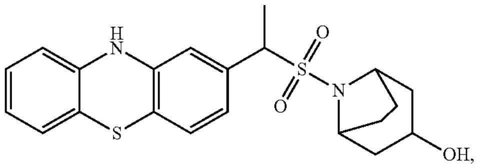
C9
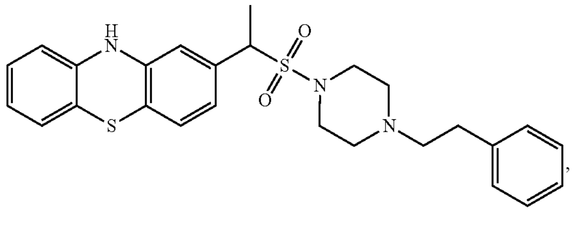
C10
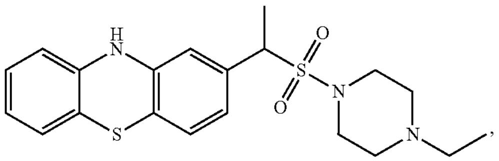
C11
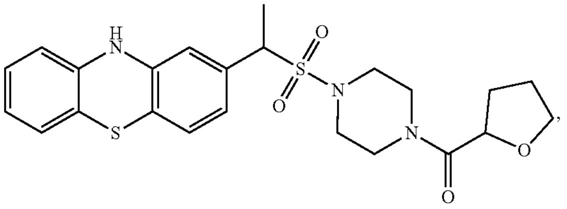
C12
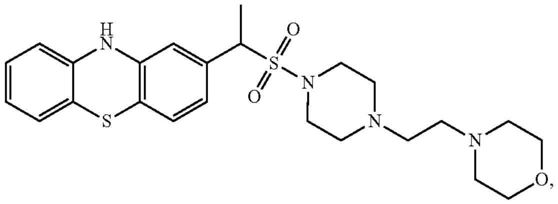
C13
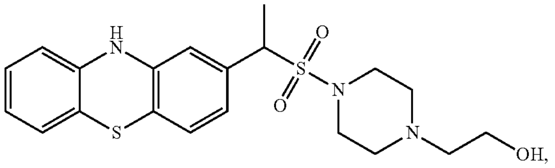
C14
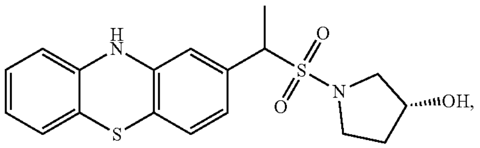
C15
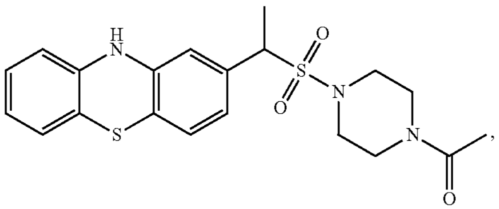
C16
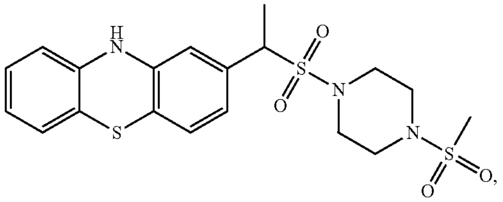

-continued
C17
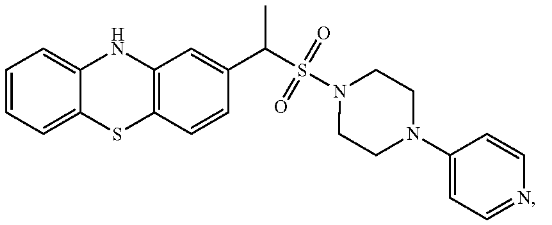,
C18
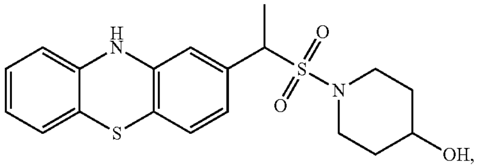,
C19
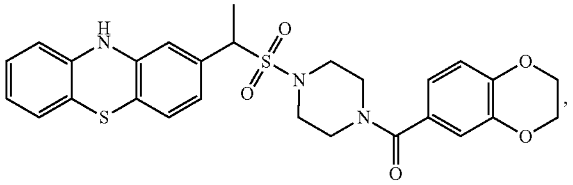,
C20
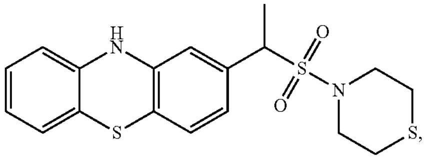,
C21
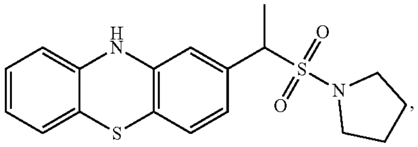,
C22
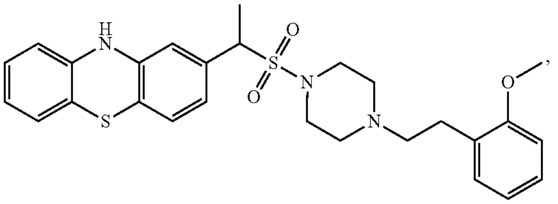,
C23
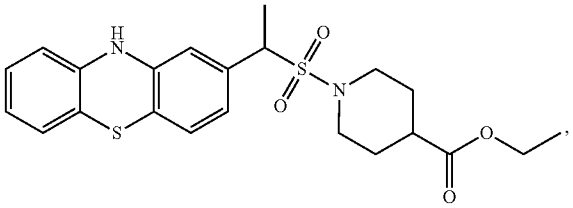,
C24
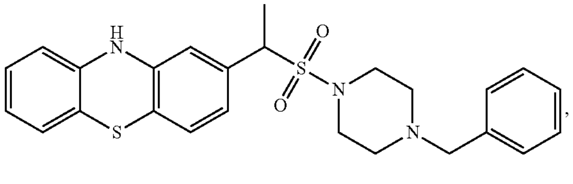,
-continued
C25
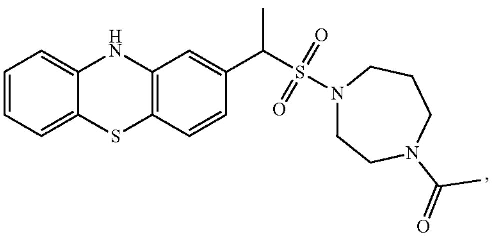,
C26
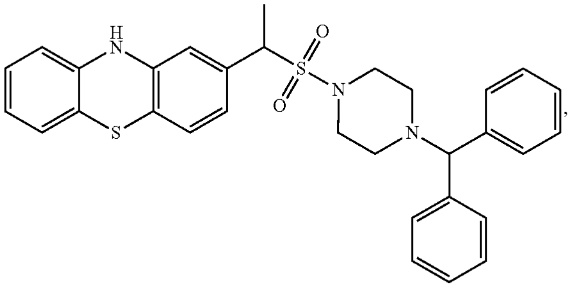,
C27
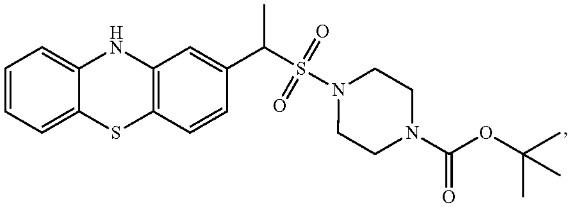,
C28
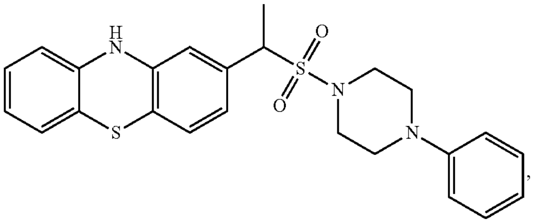,
C29
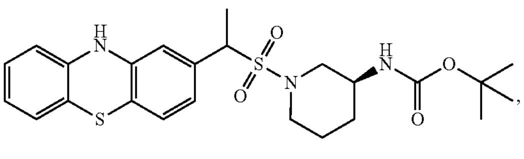,
C30
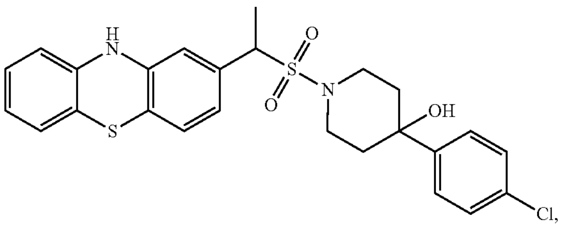, -continued
C31
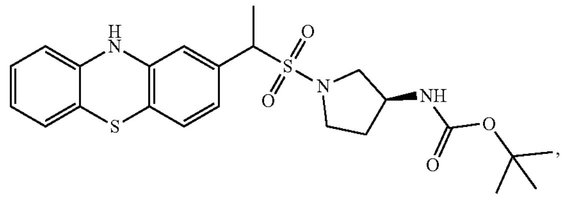,
C32
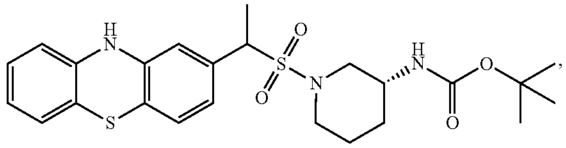,
C33
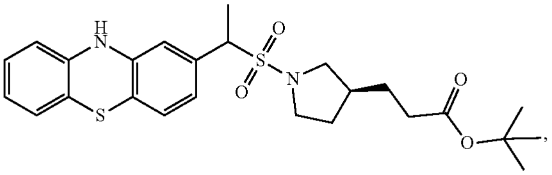,
C34
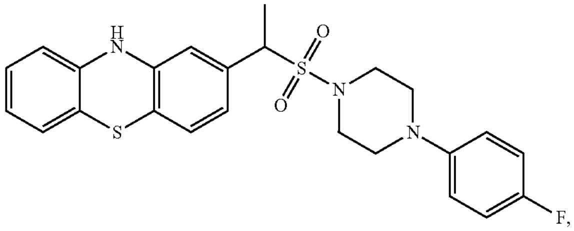,
C35
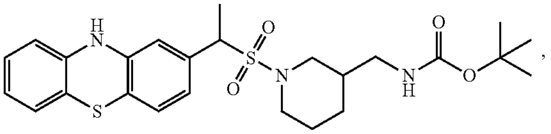,
C36
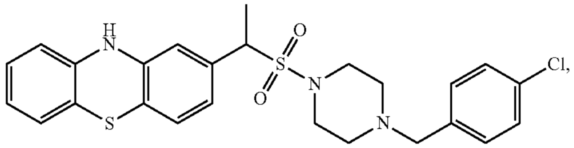,
C37
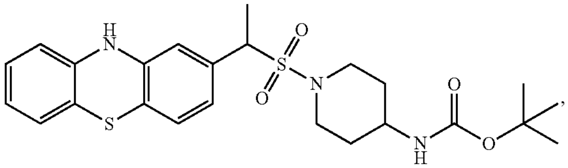,
C38
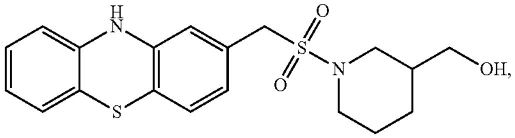,
-continued
C39
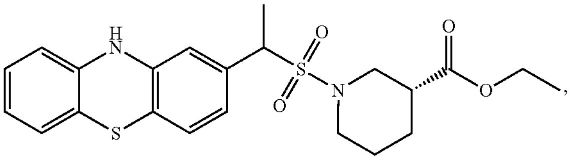,
C40
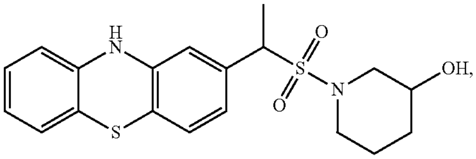,
C41
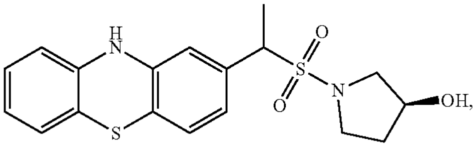,
C42
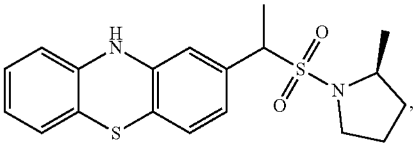,
C43
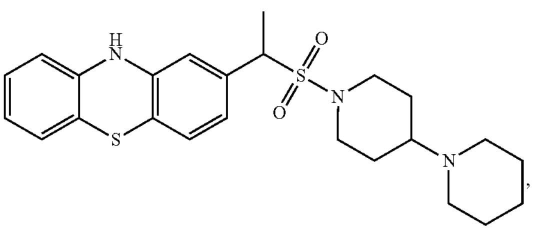,
C44
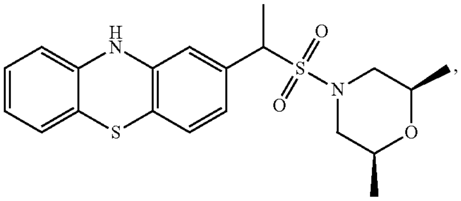,
C45
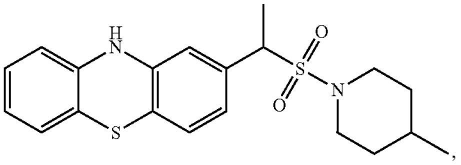,
C46
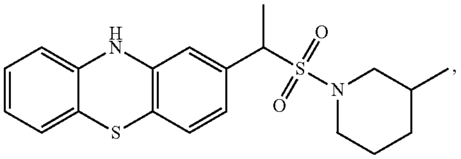, -continued
C47
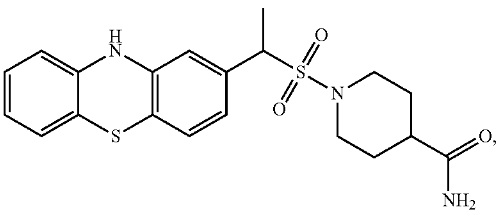
C48
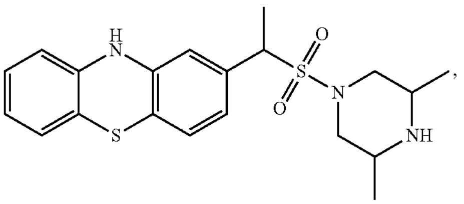
C49
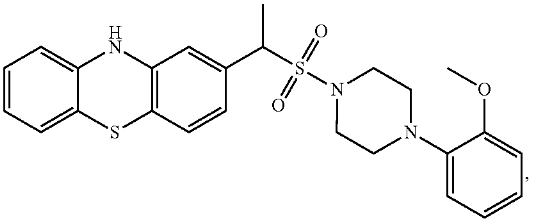
C50
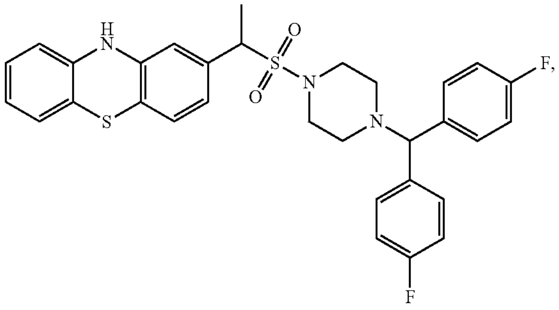
C51
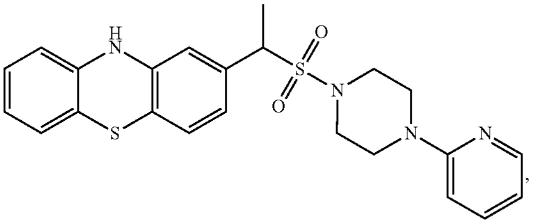
C52
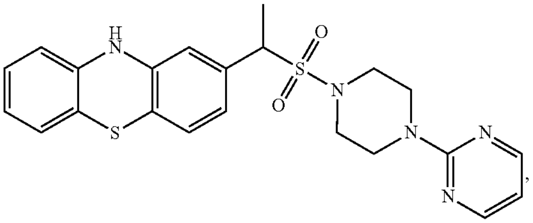
-continued
C53
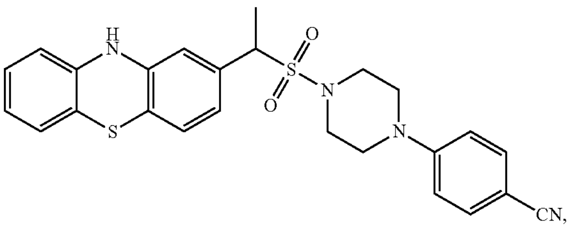
C54
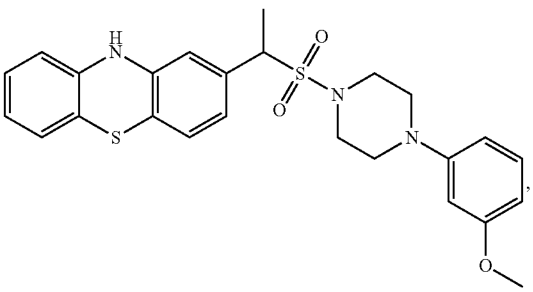
C55
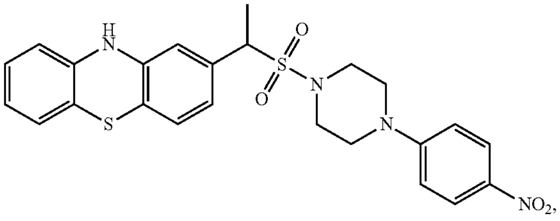
C56
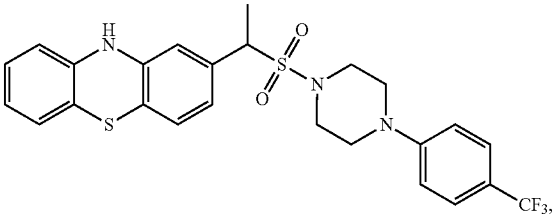
C57
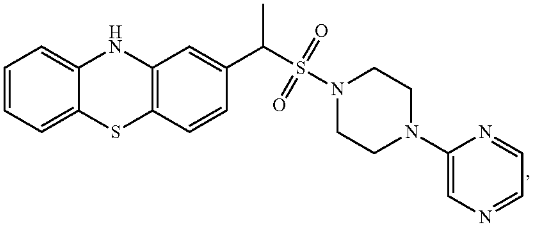
C58
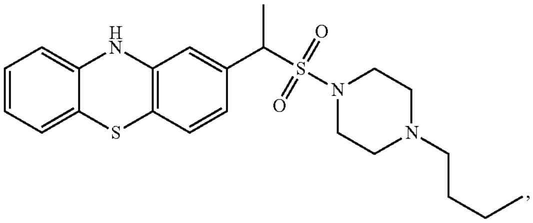

-continued

C59

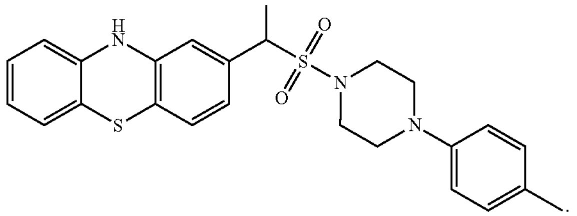

The present invention also provides the preparative method for the compound mentioned above, or a pharmaceutically acceptable salt, or crystal, or solvate thereof, that includes the following steps:

(1) 2-Acetylphenothiazine and 4-methylbenzenesulfonyl hydrazide are used as starting materials, and dissolved in MeOH, to which is then added the catalyst HOAc. The mixture is heated to 60° C. for reaction, and the progress of the reaction is monitored. After completion of the reaction, the reaction is cooled to room temperature, filtered under reduced pressure, and the filtrate is rinsed to be colorless, then dried in vacuo to obtain intermediate I;

(2) Intermediate I, starting material A, and anhydrous $K_2CO_3$ are dissolved in 1,4-dioxane, and then reacted at 110° C. The progress of the reaction is monitored. And after completion of the reaction, the mixture is cooled to room temperature and concentrated under reduced pressure to remove 1,4-dioxane.

The residue is extracted, and the organic layer is concentrated and then separated by column chromatography to obtain the target product;

Or, the method includes the following steps:

(1) 2-Acetylphenothiazine and 4-methylbenzenesulfonyl hydrazide are used as starting materials, that are dissolved in MeOH, to which is then added the catalyst HOAc. The mixture is heated to 60° C. for reaction, and the progress of the reaction is monitored. After completion of the reaction, the reaction is cooled to room temperature, filtered under reduced pressure, and the filtrate is rinsed to be colorless, then dried in vacuo to obtain intermediate I;

(2) Intermediate I, starting material A, tris(dibenzylidene-BASE acetone)dipalladium, 2-dicyclohexylphosphino-2,4,6-triisopropylbiphenyl and anhydrous t-BuOLi are dissolved in 1,4-dioxane, to which argon is purged and exchanged for 3 times. The resultant mixture is heated to 70° C. for reaction, and the reaction is monitored by TLC. After about 4 h, the reaction is completed, cooled to room temperature, filtered, concentrated under reduced pressure, and the residue is extracted. The organic layer is concentrated and separated by column chromatography to obtain the target compound;

Or, the method includes the following steps:

(1) 2-Acetylphenothiazine and 4-methylbenzenesulfonyl hydrazide are used as starting materials, that are dissolved in MeOH, to which is then added the catalyst HOAc. The mixture is heated to 60° C. for reaction, and the progress of the reaction is monitored. After completion of the reaction, the reactions are cooled to room temperature, filtered under reduced pressure, and the filtrate is rinsed to be colorless, then dried in vacuo to provide intermediate I;

(2) Intermediate I, starting material A, and DABSO are dissolved in DMSO, to which argon is purged and exchanged for 3 times. The resultant mixture is heated to 100° C. for reaction, and the reaction is monitored. After about 12 h, the reaction is completed, cooled to room temperature, filtered, concentrated under reduced pressure, and the residue is extracted. The organic layer is concentrated and separated by column chromatography to obtain the target compound.

Further, in said step (2), starting material A includes the compounds having following structures:

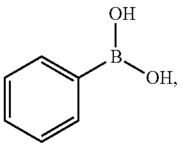
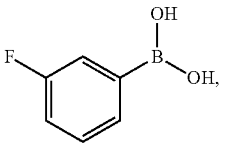
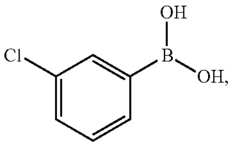
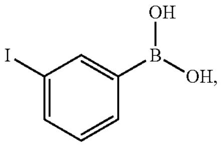
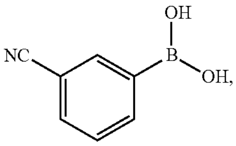
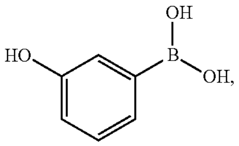
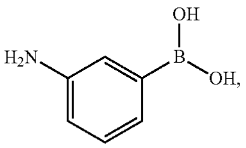
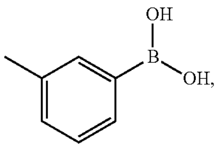
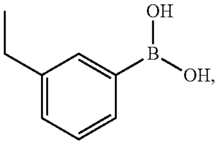
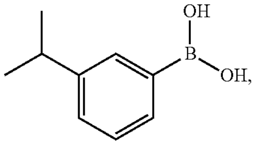
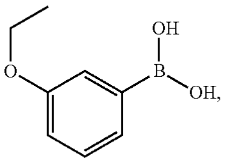
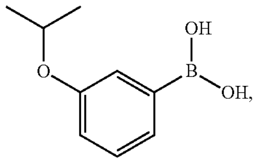
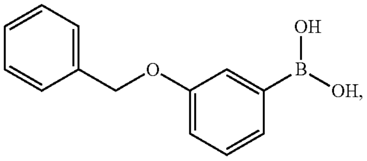
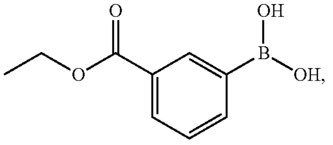
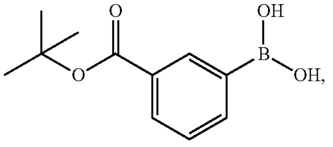
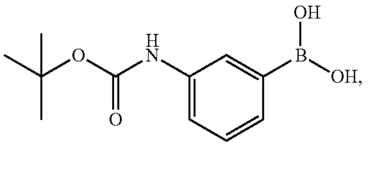

-continued
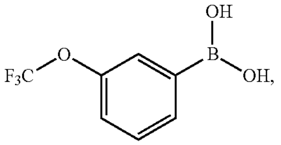
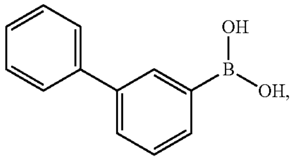
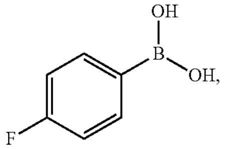
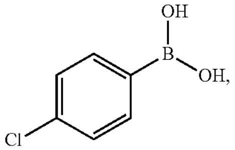
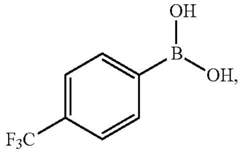
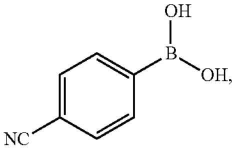
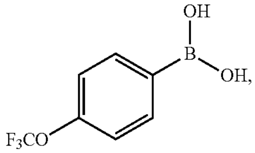
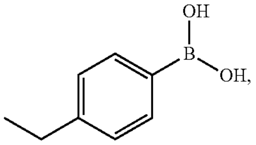
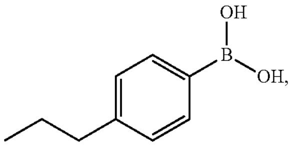
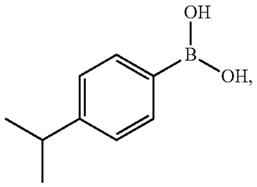
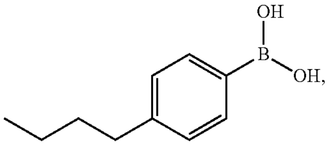
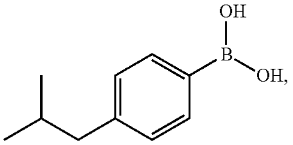
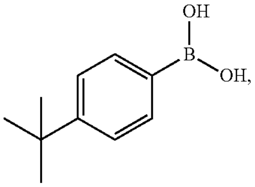
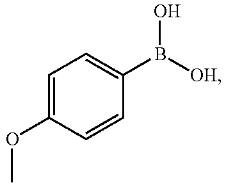
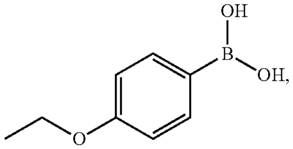
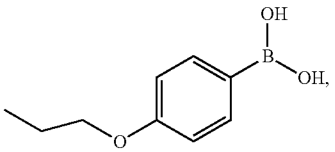
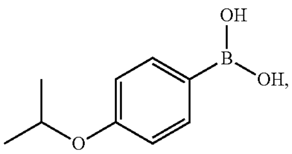
-continued
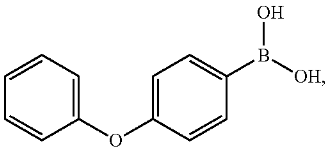
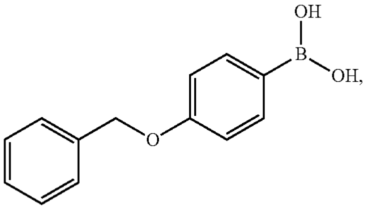
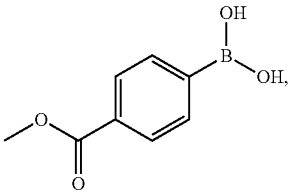
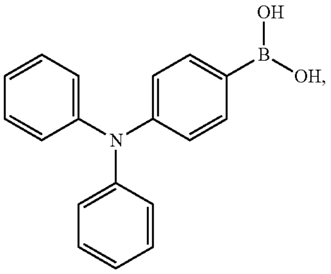
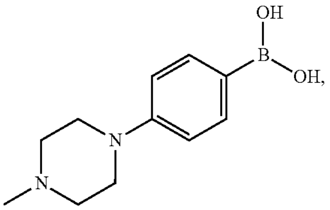
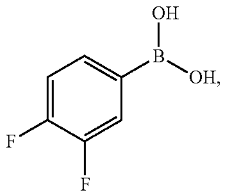
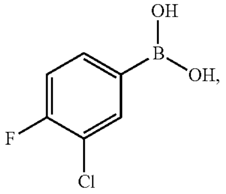
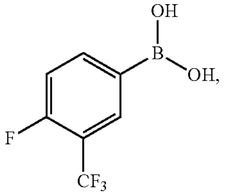
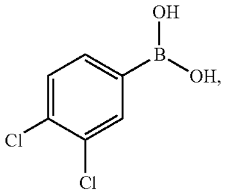
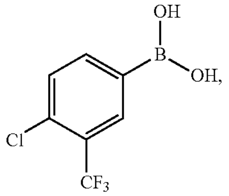
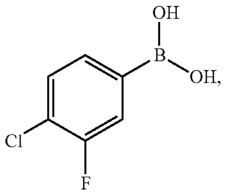
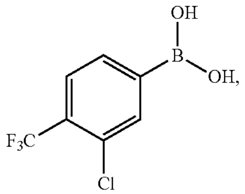

-continued
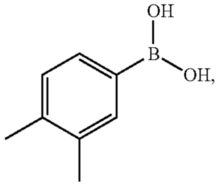
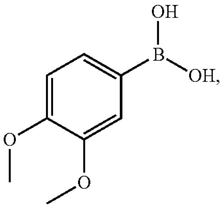
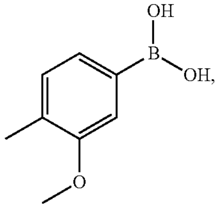
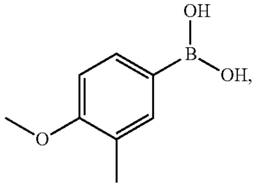
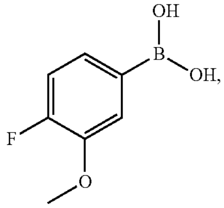
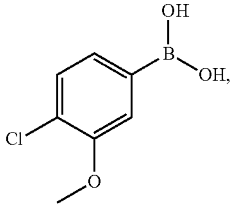
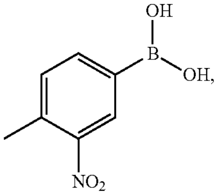
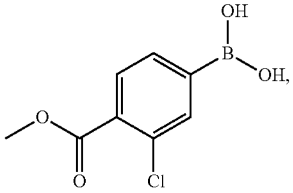
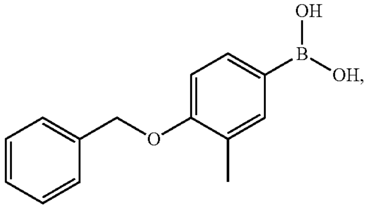
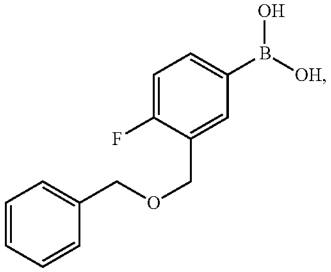
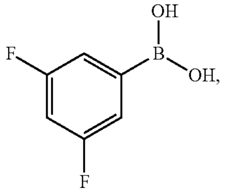
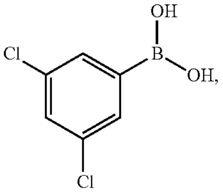
-continued
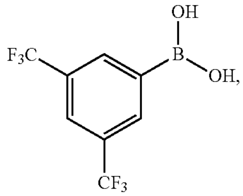
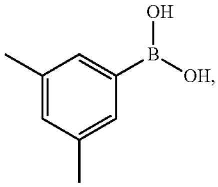
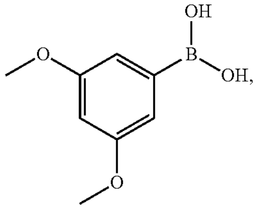
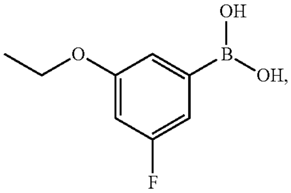
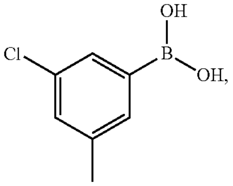
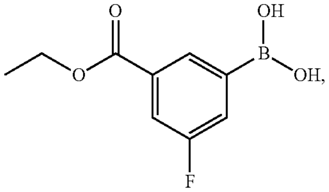
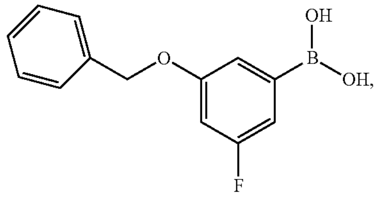
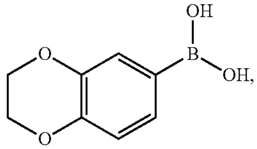
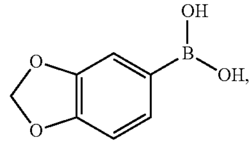
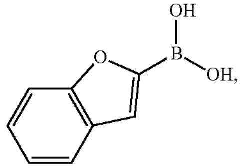
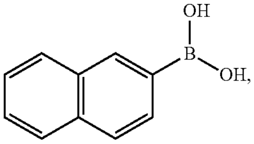
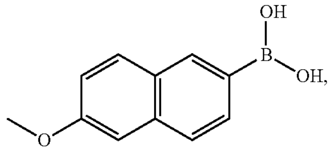
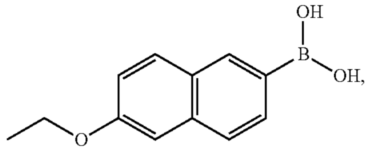
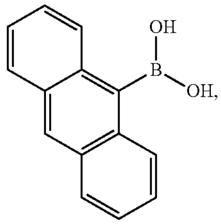
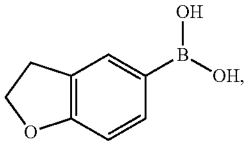

-continued
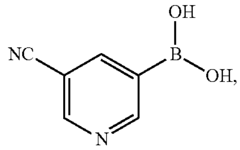 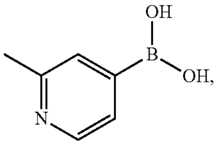
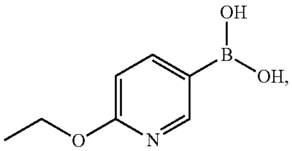 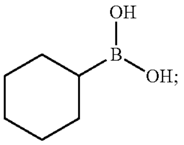
Or, in said step (2), starting material A includes the compounds having following structures:
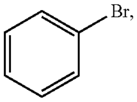 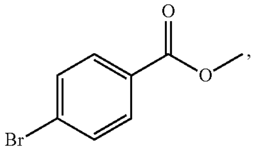
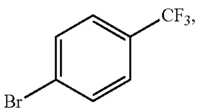 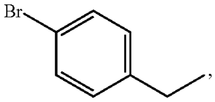
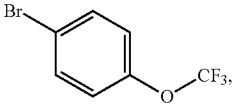 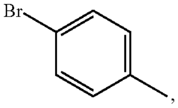
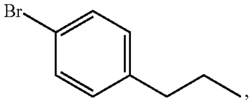 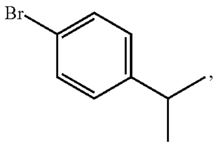
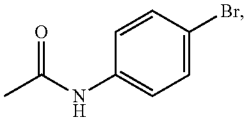 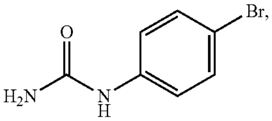
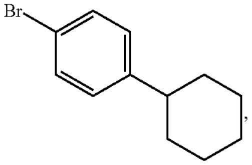 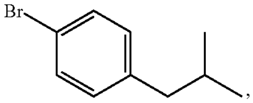
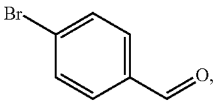 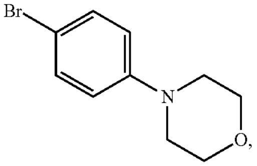
-continued
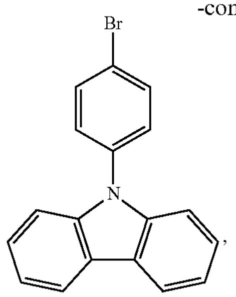 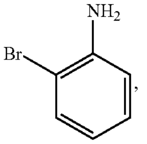
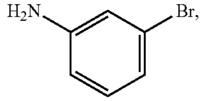 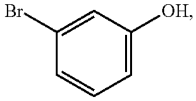
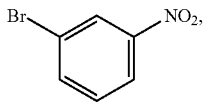 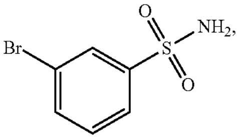
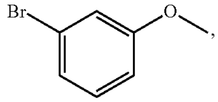 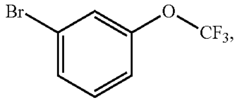
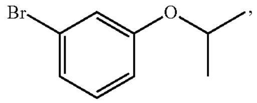 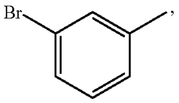
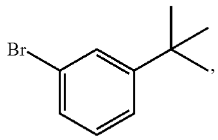 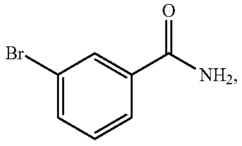
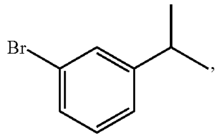 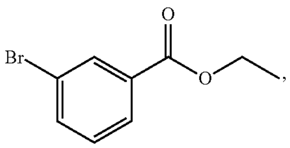
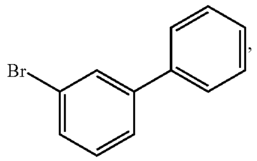 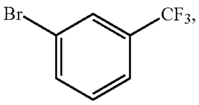
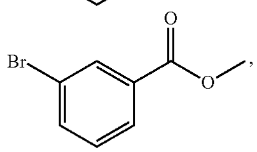 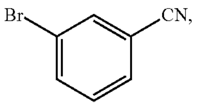
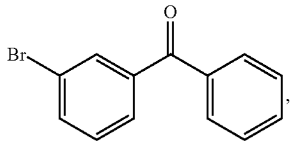 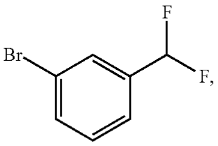
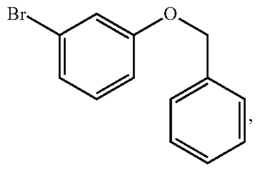 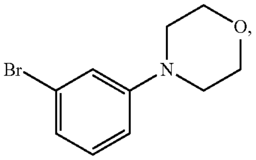

-continued
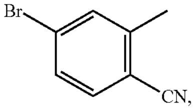
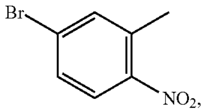
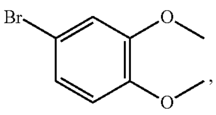
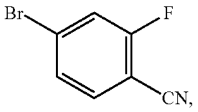
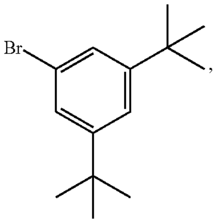
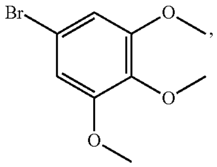
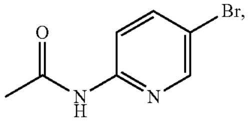
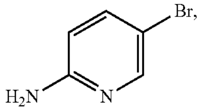
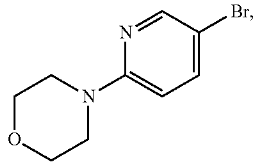
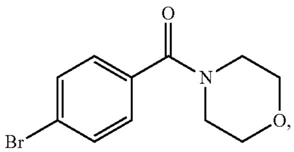
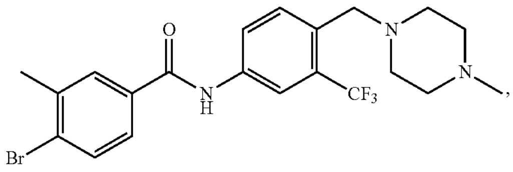
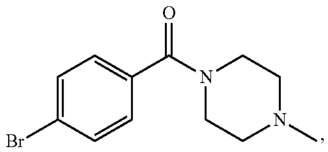
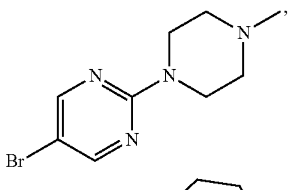
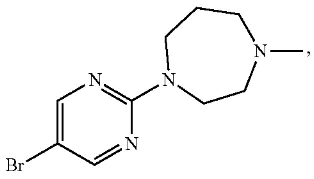
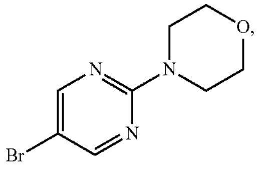
-continued
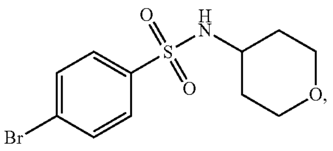
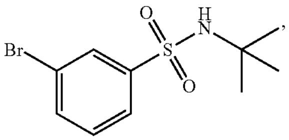
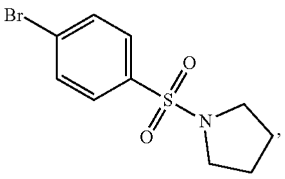
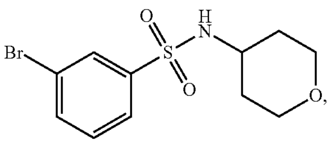
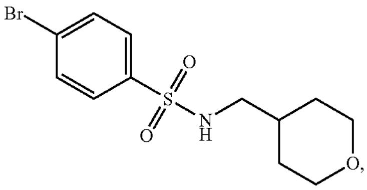
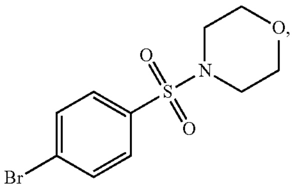
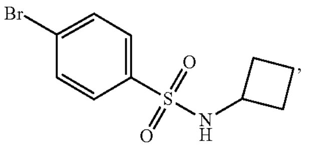
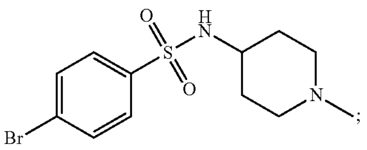
Or, in said step (2), starting material A includes the compounds having following structures:
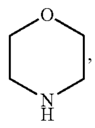
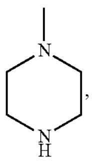
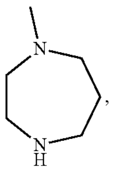
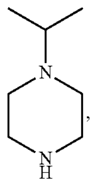

-continued
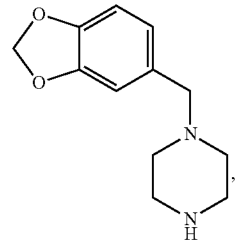,
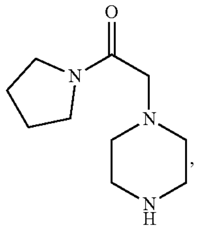,
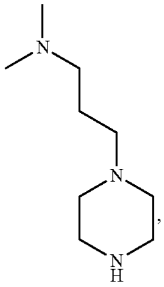,
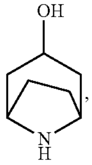,
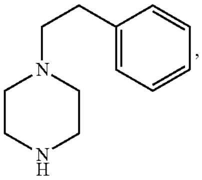,
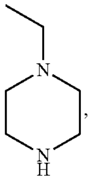,
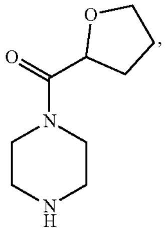
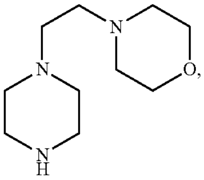
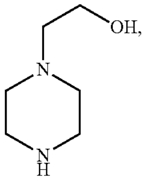
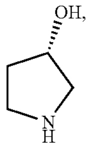
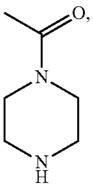
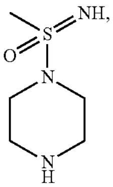
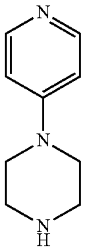
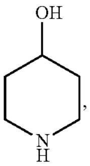,
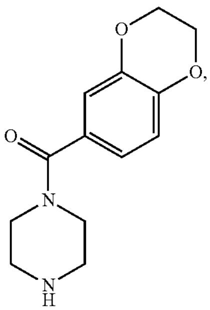,
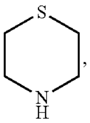
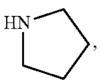,
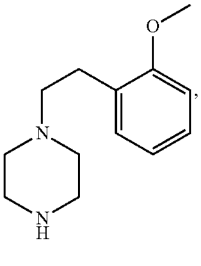,
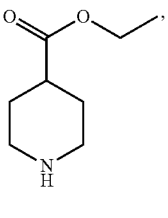,
-continued
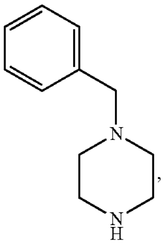,
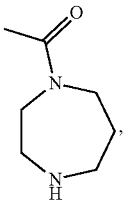,
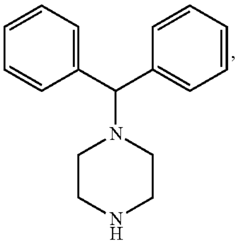,
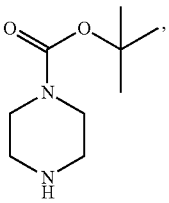,
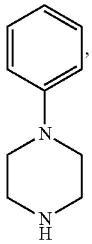,
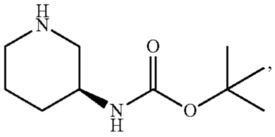,
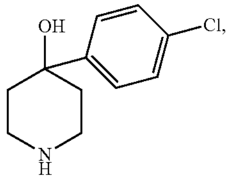,
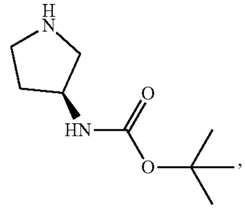
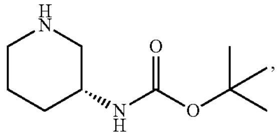,
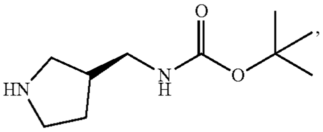,
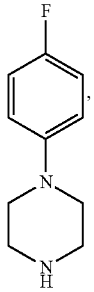,
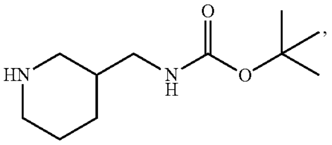,
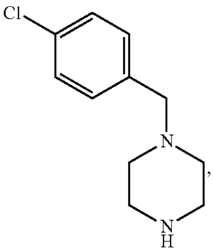, -continued

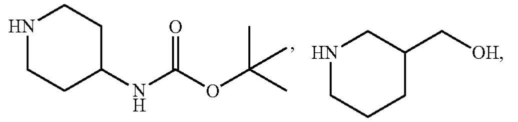

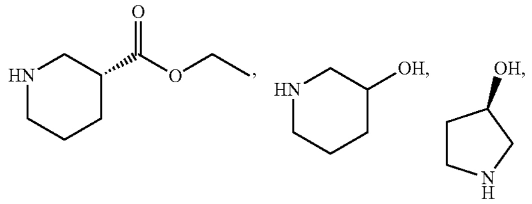

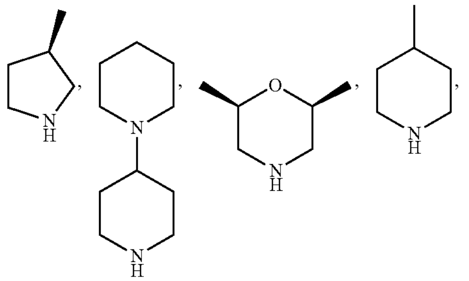

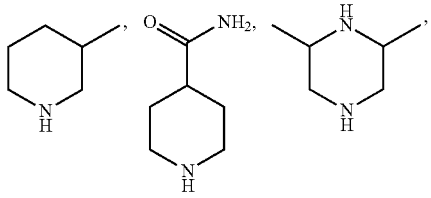

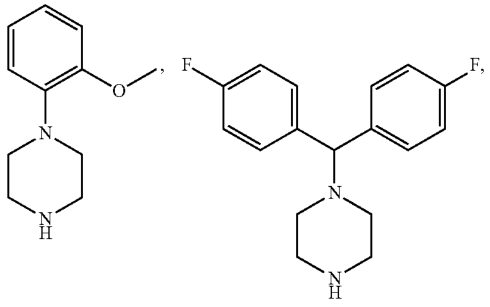

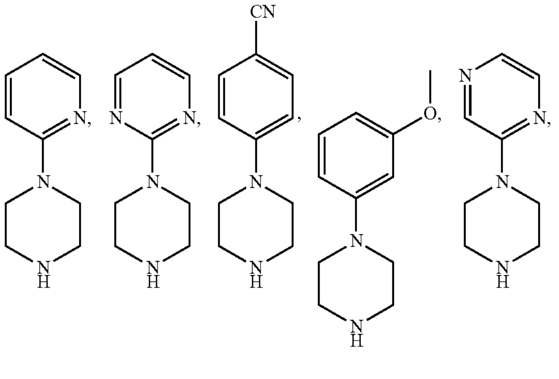

-continued

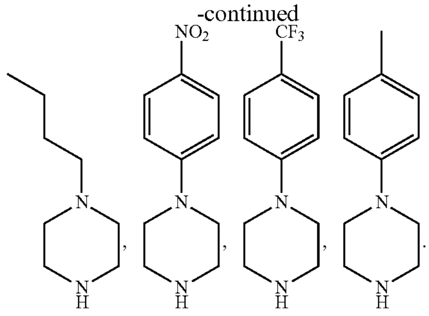

Further, in said step (1), during the rinsing process after completion of the reaction, MeOH and ethyl ether are used to wash; and/or in the step (2), during the extraction process after completion of the reaction, the extraction is carried out with saturated $NaHCO_3$/DCM; and/or, the reaction process is detected all by TLC.

The present invention provides the use of the compound mentioned above, or a pharmaceutically acceptable salt, or crystal, or solvate thereof in the preparation of ferroptosis inhibitor and/or in the preparation of drugs for treatment of stroke; wherein, said ferroptosis inhibitor is a targeted drug for inhibiting cell ferroptosis.

The present invention also provides a drug that is a preparation obtained by using the compound mentioned above, or a pharmaceutically acceptable salt, or crystal, or solvate thereof as active ingredients, with the addition of pharmaceutically acceptable excipients; wherein, said preparations are oral preparations and intravenous injection preparations.

The compounds and derivatives provided in the present invention can be named according to IUPAC (International Union of Pure and Applied Chemistry) or CAS (Chemical Abstracting Service, Columbus, Ohio) naming system.

For the definition of term used in the present the invention: unless otherwise specified, the initial definition provided for the group or the term herein is applicable to those in the whole specification; for terms not specifically defined herein, according to the disclosure content and the context, the term should have the meaning commonly given by those skilled in the field.

"Substitution" means that the hydrogen in a molecule is substituted by other different atoms or molecules.

The structure of the compound mentioned in the present invention all denotes the one that can exist stably.

In the present invention, the structure of substituent "—$C(O)R_{51}$" is

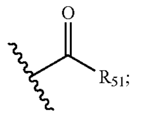

the structure of substituent "—$C(O)OR_{51}$" is

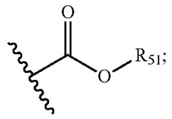

the structure of substituent "—C(O)N(H)$R_{51}$" is

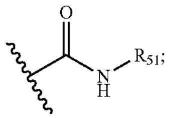

the structure of substituent "—S(O)(O)$R_{51}$" is

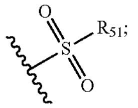

the structure of substituent "—N(H)C(O)$R_{51}$" is

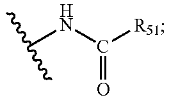

the structure of substituent "—$NR_{52}R_{53}$" is

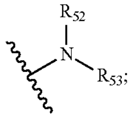

the structure of substituent "—N(H)C(O)O$R_{51}$" is

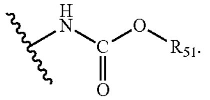

In the present invention, the minimum and the maximum for the content of carbon atoms in hydrocarbon groups are represented by prefixes, for example, the prefix ($C_a$-$C_b$) alkyls mean any alkyls containing "a"-"b" carbon atoms. Therefore, for example, $C_1$-$C_8$ alkyls denotes the straight or branched alkyls containing 1-8 carbon atoms. $C_1$-$C_8$ alkoxyls denote the alkoxyls containing 1-8 carbon atoms. In the present invention, "3-8-membered saturated cycloalkyls" denote a monocyclic or polycyclic cycloalkyl consisting of 3-8 carbon atoms, in which there isn't a double bond; 3-8 membered unsaturated cycloalkyls denote a monocyclic cycloalkyl consisting of 3-8 carbon atoms, in which there are one or more double bonds; 3-8-membered saturated heterocyclic groups denote a saturated monocyclic heterocyclic group without double bonds, in which there is at least one heteroatom selected from O, S or substituted nitrogen atom, and the remained atoms in the ring are carbons; 3-8-membered unsaturated heterocyclic groups mean an unsaturated monocyclic heterocyclic group containing double bonds, in which there is at least one heteroatom selected from O, S or substituted nitrogen atom, and the remained atoms in the ring are carbons; a benzo(saturated)heterocyclic group means a saturated heterocyclic group fused with a benzene; a benzo(unsaturated)heterocyclic group means an unsaturated heterocyclic group fused with a benzene.

In the present invention, halogen is fluorine, chlorine, bromine or iodine.

10H-phenothiazine derivatives prepared in the present invention have the effect of inhibiting ferroptosis, and ferroptosis is related to various diseases such as stroke, Parkinson's syndrome and pancreatic cancer, and it has been found that the development of the disease can be intervened by activating or inhibiting ferroptosis. Therefore, 10H-phenothiazine derivatives including bio-pharmaceutically acceptable salts, crystals, and solvates thereof can be used as the main active ingredient, together with the addition of bio-pharmaceutically acceptable excipients, to prepare the inhibitors of ferroptosis. 10H-phenothiazine derivatives or the prepared ferroptosis inhibitors can be used as the main active ingredient of the drugs for treatment of stroke.

In the present invention, a new 10H-phenothiazine derivative has been synthesized that can inhibit ferroptosis, and by study on its structure optimization and structure-activity relationship, it is confirmed that in some embodiments 10H-phenothiazine derivatives can have a better inhibitory effect on body death, and there are compounds that show better therapeutic effects on the rat focal cerebral ischemia model, which can be used as the main active ingredient for the preparation of body death inhibitors. The compounds and the inhibitors prepared by said compounds have good medicinal potential and are expected to become a new candidate drug for treatment of stroke; at the same time, the preparative method of the new compound provided by the present invention is simple, and the reaction conditions are mild, that are convenient for the operation and control. Moreover, the reactions have low consumption, high yield and low cost, and are suitable for industrialized production. The prepared compound has higher biological activity, strong selectivity, and remarkable drug-like properties, and has broad market prospects.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Figure 1:
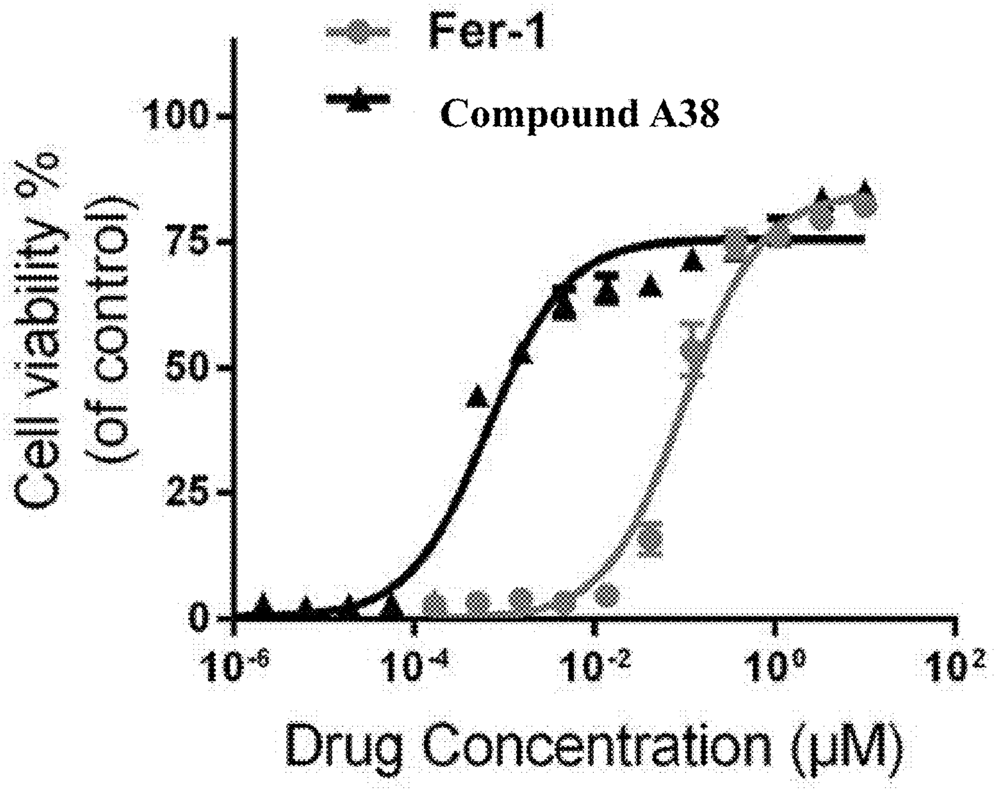
FIG. 1 shows a graph of $EC_{50}$ comparison between compound A38 of the present invention and the positive control Fer-1.

The starting materials and equipment used in the specific examples of the present invention are all known products and can be obtained by purchasing commercially available products.

Example 1 Synthesis of (E)-N'-(1-(10H-phenothiazin-2-yl)ethylidene)-4-methylbenzenesulfonyl hydrazide (Intermediate I)

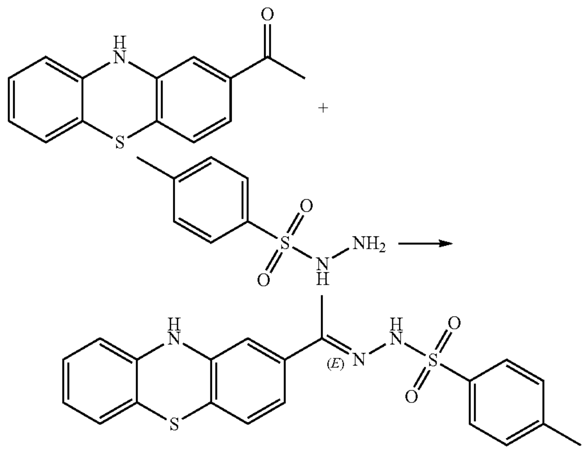

Intermediate I

2-Acetylphenothiazine (10.0 g, 41.44 mmol, 1.0 eq) and 4-methylbenzenesulfonyl hydrazide (7.72 g, 41.44 mmol, 1.0 eq) were dissolved in 100 mL MeOH, to which was added 1 mL HOAc, and the resultant mixture was heated to 60° C. for reaction. The reaction was monitored by TLC, and after about 4 h, the reaction was completed. After cooling to room temperature, a yellow solid appeared, that was collected by vacuum filtration, and then washed with MeOH and ethyl ether until the filtrate was colorless. After drying under vacuum, intermediate I (15 g) was obtained with a yield of 88.4%.

$^1$HNMR and HRMS data of intermediate I are as follows:

$^1$H NMR (400 MHz, DMSO-d$_6$) δ 10.45 (s, 1H), 8.70 (s, 1H), 7.82 (d, J=8.3 Hz, 2H), 7.40 (d, J=8.1 Hz, 2H), 7.06 (d, J=1.7 Hz, 1H), 6.98 (dd, J=8.0, 1.7 Hz, 2H), 6.89 (dd, J=7.2, 3.0 Hz, 2H), 6.75 (dd, J=7.5, 0.9 Hz, 1H), 6.72-6.62 (m, 1H), 2.37 (s, 3H), 2.08 (s, 3H).

MS m/z (ESI): 410.1 [M+H]$^+$.

Example 2 Synthesis of Compounds A1-A76 of the Present Invention

Compounds 1-76 in Example 2 were also named compounds A1-A76.

Using the intermediate I prepared in Example 1 and various substituted boronic acids as starting materials to prepare compounds 1-76, namely compounds A1-A76 Among them, the method for preparation of compounds 2-76 is the same as that of compound 1 in Example 2.

Compound 1: 2-(1-phenylethyl)-10H-phenothiazine

Synthetic route was as follows:

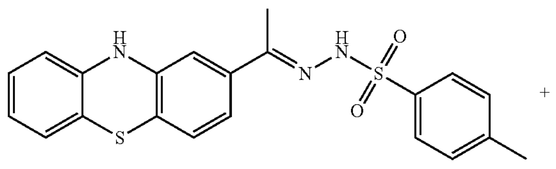

Intermediate I

-continued

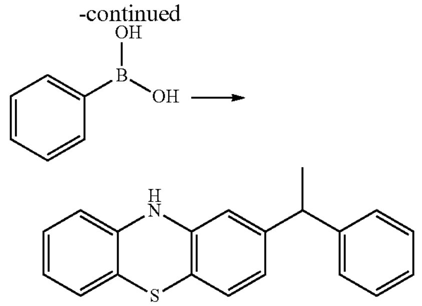

1

Intermediate I (100 mg, 0.244 mmol, 1.0 eq), phenylboronic acid (45 mg, 0.366 mmol, 1.5 eq), and anhydrous $K_2CO_3$ (51 mg, 0.366 mmol, 1.5 eq) were dissolved in 10 mL 1,4-dioxane and warmed to 110° C. for reaction, and the reaction was monitored by TLC. After about 4 h, the reaction was completed. After cooling to room temperature, the reactions were concentrated under reduced pressure to remove 1,4-dioxane, and the residue was extracted with saturated $NaHCO_3$/DCM (1:1). The organic layer was concentrated and separated by column chromatography to obtain the target product compound 1 (48 mg), with a yield of 74.8%.

$^1$HNMR and HRMS data of compound 1 are as follows:

$^1$H NMR (400 MHz, DMSO-d$_6$) δ 8.50 (s, 1H), 7.29 (t, J=7.4 Hz, 2H), 7.22 (d, J=7.1 Hz, 2H), 7.18 (d, J=7.1 Hz, 1H), 6.95 (dd, J=10.9, 4.4 Hz, 1H), 6.91-6.85 (m, 1H), 6.82 (d, J=7.9 Hz, 1H), 6.73 (td, J=7.6, 1.0 Hz, 1H), 6.71-6.62 (m, 2H), 6.54 (d, J=1.4 Hz, 1H), 4.00 (q, J=7.1 Hz, 1H), 1.50 (d, J=7.2 Hz, 3H).

HRMS m/z (ESI) calcd for $C_{20}H_{17}NS$ [M+H]$^+$ 303.1082 found: 403.1085.

Compound 2: 2-(1-(3-fluorophenyl)ethyl)-10H-phenothiazine

The synthetic route is as follows:

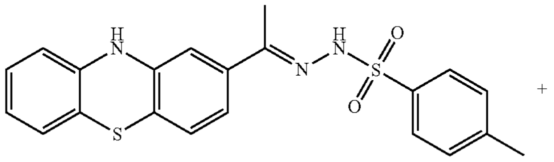

Intermediate I

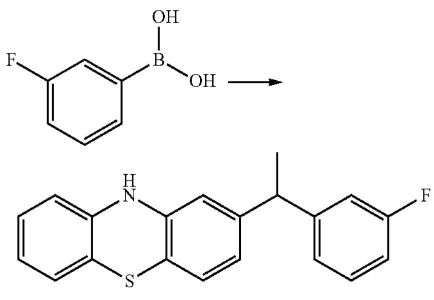

2

$^1$H NMR and HRMS data of compound 2 are as follows:

$^1$H NMR (400 MHz, DMSO-d$_6$) δ 8.50 (s, 1H), 7.33 (td, J=8.0, 6.3 Hz, 1H), 7.10-6.92 (m, 4H), 6.89 (dd, J=7.6, 1.3

Hz, 1H), 6.84 (d, J=7.9 Hz, 1H), 6.76-6.67 (m, 2H), 6.65 (dd, J=7.9, 1.1 Hz, 1H), 6.53 (d, J=1.7 Hz, 1H), 4.04 (q, J=7.2 Hz, 1H), 1.50 (d, J=7.2 Hz, 3H). HRMS m/z (ESI) calcd for $C_{20}H_{16}FNS$ $[M+H]^+$ 321.1082 found: 321.1082.

The detailed preparative method are same as that of compound 1, with a yield of 75.3%.

Compound 3: 2-(1-(3-chlorophenyl)ethyl)-10H-phenothiazine

The synthetic route is as follows:

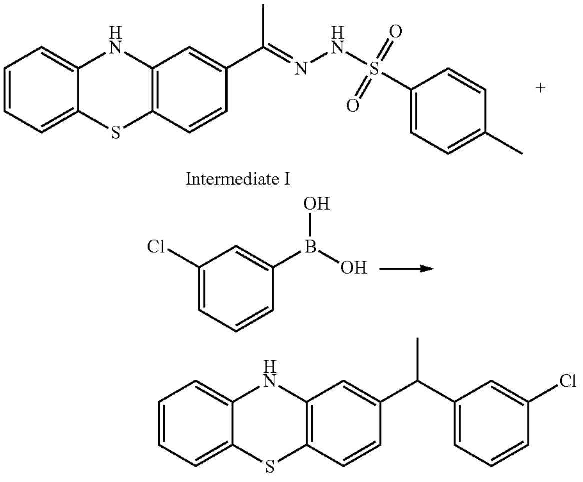

3

$^1$H NMR and HRMS data of compound 3 are as follows:

$^1$H NMR (400 MHz, DMSO-$d_6$) δ 8.49 (s, 1H), 6.96 (t, J=7.5 Hz, 1H), 6.89 (d, J=7.5 Hz, 1H), 6.82 (d, J=7.9 Hz, 2H), 6.77 (s, 1H), 6.74 (d, J=7.4 Hz, 1H), 6.67 (dd, J=15.7, 7.9 Hz, 3H), 5.95 (s, 2H), 3.93 (q, J=6.9 Hz, 1H), 1.46 (d, J=7.1 Hz, 3H).

HRMS m/z (ESI) calcd for $C_{20}H_{16}ClNS$ $[M+H]^+$ 337.0692 found: 337.0695.

The detailed preparative method is same as that of compound 1, with a yield of 73.4%.

Compound 4: 2-(1-(3-iodophenyl)ethyl)-10H-phenothiazine

The synthetic route is as follows:

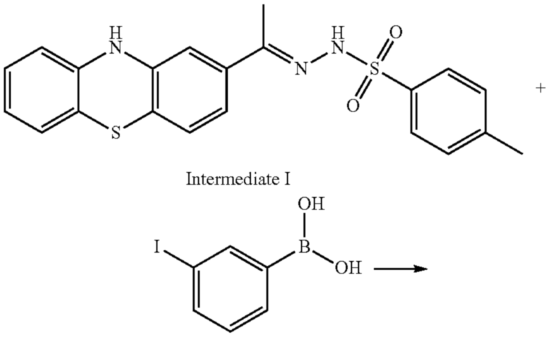

-continued

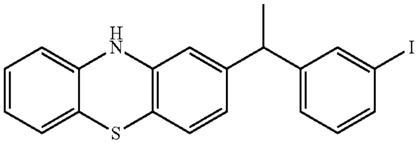

4

$^1$H NMR and HRMS data of compound 4 are as follows:

$^1$H NMR (400 MHz, DMSO-$d_6$) δ 8.51 (s, 1H), 7.59 (s, 1H), 7.55 (d, J=7.9 Hz, 1H), 7.25 (d, J=7.8 Hz, 1H), 7.10 (t, J=7.7 Hz, 1H), 7.03-6.92 (m, 1H), 6.89 (d, J=6.9 Hz, 1H), 6.83 (d, J=7.9 Hz, 1H), 6.73 (t, J=7.5 Hz, 1H), 6.70-6.61 (m, 2H), 6.51 (d, J=1.3 Hz, 1H), 3.99 (q, J=7.1 Hz, 1H), 1.48 (d, J=7.2 Hz, 3H).

HRMS m/z (ESI) calcd for $C_{20}H_{16}INS$ $[M+H]^+$ 429.0048 found: 429.0045.

The detailed preparative method is same as that of compound 1, with a yield of 63.8%.

Compound 5: 3-(1-(10H-phenothiazin-2-yl)ethyl)benzonitrile

The synthetic route is as follows:

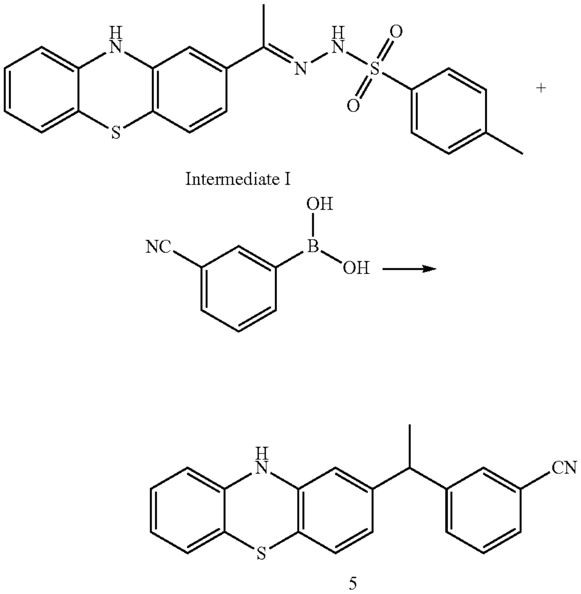

5

$^1$H NMR and HRMS data of compound 5 are as follows:

$^1$H NMR (400 MHz, DMSO-$d_6$) δ 8.51 (s, 1H), 7.73 (s, 1H), 7.67 (d, J=7.2 Hz, 1H), 7.56 (d, J=7.5 Hz, 1H), 7.52 (d, J=7.5 Hz, 1H), 6.96 (t, J=7.4 Hz, 1H), 6.89 (d, J=7.5 Hz, 1H), 6.84 (d, J=7.8 Hz, 1H), 6.72 (dd, J=15.9, 7.7 Hz, 2H), 6.65 (d, J=7.8 Hz, 1H), 6.51 (s, 1H), 4.11 (d, J=7.0 Hz, 1H), 1.52 (d, J=7.0 Hz, 3H).

HRMS m/z (ESI) calcd for $C_{21}H_{16}N_2S$ $[M+H]^+$ 328.1034 found: 328.1033.

The detailed preparative method is same as that of compound 1, with a yield of 71.4%.

Compound 6:
3-(1-(10H-phenothiazin-2-yl)ethyl)phenol

The synthetic route is as follows:

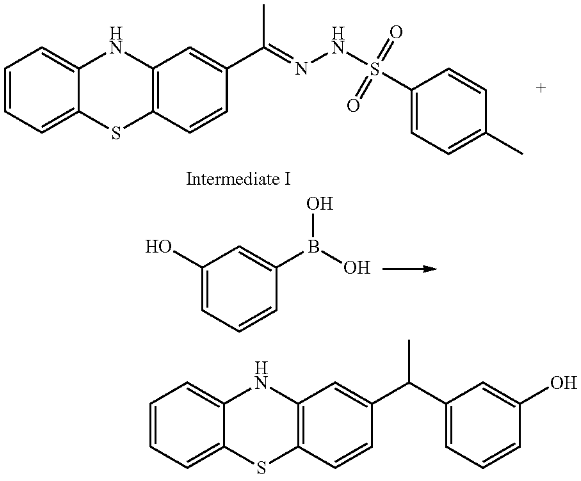

6

$^1$H NMR and HRMS data of compound 6 are as follows:

$^1$H NMR (400 MHz, DMSO-$d_6$) δ 9.25 (s, 1H), 8.52 (s, 1H), 7.07 (t, J=7.4 Hz, 1H), 6.96 (t, J=7.3 Hz, 1H), 6.89 (d, J=7.3 Hz, 1H), 6.82 (d, J=7.6 Hz, 1H), 6.78-6.70 (m, 1H), 6.65 (d, J=7.0 Hz, 3H), 6.57 (d, J=9.2 Hz, 2H), 6.53 (s, 1H), 3.90 (d, J=6.7 Hz, 1H), 1.46 (d, J=6.8 Hz, 3H).

HRMS m/z (ESI) calcd for $C_{20}H_{17}NOS$ $[M+H]^+$ 319.1031 found: 319.1034.

The detailed preparative method is same as that of compound 1, with a yield of 65.5%.

Compound 7:
3-(1-(10H-phenothiazin-2-yl)ethyl)phenylamine

The synthetic route is as follows:

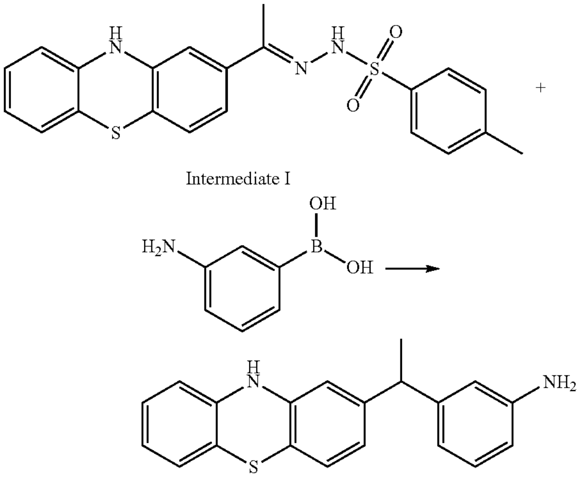

7

$^1$H NMR and HRMS data of compound 7 are as follows:

$^1$H NMR (400 MHz, DMSO-$d_6$) δ 8.50 (s, 1H), 6.95 (dd, J=7.7, 1.3 Hz, 1H), 6.89 (dd, J=11.5, 4.6 Hz, 2H), 6.81 (d, J=7.9 Hz, 1H), 6.73 (dd, J=7.5, 1.2 Hz, 1H), 6.65 (d, J=7.9 Hz, 2H), 6.52 (d, J=1.6 Hz, 1H), 6.44-6.33 (m, 3H), 4.95 (s, 2H), 3.80 (t, J=7.2 Hz, 1H), 1.42 (t, J=9.4 Hz, 3H).

HRMS m/z (ESI) calcd for $C_{20}H_{18}N_2S$ $[M+H]^+$ 318.1191 found: 318.1192.

The detailed preparative method is same as that of compound 1, with a yield of 75.5%.

Compound 8:
2-(1-(m-methylphenyl)ethyl)-10H-phenothiazine

The synthetic route is as follows:

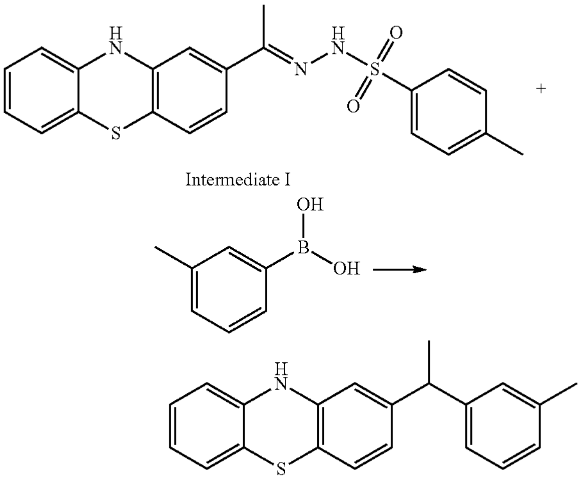

8

$^1$H NMR and HRMS data of compound 8 are as follows:

$^1$H NMR (400 MHz, DMSO-$d_6$) δ 8.49 (s, 1H), 7.17 (t, J=7.5 Hz, 1H), 7.06-6.92 (m, 4H), 6.89 (d, J=7.6 Hz, 1H), 6.82 (d, J=7.9 Hz, 1H), 6.73 (t, J=7.5 Hz, 1H), 6.66 (dd, J=13.7, 8.0 Hz, 2H), 6.53 (s, 1H), 3.95 (q, J=7.1 Hz, 1H), 2.26 (s, 3H), 1.49 (d, J=7.2 Hz, 3H).

HRMS m/z (ESI) calcd for $C_{21}H_{19}NS$ $[M+H]^+$ 317.1238 found: 317.1240.

The detailed preparative method is same as that of compound 1, with a yield of 63.8%.

Compound 9:
2-(1-(3-ethylphenyl)ethyl)-10H-phenothiazine

The synthetic route is as follows:

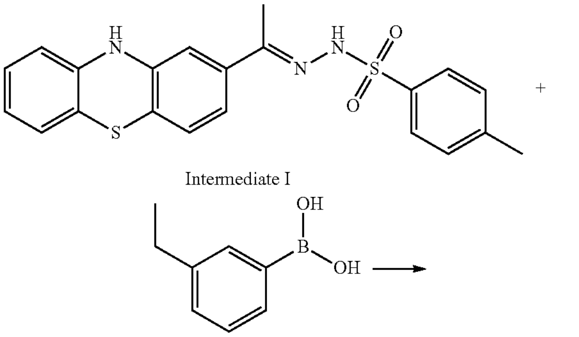

-continued

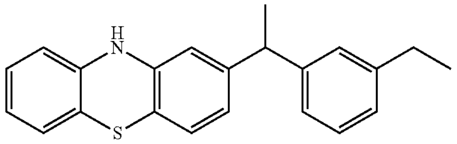

9

$^1H$ NMR and HRMS data of compound 9 are as follows:

$^1H$ NMR (400 MHz, DMSO-$d_6$) δ 8.50 (s, 1H), 7.20 (t, J=7.5 Hz, 1H), 7.06 (s, 1H), 7.02 (d, J=7.5 Hz, 2H), 6.95 (dd, J=7.6, 1.0 Hz, 1H), 6.89 (d, J=7.6 Hz, 1H), 6.82 (d, J=7.9 Hz, 1H), 6.72 (td, J=7.6, 1.0 Hz, 1H), 6.70-6.62 (m, 2H), 6.54 (d, J=1.4 Hz, 1H), 3.96 (q, J=7.1 Hz, 1H), 2.56 (q, J=7.6 Hz, 2H), 1.49 (d, J=7.2 Hz, 3H), 1.16 (t, J=7.6 Hz, 3H).

HRMS m/z (ESI) calcd for $C_{22}H_{21}NS$ $[M+H]^+$ 331.1395 found: 331.1398.

The detailed preparative method is same as that of compound 1, with a yield of 68.7%.

Compound 10: 2-(1-(3-isopropylphenyl)ethyl)-10H-phenothiazine

The synthetic route is as follows:

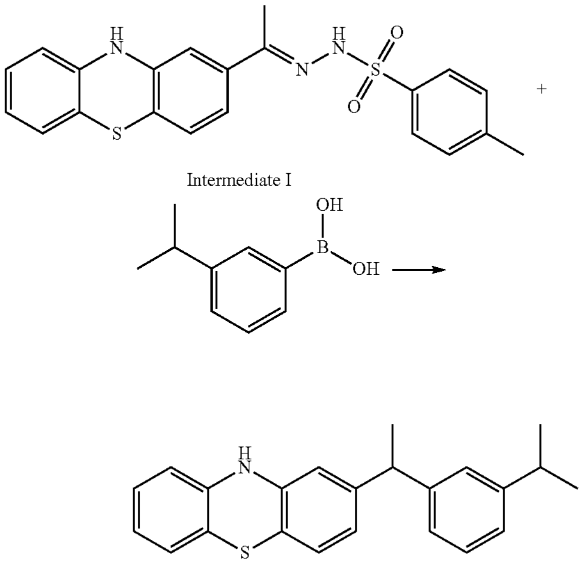

10

$^1H$ NMR and HRMS data of compound 10 are as follows:

$^1H$ NMR (400 MHz, DMSO-$d_6$) δ 8.50 (s, 1H), 7.20 (t, J=7.6 Hz, 1H), 7.10 (s, 1H), 7.04 (dd, J=15.4, 7.6 Hz, 2H), 6.96 (t, J=7.6 Hz, 1H), 6.89 (d, J=7.5 Hz, 1H), 6.82 (d, J=7.9 Hz, 1H), 6.72 (t, J=8.0 Hz, 1H), 6.71-6.61 (m, 2H), 6.55 (s, 1H), 3.97 (d, J=7.1 Hz, 1H), 2.97-2.74 (m, 1H), 1.49 (d, J=7.2 Hz, 3H), 1.20 (dd, J=17.5, 7.0 Hz, 6H).

HRMS m/z (ESI) calcd for $C_{23}H_{23}NS$ $[M+H]^+$ 345.1551 found: 345.1552.

The detailed preparative method is same as that of compound 1, with a yield of 60.8%.

Compound 11: 2-(1-(3-ethoxylphenyl)ethyl)-10H-phenothiazine

The synthetic route is as follows:

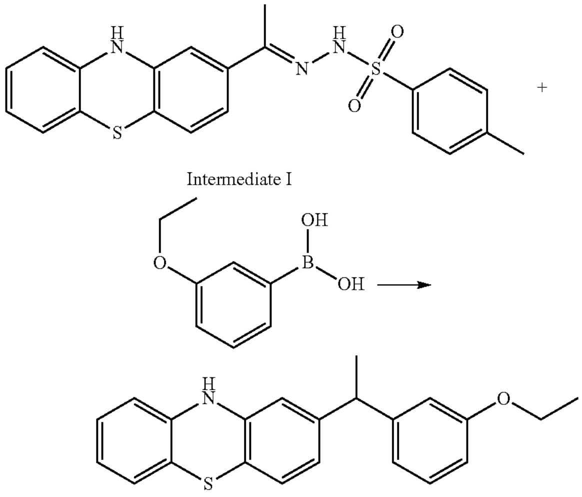

11

$^1H$ NMR and HRMS data of compound 11 are as follows:

$^1H$ NMR (400 MHz, DMSO-$d_6$) δ 8.49 (s, 1H), 7.18 (t, J=7.5 Hz, 1H), 6.96 (t, J=7.3 Hz, 1H), 6.89 (d, J=7.2 Hz, 1H), 6.82 (d, J=7.7 Hz, 1H), 6.75 (t, J=11.5 Hz, 3H), 6.67 (dd, J=16.5, 7.9 Hz, 2H), 6.53 (s, 1H), 4.07-3.87 (m, 3H), 1.48 (d, J=6.8 Hz, 3H), 1.30 (t, J=6.6 Hz, 3H).

HRMS m/z (ESI) calcd for $C_{22}H_{21}NOS$ $[M+H]^+$ 347.1344 found: 347.1345.

The detailed preparative method is same as that of compound 1, with a yield of 70.6%.

Compound 12: 2-(1-(3-isopropoxylphenyl)ethyl)-10H-phenothiazine

The synthetic route is as follows:

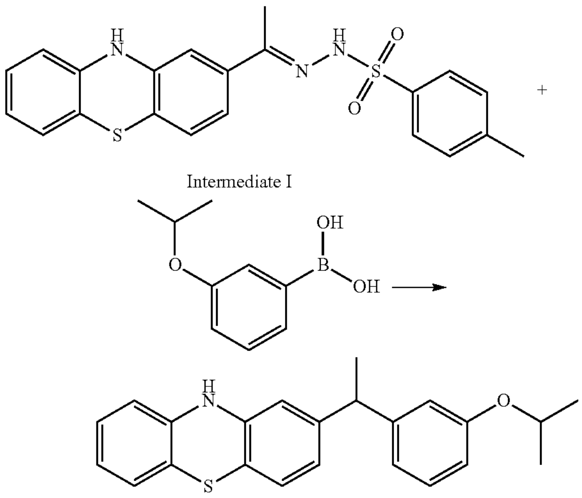

12

$^1$H NMR and HRMS data of compound 12 are as follows: $^1$H NMR (400 MHz, DMSO-$d_6$) δ 8.50 (s, 1H), 7.20 (t, J=7.6 Hz, 1H), 7.10 (s, 1H), 7.04 (dd, J=15.4, 7.6 Hz, 2H), 6.96 (t, J=7.6 Hz, 1H), 6.89 (d, J=7.5 Hz, 1H), 6.82 (d, J=7.9 Hz, 1H), 6.72 (t, J=8.0 Hz, 1H), 6.71-6.61 (m, 2H), 6.55 (s, 1H), 4.62-4.44 (m, 1H), 3.92 (d, J=7.1 Hz, 1H), 1.47 (d, J=7.2 Hz, 3H), 1.23 (d, J=6.0 Hz, 6H).

HRMS m/z (ESI) calcd for $C_{23}H_{23}NOS$ $[M+H]^+$ 361.1500 found: 361.1502.

The detailed preparative method is same as that of compound 1, with a yield of 71.9%.

Compound 13: 2-(1-(3-(benzyloxyl)phenyl)ethyl)-10H-phenothiazine

The synthetic route is as follows:

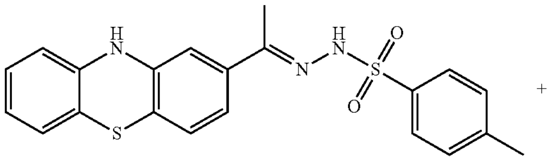

Intermediate I

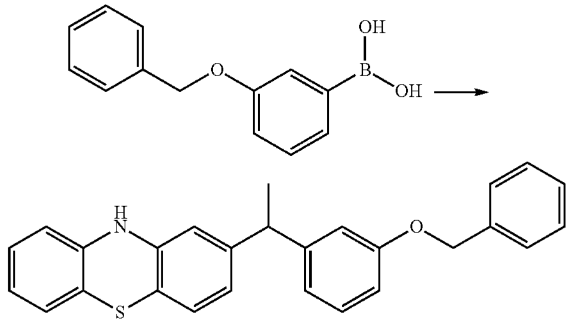

13

$^1$H NMR and HRMS data of compound 13 are as follows: $^1$H NMR (400 MHz, DMSO-$d_6$) δ 8.49 (s, 1H), 7.43 (d, J=7.0 Hz, 2H), 7.38 (dd, J=10.0, 4.7 Hz, 2H), 7.31 (d, J=7.1 Hz, 1H), 7.20 (t, J=7.9 Hz, 1H), 6.96 (td, J=7.8, 1.4 Hz, 1H), 6.92-6.84 (m, 2H), 6.85-6.78 (m, 3H), 6.73 (td, J=7.5, 1.1 Hz, 1H), 6.66 (ddd, J=12.2, 7.9, 1.3 Hz, 2H), 6.54 (d, J=1.6 Hz, 1H), 5.05 (s, 2H), 3.96 (q, J=7.1 Hz, 1H), 1.48 (d, J=7.2 Hz, 3H).

HRMS m/z (ESI) calcd for $C_{27}H_{23}NOS$ $[M+H]^+$ 409.1500 found: 409.1496.

The detailed preparative method is same as that of compound 1, with a yield of 68.8%.

Compound 14: 3-(1-(10H-phenothiazin-2-yl)ethyl)benzoic acid ethyl ester

The synthetic route is as follows:

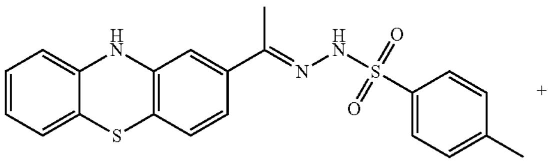

Intermediate I

-continued

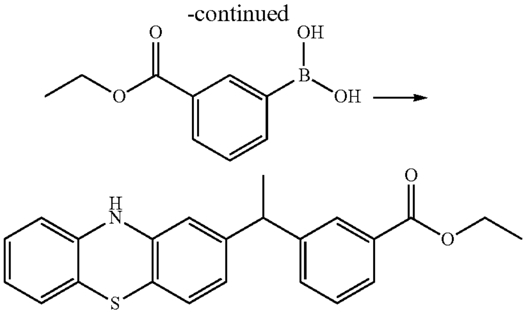

14

$^1$H NMR and HRMS data of compound 14 are as follows: $^1$H NMR (400 MHz, DMSO-$d_6$) δ 8.51 (s, 1H), 7.80 (d, J=8.8 Hz, 2H), 7.53 (d, J=7.7 Hz, 1H), 7.46 (t, J=7.6 Hz, 1H), 7.03-6.92 (m, 1H), 6.89 (d, J=7.5 Hz, 1H), 6.84 (d, J=7.9 Hz, 1H), 6.77-6.67 (m, 2H), 6.64 (d, J=7.9 Hz, 1H), 6.52 (d, J=1.3 Hz, 1H), 4.12 (q, J=7.1 Hz, 1H), 3.84 (s, 3H), 1.53 (d, J=7.2 Hz, 3H).

HRMS m/z (ESI) calcd for $C_{23}H_{21}NO_2S$ $[M+H]^+$ 375.1293 found: 375.1295.

The detailed preparative method is same as that of compound 1, with a yield of 65.2%.

Compound 15: 3-(1-(10H-phenothiazin-2-yl)ethyl)benzoic acid t-butyl ester

The synthetic route is as follows:

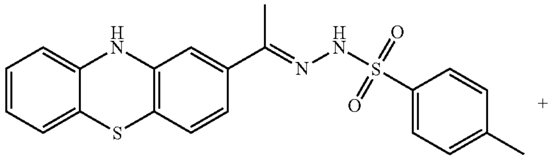

Intermediate I

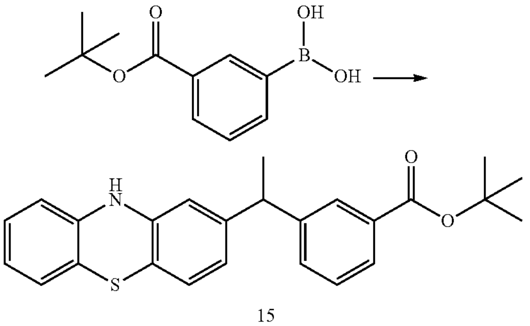

15

$^1$H NMR and HRMS data of compound 15 are as follows: $^1$H NMR (400 MHz, DMSO-$d_6$) δ 8.51 (s, 1H), 7.82-7.66 (m, 2H), 7.48 (d, J=7.8 Hz, 1H), 7.42 (t, J=7.6 Hz, 1H), 6.96 (td, J=7.9, 1.3 Hz, 1H), 6.89 (d, J=7.6 Hz, 1H), 6.84 (d, J=7.9 Hz, 1H), 6.71 (ddd, J=9.6, 7.7, 1.3 Hz, 2H), 6.64 (d, J=7.9 Hz, 1H), 6.51 (d, J=1.5 Hz, 1H), 4.10 (d, J=7.1 Hz, 1H), 1.52 (d, J=7.2 Hz, 12H).

HRMS m/z (ESI) calcd for $C_{25}H_{25}NO_2S$ $[M+H]^+$ 403.1606 found: 403.1609.

The detailed preparative method is same as that of compound 1, with a yield of 61.8%.

Compound 16: (3-(1-(10H-phenothiazin-2-yl)ethyl) phenyl)carbamic acid t-butyl ester The synthetic route is as follows:

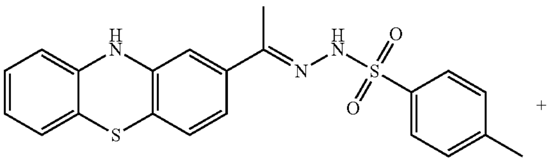

Intermediate I

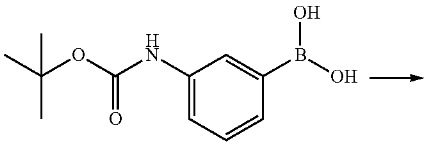

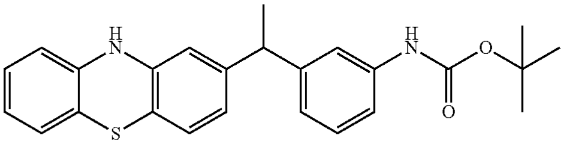

16

$^1$H NMR and HRMS data of compound 16 are as follows:

$^1$H NMR (400 MHz, DMSO-$d_6$) δ 9.24 (s, 1H), 8.50 (s, 1H), 7.35 (s, 1H), 7.25 (d, J=8.0 Hz, 1H), 7.15 (t, J=7.8 Hz, 1H), 6.95 (td, J=7.8, 1.4 Hz, 1H), 6.88 (dd, J=7.6, 1.2 Hz, 1H), 6.82 (d, J=7.9 Hz, 2H), 6.72 (td, J=7.5, 1.2 Hz, 1H), 6.68-6.60 (m, 2H), 6.50 (d, J=1.6 Hz, 1H), 3.92 (d, J=7.1 Hz, 1H), 1.46 (d, J=10.0 Hz, 11H).

HRMS m/z (ESI) calcd for $C_{25}H_{26}N_2O_2S$ $[M+H]^+$ 418.1715 found: 418.1720.

The detailed preparative method is same as that of compound 1, with a yield of 64.9%.

Compound 17: 2-(1-(3-(trifluoromethoxyl)phenyl) ethyl)-10H-phenothiazine

The synthetic route is as follows:

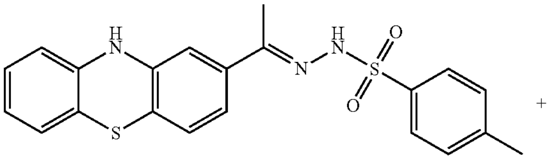

Intermediate I

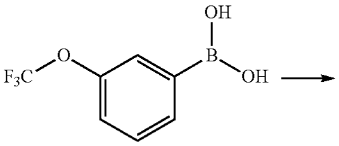

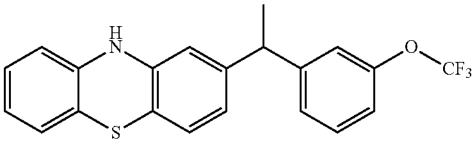

17

$^1$H NMR and HRMS data of compound 17 are as follows:

$^1$H NMR (400 MHz, DMSO-$d_6$) δ 8.52 (s, 1H), 7.43 (s, 1H), 7.27 (s, 1H), 7.20 (s, 2H), 6.96 (s, 1H), 6.92-6.79 (m, 2H), 6.70 (dd, J=17.6, 10.0 Hz, 3H), 6.54 (s, 1H), 4.10 (s, 1H), 1.52 (s, 3H).

HRMS m/z (ESI) calcd for $C_{21}H_{16}F_3NOS$ $[M+H]^+$ 387.0905 found: 387.0902.

The detailed preparative method is same as that of compound 1, with a yield of 73.4%.

Compound 18: 2-(1-([1,1'-diphenyl]-3-yl)ethyl)-10H-phenothiazine

The synthetic route is as follows:

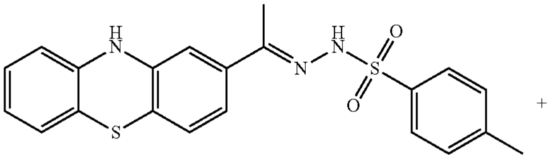

Intermediate I

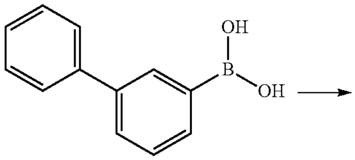

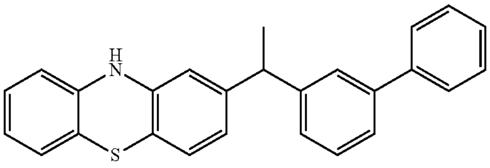

18

$^1$H NMR and HRMS data of compound 18 are as follows:

$^1$H NMR (400 MHz, DMSO-$d_6$) δ 8.51 (s, 1H), 7.69-7.59 (m, 2H), 7.52 (s, 1H), 7.46 (t, J=7.7 Hz, 3H), 7.42-7.33 (m, 2H), 7.22 (d, J=7.6 Hz, 1H), 6.95 (td, J=7.8, 1.4 Hz, 1H), 6.91-6.86 (m, 1H), 6.84 (d, J=7.9 Hz, 1H), 6.73 (ddd, J=8.5, 7.7, 1.3 Hz, 2H), 6.64 (dd, J=7.9, 0.9 Hz, 1H), 6.59 (d, J=1.5 Hz, 1H), 4.09 (q, J=7.1 Hz, 1H), 1.57 (d, J=7.2 Hz, 3H).

HRMS m/z (ESI) calcd for $C_{26}H_{21}NS$ $[M+H]^+$ 379.1395 found: 379.1398.

The detailed preparative method is same as that of compound 1, with a yield of 69.4%.

Compound 19: 2-(1-(4-fluorophenyl)ethyl)-10H-phenothiazine

The synthetic route is as follows:

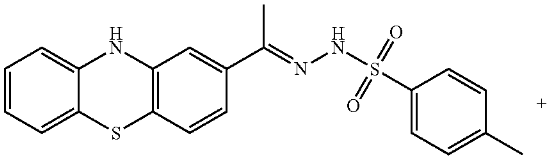

Intermediate I

-continued

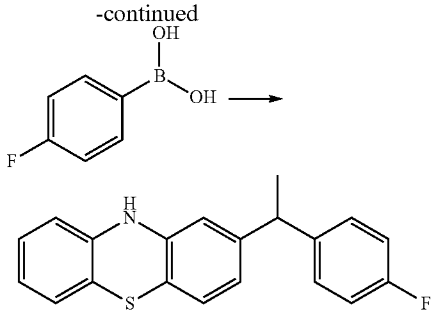

19

$^1$H NMR and HRMS data of compound 19 are as follows:

$^1$H NMR (400 MHz, DMSO-$d_6$) δ 8.50 (s, 1H), 7.35 (d, J=8.0 Hz, 2H), 7.24 (d, J=8.0 Hz, 2H), 6.96 (t, J=7.3 Hz, 1H), 6.89 (d, J=7.2 Hz, 1H), 6.83 (d, J=7.7 Hz, 1H), 6.73 (t, J=7.4 Hz, 1H), 6.70-6.60 (m, 2H), 6.50 (s, 1H), 4.02 (d, J=7.0 Hz, 1H), 1.49 (d, J=6.9 Hz, 3H).

HRMS m/z (ESI) calcd for $C_{20}H_{16}FNS$ $[M+H]^+$ 321.0987 found: 321.0989.

The detailed preparative method is same as that of compound 1, with a yield of 75.1%.

Compound 20: 2-(1-(4-chlorophenyl)ethyl)-10H-phenothiazine

The synthetic route is as follows:

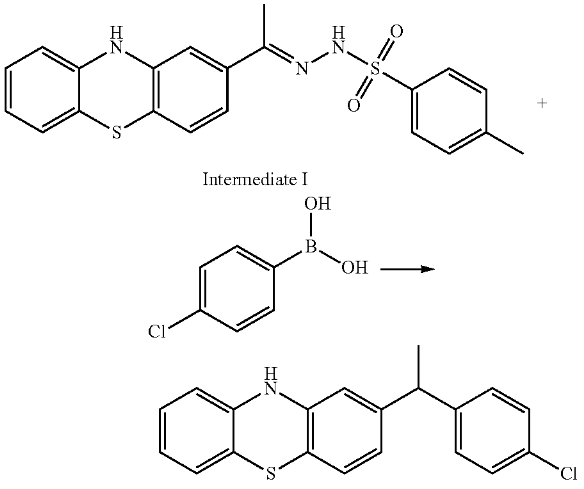

20

$^1$H NMR and HRMS data of compound 20 are as follows:

$^1$H NMR (400 MHz, DMSO-$d_6$) δ 8.50 (s, 1H), 7.35 (d, J=8.3 Hz, 2H), 7.24 (d, J=8.3 Hz, 2H), 6.96 (t, J=7.4 Hz, 1H), 6.89 (d, J=7.4 Hz, 1H), 6.83 (d, J=7.9 Hz, 1H), 6.73 (t, J=7.4 Hz, 1H), 6.66 (t, J=8.7 Hz, 2H), 6.50 (s, 1H), 4.02 (d, J=7.1 Hz, 1H), 1.49 (d, J=7.1 Hz, 3H).

HRMS m/z (ESI) calcd for $C_{20}H_{16}ClNS$ $[M+H]^+$ 337.0692 found: 337.0695.

The detailed preparative method is same as that of compound 1, with a yield of 73.5%.

Compound 21: 2-(1-(4-(trifluoromethyl)phenyl)ethyl)-10H-phenothiazine

The synthetic route is as follows:

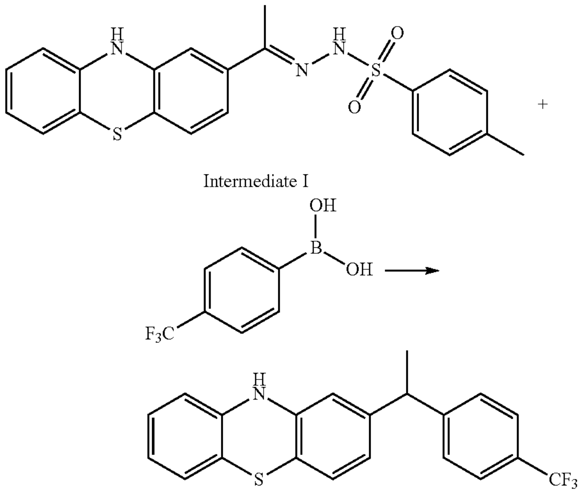

21

$^1$H NMR and HRMS data of compound 21 are as follows:

$^1$H NMR (400 MHz, DMSO-$d_6$) δ 8.53 (s, 1H), 7.66 (d, J=8.1 Hz, 2H), 7.45 (d, J=8.0 Hz, 2H), 6.96 (dd, J=11.0, 4.3 Hz, 1H), 6.87 (dd, J=17.0, 7.6 Hz, 2H), 6.76-6.68 (m, 2H), 6.65 (d, J=7.9 Hz, 1H), 6.53 (d, J=1.2 Hz, 1H), 4.13 (q, J=7.0 Hz, 1H), 1.53 (d, J=7.2 Hz, 3H).

HRMS m/z (ESI) calcd for $C_{21}H_{16}F_3NS$ $[M+H]^+$ 371.0956 found: 371.0952.

The detailed preparative method is same as that of compound 1, with a yield of 71.8%.

Compound 22: 4-(1-(10H-phenothiazin-2-yl)ethyl)benzonitrile

The synthetic route is as follows:

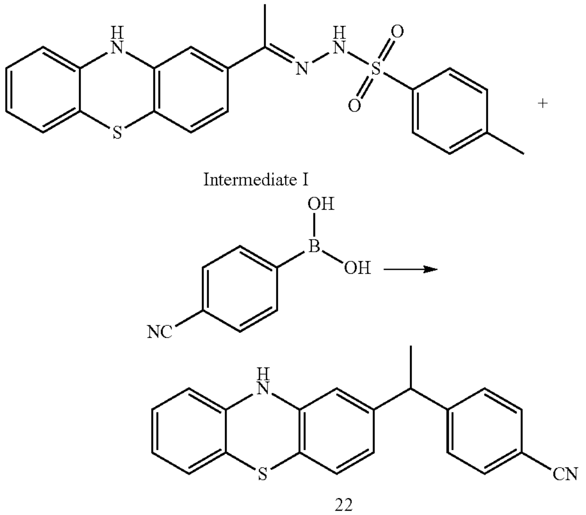

22

$^1H$ NMR and HRMS data of compound 22 are as follows:

$^1H$ NMR (400 MHz, DMSO-$d_6$) δ 8.53 (s, 1H), 7.76 (d, J=8.2 Hz, 2H), 7.43 (d, J=8.2 Hz, 2H), 6.97 (s, 1H), 6.87 (dd, J=18.4, 7.7 Hz, 2H), 6.79-6.59 (m, 3H), 6.51 (s, 1H), 4.12 (q, J=7.1 Hz, 1H), 1.52 (d, J=7.2 Hz, 3H).

HRMS m/z (ESI) calcd for $C_{21}H_{16}N_2S$ $[M+H]^+$ 329.1107 found: 329.1108.

The detailed preparative method is same as that of compound 1, with a yield of 67.8%.

Compound 23: 2-(1-(4-(trifluoromethoxyl)phenyl) ethyl)-10H-phenothiazine

The synthetic route is as follows:

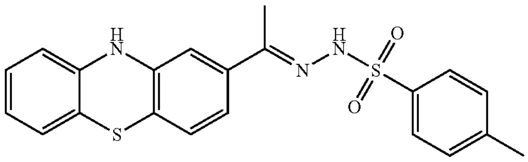

+

Intermediate I

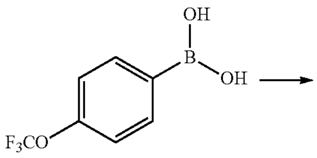

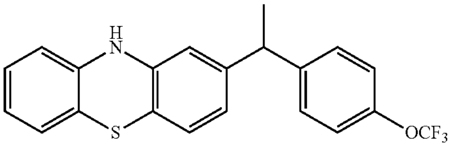

23

$^1H$ NMR and HRMS data of compound 23 are as follows:

$^1H$ NMR (400 MHz, DMSO-$d_6$) δ 8.51 (s, 1H), 7.35 (d, J=8.7 Hz, 2H), 7.28 (d, J=8.2 Hz, 2H), 6.95 (dd, J=7.6, 1.3 Hz, 1H), 6.89 (dd, J=7.6, 1.2 Hz, 1H), 6.84 (d, J=7.9 Hz, 1H), 6.74 (dd, J=7.5, 1.1 Hz, 1H), 6.69 (dd, J=7.9, 1.6 Hz, 1H), 6.64 (dd, J=7.9, 1.0 Hz, 1H), 6.52 (d, J=1.6 Hz, 1H), 4.07 (d, J=7.1 Hz, 1H), 1.51 (d, J=7.2 Hz, 3H).

HRMS m/z (ESI) calcd for $C_{21}H_{16}F_3NOS$ $[M+H]^+$ 387.0905 found: 387.0903.

The detailed preparative method is same as that of compound 1, with a yield of 55.2%.

Compound 24: 2-(1-(4-ethylphenyl)ethyl)-10H-phenothiazine

The synthetic route is as follows:

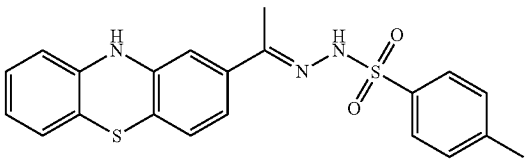

+

Intermediate I

-continued

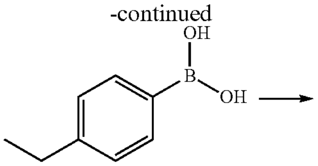

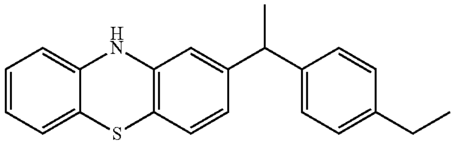

24

$^1H$ NMR and HRMS data of compound 24 are as follows:

$^1H$ NMR (400 MHz, DMSO-$d_6$) δ 8.49 (s, 1H), 7.12 (s, 4H), 6.96 (td, J=7.8, 1.3 Hz, 1H), 6.91-6.85 (m, 1H), 6.81 (d, J=7.9 Hz, 1H), 6.72 (td, J=7.5, 1.1 Hz, 1H), 6.70-6.61 (m, 2H), 6.52 (d, J=1.6 Hz, 1H), 3.95 (q, J=7.2 Hz, 1H), 2.55 (q, J=7.6 Hz, 2H), 1.48 (d, J=7.2 Hz, 3H), 1.15 (t, J=7.6 Hz, 3H).

HRMS m/z (ESI) calcd for $C_{22}H_{21}NS$ $[M+H]^+$ 331.1395 found: 331.1391.

The detailed preparative method is same as that of compound 1, with a yield of 60.8%.

Compound 25: 2-(1-(4-propylphenyl)ethyl)-10H-phenothiazine

The synthetic route is as follows:

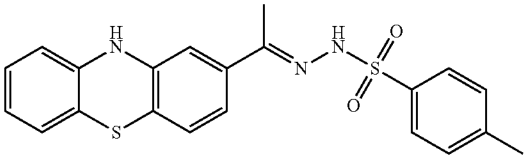

+

Intermediate I

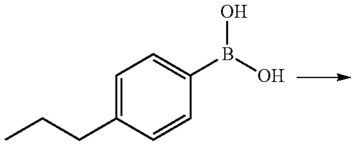

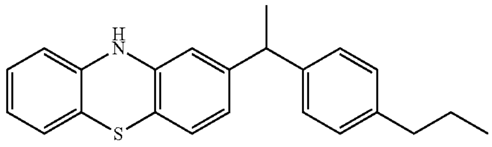

25

$^1H$ NMR and HRMS data of compound 25 are as follows:

$^1H$ NMR (400 MHz, DMSO-$d_6$) δ 8.49 (s, 1H), 7.17-7.06 (m, 4H), 6.96 (td, J=7.8, 1.4 Hz, 1H), 6.92-6.86 (m, 1H), 6.81 (d, J=7.9 Hz, 1H), 6.72 (td, J=7.5, 1.1 Hz, 1H), 6.66 (ddd, J=10.5, 8.0, 1.3 Hz, 2H), 6.53 (d, J=1.6 Hz, 1H), 3.95 (d, J=7.2 Hz, 1H), 1.55 (dd, J=15.1, 7.5 Hz, 2H), 1.50 (dd, J=11.8, 7.4 Hz, 3H), 0.88 (t, J=7.3 Hz, 3H).

HRMS m/z (ESI) calcd for $C_{23}H_{23}NS$ $[M+H]^+$ 345.1551 found: 345.1555.

The detailed preparative method is same as that of compound 1, with a yield of 69.5%.

Compound 26: 2-(1-(4-isopropylphenyl)ethyl)-10H-phenothiazine

The synthetic route is as follows:

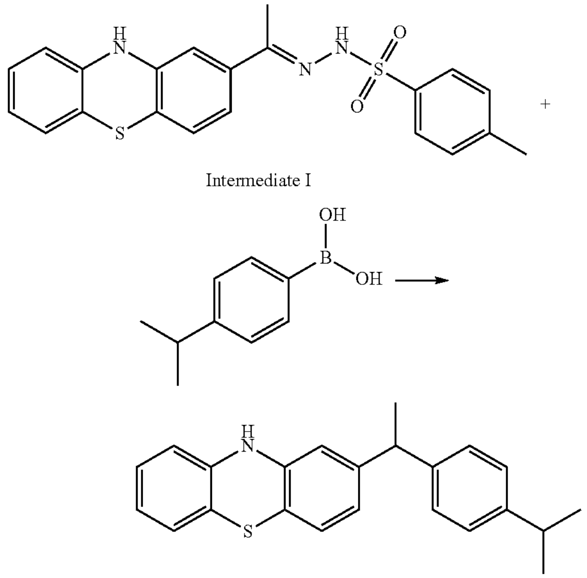

26

$^1$H NMR and HRMS data of compound 26 are as follows:

$^1$H NMR (400 MHz, DMSO-$d_6$) δ 8.49 (s, 1H), 7.10 (d, J=8.6 Hz, 2H), 7.00-6.93 (m, 1H), 6.89 (d, J=7.6 Hz, 1H), 6.85-6.78 (m, 3H), 6.73 (d, J=7.5 Hz, 1H), 6.66 (dd, J=10.6, 4.3 Hz, 2H), 6.52 (d, J=1.4 Hz, 1H), 3.97 (d, J=7.1 Hz, 1H), 2.97-2.74 (m, 1H), 1.49 (d, J=7.2 Hz, 3H), 1.20 (dd, J=17.5, 7.0 Hz, 6H).

HRMS m/z (ESI) calcd for $C_{23}H_{23}NS$ $[M+H]^+$ 345.1551 found: 345.1557.

The detailed preparative method is same as that of compound 1, with a yield of 75.5%.

Compound 27: 2-(1-(4-butylphenyl)ethyl)-10H-phenothiazine

The synthetic route is as follows:

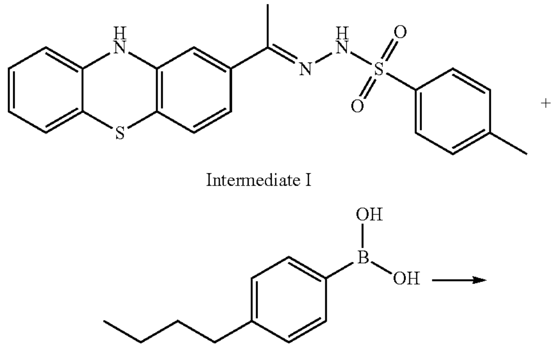

-continued

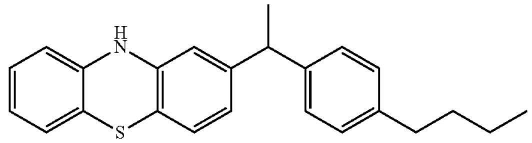

27

$^1$H NMR and HRMS data of compound 27 are as follows:

$^1$H NMR (400 MHz, DMSO-$d_6$) δ 8.49 (s, 1H), 7.19-7.05 (m, 4H), 7.01-6.91 (m, 1H), 6.88 (d, J=7.5 Hz, 1H), 6.81 (d, J=7.9 Hz, 1H), 6.73 (d, J=7.4 Hz, 1H), 6.66 (dd, J=12.7, 4.6 Hz, 2H), 6.53 (d, J=1.2 Hz, 1H), 3.95 (q, J=7.1 Hz, 1H), 1.61-1.40 (m, 5H), 1.28 (tt, J=9.3, 4.6 Hz, 3H), 0.88 (t, J=7.3 Hz, 3H).

HRMS m/z (ESI) calcd for $C_{23}H_{23}NS$ $[M+H]^+$ 359.1708 found: 359.1715.

The detailed preparative method is same as that of compound 1, with a yield of 71.4%.

Compound 28: 2-(1-(4-isobutylphenyl)ethyl)-10H-phenothiazine

The synthetic route is as follows:

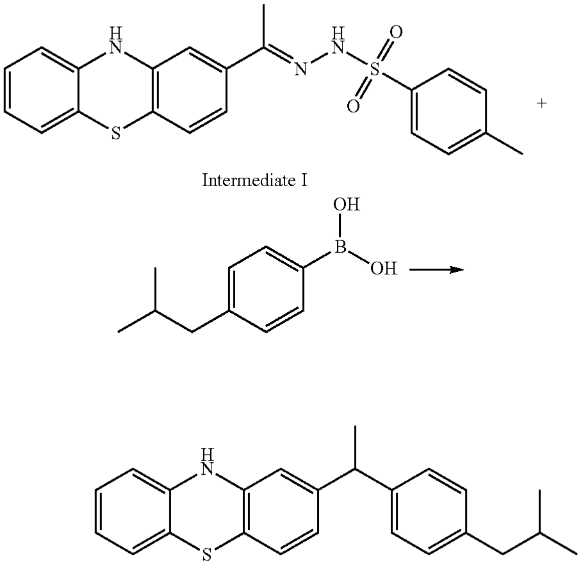

28

$^1$H NMR and HRMS data of compound 28 are as follows:

$^1$H NMR (400 MHz, DMSO-$d_6$) δ 8.49 (s, 1H), 7.12 (d, J=7.8 Hz, 2H), 7.06 (d, J=7.8 Hz, 2H), 6.96 (t, J=7.4 Hz, 1H), 6.88 (d, J=7.5 Hz, 1H), 6.81 (d, J=7.8 Hz, 1H), 6.72 (t, J=7.4 Hz, 1H), 6.66 (t, J=8.3 Hz, 2H), 6.54 (s, 1H), 3.95 (q, J=6.8 Hz, 1H), 2.39 (d, J=7.0 Hz, 2H), 1.79 (dt, J=13.4, 6.6 Hz, 1H), 1.49 (d, J=7.1 Hz, 3H), 0.84 (d, J=6.5 Hz, 6H).

HRMS m/z (ESI) calcd for $C_{24}H_{25}NS$ $[M+H]^+$ 359.1708 found: 359.1711.

The detailed preparative method is same as that of compound 1, with a yield of 72.8%.

Compound 29: 2-(1-(4-t-butylphenyl)ethyl)-10H-phenothiazine

The synthetic route is as follows:

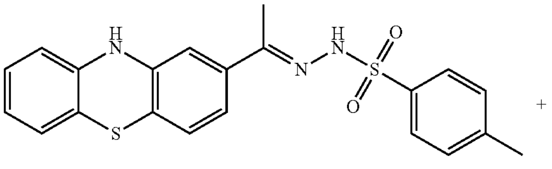

Intermediate I

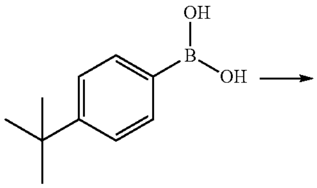

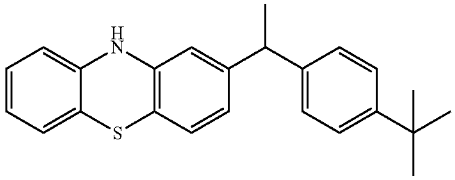

29

$^1$H NMR and HRMS data of compound 29 are as follows:

$^1$H NMR (400 MHz, DMSO-$d_6$) δ 8.50 (s, 1H), 7.30 (d, J=8.3 Hz, 2H), 7.14 (d, J=8.3 Hz, 2H), 6.96 (td, J=7.8, 1.4 Hz, 1H), 6.88 (dd, J=7.6, 1.1 Hz, 1H), 6.82 (d, J=7.9 Hz, 1H), 6.77-6.59 (m, 3H), 6.54 (d, J=1.6 Hz, 1H), 3.95 (q, J=7.1 Hz, 1H), 1.49 (d, J=7.2 Hz, 3H), 1.29-1.15 (m, 10H).

HRMS m/z (ESI) calcd for $C_{24}H_{25}NS$ $[M+H]^+$ 359.1708 found: 359.1710.

The detailed preparative method is same as that of compound 1, with a yield of 68.8%.

Compound 30: 2-(1-(4-methoxylphenyl)ethyl)-10H-phenothiazine

The synthetic route is as follows:

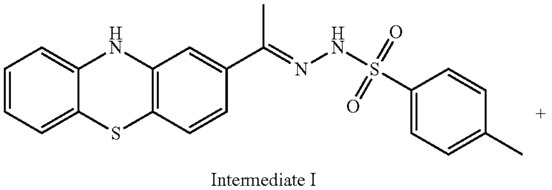

Intermediate I

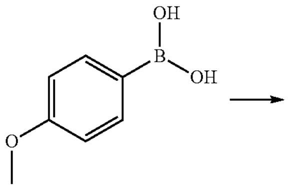

-continued

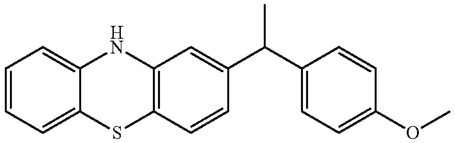

30

$^1$H NMR and HRMS data of compound 30 are as follows:

$^1$H NMR (400 MHz, DMSO-$d_6$) δ 8.48 (s, 1H), 7.13 (d, J=8.6 Hz, 2H), 6.96 (t, J=7.6 Hz, 1H), 6.92-6.79 (m, 4H), 6.72 (t, J=7.4 Hz, 1H), 6.69-6.61 (m, 2H), 6.51 (s, 1H), 3.94 (q, J=7.1 Hz, 1H), 3.71 (s, 3H), 1.47 (d, J=7.2 Hz, 3H).

HRMS m/z (ESI) calcd for $C_{21}H_{19}NOS$ $[M+H]^+$ 333.1187 found: 333.1186.

The detailed preparative method is same as that of compound 1, with a yield of 67.8%.

Compound 31: 2-(1-(4-ethoxylphenyl)ethyl)-10H-phenothiazine

The synthetic route is as follows:

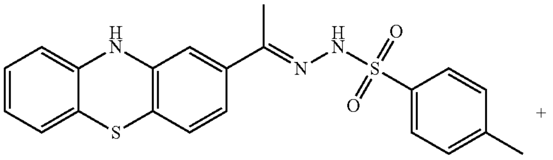

Intermediate I

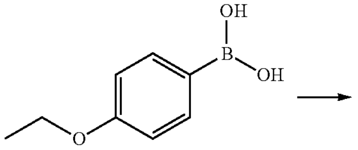

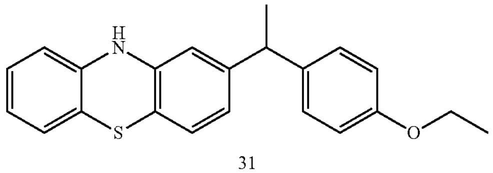

31

$^1$H NMR and HRMS data of compound 31 are as follows:

$^1$H NMR (400 MHz, DMSO-$d_6$) δ 8.48 (s, 1H), 7.11 (d, J=8.6 Hz, 2H), 6.96 (d, J=0.9 Hz, 1H), 6.91-6.86 (m, 1H), 6.82 (t, J=8.1 Hz, 3H), 6.72 (d, J=1.0 Hz, 1H), 6.68-6.61 (m, 2H), 6.51 (d, J=1.5 Hz, 1H), 4.06-3.86 (m, 3H), 1.47 (d, J=7.2 Hz, 3H), 1.30 (t, J=7.0 Hz, 3H).

HRMS m/z (ESI) calcd for $C_{22}H_{21}NOS$ $[M+H]^+$ 347.1344 found: 347.1341.

The detailed preparative method is same as that of compound 1, with a yield of 61.9%.

Compound 32: 2-(1-(4-propoxylphenyl)ethyl)-10H-phenothiazine

The synthetic route is as follows:

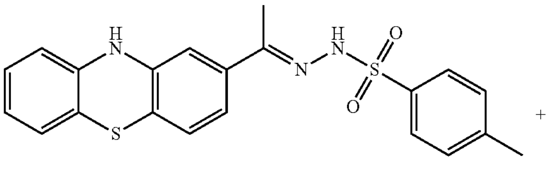

Intermediate I

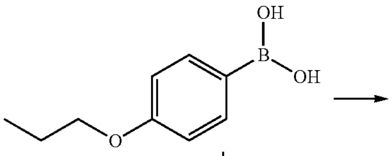

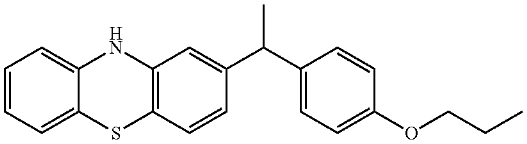

32

$^1$H NMR and HRMS data of compound 32 are as follows:

$^1$H NMR (400 MHz, DMSO-$d_6$) δ 8.48 (s, 1H), 7.11 (d, J=8.6 Hz, 2H), 6.95 (dd, J=11.3, 4.0 Hz, 1H), 6.89 (d, J=7.6 Hz, 1H), 6.82 (dd, J=10.4, 8.3 Hz, 3H), 6.72 (t, J=7.5 Hz, 1H), 6.69-6.60 (m, 2H), 6.51 (d, J=1.2 Hz, 1H), 3.93 (d, J=7.1 Hz, 1H), 3.87 (t, J=6.5 Hz, 2H), 1.70 (dd, J=14.0, 6.9 Hz, 2H), 1.47 (d, J=7.2 Hz, 3H), 0.96 (t, J=7.4 Hz, 3H).

HRMS m/z (ESI) calcd for $C_{23}H_{23}NOS$ $[M+H]^+$ 361.1500 found: 361.1501.

The detailed preparative method is same as that of compound 1, with a yield of 59.2%.

Compound 33: 2-(1-(4-isopropoxylphenyl)ethyl)-10H-phenothiazine

The synthetic route is as follows:

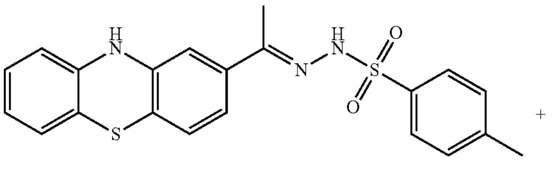

Intermediate I

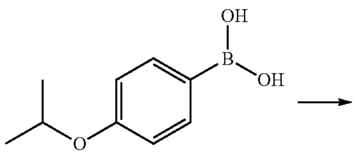

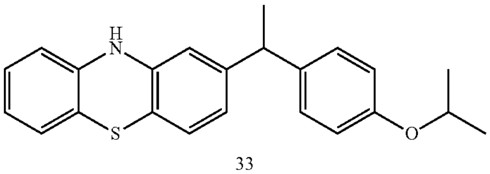

33

$^1$H NMR and HRMS data of compound 33 are as follows:

$^1$H NMR (400 MHz, DMSO-$d_6$) δ 8.49 (s, 1H), 7.10 (d, J=8.6 Hz, 2H), 7.00-6.93 (m, 1H), 6.89 (d, J=7.6 Hz, 1H), 6.85-6.78 (m, 3H), 6.73 (d, J=7.5 Hz, 1H), 6.66 (dd, J=10.6, 4.3 Hz, 2H), 6.52 (d, J=1.4 Hz, 1H), 4.62-4.44 (m, 1H), 3.92 (d, J=7.1 Hz, 1H), 1.47 (d, J=7.2 Hz, 3H), 1.23 (d, J=6.0 Hz, 6H).

HRMS m/z (ESI) calcd for $C_{23}H_{23}NOS$ $[M+H]^+$ 361.1500 found: 361.1547.

The detailed preparative method is same as that of compound 1, with a yield of 68.4%.

Compound 34: 2-(1-(4-isopropoxylphenyl)ethyl)-10H-phenothiazine

The synthetic route is as follows:

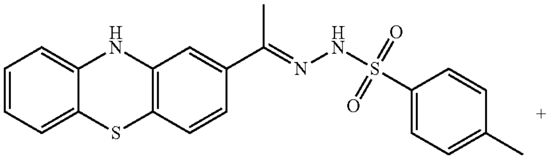

Intermediate I

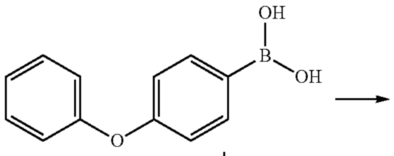

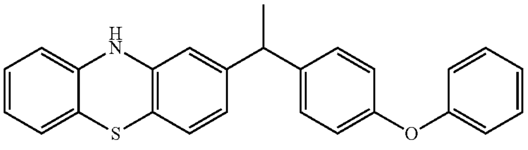

34

$^1$H NMR and HRMS data of compound 34 are as follows:

$^1$H NMR (400 MHz, $CDCl_3$) δ 7.31 (t, J=7.6 Hz, 2H), 7.14 (d, J=8.2 Hz, 2H), 7.08 (t, J=7.2 Hz, 1H), 7.04-6.87 (m, 7H), 6.76 (d, J=24.8 Hz, 2H), 6.51 (s, 1H), 6.37 (s, 1H), 5.74 (s, 1H), 3.98 (d, J=6.5 Hz, 1H), 1.60-1.53 (m, 3H).

HRMS m/z (ESI) calcd for $C_{26}H_{21}NOS$ $[M+H]^+$ 395.1344 found: 395.1345.

The detailed preparative method is same as that of compound 1, with a yield of 63.8%.

Compound 35: 2-(1-(4-(benzyloxyl)phenyl)ethyl)-10H-phenothiazine

The synthetic route is as follows:

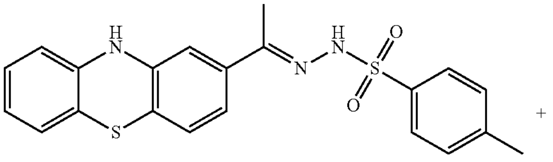

Intermediate I

-continued

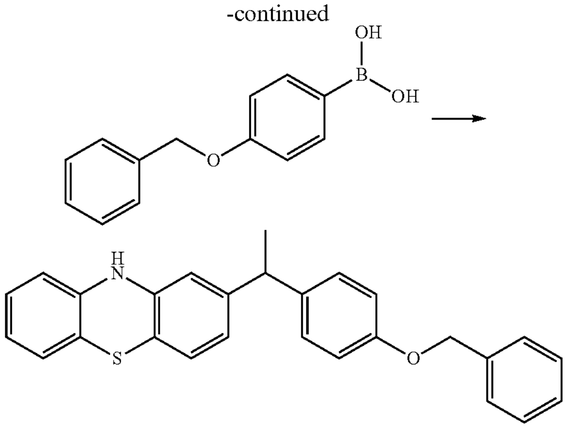

35

$^1$H NMR and HRMS data of compound 35 are as follows: $^1$H NMR (400 MHz, DMSO-$d_6$) δ 8.48 (s, 1H), 7.43 (d, J=7.0 Hz, 2H), 7.38 (t, J=7.3 Hz, 2H), 7.32 (d, J=7.1 Hz, 1H), 7.13 (d, J=8.6 Hz, 2H), 6.99-6.85 (m, 4H), 6.81 (d, J=7.9 Hz, 1H), 6.73 (dd, J=7.5, 0.9 Hz, 1H), 6.68-6.61 (m, 2H), 6.51 (d, J=1.4 Hz, 1H), 5.05 (s, 2H), 3.94 (d, J=7.1 Hz, 1H), 1.47 (d, J=7.2 Hz, 3H).

HRMS m/z (ESI) calcd for $C_{27}H_{23}NOS$ $[M+H]^+$ 409.1500 found: 409.1502.

The detailed preparative method is same as that of compound 1, with a yield of 62.9%.

Compound 36: 4-(1-(10H-phenothiazin-2-yl)ethyl)benzoic acid methyl ester

The synthetic route is as follows: 4-(1-(10H-phenothiazin-2-yl)ethyl)benzoic acid methyl ester

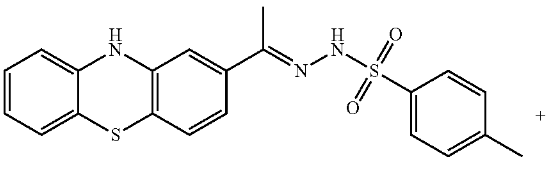

Intermediate I

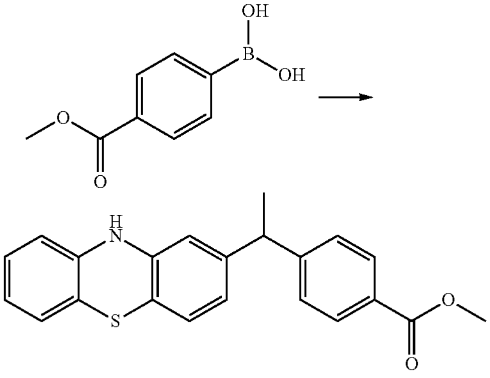

36

$^1$H NMR and HRMS data of compound 36 are as follows: $^1$H NMR (400 MHz, DMSO-$d_6$) δ 8.50 (s, 1H), 7.90 (d, J=7.4 Hz, 2H), 7.38 (d, J=7.4 Hz, 2H), 6.95 (d, J=6.9 Hz, 1H), 6.89 (d, J=7.2 Hz, 1H), 6.84 (d, J=7.5 Hz, 1H), 6.80-6.57 (m, 3H), 6.51 (s, 1H), 4.11 (d, J=6.5 Hz, 1H), 3.83 (s, 3H), 1.52 (d, J=6.6 Hz, 3H).

HRMS m/z (ESI) calcd for $C_{22}H_{19}NO_2S$ $[M+H]^+$ 361.1136 found: 361.1132.

The detailed preparative method is same as that of compound 1, with a yield of 63.3%.

Compound 37: 4-(1-(10H-phenothiazin-2-yl)ethyl)-N,N-diphenylphenylamine

The synthetic route is as follows:

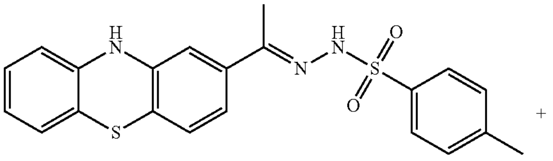

Intermediate I

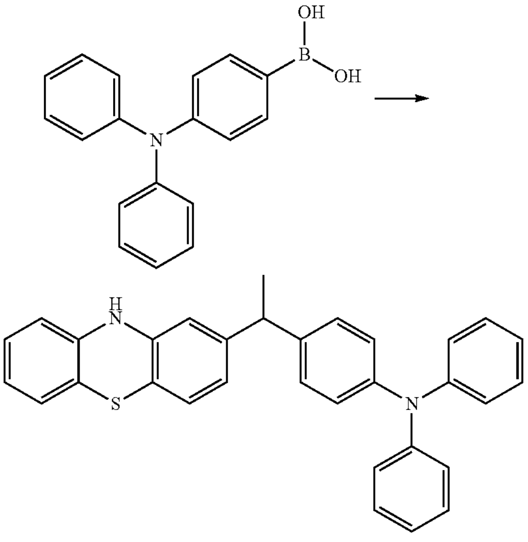

37

$^1$H NMR and HRMS data of compound 37 are as follows: $^1$H NMR (400 MHz, DMSO-$d_6$) δ 8.52 (s, 1H), 7.27 (dd, J=8.3, 7.5 Hz, 4H), 7.16 (d, J=8.5 Hz, 2H), 7.05-6.86 (m, 10H), 6.83 (d, J=7.9 Hz, 1H), 6.77-6.62 (m, 3H), 6.58 (d, J=1.6 Hz, 1H), 3.95 (q, J=7.1 Hz, 1H), 1.49 (t, J=6.1 Hz, 3H).

HRMS m/z (ESI) calcd for $C_{32}H_{26}N_2S$ $[M+H]^+$ 470.1817 found: 470.1818.

The detailed preparative method is same as that of compound 1, with a yield of 64.8%.

Compound 38: 2-(1-(4-(4-methylpiperazin-1-yl)phenyl)ethyl)-10H-phenothiazine

The synthetic route is as follows:

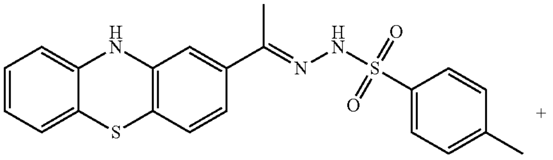

Intermediate I

-continued

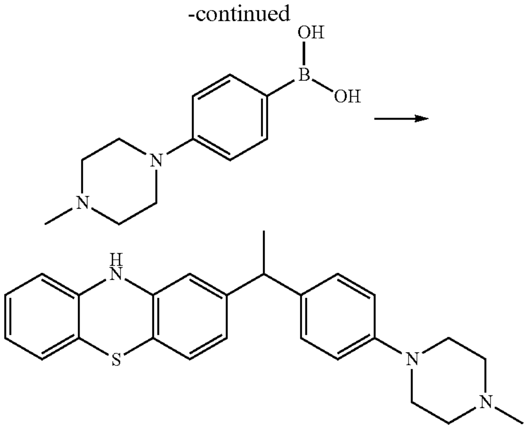

38

$^1$H NMR and HRMS data of compound 38 are as follows: $^1$H NMR (400 MHz, DMSO) δ 8.48 (s, 1H), 7.06 (s, 1H), 7.04 (s, 1H), 6.95 (td, J=7.8, 1.4 Hz, 1H), 6.88 (dd, J=7.6, 1.1 Hz, 1H), 6.86 (s, 1H), 6.84 (s, 1H), 6.80 (d, J=7.9 Hz, 1H), 6.72 (td, J=7.5, 1.1 Hz, 1H), 6.65 (ddd, J=7.9, 4.2, 1.3 Hz, 2H), 6.50 (d, J=1.6 Hz, 1H), 3.89 (q, J=7.1 Hz, 1H), 3.09-3.00 (m, 4H), 2.46-2.36 (m, 4H), 2.21 (d, J=4.3 Hz, 3H), 1.45 (d, J=7.2 Hz, 3H).

HRMS m/z (ESI) calcd for $C_{22}H_{21}NS$ $[M+H]^+$ 401.1926 found: 401.1926.

The detailed preparative method is same as that of compound 1, with a yield of 73.7%.

Compound 39: 2-(1-(3,4-difluorophenyl)ethyl)-10H-phenothiazine

The synthetic route is as follows:

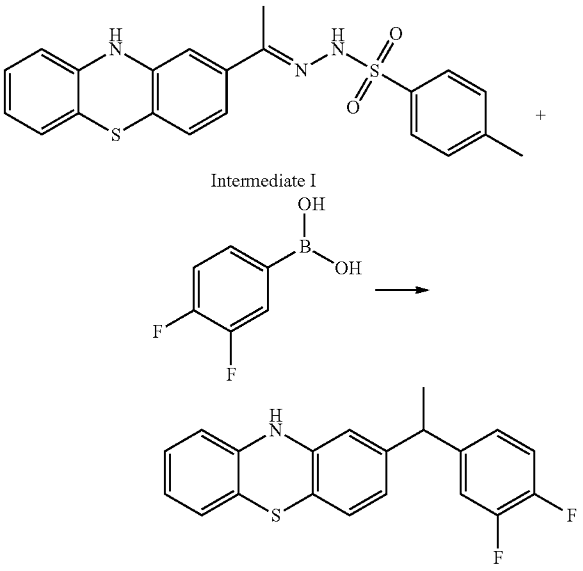

39

$^1$H NMR and HRMS data of compound 39 are as follows: $^1$H NMR (400 MHz, DMSO-$d_6$) δ 8.50 (s, 1H), 7.38-7.26 (m, 2H), 7.10-7.01 (m, 1H), 6.96 (td, J=7.8, 1.4 Hz, 1H), 6.89 (dd, J=7.6, 1.2 Hz, 1H), 6.84 (d, J=7.9 Hz, 1H), 6.73 (td, J=7.5, 1.2 Hz, 1H), 6.68 (dd, J=7.9, 1.7 Hz, 1H), 6.64 (dd, J=7.9, 1.0 Hz, 1H), 6.50 (d, J=1.7 Hz, 1H), 4.03 (t, J=7.2 Hz, 1H), 1.49 (d, J=7.2 Hz, 3H).

HRMS m/z (ESI) calcd for $C_{20}H_{15}F_2NS$ $[M+H]^+$ 339.0893 found: 339.0891.

The detailed preparative method is same as that of compound 1, with a yield of 78.4%.

Compound 40: 2-(1-(3-chloro-4-fluorophenyl) ethyl)-10H-phenothiazine

The synthetic route is as follows:

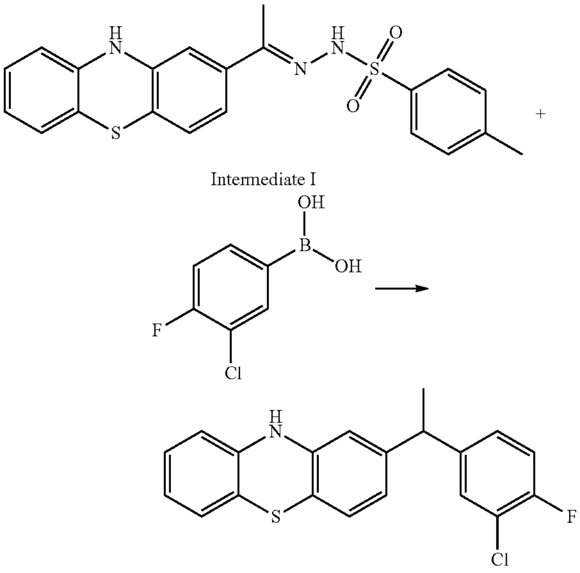

40

$^1$H NMR and HRMS data of compound 40 are as follows: $^1$H NMR (400 MHz, DMSO-$d_6$) δ 8.53 (s, 1H), 7.61-7.09 (m, 3H), 7.08-6.79 (m, 3H), 6.68 (d, J=18.8 Hz, 3H), 6.50 (s, 1H), 4.06 (s, 1H), 1.50 (s, 3H).

HRMS m/z (ESI) calcd for $C_{20}H_{15}ClFNS$ $[M+H]^+$ 355.0598 found: 355.0592.

The detailed preparative method is same as that of compound 1, with a yield of 80.5%.

Compound 41: 2-(1-(4-fluoro-3-(trifluoromethyl) phenyl)ethyl)-10H-phenothiazine

The synthetic route is as follows:

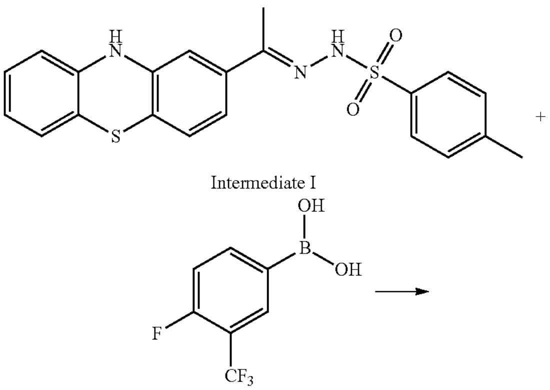

-continued

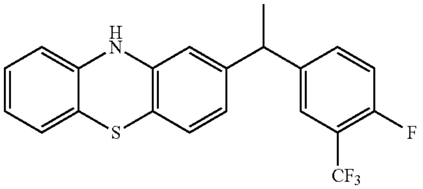

41

$^1H$ NMR and HRMS data of compound 41 are as follows:

$^1H$ NMR (400 MHz, DMSO-$d_6$) δ 8.51 (s, 1H), 7.59 (t, J=7.2 Hz, 2H), 7.51-7.37 (m, 1H), 6.96 (t, J=7.6 Hz, 1H), 6.87 (dd, J=15.4, 7.7 Hz, 2H), 6.72 (dd, J=15.1, 7.6 Hz, 2H), 6.64 (d, J=7.9 Hz, 1H), 6.51 (s, 1H), 4.16 (d, J=7.1 Hz, 1H), 1.52 (d, J=7.2 Hz, 3H).

HRMS m/z (ESI) calcd for $C_{21}H_{15}F_4NS$ $[M+H]^+$ 389.0861 found: 389.0863.

The detailed preparative method is same as that of compound 1, with a yield of 79.6%.

Compound 42: 2-(1-(3,4-dichlorophenyl)ethyl)-10H-phenothiazine

The synthetic route is as follows:

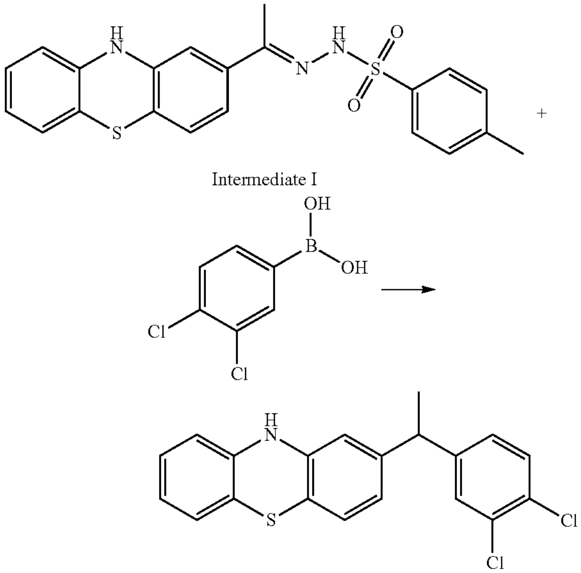

42

$^1H$ NMR and HRMS data of compound 42 are as follows:

$^1H$ NMR (400 MHz, DMSO-$d_6$) δ 8.51 (s, 1H), 7.55 (d, J=8.3 Hz, 1H), 7.49 (s, 1H), 7.21 (d, J=8.2 Hz, 1H), 6.95 (d, J=7.5 Hz, 1H), 6.89 (d, J=7.5 Hz, 1H), 6.84 (d, J=7.9 Hz, 1H), 6.72 (dd, J=19.7, 7.8 Hz, 2H), 6.65 (d, J=7.8 Hz, 1H), 6.50 (s, 1H), 4.06 (d, J=7.1 Hz, 1H), 1.50 (d, J=7.1 Hz, 3H).

HRMS m/z (ESI) calcd for $C_{20}H_{15}Cl_2NS$ $[M+H]^+$ 371.0302 found: 371.0305.

The detailed preparative method is same as that of compound 1, with a yield of 72.7%.

Compound 43: 2-(1-(4-chloro-3-(trifluoromethyl)phenyl)ethyl)-10H-phenothiazine

The synthetic route is as follows:

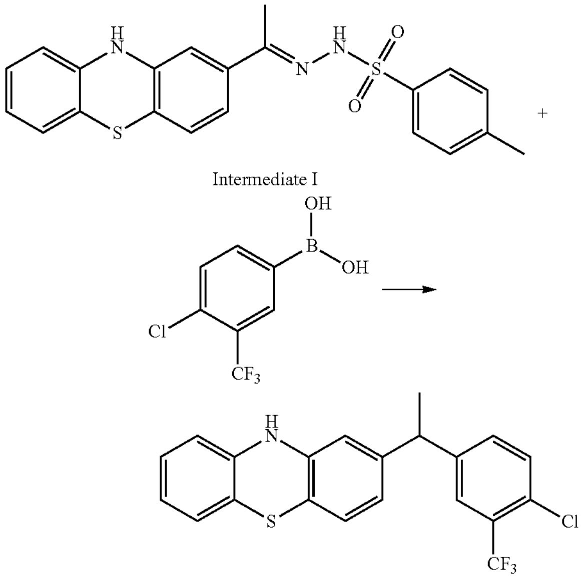

43

$^1H$ NMR and HRMS data of compound 43 are as follows:

$^1H$ NMR (400 MHz, DMSO-$d_6$) δ 8.51 (s, 1H), 7.69 (d, J=1.9 Hz, 1H), 7.66 (d, J=8.3 Hz, 1H), 7.53 (dd, J=8.3, 1.9 Hz, 1H), 6.96 (td, J=7.8, 1.4 Hz, 1H), 6.92-6.82 (m, 2H), 6.72 (ddd, J=15.6, 7.8, 1.4 Hz, 2H), 6.64 (dd, J=7.9, 1.0 Hz, 1H), 6.50 (d, J=1.7 Hz, 1H), 4.17 (q, J=7.2 Hz, 1H), 1.52 (d, J=7.2 Hz, 3H).

HRMS m/z (ESI) calcd for $C_{21}H_{15}ClF_3NS$ $[M+H]^+$ 405.0566 found: 405.0562.

The detailed preparative method is same as that of compound 1, with a yield of 63.4%.

Compound 44: 2-(1-(4-chloro-3-fluorophenyl)ethyl)-10H-phenothiazine

The synthetic route is as follows:

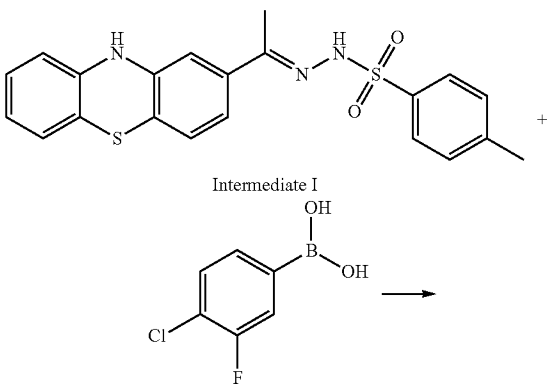

-continued

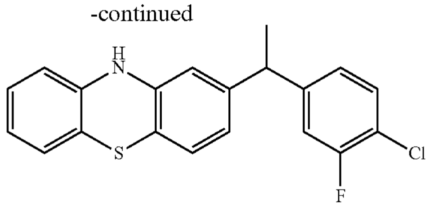

44

$^1$H NMR and HRMS data of compound 44 are as follows:

$^1$H NMR (400 MHz, DMSO-$d_6$) δ 8.50 (s, 1H), 7.50 (t, J=8.1 Hz, 1H), 7.29 (dd, J=10.8, 1.9 Hz, 1H), 7.08 (dd, J=8.3, 1.8 Hz, 1H), 6.96 (td, J=7.8, 1.4 Hz, 1H), 6.89 (dd, J=7.6, 1.1 Hz, 1H), 6.84 (d, J=7.9 Hz, 1H), 6.74 (dd, J=7.5, 1.1 Hz, 1H), 6.72-6.67 (m, 1H), 6.65 (dd, J=7.9, 1.0 Hz, 1H), 6.50 (d, J=1.6 Hz, 1H), 4.06 (q, J=7.1 Hz, 1H), 1.50 (d, J=7.2 Hz, 3H).

HRMS m/z (ESI) calcd for $C_{20}H_{15}ClFNS$ $[M+H]^+$ 355.0598 found: 355.0592.

The detailed preparative method is same as that of compound 1, with a yield of 69.1%.

Compound 45: 2-(1-(3-chloro-4-(trifluoromethyl)phenyl)ethyl)-10H-phenothiazine The synthetic route is as follows:

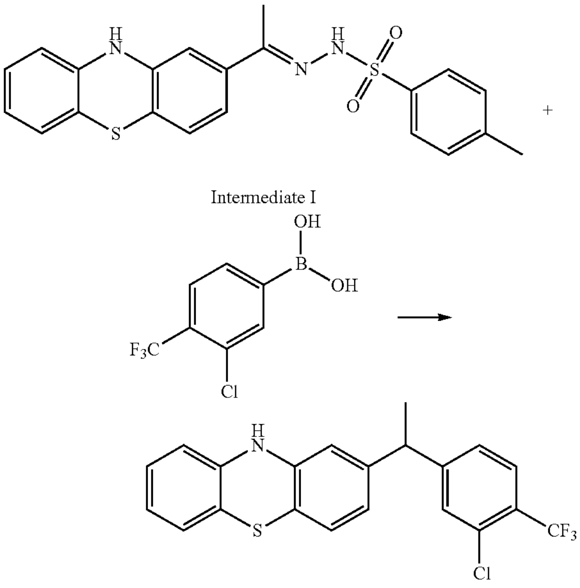

45

$^1$H NMR and HRMS data of compound 45 are as follows:

$^1$H NMR (400 MHz, DMSO-$d_6$) δ 8.53 (s, 1H), 7.78 (d, J=8.2 Hz, 1H), 7.59 (s, 1H), 7.39 (d, J=8.1 Hz, 1H), 6.96 (dd, J=11.1, 4.2 Hz, 1H), 6.88 (dd, J=12.5, 7.7 Hz, 2H), 6.74 (d, J=10.7 Hz, 2H), 6.65 (d, J=7.8 Hz, 1H), 6.52 (s, 1H), 4.23-4.06 (m, 1H), 1.53 (d, J=7.2 Hz, 3H).

HRMS m/z (ESI) calcd for $C_{21}H_{15}ClF_3NS$ $[M+H]^+$ 405.0566 found: 405.0563.

The detailed preparative method is same as that of compound 1, with a yield of 68.3%.

Compound 46: 2-(1-(3,4-dimethylphenyl)ethyl)-10H-phenothiazine

The synthetic route is as follows:

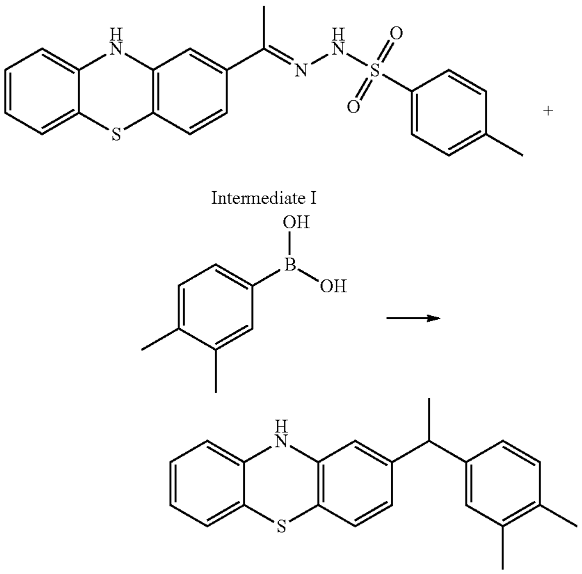

46

$^1$H NMR and HRMS data of compound 46 are as follows:

$^1$H NMR (400 MHz, DMSO-$d_6$) δ 8.47 (s, 1H), 7.04 (d, J=7.7 Hz, 1H), 6.97 (s, 1H), 6.93 (t, J=8.0 Hz, 2H), 6.88 (d, J=7.6 Hz, 1H), 6.81 (d, J=7.9 Hz, 1H), 6.72 (td, J=7.6, 1.0 Hz, 1H), 6.66 (dd, J=12.2, 4.3 Hz, 2H), 6.50 (d, J=1.5 Hz, 1H), 3.91 (d, J=7.2 Hz, 1H), 2.16 (d, J=5.8 Hz, 6H), 1.44 (t, J=15.8 Hz, 3H).

HRMS m/z (ESI) calcd for $C_{22}H_{21}NS$ $[M+H]^+$ 331.1395 found: 331.1394.

The detailed preparative method is same as that of compound 1, with a yield of 80.1%.

Compound 47: 2-(1-(3,4-dimethoxylphenyl)ethyl)-10H-phenothiazine

The synthetic route is as follows:

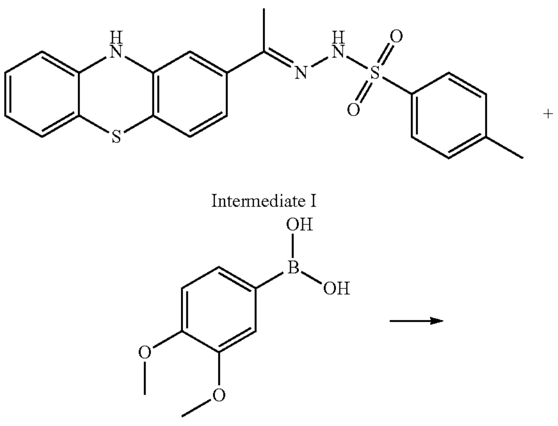

-continued

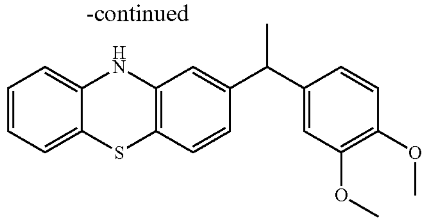

47

$^1$H NMR and HRMS data of compound 47 are as follows: $^1$H NMR (400 MHz, DMSO-$d_6$) δ 8.48 (s, 1H), 7.02-6.92 (m, 1H), 6.88 (t, J=7.6 Hz, 2H), 6.81 (d, J=8.0 Hz, 2H), 6.74 (d, J=2.1 Hz, 1H), 6.72 (d, J=3.2 Hz, 1H), 6.71-6.67 (m, 1H), 6.67-6.63 (m, 1H), 6.51 (d, J=1.2 Hz, 1H), 3.93 (q, J=7.1 Hz, 1H), 3.71 (d, J=3.2 Hz, 6H), 1.48 (d, J=7.1 Hz, 3H).

HRMS m/z (ESI) calcd for $C_{22}H_{21}NO_2S$ $[M+H]^+$ 363.1293 found: 363.1296.

The detailed preparative method is same as that of compound 1, with a yield of 78.9%.

Compound 48: 2-(1-(3-methoxyl-4-methylphenyl) ethyl)-10H-phenothiazine

The synthetic route is as follows:

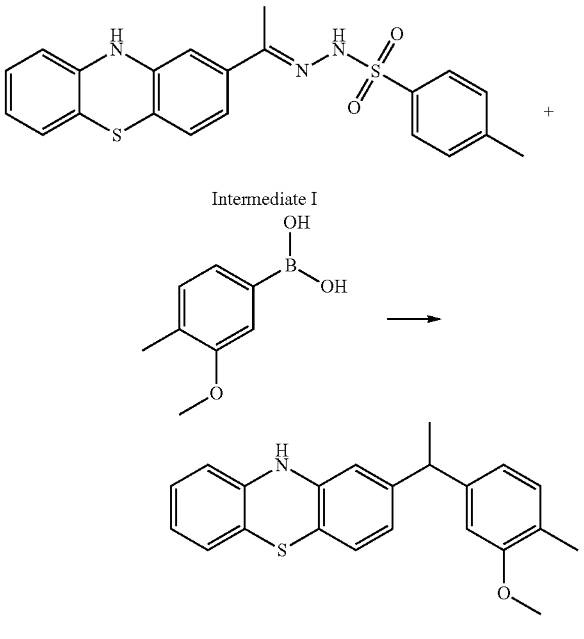

48

$^1$H NMR and HRMS data of compound 48 are as follows: $^1$H NMR (400 MHz, DMSO-$d_6$) δ 8.48 (s, 1H), 7.03 (d, J=7.7 Hz, 1H), 6.99-6.92 (m, 1H), 6.92-6.85 (m, 1H), 6.85-6.76 (m, 2H), 6.73 (dd, J=7.5, 1.0 Hz, 1H), 6.69 (dd, J=8.1, 2.2 Hz, 2H), 6.66-6.61 (m, 1H), 6.52 (d, J=1.5 Hz, 1H), 3.96 (q, J=7.2 Hz, 1H), 3.75 (s, 3H), 2.09 (s, 3H), 1.49 (d, J=7.2 Hz, 3H).

HRMS m/z (ESI) calcd for $C_{22}H_{21}NOS$ $[M+H]^+$ 347.1344 found: 347.1345.

The detailed preparative method is same as that of compound 1, with a yield of 79.1%.

Compound 49: 2-(1-(4-methoxyl-3-methylphenyl) ethyl)-10H-phenothiazine

The synthetic route is as follows:

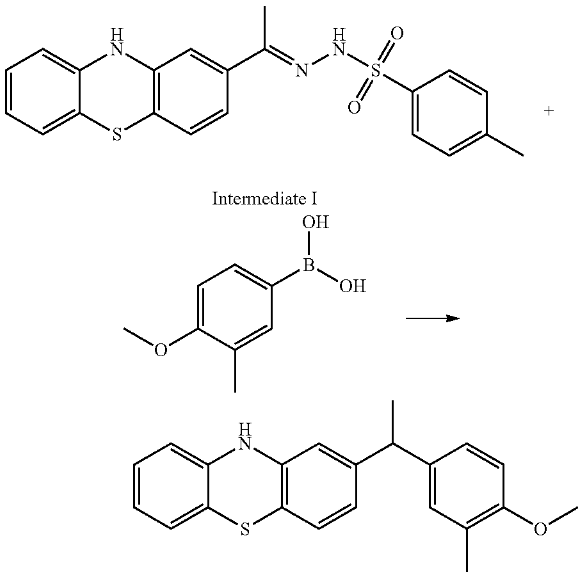

49

$^1$H NMR and HRMS data of compound 49 are as follows:

$^1$H NMR (400 MHz, DMSO-$d_6$) δ 8.48 (s, 1H), 7.03-6.92 (m, 3H), 6.88 (d, J=7.6 Hz, 1H), 6.82 (dd, J=10.8, 8.2 Hz, 2H), 6.72 (td, J=7.5, 1.0 Hz, 1H), 6.69-6.61 (m, 2H), 6.50 (d, J=1.4 Hz, 1H), 3.90 (d, J=7.2 Hz, 1H), 3.74 (s, 3H), 2.10 (s, 3H), 1.46 (d, J=7.2 Hz, 3H).

HRMS m/z (ESI) calcd for $C_{22}H_{21}NOS$ $[M+H]^+$ 347.1344 found: 347.1347.

The detailed preparative method is same as that of compound 1, with a yield of 72.9%.

Compound 50: 2-(1-(4-chloro-3-methoxylphenyl) ethyl)-10H-phenothiazine

The synthetic route is as follows:

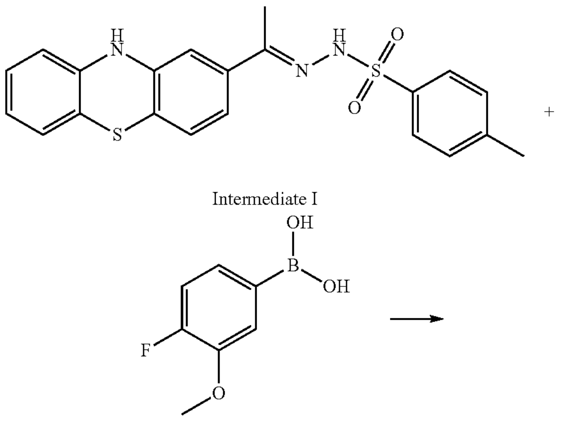

-continued

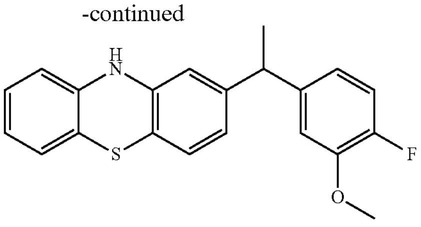

50

$^1$H NMR and HRMS data of compound 50 are as follows:

$^1$H NMR (400 MHz, DMSO-$d_6$) δ 8.49 (s, 1H), 7.32 (d, J=8.1 Hz, 1H), 7.02 (s, 1H), 6.96 (t, J=7.2 Hz, 1H), 6.89 (d, J=7.4 Hz, 1H), 6.83 (d, J=7.9 Hz, 1H), 6.79 (d, J=8.1 Hz, 1H), 6.72 (dd, J=14.2, 7.3 Hz, 2H), 6.64 (d, J=7.8 Hz, 1H), 6.51 (s, 1H), 4.02 (q, J=6.9 Hz, 1H), 3.83 (s, 3H), 1.51 (d, J=7.2 Hz, 3H).

HRMS m/z (ESI) calcd for $C_{21}H_{18}ClNOS$ $[M+H]^+$ 367.0798 found: 367.0795.

The detailed preparative method is same as that of compound 1, with a yield of 62.4%.

Compound 51: 2-(1-(4-fluoro-3-methoxylphenyl) ethyl)-10H-phenothiazine

The synthetic route is as follows:

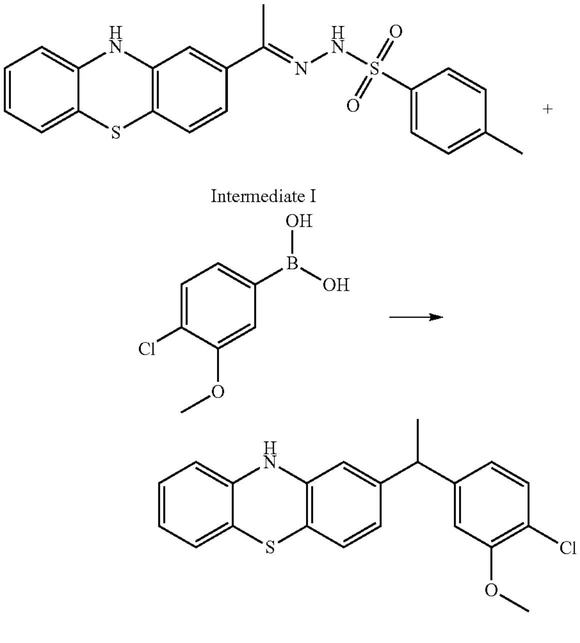

51

$^1$H NMR and HRMS data of compound 51 are as follows:

$^1$H NMR (400 MHz, DMSO-$d_6$) δ 8.49 (s, 1H), 7.11 (dd, J=11.5, 8.3 Hz, 1H), 7.01 (dd, J=8.4, 1.9 Hz, 1H), 6.96 (td, J=7.8, 1.4 Hz, 1H), 6.89 (d, J=7.6 Hz, 1H), 6.83 (d, J=7.9 Hz, 1H), 6.79-6.72 (m, 2H), 6.69 (dd, J=8.1, 1.7 Hz, 1H), 6.67-6.61 (m, 1H), 6.51 (d, J=1.5 Hz, 1H), 4.00 (q, J=7.1 Hz, 1H), 3.81 (s, 3H), 1.50 (d, J=7.2 Hz, 3H).

HRMS m/z (ESI) calcd for $C_{21}H_{18}FNOS$ $[M+H]^+$ 351.1093 found: 351.1098.

The detailed preparative method is same as that of compound 1, with a yield of 64.8%.

Compound 52: 2-(1-(4-methyl-3-nitrophenyl)ethyl)-10H-phenothiazine

The synthetic route is as follows:

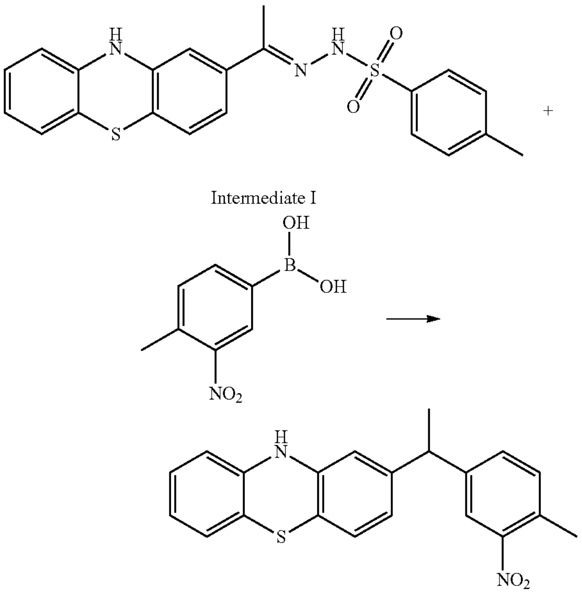

52

$^1$H NMR and HRMS data of compound 52 are as follows:

$^1$H NMR (400 MHz, DMSO-$d_6$) δ 8.53 (s, 1H), 8.03 (s, 1H), 7.66-7.53 (m, 1H), 7.41 (d, J=8.1 Hz, 1H), 6.96 (s, 1H), 6.88 (d, J=7.5 Hz, 1H), 6.83 (s, 2H), 6.78 (s, 1H), 6.73 (d, J=7.5 Hz, 1H), 6.64 (d, J=7.8 Hz, 1H), 5.96 (s, 1H), 2.47 (s, 3H), 1.79 (s, 3H).

HRMS m/z (ESI) calcd for $C_{21}H_{18}N_2O_2S$ $[M+H]^+$ 362.1089 found: 362.1085.

The detailed preparative method is same as that of compound 1, with a yield of 66.5%.

Compound 53: 4-(1-(10H-phenothiazin-2-yl)ethyl)-2-chlorobenzoic acid methyl ester The synthetic route is as follows:

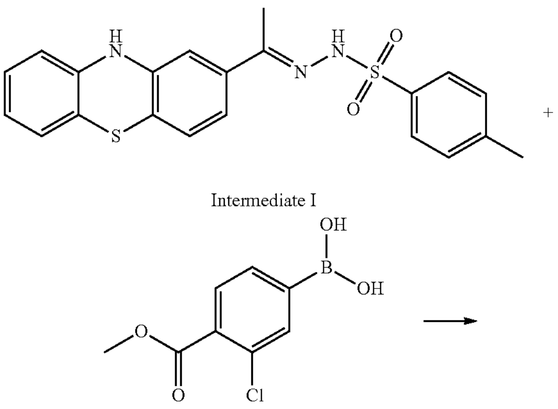

-continued

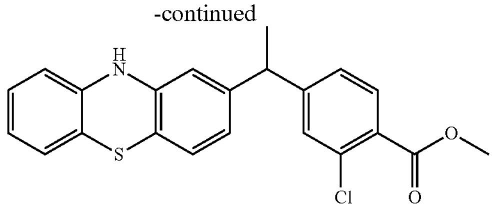

53

$^1$H NMR and HRMS data of compound 53 are as follows:

$^1$H NMR (400 MHz, DMSO-$d_6$) δ 8.52 (s, 1H), 7.76 (d, J=8.0 Hz, 1H), 7.43 (s, 1H), 7.30 (d, J=8.1 Hz, 1H), 6.96 (t, J=7.3 Hz, 1H), 6.87 (dd, J=15.4, 7.7 Hz, 2H), 6.72 (dd, J=15.7, 7.7 Hz, 2H), 6.64 (d, J=7.8 Hz, 1H), 6.50 (s, 1H), 4.11 (d, J=7.1 Hz, 1H), 3.84 (s, 3H), 1.51 (d, J=7.1 Hz, 3H).

HRMS m/z (ESI) calcd for $C_{22}H_{18}ClNO_2S$ $[M+H]^+$ 395.0747 found: 395.0743.

The detailed preparative method is same as that of compound 1, with a yield of 69.8%.

Compound 54: 2-(1-(4-(benzyloxyl)-3-methylphenyl)ethyl)-10H-phenothiazine

The synthetic route is as follows:

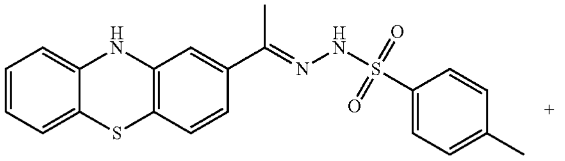

Intermediate I

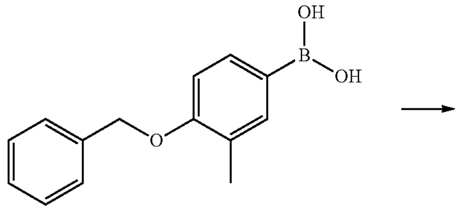

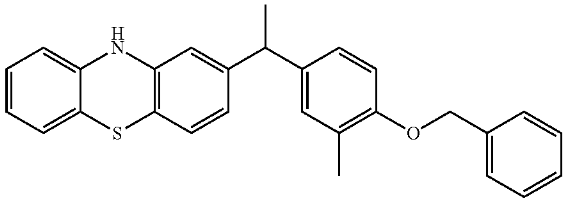

54

$^1$H NMR and HRMS data of compound 54 are as follows:

$^1$H NMR (400 MHz, DMSO-$d_6$) δ 8.49 (s, 1H), 7.44 (d, J=7.1 Hz, 2H), 7.39 (t, J=7.4 Hz, 2H), 7.32 (d, J=7.2 Hz, 1H), 6.98 (d, J=8.7 Hz, 2H), 6.95 (dd, J=7.7, 1.2 Hz, 1H), 6.93-6.86 (m, 2H), 6.81 (d, J=7.9 Hz, 1H), 6.72 (td, J=7.5, 1.1 Hz, 1H), 6.68-6.61 (m, 2H), 6.51 (d, J=1.5 Hz, 1H), 5.07 (s, 2H), 3.90 (q, J=7.1 Hz, 1H), 2.16 (s, 3H), 1.46 (d, J=7.2 Hz, 3H).

HRMS m/z (ESI) calcd for $C_{28}H_{25}NOS$ $[M+H]^+$ 423.1657 found: 423.1652.

The detailed preparative method is same as that of compound 1, with a yield of 77.1%.

Compound 55: 2-(1-(3-(benzyloxyl)-4-fluorophenyl)ethyl)-10H-phenothiazine

The synthetic route is as follows:

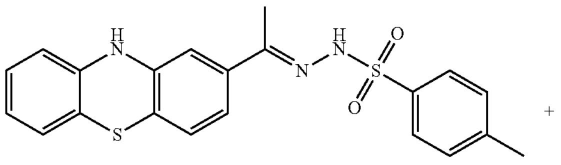

Intermediate I

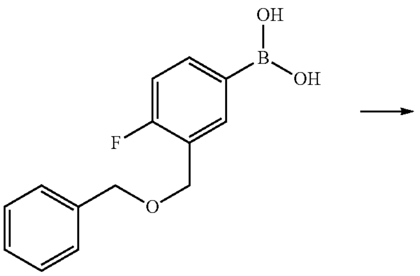

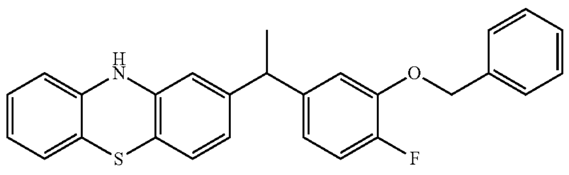

55

$^1$H NMR and HRMS data of compound 55 are as follows:

$^1$H NMR (400 MHz, DMSO-$d_6$) δ 8.49 (s, 1H), 7.42 (d, J=7.1 Hz, 2H), 7.37 (t, J=7.4 Hz, 2H), 7.30 (d, J=7.1 Hz, 1H), 7.18-7.07 (m, 2H), 6.96 (d, J=7.2 Hz, 1H), 6.90 (d, J=7.5 Hz, 1H), 6.82 (d, J=7.9 Hz, 1H), 6.78 (ddd, J=6.6, 4.2, 2.0 Hz, 1H), 6.75 (dd, J=7.3, 4.9 Hz, 1H), 6.66 (d, J=7.8 Hz, 2H), 6.51 (s, 1H), 5.14 (s, 2H), 3.97 (d, J=7.1 Hz, 1H), 1.48 (d, J=7.2 Hz, 3H).

HRMS m/z (ESI) calcd for $C_{27}H_{22}FNOS$ $[M+H]^+$ 427.1406 found: 427.1402.

The detailed preparative method is same as that of compound 1, with a yield of 74.9%.

Compound 56: 2-(1-(3,5-difluorophenyl)ethyl)-10H-phenothiazine

The synthetic route is as follows:

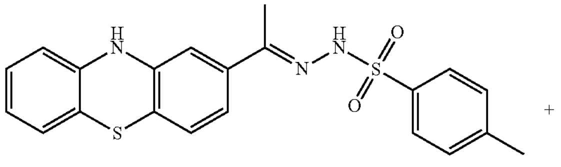

Intermediate I

-continued

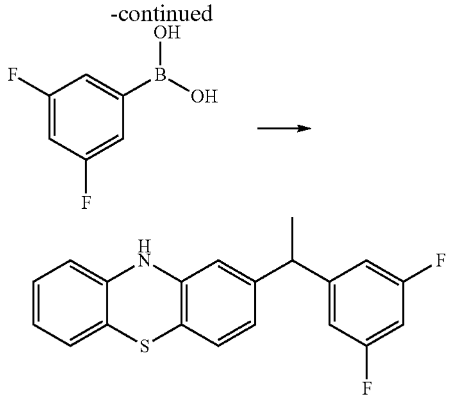

56

$^1$H NMR and HRMS data of compound 56 are as follows: $^1$H NMR (400 MHz, DMSO-$d_6$) δ 8.51 (s, 1H), 7.14-7.00 (m, 1H), 7.00-6.91 (m, 3H), 6.92-6.80 (m, 2H), 6.78-6.68 (m, 2H), 6.65 (dd, J=7.9, 1.0 Hz, 1H), 6.52 (d, J=1.6 Hz, 1H), 4.06 (q, J=7.2 Hz, 1H), 1.51 (t, J=8.2 Hz, 3H).

HRMS m/z (ESI) calcd for $C_{20}H_{15}F_2NS$ $[M+H]^+$ 339.0893 found: 339.0896.

The detailed preparative method is same as that of compound 1, with a yield of 69.9%.

Compound 57: 2-(1-(3,5-dichlorophenyl)ethyl)-10H-phenothiazine

The synthetic route is as follows:

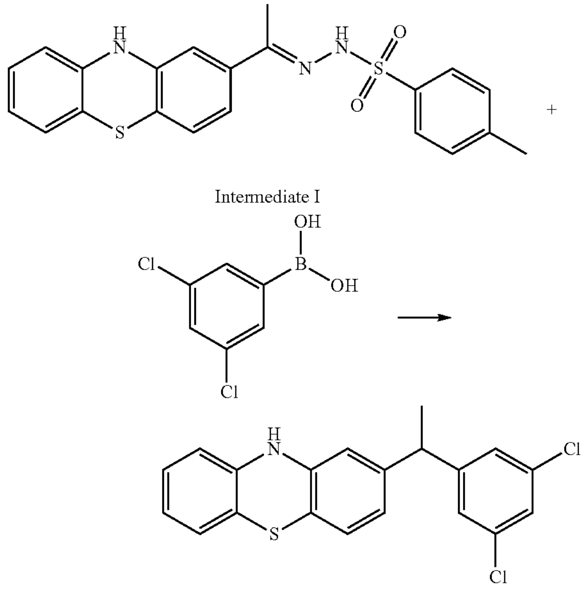

57

$^1$H NMR and HRMS data of compound 57 are as follows: $^1$H NMR (400 MHz, DMSO-$d_6$) δ 8.52 (s, 1H), 7.43 (s, 1H), 7.28 (d, J=1.6 Hz, 2H), 7.03-6.93 (m, 1H), 6.87 (dd, J=15.5, 7.7 Hz, 2H), 6.79-6.68 (m, 2H), 6.65 (d, J=7.9 Hz, 1H), 6.51 (s, 1H), 4.07 (d, J=7.1 Hz, 1H), 1.50 (d, J=7.2 Hz, 3H).

HRMS m/z (ESI) calcd for $C_{20}H_{15}Cl_2NS$ $[M+H]^+$ 371.0302 found: 371.0305.

The detailed preparative method is same as that of compound 1, with a yield of 79.9%.

Compound 58: 2-(1-(3,5-bis(trifluoromethyl)phenyl) ethyl)-10H-phenothiazine

The synthetic route is as follows:

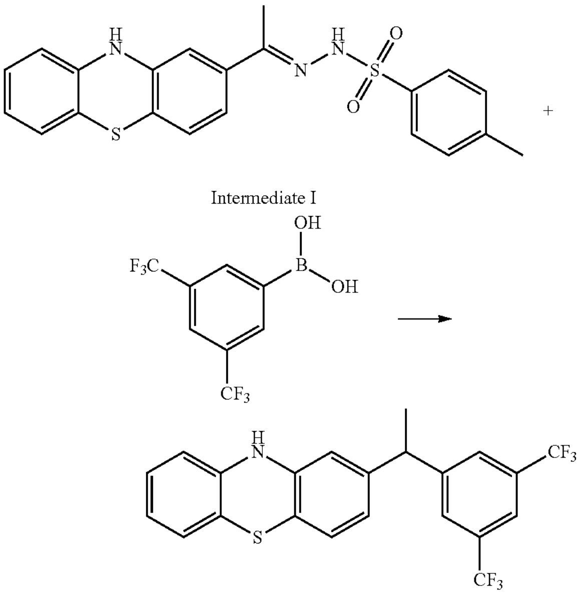

58

$^1$H NMR and HRMS data of compound 58 are as follows: $^1$H NMR (400 MHz, DMSO-$d_6$) δ 8.52 (s, 1H), 7.95 (s, 1H), 7.92 (s, 2H), 6.96 (td, J=7.8, 1.4 Hz, 1H), 6.88 (dd, J=11.5, 4.6 Hz, 2H), 6.79-6.69 (m, 2H), 6.65 (dd, J=7.9, 1.0 Hz, 1H), 6.54 (d, J=1.6 Hz, 1H), 4.33 (q, J=7.1 Hz, 1H), 1.58 (d, J=7.2 Hz, 3H).

HRMS m/z (ESI) calcd for $C_{22}H_{15}F_6NS$ $[M+H]^+$ 439.0829 found: 439.0825.

The detailed preparative method is same as that of compound 1, with a yield of 80.0%.

Compound 59: 2-(1-(3,5-dimethylphenyl)ethyl)-10H-phenothiazine

The synthetic route is as follows:

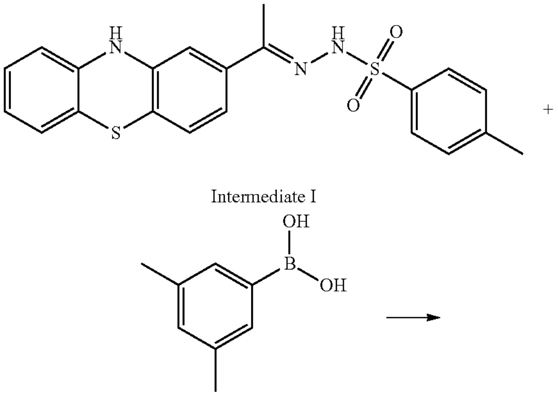

-continued

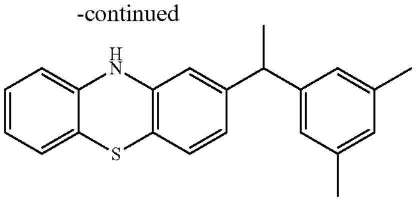

59

$^1$H NMR and HRMS data of compound 59 are as follows:

$^1$H NMR (400 MHz, DMSO-$d_6$) δ 8.49 (s, 1H), 6.95 (dd, J=7.6, 1.3 Hz, 1H), 6.91-6.86 (m, 1H), 6.84-6.78 (m, 3H), 6.73 (dd, J=7.5, 1.1 Hz, 1H), 6.66 (ddd, J=11.4, 7.9, 1.3 Hz, 2H), 6.51 (d, J=1.6 Hz, 1H), 3.90 (d, J=7.2 Hz, 1H), 2.22 (s, 5H), 1.47 (d, J=7.2 Hz, 3H).

HRMS m/z (ESI) calcd for $C_{22}H_{21}NS$ $[M+H]^+$ 331.1395 found: 331.1390.

The detailed preparative method is same as that of compound 1, with a yield of 64.8%.

Compound 60: 2-(1-(3,5-dimethoxylphenyl)ethyl)-10H-phenothiazine

The synthetic route is as follows:

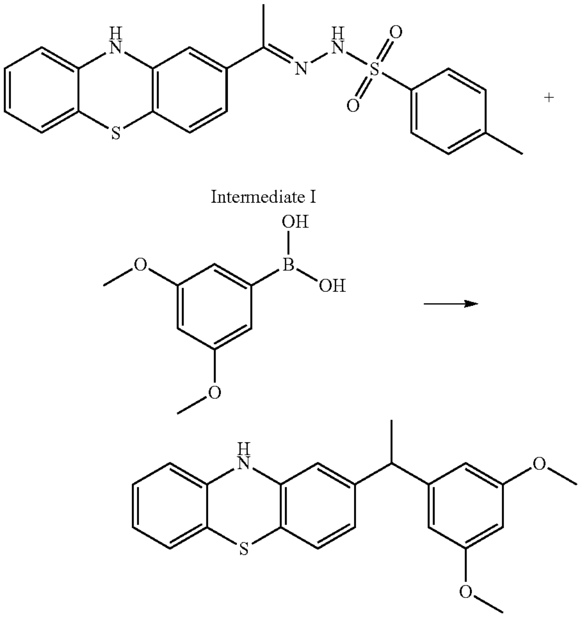

60

$^1$H NMR and HRMS data of compound 60 are as follows:

$^1$H NMR (400 MHz, DMSO-$d_6$) δ 8.49 (s, 1H), 6.95 (d, J=7.4 Hz, 1H), 6.89 (d, J=7.5 Hz, 1H), 6.82 (d, J=7.9 Hz, 1H), 6.72 (dd, J=15.9, 7.7 Hz, 2H), 6.65 (d, J=7.9 Hz, 1H), 6.53 (s, 1H), 6.37 (d, J=1.9 Hz, 2H), 6.33 (d, J=2.0 Hz, 1H), 3.92 (d, J=7.1 Hz, 1H), 3.70 (s, 6H), 1.47 (d, J=7.2 Hz, 3H).

HRMS m/z (ESI) calcd for $C_{22}H_{21}NO_2S$ $[M+H]^+$ 363.1293 found: 363.1295.

The detailed preparative method is same as that of compound 1, with a yield of 77.2%.

Compound 61: 2-(1-(3-ethoxyl-5-fluorophenyl)ethyl)-10H-phenothiazine

The synthetic route is as follows:

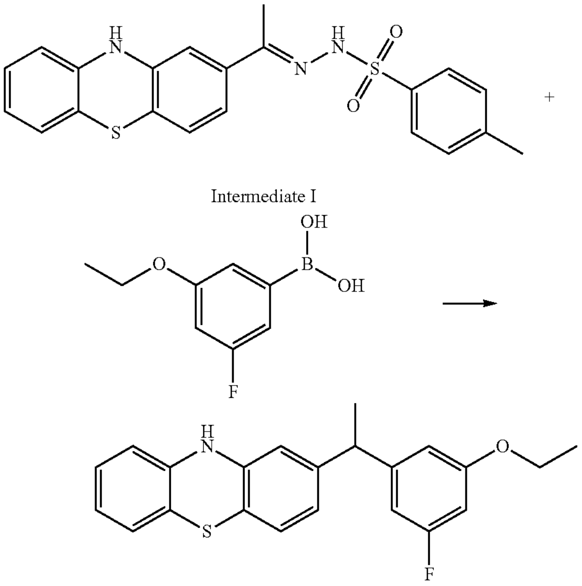

61

$^1$H NMR and HRMS data of compound 61 are as follows:

$^1$H NMR (400 MHz, DMSO-$d_6$) δ 8.50 (s, 1H), 7.02-6.93 (m, 1H), 6.89 (d, J=7.6 Hz, 1H), 6.83 (d, J=7.9 Hz, 1H), 6.72 (ddd, J=9.7, 7.7, 1.2 Hz, 2H), 6.69-6.57 (m, 4H), 6.52 (d, J=1.4 Hz, 1H), 3.99 (dd, J=14.0, 7.0 Hz, 3H), 1.47 (d, J=7.2 Hz, 3H), 1.29 (t, J=7.0 Hz, 3H).

HRMS m/z (ESI) calcd for $C_{22}H_{20}FNOS$ $[M+H]^+$ 365.1250 found: 365.1253.

The detailed preparative method is same as that of compound 1, with a yield of 64.8%.

Compound 62: 2-(1-(3-chloro-5-methylphenyl)ethyl)-10H-phenothiazine

The synthetic route is as follows:

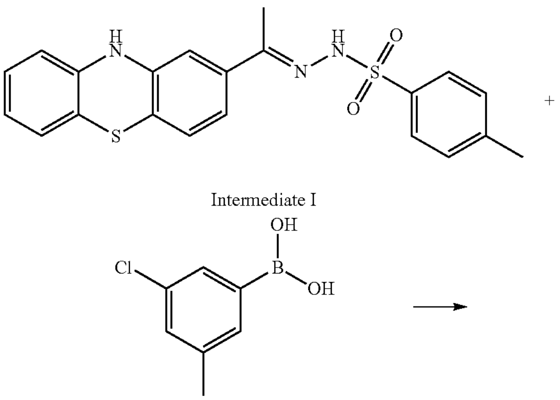

-continued

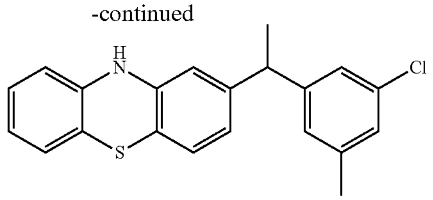

62

$^1$H NMR and HRMS data of compound 62 are as follows: $^1$H NMR (400 MHz, DMSO-$d_6$) δ 8.50 (s, 1H), 7.07 (d, J=7.7 Hz, 2H), 7.00 (s, 1H), 6.99-6.93 (m, 1H), 6.89 (d, J=6.7 Hz, 1H), 6.83 (d, J=7.9 Hz, 1H), 6.74 (d, J=7.5 Hz, 1H), 6.72-6.67 (m, 1H), 6.66-6.62 (m, 1H), 6.51 (d, J=1.5 Hz, 1H), 3.98 (q, J=7.1 Hz, 1H), 2.27 (s, 3H), 1.48 (d, J=7.2 Hz, 3H).

HRMS m/z (ESI) calcd for $C_{21}H_{18}ClNS$ $[M+H]^+$ 351.0848 found: 351.0852.

The detailed preparative method is same as that of compound 1, with a yield of 66.8%.

Compound 63: 3-(1-(10H-phenothiazin-2-yl)ethyl)-5-fluorobenzoic acid methyl ester The synthetic route is as follows:

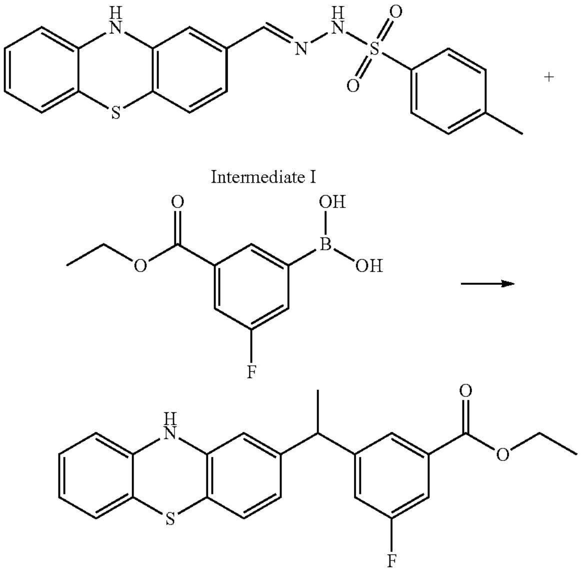

63

$^1$H NMR and HRMS data of compound 63 are as follows: $^1$H NMR (400 MHz, DMSO-$d_6$) δ 8.51 (s, 1H), 7.65 (s, 1H), 7.57-7.48 (m, 1H), 7.43 (d, J=9.8 Hz, 1H), 6.96 (td, J=7.8, 1.3 Hz, 1H), 6.87 (dd, J=15.2, 7.8 Hz, 2H), 6.77-6.68 (m, 2H), 6.64 (d, J=7.9 Hz, 1H), 6.51 (d, J=1.5 Hz, 1H), 4.16 (q, J=7.1 Hz, 1H), 3.84 (d, J=7.2 Hz, 3H), 1.53 (d, J=7.2 Hz, 3H).

HRMS m/z (ESI) calcd for $C_{21}H_{18}FNO_2S$ $[M+H]^+$ 379.1042 found: 379.1046.

The detailed preparative method is same as that of compound 1, with a yield of 80.3%.

Compound 64: 2-(1-(3-(benzyloxyl)-5-fluorophenyl)ethyl)-10H-phenothiazine

The synthetic route is as follows:

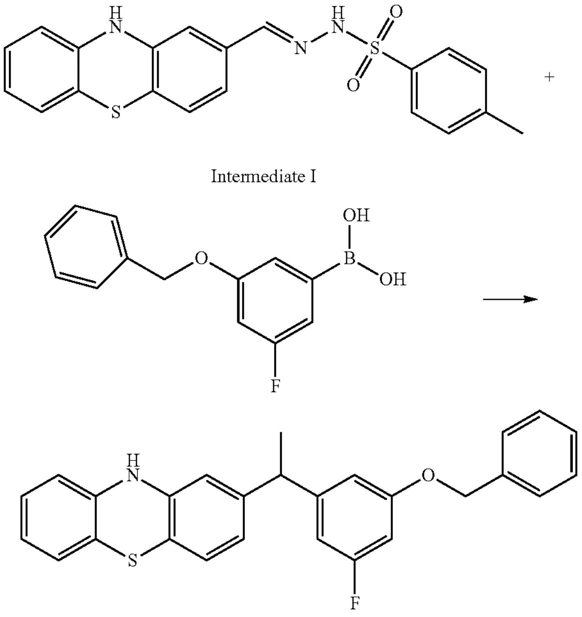

64

$^1$H NMR and HRMS data of compound 64 are as follows: $^1$H NMR (400 MHz, DMSO-$d_6$) δ 8.50 (s, 1H), 7.55-7.24 (m, 5H), 7.05-6.80 (m, 3H), 6.79-6.58 (m, 6H), 6.53 (s, 1H), 5.07 (s, 2H), 3.98 (d, J=6.6 Hz, 1H), 1.48 (d, J=6.5 Hz, 3H).

HRMS m/z (ESI) calcd for $C_{27}H_{22}FNOS$ $[M+H]^+$ 427.1406 found: 427.1402.

The detailed preparative method is same as that of compound 1, with a yield of 45.2%.

Compound 65: 2-(1-(2,3-dihydrobenzo[b][1,4]dioxa-6-yl)ethyl)-10H-phenothiazine

The synthetic route is as follows:

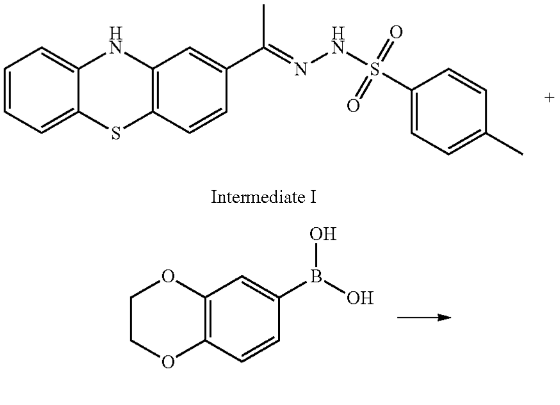

-continued

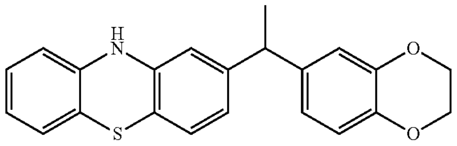

65

$^1$H NMR and HRMS data of compound 65 are as follows:

$^1$H NMR (400 MHz, DMSO-$d_6$) δ 8.50 (s, 1H), 6.96 (t, J=7.6 Hz, 1H), 6.89 (d, J=7.5 Hz, 1H), 6.81 (d, J=7.9 Hz, 1H), 6.74 (dd, J=15.0, 7.8 Hz, 2H), 6.70-6.62 (m, 4H), 6.52 (s, 1H), 4.19 (s, 4H), 3.98-3.77 (m, 1H), 1.55-1.40 (m, 3H).

HRMS m/z (ESI) calcd for $C_{22}H_{19}NO_2S$ $[M+H]^+$ 361.1136 found: 361.1133.

The detailed preparative method is same as that of compound 1, with a yield of 71.8%.

Compound 66: 2-(1-(benzo[d][1,3]dioxin-5-yl) ethyl)-10H-phenothiazine

The synthetic route is as follows:

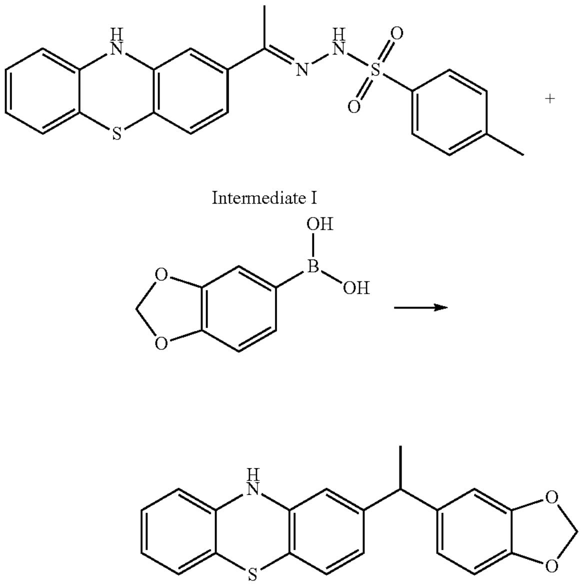

66

$^1$H NMR and HRMS data of compound 66 are as follows:

$^1$H NMR (400 MHz, DMSO-$d_6$) δ 8.51 (s, 1H), 7.32 (t, J=7.7 Hz, 1H), 7.28-7.22 (m, 2H), 7.19 (d, J=7.6 Hz, 1H), 6.96 (t, J=7.3 Hz, 1H), 6.89 (d, J=7.5 Hz, 1H), 6.84 (d, J=7.9 Hz, 1H), 6.72 (dd, J=17.7, 7.8 Hz, 2H), 6.65 (d, J=7.9 Hz, 1H), 6.52 (s, 1H), 4.04 (d, J=7.1 Hz, 1H), 1.50 (d, J=7.2 Hz, 3H).

HRMS m/z (ESI) calcd for $C_{21}H_{17}NO_2S$ $[M+H]^+$ 347.0980 found: 347.0985.

The detailed preparative method is same as that of compound 1, with a yield of 59.8%.

Compound 67: 2-(1-(benzofuran-2-yl)ethyl)-10H-phenothiazine

The synthetic route is as follows:

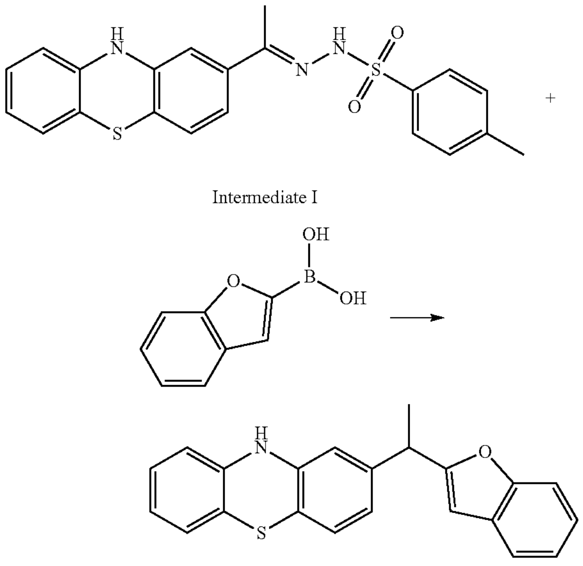

67

$^1$H NMR and HRMS data of compound 67 are as follows:

$^1$H NMR (400 MHz, DMSO-$d_6$) δ 8.54 (s, 1H), 7.57 (d, J=6.4 Hz, 1H), 7.46 (d, J=6.9 Hz, 1H), 7.21 (s, 2H), 6.95 (d, J=7.4 Hz, 1H), 6.93-6.79 (m, 2H), 6.72 (d, J=10.1 Hz, 3H), 6.64 (d, J=7.6 Hz, 1H), 6.56 (s, 1H), 4.18 (d, J=6.5 Hz, 1H), 1.57 (d, J=6.7 Hz, 3H).

HRMS m/z (ESI) calcd for $C_{22}H_{17}NOS$ $[M+H]^+$ 343.1031 found: 343.1036.

The detailed preparative method is same as that of compound 1, with a yield of 69.8%.

Compound 68: 2-(1-(naphthalen-2-yl)ethyl)-10H-phenothiazine

The synthetic route is as follows:

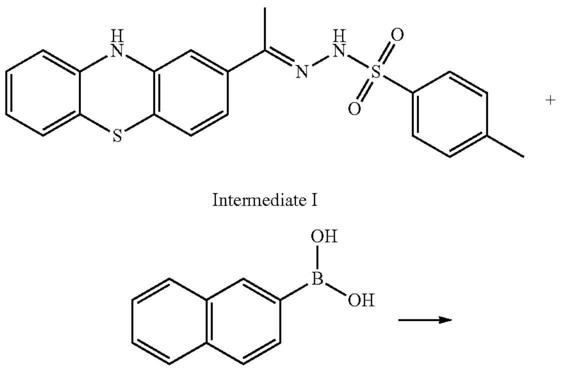

-continued

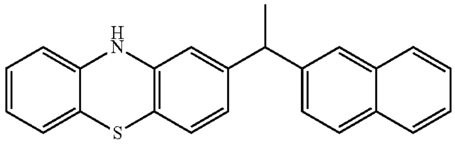

68

$^1$H NMR and HRMS data of compound 68 are as follows:

$^1$H NMR (400 MHz, DMSO-$d_6$) δ 8.48 (s, 1H), 7.93-7.80 (m, 3H), 7.78 (s, 1H), 7.58-7.41 (m, 2H), 7.33 (d, J=8.5 Hz, 1H), 6.94 (t, J=7.6 Hz, 1H), 6.88 (d, J=7.5 Hz, 1H), 6.84 (d, J=7.9 Hz, 1H), 6.73 (dd, J=13.6, 6.9 Hz, 2H), 6.62 (d, J=7.8 Hz, 1H), 6.54 (s, 1H), 4.18 (q, J=7.1 Hz, 1H), 1.61 (d, J=7.1 Hz, 3H).

HRMS m/z (ESI) calcd for $C_{24}H_{19}NS$ $[M+H]^+$ 353.1238 found: 353.1242.

The detailed preparative method is same as that of compound 1, with a yield of 57.8%.

Compound 69: 2-(1-(6-methoxylnaphthalen-2-yl) ethyl)-10H-phenothiazine

The synthetic route is as follows:

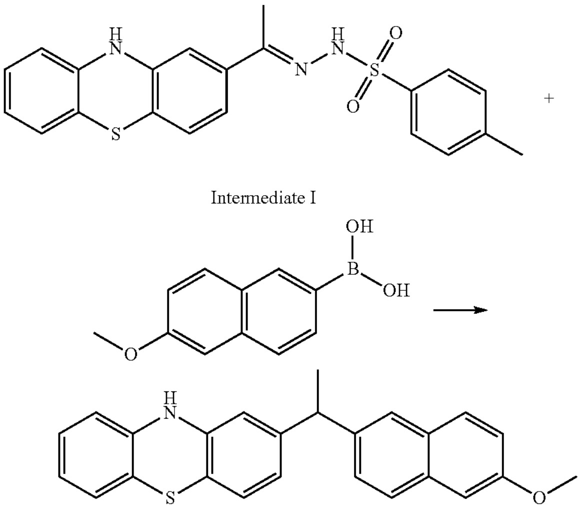

69

$^1$H NMR and HRMS data of compound 69 are as follows:

$^1$H NMR (400 MHz, DMSO-$d_6$) δ 8.47 (s, 1H), 7.79 (d, J=9.0 Hz, 1H), 7.76-7.67 (m, 2H), 7.27 (dd, J=10.7, 1.9 Hz, 2H), 7.13 (dd, J=8.9, 2.5 Hz, 1H), 6.99-6.91 (m, 1H), 6.88 (d, J=7.6 Hz, 1H), 6.83 (d, J=7.9 Hz, 1H), 6.71 (dd, J=11.7, 4.3 Hz, 2H), 6.62 (d, J=7.9 Hz, 1H), 6.52 (s, 1H), 4.13 (q, J=7.1 Hz, 1H), 3.85 (s, 3H), 1.59 (d, J=7.1 Hz, 3H).

HRMS m/z (ESI) calcd for $C_{25}H_{21}NOS$ $[M+H]^+$ 383.1344 found: 383.1350.

The detailed preparative method is same as that of compound 1, with a yield of 59.8%.

Compound 70: 2-(1-(6-ethoxylnaphthalen-2-yl) ethyl)-10H-phenothiazine

The synthetic route is as follows:

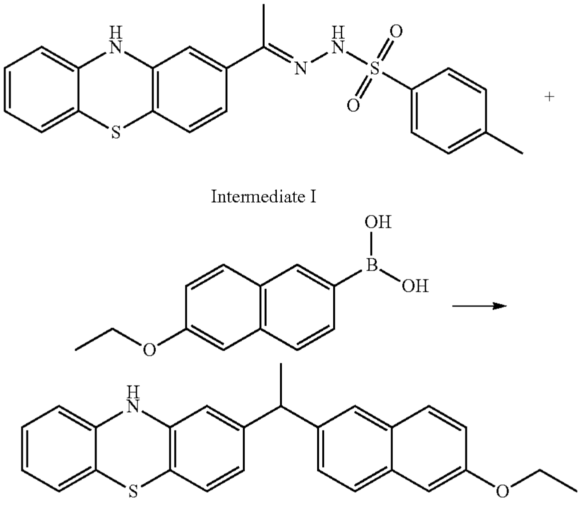

70

$^1$H NMR and HRMS data of compound 70 are as follows:

$^1$H NMR (400 MHz, DMSO-$d_6$) δ 8.47 (s, 1H), 7.78 (d, J=9.0 Hz, 1H), 7.70 (d, J=9.1 Hz, 2H), 7.33-7.21 (m, 2H), 7.12 (dd, J=8.9, 2.5 Hz, 1H), 6.94 (td, J=7.8, 1.3 Hz, 1H), 6.91-6.86 (m, 1H), 6.83 (d, J=7.9 Hz, 1H), 6.72 (td, J=7.7, 1.2 Hz, 2H), 6.62 (dd, J=7.9, 0.9 Hz, 1H), 6.53 (d, J=1.5 Hz, 1H), 4.12 (dt, J=9.4, 5.6 Hz, 3H), 1.58 (d, J=7.2 Hz, 3H), 1.38 (t, J=7.0 Hz, 3H).

HRMS m/z (ESI) calcd for $C_{26}H_{23}NOS$ $[M+H]^+$ 397.1500 found: 397.1496.

The detailed preparative method is same as that of compound 1, with a yield of 64.3%.

Compound 71: 2-(1-(anthrathen-9-yl)ethyl)-10H-phenothiazine

The synthetic route is as follows:

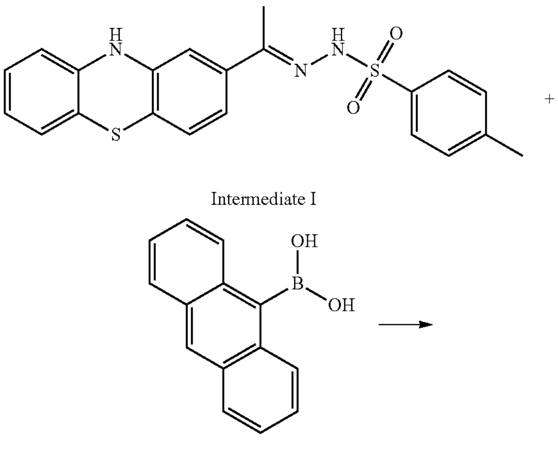

-continued

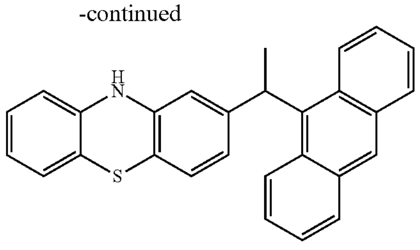

71

$^1$H NMR and HRMS data of compound 71 are as follows:

$^1$H NMR (400 MHz, DMSO-$d_6$) δ 8.86 (d, J=8.0 Hz, 1H), 8.81 (d, J=8.8 Hz, 1H), 8.36 (s, 1H), 8.05 (dd, J=8.3, 4.4 Hz, 2H), 7.89 (s, 1H), 7.75-7.60 (m, 3H), 7.56 (t, J=7.4 Hz, 1H), 6.96-6.79 (m, 4H), 6.69 (t, J=7.4 Hz, 1H), 6.53 (d, J=7.9 Hz, 1H), 6.41 (s, 1H), 4.79 (q, J=6.4 Hz, 1H), 1.73 (d, J=6.9 Hz, 3H).

HRMS m/z (ESI) calcd for $C_{28}H_{21}NS$ $[M+H]^+$ 403.1395 found: 403.1392.

The detailed preparative method is same as that of compound 1, with a yield of 74.8%.

Compound 72: 2-(1-(2,3-dihydrobenzofuran-5-yl)ethyl)-10H-phenothiazine

The synthetic route is as follows:

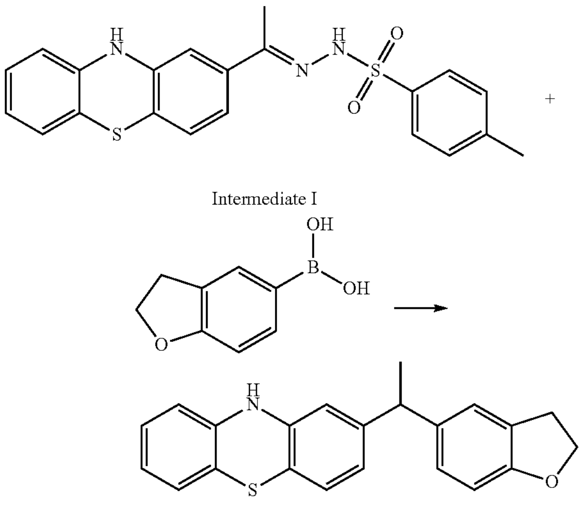

72

$^1$H NMR and HRMS data of compound 72 are as follows:

$^1$H NMR (400 MHz, DMSO-$d_6$) δ 8.48 (s, 1H), 7.05 (s, 1H), 7.01-6.91 (m, 2H), 6.89 (d, J=7.4 Hz, 1H), 6.81 (d, J=7.7 Hz, 1H), 6.77-6.70 (m, 1H), 6.66 (d, J=5.0 Hz, 3H), 6.52 (s, 1H), 4.46 (t, J=8.5 Hz, 2H), 3.92 (d, J=6.8 Hz, 1H), 3.11 (t, J=8.3 Hz, 2H), 1.46 (d, J=6.9 Hz, 3H).

HRMS m/z (ESI) calcd for $C_{22}H_{19}NOS$ $[M+H]^+$ 345.1187 found: 345.1183.

The detailed preparative method is same as that of compound 1, with a yield of 78.5%.

Compound 73: 5-(1-(10H-phenothiazin-2-yl)ethyl)nicotinonitrile

The synthetic route is as follows:

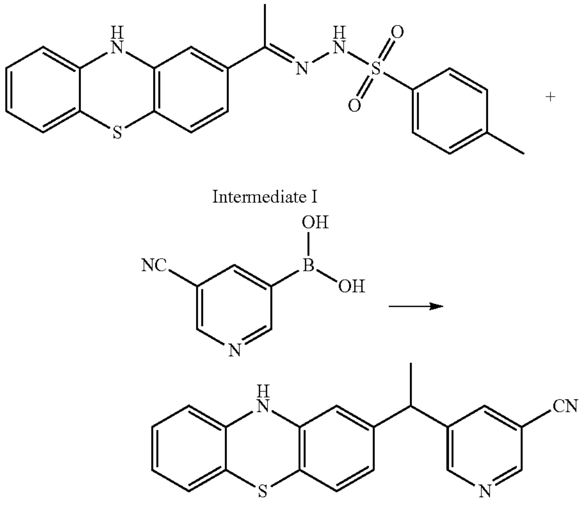

73

$^1$H NMR and HRMS data of compound 73 are as follows:

$^1$H NMR (400 MHz, DMSO-$d_6$) δ 8.87 (d, J=1.5 Hz, 1H), 8.77 (d, J=1.7 Hz, 1H), 8.51 (s, 1H), 8.23 (s, 1H), 6.96 (t, J=7.6 Hz, 1H), 6.87 (dd, J=11.7, 7.6 Hz, 2H), 6.73 (t, J=8.4 Hz, 2H), 6.64 (d, J=7.9 Hz, 1H), 6.51 (s, 1H), 4.17 (q, J=7.2 Hz, 1H), 1.56 (d, J=7.2 Hz, 3H).

HRMS m/z (ESI) calcd for $C_{20}H_{15}N_3S$ $[M+H]^+$ 329.0987 found: 329.0986.

The detailed preparative method is same as that of compound 1, with a yield of 71.8%.

Compound 74: 2-(1-(2-methylpyridin-4-yl)ethyl)-10H-phenothiazine

The synthetic route is as follows:

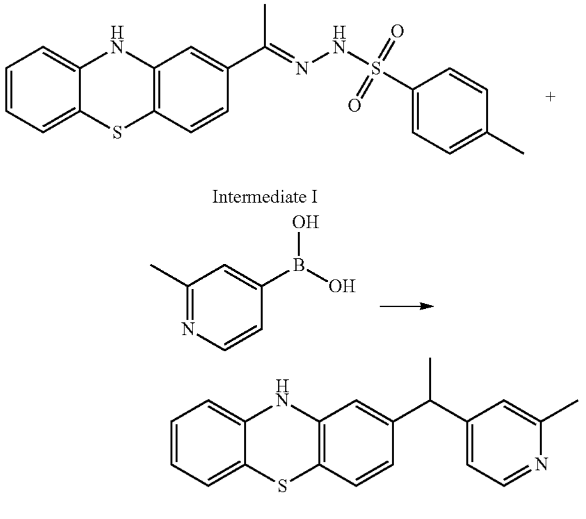

74

$^1$H NMR and HRMS data of compound 74 are as follows:

$^1$H NMR (400 MHz, DMSO-$d_6$) δ 8.51 (s, 1H), 8.33 (d, J=5.1 Hz, 1H), 7.10 (s, 1H), 7.02 (d, J=4.8 Hz, 1H), 6.96 (t, J=7.6 Hz, 1H), 6.89 (d, J=7.5 Hz, 1H), 6.84 (d, J=7.8 Hz, 1H), 6.73 (t, J=7.5 Hz, 1H), 6.68 (d, J=8.0 Hz, 1H), 6.64 (d, J=7.9 Hz, 1H), 6.50 (s, 1H), 3.97 (q, J=6.9 Hz, 1H), 2.42 (s, 3H), 1.49 (d, J=7.1 Hz, 3H).

HRMS m/z (ESI) calcd for $C_{20}H_{18}N_2S$ $[M+H]^+$ 318.1191 found: 318.1194.

The detailed preparative method is same as that of compound 1, with a yield of 50.1%.

Compound 75: 2-(1-(6-ethoxylpyridin-3-yl)ethyl)-10H-phenothiazine

The synthetic route is as follows:

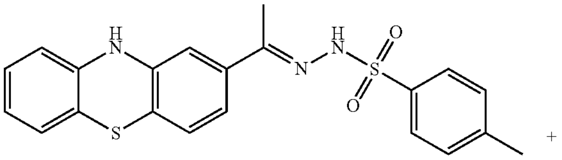

Intermediate I

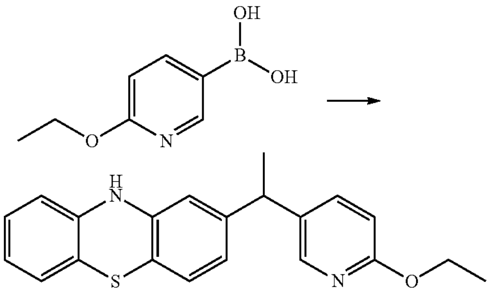

75

$^1$H NMR and HRMS data of compound 75 are as follows:

$^1$H NMR (400 MHz, DMSO-$d_6$) δ 8.50 (s, 1H), 8.04 (d, J=2.5 Hz, 1H), 7.50 (dd, J=8.6, 2.5 Hz, 1H), 6.96 (td, J=7.7, 1.4 Hz, 1H), 6.89 (dd, J=7.7, 1.3 Hz, 1H), 6.83 (d, J=7.9 Hz, 1H), 6.76-6.66 (m, 3H), 6.64 (dd, J=7.9, 1.1 Hz, 1H), 6.51 (d, J=1.7 Hz, 1H), 4.26 (q, J=7.0 Hz, 2H), 3.98 (q, J=7.1 Hz, 1H), 1.49 (d, J=7.2 Hz, 3H), 1.29 (t, J=7.0 Hz, 3H).

HRMS m/z (ESI) calcd for $C_{21}H_{20}N_2OS$ $[M+H]^+$ 348.1296 found: 348.1291.

The detailed preparative method is same as that of compound 1, with a yield of 71.7%.

Compound 76: 2-(1-cyclohexylethyl)-10H-phenothiazine

The synthetic route is as follows:

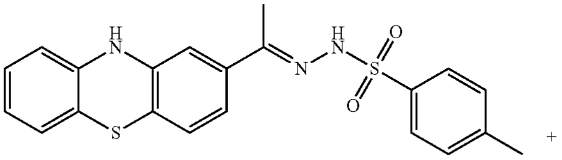

Intermediate I

-continued

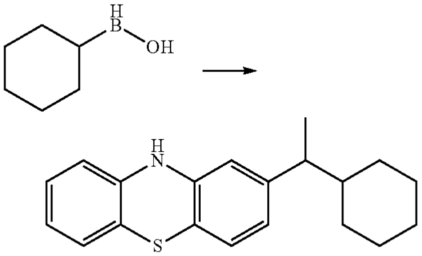

76

$^1$H NMR and HRMS data of compound 76 are as follows:

$^1$H NMR (400 MHz, DMSO-$d_6$) δ 8.50 (s, 1H), 6.98 (td, J=7.8, 1.4 Hz, 1H), 6.94-6.86 (m, 1H), 6.80 (d, J=7.8 Hz, 1H), 6.74 (td, J=7.5, 1.1 Hz, 1H), 6.67 (d, J=7.9 Hz, 1H), 6.56 (dd, J=7.9, 1.6 Hz, 1H), 6.49 (d, J=1.5 Hz, 1H), 2.36-2.22 (m, 1H), 1.79 (d, J=12.3 Hz, 1H), 1.69 (d, J=12.9 Hz, 1H), 1.58 (s, 2H), 1.42 (d, J=14.5 Hz, 1H), 1.36-1.23 (m, 1H), 1.17 (d, J=12.5 Hz, 1H), 1.11 (d, J=7.0 Hz, 3H), 1.07 (d, J=7.9 Hz, 2H), 0.97-0.68 (m, 3H).

HRMS m/z (ESI) calcd for $C_{20}H_{23}NS$ $[M+H]^+$ 309.1551 found: 309.1554.

The detailed preparative method is same as that of compound 1, with a yield of 64.7%.

Example 3 Synthesis of Compounds B1-B59 of the Present Invention

Compounds 1-59 in Example 3 were also named compounds B1-B59.

Using the intermediate I prepared in Example 1 and various substituted bromides as starting materials, to prepare compounds 1-59, namely compounds B1-B59. Among them, the method for preparation of compounds 2-59 is the same as that of compound 1 in Example 3.

Compound 1: 2-(1-phenylethyl)-10H-phenothiazine

The synthetic route was as follows:

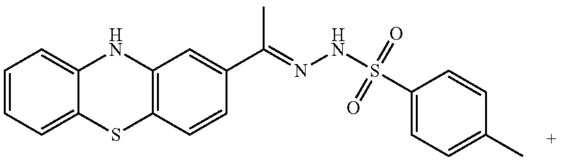

Intermediate I

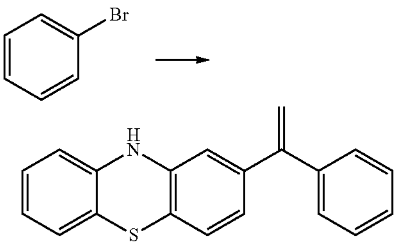

1

Intermediate I (120 mg, 0.293 mmol, 1.2 eq), bromobenzene (38 mg, 0.244 mmol, 1.0 eq), tris (dibenzylidene-BASE acetone)dipalladium(0) $Pd_2(dpa)_3$ (24 mg, 0.03 mmol, 0.1 eq), 2-dicyclohexyl phosphorus-2,4,6-triisopropylbiphenyl X-phos (25 mg, 0.03 mmol, 0.2 eq) and anhydrous t-BuOLi (43 mg, 0.537 mmol, 2.2 eq) were dissolved in 10 mL 1,4-dioxane, and argon was purged and exchanged 3 times. The resultant mixture was heated to 70° C. for reaction, and the reaction was monitored by TLC. After about 4 h, the reaction was completed, and cooled to room temperature, then filtered with Celite. The reaction solution was concentrated under reduced pressure, and the residue was extracted with water/DCM (1:1). The organic layer was concentrated and separated by column chromatography to obtain the target product compound 1 (58 mg), with a yield of 74.8%.

$^1$H NMR and HRMS data of compound 1 are as follows:

1H NMR (400 MHz, DMSO-$d_6$) δ 8.56 (s, 1H), 7.43-7.33 (m, 3H), 7.30 (dd, J=7.8, 1.7 Hz, 2H), 7.01-6.88 (m, 3H), 6.79-6.71 (m, 2H), 6.62 (dd, J=7.9, 1.0 Hz, 1H), 6.57 (d, J=1.8 Hz, 1H), 5.44 (s, 1H), 5.39 (d, J=0.7 Hz, 1H).

HRMS m/z (ESI) calcd for $C_{20}H_{15}NS$ [M+H]+ 302.0998 found: 302.0997.

Compound 2: methyl 4-(1-(10H-phenothiazin-2-yl)ethenyl)benzoic acid

The synthetic route is as follows:

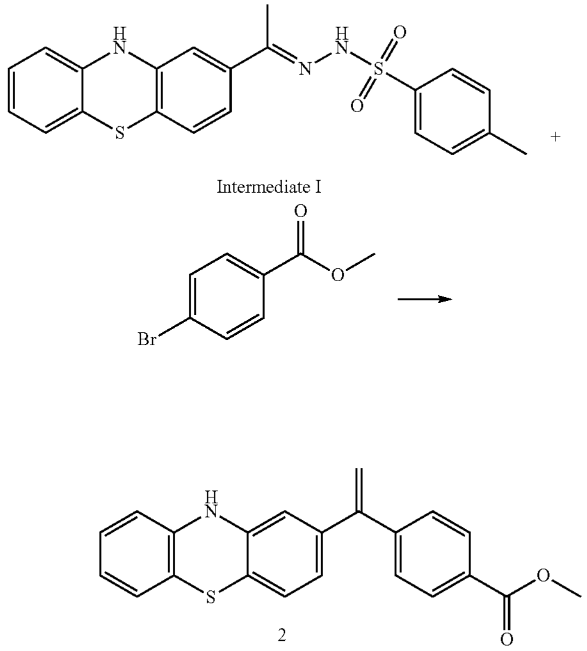

Intermediate I

2

$^1$H NMR and HRMS data of compound 2 are as follows:

$^1$H NMR (400 MHz, DMSO-$d_6$) δ 8.57 (s, 1H), 7.97 (d, =8. J 0 Hz, 2H), 7.46 (d, J=7.8 Hz, 2H), 7.02-6.95 (m, 1H), 6.93 (dd, J=13.6, 6.1 Hz, 2H), 6.75 (t, J=6.6 Hz, 2H), 6.63 (d, J=7.7 Hz, 1H), 6.55 (s, 1H), 5.54 (d, J=14.4 Hz, 2H), 3.87 (s, 3H).

HRMS m/z (ESI) calcd for $C_{22}H_{17}NO_2S$ $[M+H]^+$ 360.1058 found: 360.1062.

The detailed preparative method is same as that of compound 1, with a yield of 84.1%.

Compound 3: 2-(1-(4-(trifluoromethyl)phenyl)ethenyl)-10H-phenothiazine

The synthetic route is as follows:

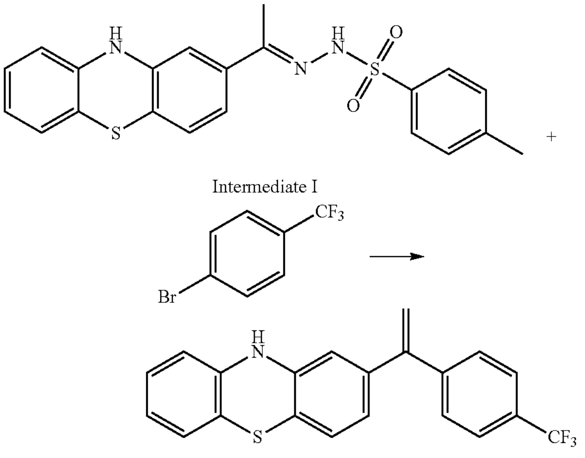

Intermediate I

3

$^1$H NMR and HRMS data of compound 3 are as follows:

$^1$H NMR (400 MHz, DMSO-$d_6$) δ 8.57 (s, 1H), 7.75 (d, J=8.2 Hz, 2H), 7.53 (d, J=8.0 Hz, 2H), 7.01-6.88 (m, 3H), 6.81-6.72 (m, 2H), 6.62 (dd, J=7.9, 0.9 Hz, 1H), 6.54 (d, J=1.7 Hz, 1H), 5.59 (s, 1H), 5.51 (s, 1H).

HRMS m/z (ESI) calcd for $C_{21}H_{14}F_3NS$ $[M+H]^+$ 370.0877 found: 370.0875.

The detailed preparative method is same as that of compound 1, with a yield of 73.1%.

Compound 4: 2-(1-(4-ethylphenyl)ethenyl)-10H-phenothiazine

The synthetic route is as follows:

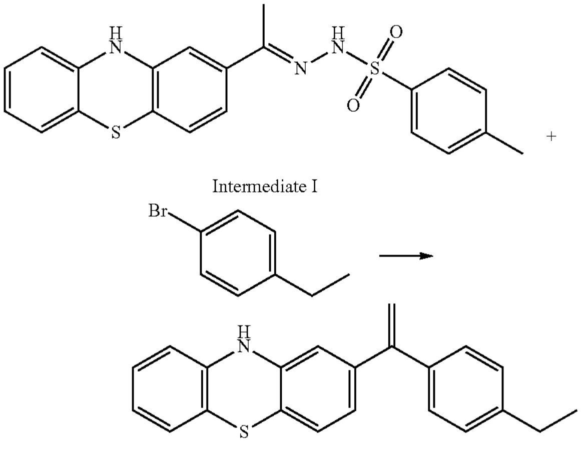

Intermediate I

4

$^1$H NMR and HRMS data of compound 4 are as follows:

$^1$H NMR (400 MHz, DMSO-$d_6$) δ 8.56 (s, 1H), 7.22 (s, 4H), 6.96 (dd, J=7.6, 1.3 Hz, 1H), 6.91 (d, J=7.9 Hz, 2H), 6.75 (dd, J=7.6, 1.4 Hz, 2H), 6.63 (dd, J=7.9, 1.0 Hz, 1H), 6.58 (d, J=1.8 Hz, 1H), 5.37 (dd, J=11.5, 0.9 Hz, 2H), 2.62 (q, J=7.6 Hz, 2H), 1.20 (t, J=7.6 Hz, 3H).

HRMS m/z (ESI) calcd for $C_{22}H_{19}NS$ $[M+H]^+$ 330.1316 found: 330.1318.

The detailed preparative method is same as that of compound 1, with a yield of 72.8%.

Compound 5: 2-(1-(4-trifluoromethoxylphenyl)ethenyl)-10H-phenothiazine

The synthetic route is as follows:

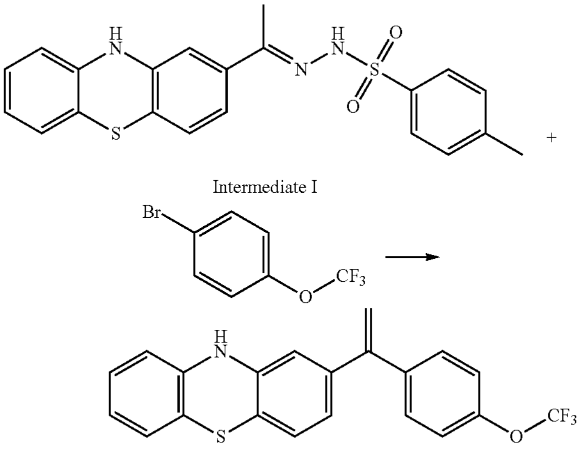

5

$^1H$ NMR and HRMS data of compound 5 are as follows: $^1H$ NMR (400 MHz, DMSO-$d_6$) δ 8.57 (s, 1H), 7.44 (d, J=8.8 Hz, 2H), 7.37 (d, J=8.4 Hz, 2H), 6.98 (dd, J=11.3, 3.9 Hz, 1H), 6.96-6.88 (m, 2H), 6.81-6.70 (m, 2H), 6.62 (d, J=7.9 Hz, 1H), 6.56 (d, J=1.6 Hz, 1H), 5.47 (d, J=20.6 Hz, 2H).

HRMS m/z (ESI) calcd for $C_{22}H_{19}NS$ $[M+H]^+$ 386.4122 found: 386.4125.

The detailed preparative method is same as that of compound 1, with a yield of 63.4%.

Compound 6: 2-(1-(p-methylphenyl)ethenyl)-10H-phenothiazine

The synthetic route is as follows:

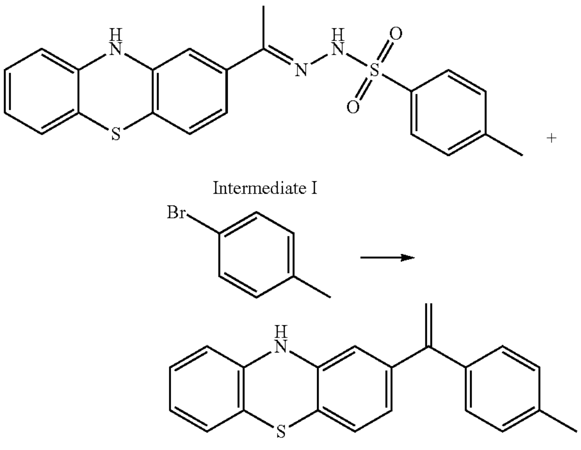

6

$^1H$ NMR and HRMS data of compound 6 are as follows: $^1H$ NMR (400 MHz, DMSO-$d_6$) δ 8.55 (s, 1H), 7.19 (s, 4H), 6.97 (dd, J=11.3, 3.9 Hz, 1H), 6.95-6.88 (m, 2H), 6.81-6.70 (m, 2H), 6.62 (d, J=7.9 Hz, 1H), 6.57 (d, J=1.6 Hz, 1H), 5.36 (d, J=13.4 Hz, 2H), 2.32 (s, 3H).

HRMS m/z (ESI) calcd for $C_{21}H_{17}NS$ $[M+H]^+$ 316.1160 found: 316.1163.

The detailed preparative method is same as that of compound 1, with a yield of 83.5%.

Compound 7: 2-(1-(4-butylphenyl)ethenyl)-10H-phenothiazine

The synthetic route is as follows:

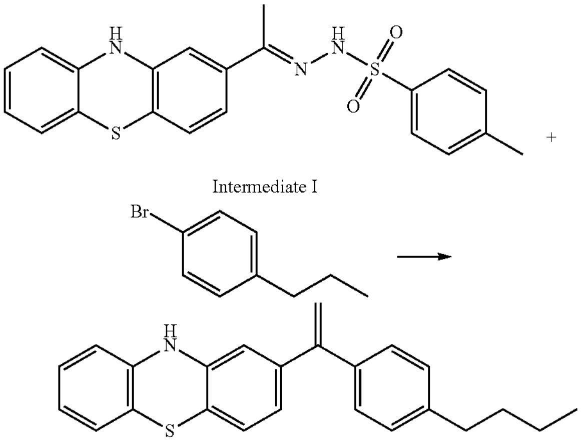

7

$^1H$ NMR and HRMS data of compound 7 are as follows: $^1H$ NMR (400 MHz, DMSO-$d_6$) δ 8.56 (s, 1H), 7.27-7.15 (m, 4H), 7.05-6.94 (m, 1H), 6.91 (d, J=7.9 Hz, 2H), 6.83-6.71 (m, 2H), 6.63 (d, J=7.9 Hz, 1H), 6.58 (d, J=1.6 Hz, 1H), 5.37 (d, J=4.9 Hz, 2H), 2.64-2.55 (m, 2H), 1.56 (dd, J=15.2, 7.8 Hz, 2H), 1.33 (dd, J=14.8, 7.4 Hz, 2H), 0.91 (t, J=7.3 Hz, 3H).

HRMS m/z (ESI) calcd for $C_{24}H_{23}NS$ $[M+H]^+$ 358.1629 found: 358.1630.

The detailed preparative method is same as that of compound 1, with a yield of 68.5%.

Compound 8: 2-(1-(4-isopropylphenyl)ethenyl)-10H-phenothiazine

The synthetic route is as follows:

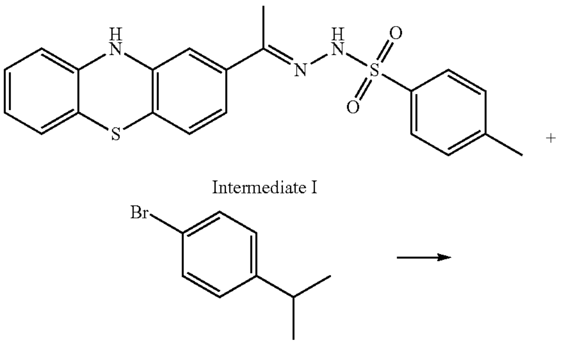

-continued

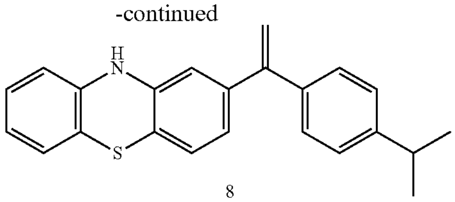

8

$^1$H NMR and HRMS data of compound 8 are as follows:

$^1$H NMR (400 MHz, DMSO-$d_6$) δ 8.57 (s, 1H), 7.34-7.16 (m, 4H), 6.97 (td, J=7.9, 1.3 Hz, 1H), 6.91 (d, J=7.9 Hz, 2H), 6.75 (dd, J=10.8, 4.4 Hz, 2H), 6.63 (d, J=7.9 Hz, 1H), 6.59 (d, J=1.7 Hz, 1H), 5.37 (d, J=8.4 Hz, 2H), 3.00-2.81 (m, 1H), 1.22 (d, J=6.9 Hz, 6H).

HRMS m/z (ESI) calcd for $C_{23}H_{21}NS$ $[M+H]^+$ 344.1473 found: 344.1476.

The detailed preparative method is same as that of compound 1, with a yield of 76.2%.

Compound 9: N-(4-(1-(10H-phenothiazin-2-yl)ethenyl)phenyl)acetylamine

The synthetic route is as follows:

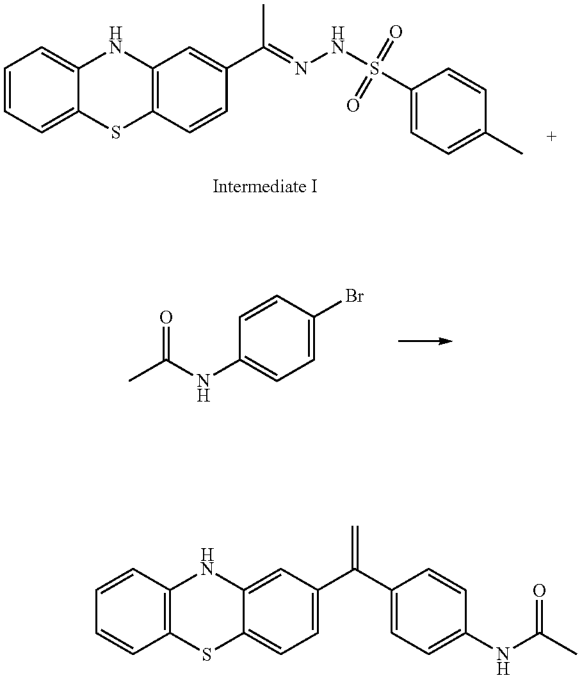

9

$^1$H NMR and HRMS data of compound 9 are as follows:

$^1$H NMR (400 MHz, DMSO-$d_6$) δ 10.00 (s, 1H), 8.56 (s, 1H), 7.58 (d, J=8.5 Hz, 2H), 7.24 (d, J=8.5 Hz, 2H), 7.01-6.94 (m, 1H), 6.91 (d, J=7.9 Hz, 2H), 6.75 (dd, J=7.8, 1.9 Hz, 2H), 6.63 (d, J=7.4 Hz, 1H), 6.58 (d, J=1.6 Hz, 1H), 5.35 (s, 2H), 2.05 (s, 3H).

HRMS m/z (ESI) calcd for $C_{22}H_{18}N_2OS$ $[M+H]^+$ 359.1218 found: 359.1220.

The detailed preparative method is same as that of compound 1, with a yield of 75.7%.

Compound 10: N-(4-(1-(10H-phenothiazin-2-yl)ethenyl)phenyl)urea

The synthetic route is as follows:

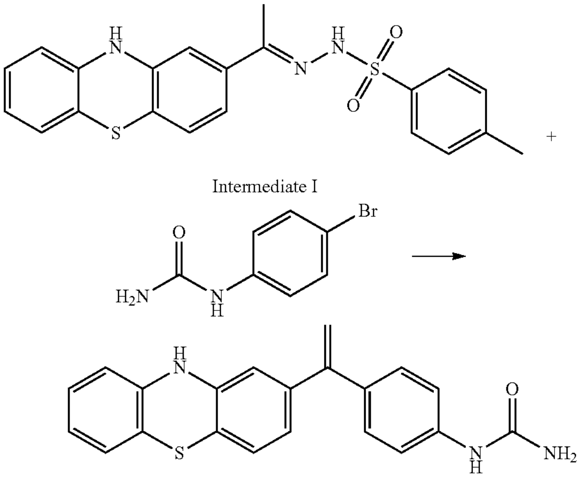

10

$^1$H NMR and HRMS data of compound 10 are as follows:

$^1$H NMR (400 MHz, DMSO-$d_6$) δ 8.61 (s, 1H), 8.55 (s, 1H), 7.40 (d, J=8.6 Hz, 2H), 7.17 (d, J=8.6 Hz, 2H), 7.05-6.94 (m, 1H), 6.94-6.87 (m, 2H), 6.78-6.71 (m, 2H), 6.66-6.61 (m, 1H), 6.59 (d, J=1.7 Hz, 1H), 5.85 (s, 2H), 5.31 (d, J=5.7 Hz, 2H).

HRMS m/z (ESI) calcd for $C_{21}H_{17}N_3OS$ $[M+H]^+$ 360.1171 found: 360.1174.

The detailed preparative method is same as that of compound 1, with a yield of 84.8%.

Compound 11: 2-(1-(4-cyclohexylphenyl)ethenyl)-10H-phenothiazine

The synthetic route is as follows:

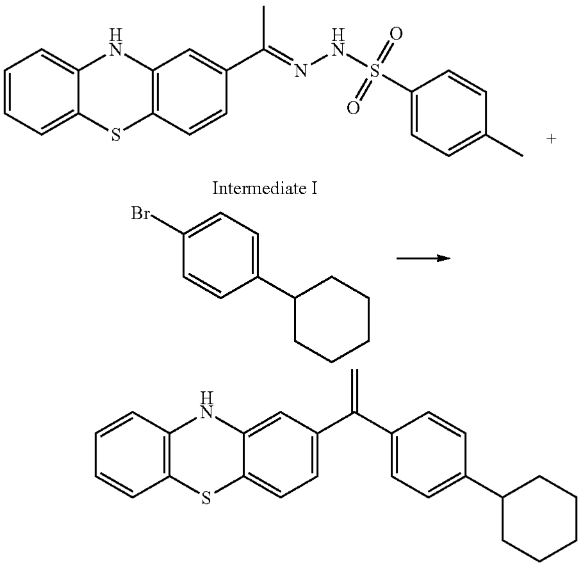

11

$^1$H NMR and HRMS data of compound 11 are as follows:

$^1$H NMR (400 MHz, DMSO-$d_6$) δ 8.57 (s, 1H), 7.22 (s, 4H), 6.97 (t, J=7.6 Hz, 1H), 6.91 (d, J=7.9 Hz, 2H), 6.79-6.70 (m, 2H), 6.62 (d, J=7.8 Hz, 1H), 6.58 (d, J=1.6 Hz, 1H), 5.36 (d, J=2.6 Hz, 2H), 1.80 (d, J=9.5 Hz, 4H), 1.70 (d, J=12.7 Hz, 1H), 1.39 (d, J=8.5 Hz, 4H), 1.29-1.18 (m, 1H).

HRMS m/z (ESI) calcd for $C_{26}H_{25}NS$ $[M+H]^+$ 384.1786 found: 384.1788.

The detailed preparative method is same as that of compound 1, with a yield of 62.8%.

Compound 12: 2-(1-(4-isobutylphenyl)ethenyl)-10H-phenothiazine

The synthetic route is as follows:

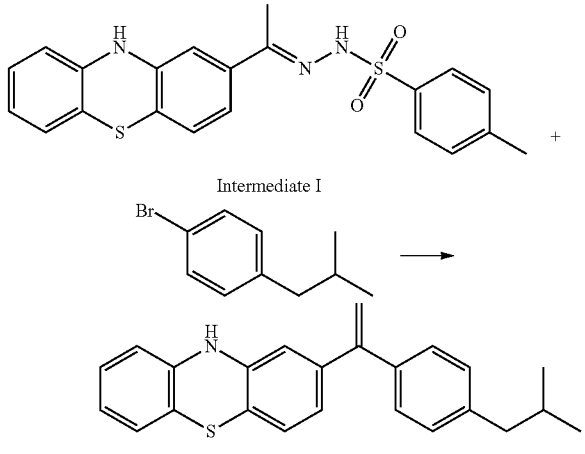

12

$^1$H NMR and HRMS data of compound 12 are as follows:

$^1$H NMR (400 MHz, DMSO-$d_6$) δ 8.56 (s, 1H), 7.22 (d, J=8.1 Hz, 2H), 7.16 (d, J=8.1 Hz, 2H), 6.96 (dd, J=10.8, 4.5 Hz, 1H), 6.91 (d, J=7.9 Hz, 2H), 6.74 (dd, J=12.2, 4.2 Hz, 2H), 6.70-6.61 (m, 1H), 6.59 (d, J=1.7 Hz, 1H), 5.37 (s, 2H), 2.46 (d, J=7.1 Hz, 2H), 1.85 (dt, J=13.5, 6.8 Hz, 1H), 0.88 (d, J=6.6 Hz, 6H).

HRMS m/z (ESI) calcd for $C_{24}H_{23}NS$ $[M+H]^+$ 358.1629 found: 358.1633.

The detailed preparative method is same as that of compound 1, with a yield of 76.4%.

Compound 13: 4-(1-(10H-phenothiazin-2-yl)ethenyl)benzaldehyde

The synthetic route is as follows:

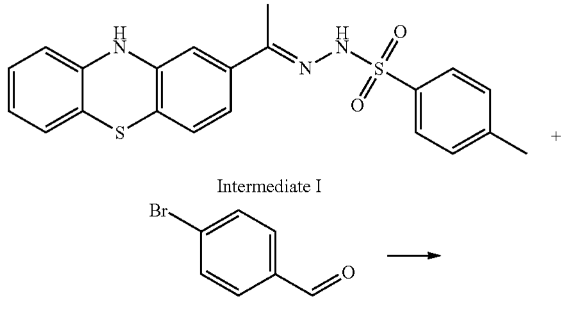

-continued

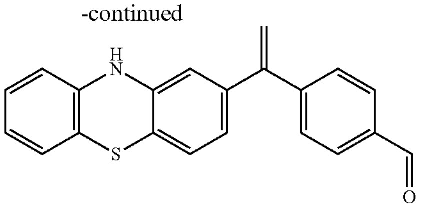

13

$^1$H NMR and HRMS data of compound 13 are as follows:

$^1$H NMR (400 MHz, DMSO-$d_6$) δ 10.04 (s, 1H), 8.57 (s, 1H), 7.93 (d, J=8.2 Hz, 2H), 7.54 (d, J=8.1 Hz, 2H), 6.96 (dt, J=17.1, 5.1 Hz, 3H), 6.79-6.72 (m, 2H), 6.62 (d, J=7.9 Hz, 1H), 6.55 (d, J=1.6 Hz, 1H), 5.59 (s, 1H), 5.56 (s, 1H).

HRMS m/z (ESI) calcd for $C_{21}H_{15}NOS$ $[M+H]^+$ 330.0953 found: 330.0955.

The detailed preparative method is same as that of compound 1, with a yield of 79.8%.

Compound 14: 4-(4-(1-(10H-phenothiazin-2-yl)ethenyl)phenyl)morpholine

The synthetic route is as follows:

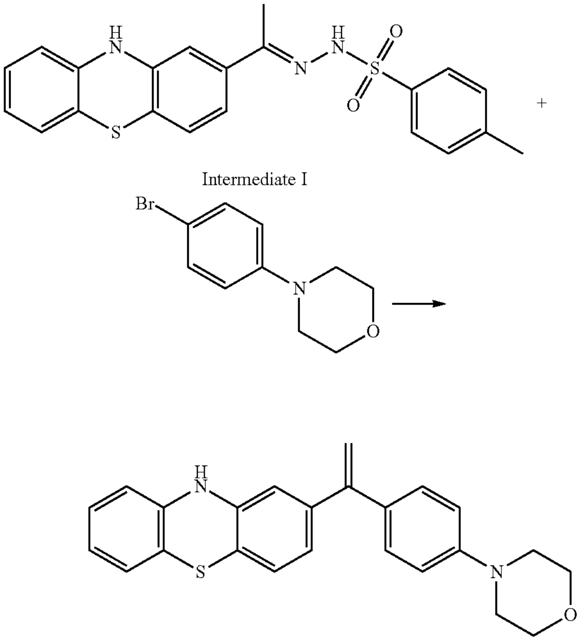

14

$^1$H NMR and HRMS data of compound 14 are as follows:

$^1$H NMR (400 MHz, DMSO-$d_6$) δ 8.55 (s, 1H), 7.17 (d, J=8.7 Hz, 2H), 7.00-6.87 (m, 5H), 6.78-6.71 (m, 2H), 6.63 (d, J=7.1 Hz, 1H), 6.59 (d, J=1.6 Hz, 1H), 5.27 (d, J=18.8 Hz, 2H), 3.80-3.65 (m, 4H), 3.21-3.10 (m, 4H).

HRMS m/z (ESI) calcd for $C_{24}H_{22}N_2OS$ $[M+H]^+$ 387.1531 found: 387.1533.

The detailed preparative method is same as that of compound 1, with a yield of 74.2%.

Compound 15: 4-(4-(1-(10H-phenothiazin-2-yl)ethenyl)phenyl)morpholine

The synthetic route is as follows:

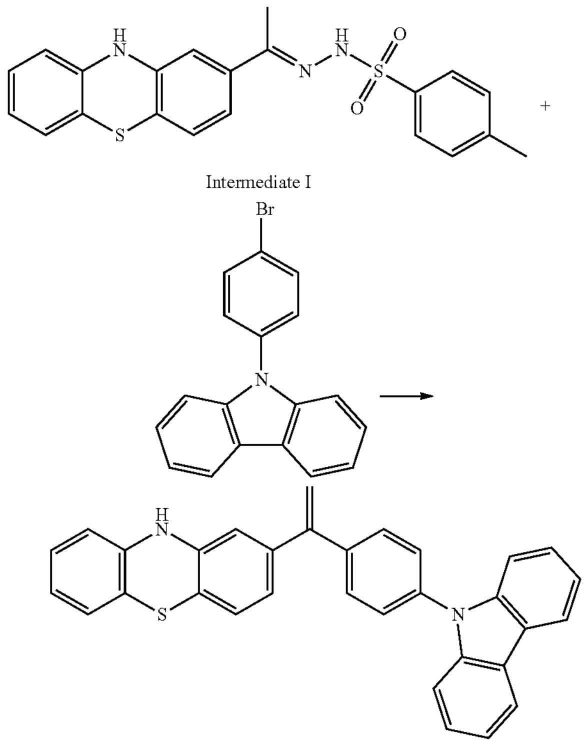

Intermediate I

15

$^1$H NMR and HRMS data of compound 15 are as follows:

$^1$H NMR (400 MHz, DMSO-$d_6$) δ 8.63 (s, 1H), 8.26 (d, J=7.7 Hz, 2H), 7.64 (dd, J=19.7, 8.5 Hz, 4H), 7.46 (d, J=3.6 Hz, 4H), 7.31 (dt, J=7.9, 4.1 Hz, 2H), 6.98 (d, J=7.9 Hz, 2H), 6.93 (d, J=7.6 Hz, 1H), 6.85 (dd, J=7.9, 1.7 Hz, 1H), 6.76 (s, 1H), 6.71 (d, J=1.6 Hz, 1H), 6.66 (d, J=7.9 Hz, 1H), 5.56 (d, J=16.8 Hz, 2H).

HRMS m/z (ESI) calcd for $C_{32}H_{22}N_2S$ $[M+H]^+$ 467.1582 found: 467.1583.

The detailed preparative method is same as that of compound 1, with a yield of 79.8%.

Compound 16: 2-(1-(10H-phenothiazin-2-yl)ethenyl)phenylamine

The synthetic route is as follows:

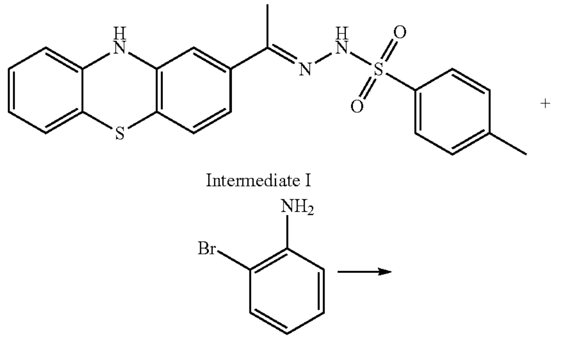

Intermediate I

-continued

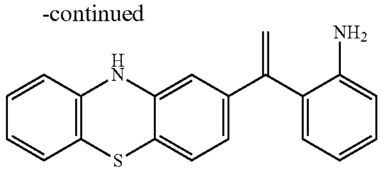

16

$^1$H NMR and HRMS data of compound 16 are as follows:

$^1$H NMR (400 MHz, DMSO-$d_6$) δ 8.56 (s, 1H), 7.09-7.02 (m, 1H), 6.99-6.91 (m, 2H), 6.91-6.85 (m, 2H), 6.81 (dd, J=8.0, 1.7 Hz, 1H), 6.73 (td, J=7.6, 1.1 Hz, 1H), 6.69 (d, J=8.0 Hz, 1H), 6.66-6.57 (m, 2H), 6.55 (d, J=1.7 Hz, 1H), 5.69 (d, J=1.2 Hz, 1H), 5.17 (d, J=1.1 Hz, 1H), 4.48 (s, 2H).

HRMS m/z (ESI) calcd for $C_{20}H_{16}N_2S$ $[M+H]^+$ 317.1112 found: 317.1114.

The detailed preparative method is same as that of compound 1, with a yield of 86.9%.

Compound 17: 3-(1-(10H-phenothiazin-2-yl)ethenyl)phenylamine

The synthetic route is as follows:

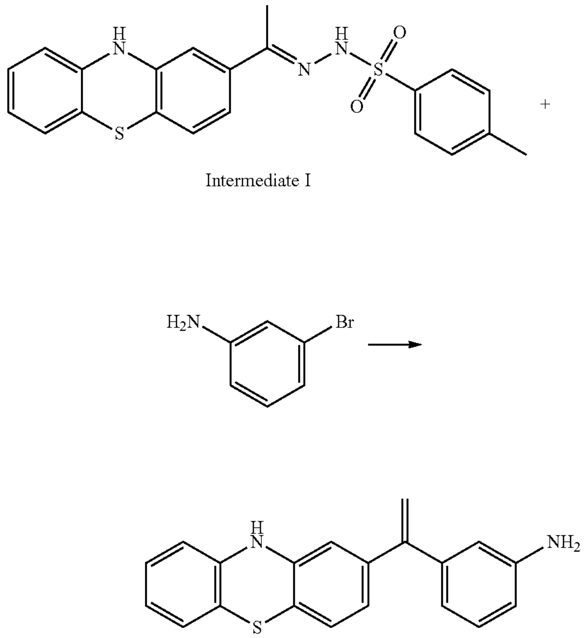

Intermediate I

17

$^1$H NMR and HRMS data of compound 17 are as follows:

$^1$H NMR (400 MHz, DMSO-$d_6$) δ 8.57 (s, 1H), 6.98 (dd, J=18.2, 8.0 Hz, 2H), 6.91 (d, J=2.8 Hz, 1H), 6.90 (d, J=3.9 Hz, 1H), 6.79-6.76 (m, 1H), 6.75 (d, J=3.0 Hz, 1H), 6.64 (d, J=7.8 Hz, 1H), 6.59 (d, J=1.4 Hz, 1H), 6.53 (d, J=7.9 Hz, 1H), 6.47 (d, J=1.6 Hz, 2H), 5.30 (d, J=14.9 Hz, 2H), 5.08 (s, 2H).

HRMS m/z (ESI) calcd for $C_{20}H_{16}N_2S$ $[M+H]^+$ 317.1112 found: 317.1115.

The detailed preparative method is same as that of compound 1, with a yield of 67.4%.

Compound 18: 3-(1-(10H-phenothiazin-2-yl)ethenyl)phenol

The synthetic route is as follows:

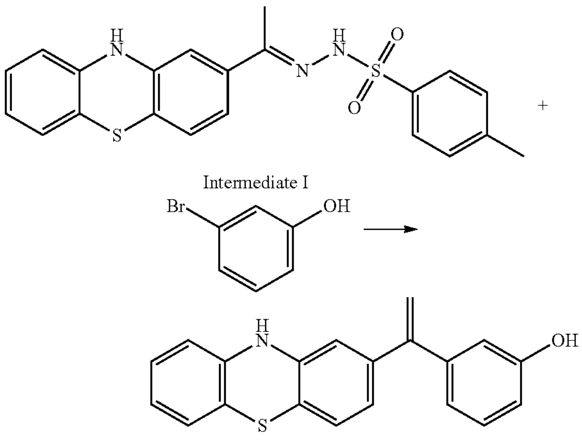

18

$^1$H NMR and HRMS data of compound 18 are as follows: $^1$H NMR (400 MHz, DMSO-$d_6$) δ 8.57 (s, 1H), 7.99 (s, 1H), 7.89 (d, J=8.3 Hz, 2H), 7.37 (d, J=8.3 Hz, 3H), 6.95 (ddd, J=18.4, 10.9, 3.3 Hz, 3H), 6.84-6.70 (m, 2H), 6.62 (d, J=7.9 Hz, 1H), 6.56 (d, J=1.7 Hz, 1H), 5.49 (d, J=16.9 Hz, 2H).

HRMS m/z (ESI) calcd for $C_{20}H_{15}NOS$ $[M+H]^+$ 318.0953 found: 318.0955.

The detailed preparative method is same as that of compound 1, with a yield of 83.4%.

Compound 19: 2-(1-(3-nitrophenyl)ethenyl)-10H-phenothiazine

The synthetic route is as follows:

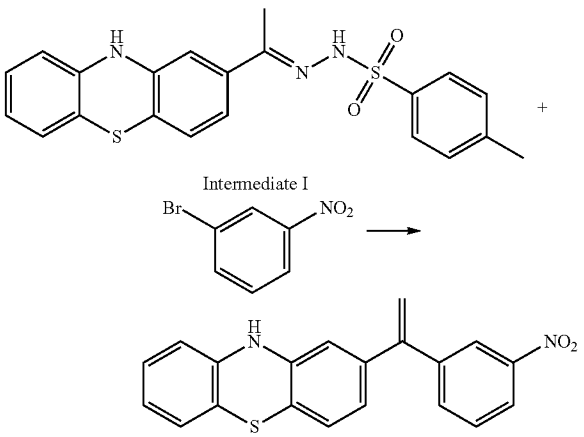

19

$^1$H NMR and HRMS data of compound 19 are as follows: $^1$H NMR (400 MHz, DMSO-$d_6$) δ 8.59 (s, 1H), 8.23 (d, J=7.1 Hz, 1H), 8.07 (s, 1H), 7.78 (d, J=7.7 Hz, 1H), 7.71 (d, J=7.9 Hz, 1H), 7.06-6.87 (m, 3H), 6.76 (t, J=7.0 Hz, 2H), 6.63 (d, J=7.8 Hz, 1H), 6.59 (s, 1H), 5.60 (d, J=11.2 Hz, 2H).

HRMS m/z (ESI) calcd for $C_{20}H_{14}N_2O_2S$ $[M+H]^+$ 347.0854 found: 347.0824.

The detailed preparative method is same as that of compound 1, with a yield of 64.1%.

Compound 20: 3-(1-(10H-phenothiazin-2-yl)ethenyl)benzenesulfonamide

The synthetic route is as follows:

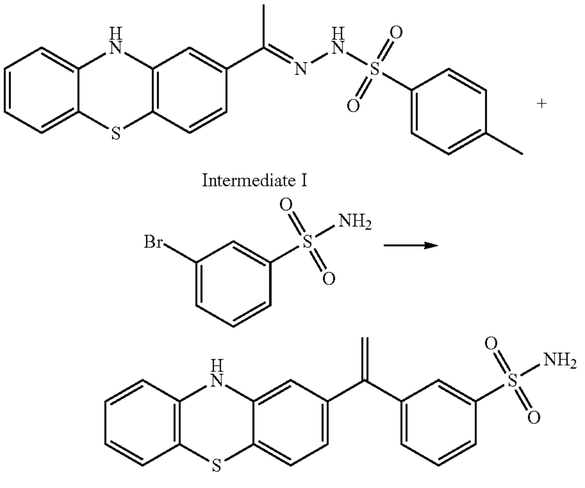

20

$^1$H NMR and HRMS data of compound 20 are as follows: $^1$H NMR (400 MHz, DMSO-$d_6$) δ 8.59 (s, 1H), 7.81 (d, J=7.7 Hz, 1H), 7.74 (s, 1H), 7.64-7.50 (m, 2H), 7.39 (s, 2H), 7.05-6.87 (m, 3H), 6.74 (dd, J=10.9, 4.4 Hz, 2H), 6.63 (d, J=7.8 Hz, 1H), 6.56 (d, J=1.6 Hz, 1H), 5.55 (s, 1H), 5.46 (s, 1H).

HRMS m/z (ESI) calcd for $C_{20}H_{16}N_2O_2S_2$ $[M+H]^+$ 381.0731 found: 381.0733.

The detailed preparative method is same as that of compound 1, with a yield of 87.5%.

Compound 21: 2-(1-(3-methoxylphenyl)ethenyl)-10H-phenothiazine

The synthetic route is as follows:

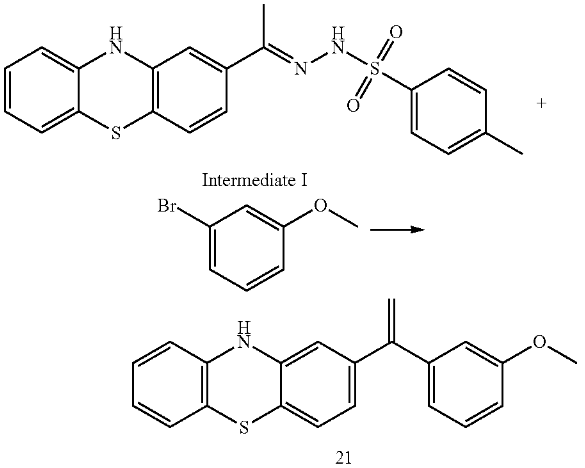

21

$^1$H NMR and HRMS data of compound 21 are as follows:

$^1$H NMR (400 MHz, DMSO-$d_6$) δ 8.56 (s, 1H), 7.30 (t, J=7.9 Hz, 1H), 6.95 (dd, J=7.6, 4.5 Hz, 2H), 6.91 (d, J=7.9 Hz, 2H), 6.84 (dd, J=8.3, 4.9 Hz, 2H), 6.75 (dd, J=7.8, 1.4 Hz, 2H), 6.62 (d, J=7.1 Hz, 1H), 6.58 (d, J=1.7 Hz, 1H), 5.42 (d, J=16.3 Hz, 2H), 3.75 (s, 3H).

HRMS m/z (ESI) calcd for $C_{21}H_{17}NOS$ $[M+H]^+$ 332.1109 found: 332.1105.

The detailed preparative method is same as that of compound 1, with a yield of 65.8%.

Compound 22: 2-(1-(3-trifluoromethoxylphenyl)ethenyl)-10H-phenothiazine

The synthetic route is as follows:

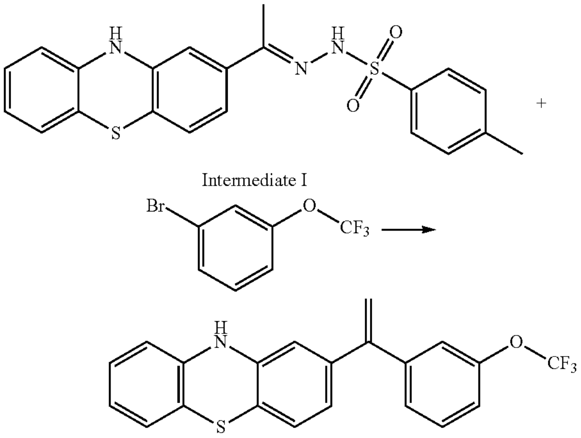

Intermediate I

22

$^1$H NMR and HRMS data of compound 22 are as follows:

$^1$H NMR (400 MHz, DMSO-$d_6$) δ 8.59 (s, 1H), 7.53 (t, J=8.0 Hz, 1H), 7.48-7.31 (m, 2H), 7.26 (s, 1H), 6.95 (dt, J=14.3, 6.9 Hz, 3H), 6.75 (t, J=7.2 Hz, 2H), 6.64 (d, J=7.8 Hz, 1H), 6.58 (s, 1H), 5.52 (d, J=13.2 Hz, 2H).

HRMS m/z (ESI) calcd for $C_{21}H_{14}F_3NOS$ $[M+H]^+$ 386.0826 found: 386.0829.

The detailed preparative method is same as that of compound 1, with a yield of 75.8%.

Compound 23: 2-(1-(3-isopropoxylphenyl)ethenyl)-10H-phenothiazine

The synthetic route is as follows:

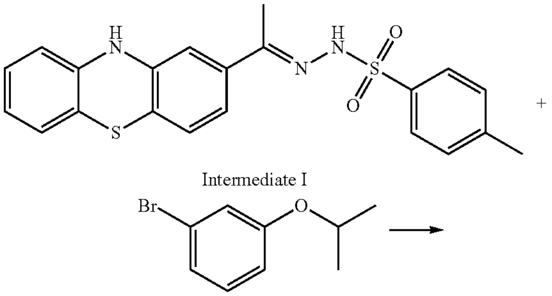

Intermediate I

-continued

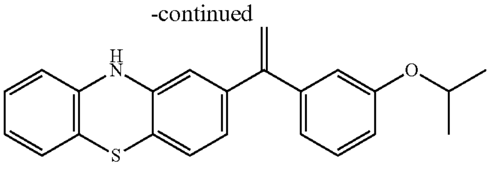

23

$^1$H NMR and HRMS data of compound 23 are as follows:

$^1$H NMR (400 MHz, DMSO-$d_6$) δ 8.60 (s, 1H), 7.27 (t, J=7.9 Hz, 1H), 6.97 (t, J=7.6 Hz, 1H), 6.90 (t, J=6.6 Hz, 3H), 6.85 (d, J=7.6 Hz, 1H), 6.76 (dd, J=15.9, 8.1 Hz, 3H), 6.65 (d, J=7.9 Hz, 1H), 6.62 (d, J=1.1 Hz, 1H), 5.41 (d, J=11.3 Hz, 2H), 4.58 (dd, J=12.0, 6.0 Hz, 1H), 1.25 (d, J=6.0 Hz, 7H).

HRMS m/z (ESI) calcd for $C_{23}H_{21}NOS$ $[M+H]^+$ 360.1422 found: 360.1425.

The detailed preparative method is same as that of compound 1, with a yield of 62.2%.

Compound 24: 2-(1-(m-methylphenyl)ethenyl)-10H-phenothiazine

The synthetic route is as follows:

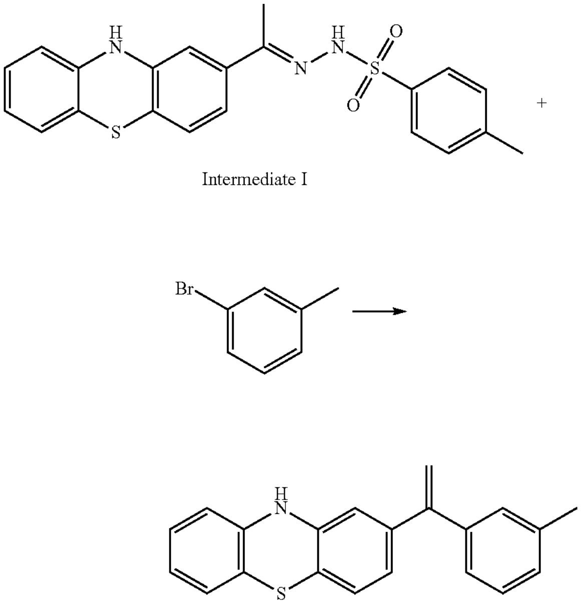

Intermediate I

24

$^1$H NMR and HRMS data of compound 24 are as follows:

$^1$H NMR (400 MHz, DMSO-$d_6$) δ 8.57 (s, 1H), 7.27 (t, J=7.6 Hz, 1H), 7.16 (d, J=7.6 Hz, 1H), 7.14-7.03 (m, 2H), 7.01-6.94 (m, 1H), 6.93 (dd, J=16.7, 4.6 Hz, 2H), 6.82-6.71 (m, 2H), 6.63 (d, J=7.9 Hz, 1H), 6.57 (d, J=1.6 Hz, 1H), 5.41 (s, 1H), 5.36 (s, 1H), 2.31 (s, 3H).

HRMS m/z (ESI) calcd for $C_{21}H_{17}NS$ $[M+H]^+$ 316.1160 found: 316.1165.

The detailed preparative method is same as that of compound 1, with a yield of 73.8%.

Compound 25: 2-(1-(3-t-butylphenyl)ethenyl)-10H-phenothiazine

The synthetic route is as follows:

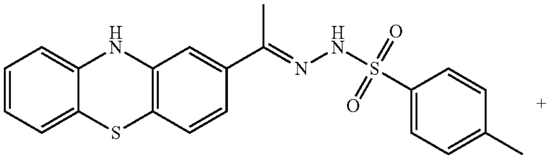

Intermediate I

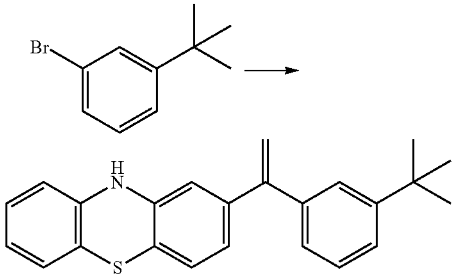

25

$^1$H NMR and HRMS data of compound 25 are as follows: $^1$H NMR (400 MHz, DMSO-$d_6$) δ 8.58 (s, 1H), 7.39 (d, J=7.9 Hz, 1H), 7.31 (dd, J=13.9, 6.2 Hz, 2H), 7.07 (d, J=7.6 Hz, 1H), 6.96 (dd, J=7.6, 1.1 Hz, 1H), 6.91 (d, J=7.9 Hz, 2H), 6.75 (dd, J=7.6, 1.3 Hz, 2H), 6.62 (dd, J=11.6, 4.8 Hz, 2H), 5.44 (s, 1H), 5.38 (s, 1H), 1.28 (s, 9H).

HRMS m/z (ESI) calcd for $C_{24}H_{23}NS$ [M+H]$^+$ 358.1629 found: 358.1625.

The detailed preparative method is same as that of compound 1, with a yield of 69.5%.

Compound 26: 3-(1-(10H-phenothiazin-2-yl)ethenyl)benzamide

The synthetic route is as follows:

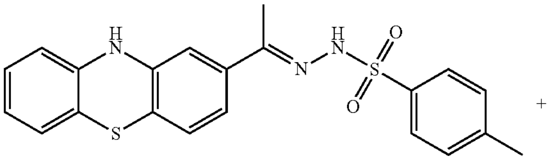

Intermediate I

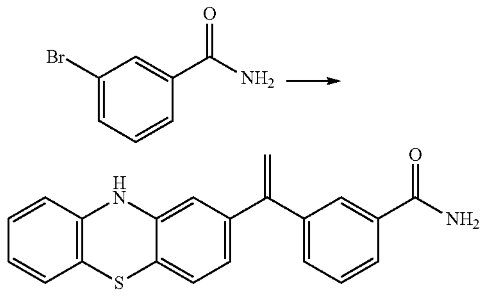

26

$^1$H NMR and HRMS data of compound 26 are as follows: $^1$H NMR (400 MHz, DMSO-$d_6$) δ 8.57 (s, 1H), 8.03 (s, 1H), 7.86 (d, J=7.2 Hz, 1H), 7.83 (s, 1H), 7.50-7.41 (m, 2H), 7.38 (s, 1H), 6.95 (ddd, J=18.0, 11.0, 3.4 Hz, 3H), 6.75 (dd, J=12.2, 4.3 Hz, 2H), 6.62 (d, J=7.9 Hz, 1H), 6.56 (d, J=1.6 Hz, 1H), 5.48 (d, J=20.9 Hz, 2H).

HRMS m/z (ESI) calcd for $C_{21}H_{16}N_2OS$ [M+H]$^+$ 345.1062 found: 345.1064.

The detailed preparative method is same as that of compound 1, with a yield of 69.5%.

Compound 27: 2-(1-(3-isopropylphenyl)ethenyl)-10H-phenothiazine

The synthetic route is as follows:

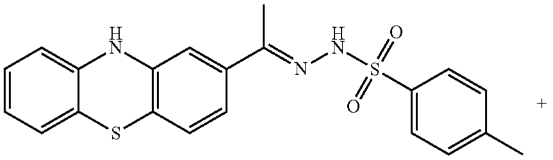

Intermediate I

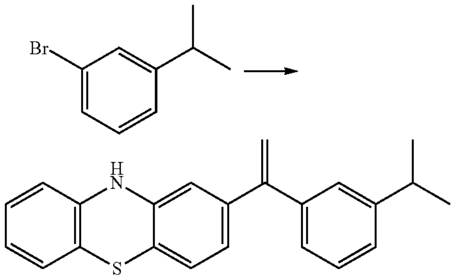

27

$^1$H NMR and HRMS data of compound 27 are as follows: $^1$H NMR (400 MHz, DMSO-$d_6$) δ 8.57 (s, 1H), 7.29 (d, J=7.5 Hz, 1H), 7.23 (d, J=7.8 Hz, 1H), 7.18 (s, 1H), 7.08 (d, J=7.5 Hz, 1H), 6.96 (dd, J=7.6, 1.2 Hz, 1H), 6.95-6.88 (m, 2H), 6.75 (dd, J=7.8, 1.8 Hz, 2H), 6.63 (dd, J=7.9, 0.9 Hz, 1H), 6.59 (d, J=1.7 Hz, 1H), 5.49-5.31 (m, 2H), 3.01-2.81 (m, 1H), 1.22 (dd, J=16.0, 8.7 Hz, 6H).

HRMS m/z (ESI) calcd for $C_{23}H_{21}NS$ [M+H]$^+$ 344.1473 found: 344.1475.

The detailed preparative method is same as that of compound 1, with a yield of 75.4%.

Compound 28: ethyl3-(1-(10H-phenothiazin-2-yl)ethenyl)benzoic acid

The synthetic route is as follows:

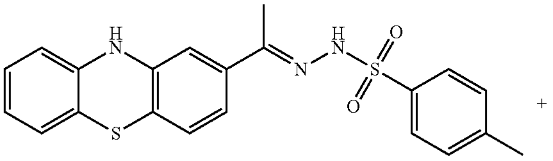

Intermediate I

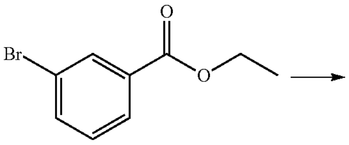

-continued

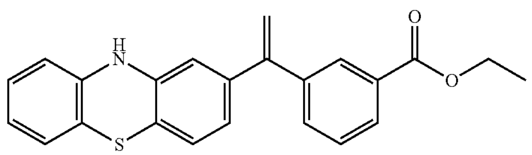

28

$^1H$ NMR and HRMS data of compound 28 are as follows:

$^1H$ NMR (400 MHz, DMSO-$d_6$) δ 8.57 (s, 1H), 7.96 (d, J=7.4 Hz, 1H), 7.84 (s, 1H), 7.57 (dt, J=15.1, 7.7 Hz, 2H), 7.01-6.95 (m, 1H), 6.92 (t, J=7.0 Hz, 2H), 6.75 (t, J=7.5 Hz, 2H), 6.63 (d, J=7.8 Hz, 1H), 6.56 (d, J=1.5 Hz, 1H), 5.54 (s, 1H), 5.45 (s, 1H), 4.32 (q, J=7.1 Hz, 2H), 1.28 (dt, J=8.0, 6.2 Hz, 3H).

HRMS m/z (ESI) calcd for $C_{23}H_{19}NO_2S$ $[M+H]^+$ 374.1215 found: 374.1212.

The detailed preparative method is same as that of compound 1, with a yield of 68.2%.

Compound 29: 2-(1-([1,1'-diphenyl]-3-yl)ethenyl)-10H-phenothiazine

The synthetic route is as follows:

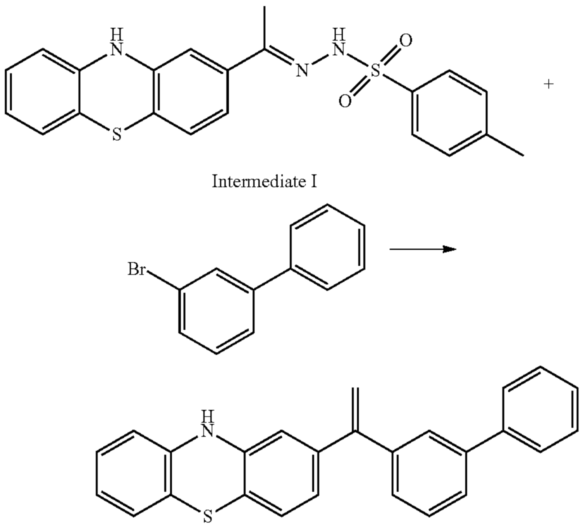

29

$^1H$ NMR and HRMS data of compound 29 are as follows:

$^1H$ NMR (400 MHz, DMSO-$d_6$) δ 8.58 (s, 1H), 7.65 (dd, J=9.4, 2.2 Hz, 3H), 7.55 (s, 1H), 7.48 (dd, J=16.8, 7.8 Hz, 3H), 7.38 (d, J=7.3 Hz, 1H), 7.29 (d, J=7.8 Hz, 1H), 6.94 (dt, J=15.3, 4.2 Hz, 3H), 6.81 (dd, J=8.0, 1.8 Hz, 1H), 6.75 (dd, J=7.5, 1.0 Hz, 1H), 6.62 (dd, J=8.6, 1.2 Hz, 2H), 5.50 (d, J=3.1 Hz, 2H).

HRMS m/z (ESI) calcd for $C_{26}H_{19}NS$ $[M+H]^+$ 378.1316 found: 378.1318.

The detailed preparative method is same as that of compound 1, with a yield of 76.8%.

Compound 30: 2-(1-(3-(trifluoromethyl)phenyl) ethenyl)-10H-phenothiazine

The synthetic route is as follows:

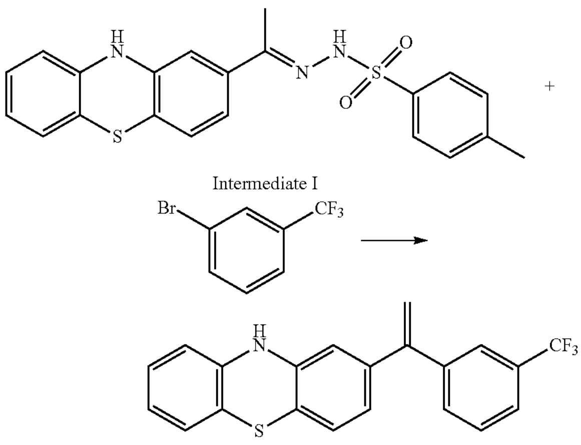

30

$^1H$ NMR and HRMS data of compound 30 are as follows:

$^1H$ NMR (400 MHz, DMSO-$d_6$) 8.58 (s, 1H), 7.74 (d, J=7.5 Hz, 1H), 7.62 (dd, J=10.9, 7.1 Hz, 3H), 7.03-6.87 (m, 3H), 6.82-6.71 (m, 2H), 6.66-6.59 (m, 1H), 6.55 (d, J=1.7 Hz, 1H), 5.54 (d, J=20.9 Hz, 2H).

HRMS m/z (ESI) calcd for $C_{21}H_{15}F_3NS$ $[M+H]^+$ 370.0877 found: 370.0879.

The detailed preparative method is same as that of compound 1, with a yield of 67.8%.

Compound 31: methyl 3-(1-(10H-phenothiazin-2-yl)ethenyl)benzoic acid

The synthetic route is as follows:

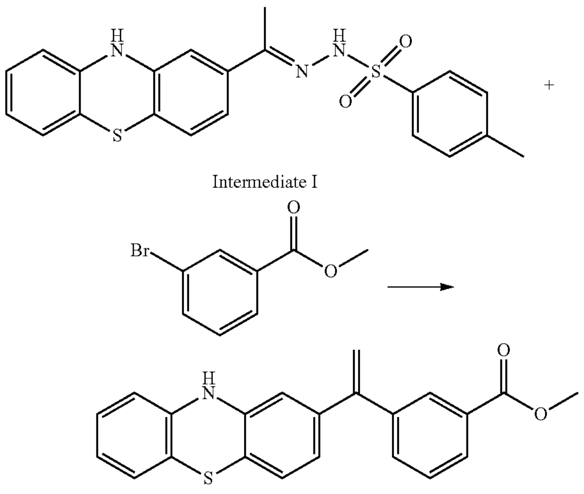

31

$^1H$ NMR and HRMS data of compound 31 are as follows:

$^1H$ NMR (400 MHz, DMSO-$d_6$) δ 8.56 (s, 1H), 8.01-7.90 (m, 1H), 7.83 (d, J=1.5 Hz, 1H), 7.67-7.60 (m, 1H), 7.56 (t, J=7.7 Hz, 1H), 6.97 (td, J=7.8, 1.4 Hz, 1H), 6.92 (t, J=7.3

Hz, 2H), 6.75 (td, J=7.5, 1.4 Hz, 2H), 6.62 (dd, J=7.9, 0.9 Hz, 1H), 6.56 (d, J=1.8 Hz, 1H), 5.49 (d, J=26.7 Hz, 2H), 3.85 (s, 3H).

HRMS m/z (ESI) calcd for $C_{22}H_{17}N_2S$ $[M+H]^+$ 360.1058 found: 360.1055.

The detailed preparative method is same as that of compound 1, with a yield of 61.9%.

Compound 32: 3-(1-(10H-phenothiazin-2-yl)ethenyl)benzonitrile

The synthetic route is as follows:

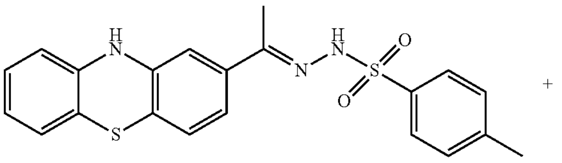

Intermediate I

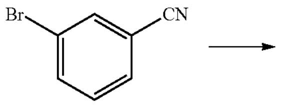

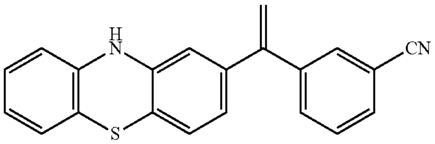

32

$^1H$ NMR and HRMS data of compound 32 are as follows:

$^1H$ NMR (400 MHz, DMSO-$d_6$) δ 8.58 (s, 1H), 7.87-7.81 (m, 1H), 7.78 (s, 1H), 7.64-7.58 (m, 2H), 7.03-6.95 (m, 1H), 6.92 (t, J=7.6 Hz, 2H), 6.79-6.70 (m, 2H), 6.67-6.59 (m, 1H), 6.54 (d, J=1.7 Hz, 1H), 5.55 (d, J=17.8 Hz, 2H).

HRMS m/z (ESI) calcd for $C_{21}H_{14}N_2S$ $[M+H]^+$ 327.0956 found: 327.0959.

The detailed preparative method is same as that of compound 1, with a yield of 73.2%.

Compound 33: (3-(1-(10H-phenothiazin-2-yl)ethenyl)phenyl)benzophenone

The synthetic route is as follows:

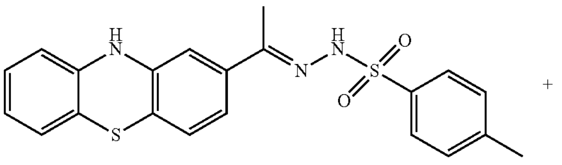

Intermediate I

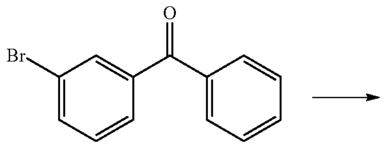

-continued

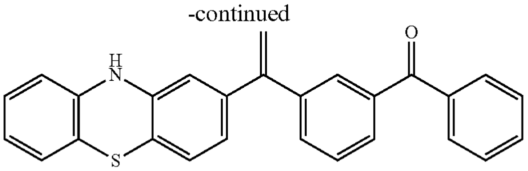

33

$^1H$ NMR and HRMS data of compound 33 are as follows:

$^1H$ NMR (400 MHz, DMSO-$d_6$) δ 8.62 (s, 1H), 7.76 (t, J=6.8 Hz, 3H), 7.70-7.64 (m, 2H), 7.62 (d, J=7.7 Hz, 1H), 7.59 (s, 1H), 7.54 (t, J=7.6 Hz, 2H), 6.98 (dd, J=10.8, 4.4 Hz, 1H), 6.92 (dd, J=7.3, 4.4 Hz, 2H), 6.84-6.72 (m, 2H), 6.65 (dd, J=10.6, 4.8 Hz, 2H), 5.52 (d, J=17.4 Hz, 2H).

HRMS m/z (ESI) calcd for $C_{27}H_{19}NOS$ $[M+H]^+$ 406.1266 found: 406.1261.

The detailed preparative method is same as that of compound 1, with a yield of 76.4%.

Compound 34: 2-(1-(3-(difluoromethyl)phenyl)ethenyl)-10H-phenothiazine

The synthetic route is as follows:

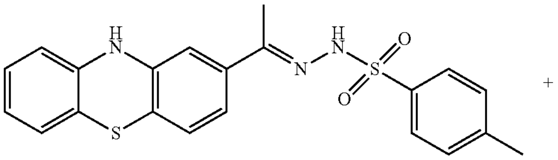

Intermediate I

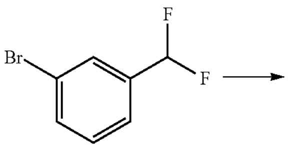

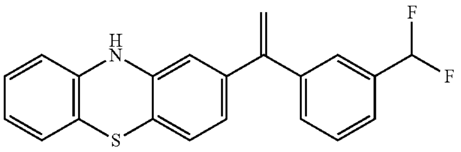

34

$^1H$ NMR and HRMS data of compound 34 are as follows:

$^1H$ NMR (400 MHz, DMSO-$d_6$) δ 8.59 (s, 1H), 7.57 (s, 1H), 7.47 (d, J=6.5 Hz, 3H), 6.95 (dt, J=15.3, 7.2 Hz, 3H), 6.76 (d, J=5.9 Hz, 2H), 6.63 (d, J=7.8 Hz, 1H), 6.57 (s, 1H), 5.49 (d, J=25.2 Hz, 2H).

HRMS m/z (ESI) calcd for $C_{21}H_{15}F_2NS$ $[M+H]^+$ 352.0972 found: 352.0975.

The detailed preparative method is same as that of compound 1, with a yield of 83.8%.

Compound 35: 2-(1-(3-(benzyloxyl)phenyl)ethenyl)-10H-phenothiazine

The synthetic route is as follows:

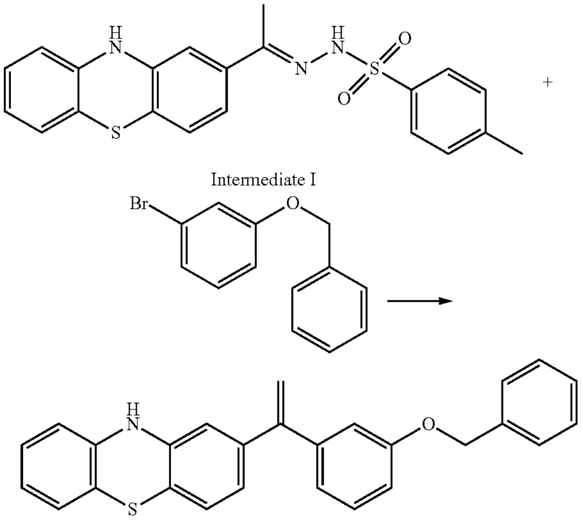

35

$^1H$ NMR and HRMS data of compound 35 are as follows:

$^1H$ NMR (400 MHz, DMSO) δ 8.58 (s, 1H), 7.44 (d, J=7.3 Hz, 2H), 7.38 (t, J=7.4 Hz, 2H), 7.31 (m, 2H), 6.99 (m, 2H), 6.90 (m, 4H), 6.74 (dd, J=12.3, 4.5 Hz, 2H), 6.64 (d, J=7.8 Hz, 1H), 6.59 (d, J=1.4 Hz, 1H), 5.43 (s, 1H), 5.40 (s, 1H), 5.10 (s, 2H).

HRMS m/z (ESI) calcd for $C_{27}H_{21}NOS$ $[M+H]^+$ 408.1422 found: 408.1425.

The detailed preparative method is same as that of compound 1, with a yield of 68.9%.

Compound 36: 4-(3-(1-(10H-phenothiazin-2-yl) ethenyl)phenyl)morpholine

The synthetic route is as follows:

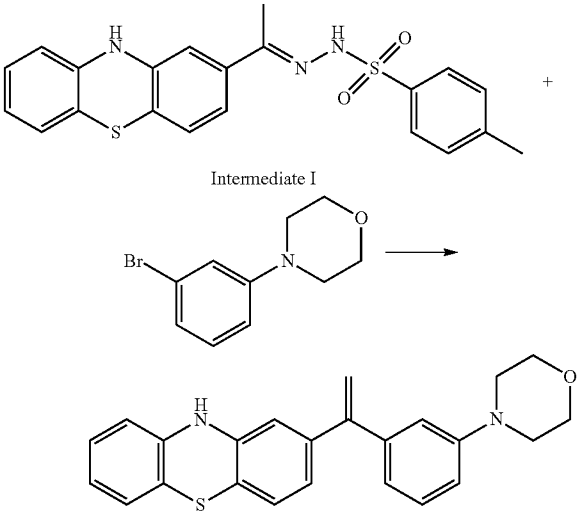

36

$^1H$ NMR and HRMS data of compound 36 are as follows:

$^1H$ NMR (400 MHz, DMSO-$d_6$) δ 8.56 (s, 1H), 7.23 (t, J=7.9 Hz, 1H), 7.02-6.87 (m, 4H), 6.83 (s, 1H), 6.80-6.68 (m, 3H), 6.61 (dd, J=14.3, 4.7 Hz, 2H), 5.39 (d, J=23.4 Hz, 2H), 3.84-3.63 (m, 4H), 3.18-2.98 (m, 4H).

HRMS m/z (ESI) calcd for $C_{24}H_{22}N_2OS$ $[M+H]^+$ 387.1531 found: 387.1533.

The detailed preparative method is same as that of compound 1, with a yield of 83.3%.

Compound 37: 4-(1-(10H-phenothiazin-2-yl)ethenyl)-2-methylbenzonitrile

The synthetic route is as follows:

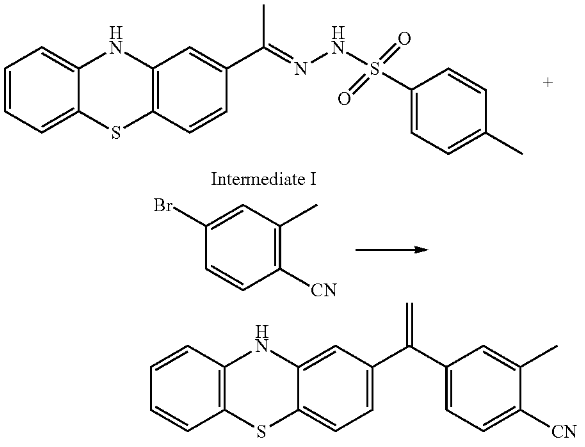

37

$^1H$ NMR and HRMS data of compound 37 are as follows:

$^1H$ NMR (400 MHz, DMSO-$d_6$) δ 8.57 (s, 1H), 7.77 (d, J=8.0 Hz, 1H), 7.41 (s, 1H), 7.29 (d, J=8.0 Hz, 1H), 6.97 (dd, J=10.9, 4.4 Hz, 1H), 6.92 (t, J=7.1 Hz, 2H), 6.79-6.70 (m, 2H), 6.65-6.59 (m, 1H), 6.53 (d, J=1.7 Hz, 1H), 5.58 (s, 1H), 5.51 (s, 1H), 2.49 (s, 3H).

HRMS m/z (ESI) calcd for $C_{22}H_{16}N_2S$ $[M+H]^+$ 341.1112 found: 341.1115.

The detailed preparative method is same as that of compound 1, with a yield of 75.8%.

Compound 38: 2-(1-(3-methyl-4-nitrophenyl)ethenyl)-10H-phenothiazine

The synthetic route is as follows:

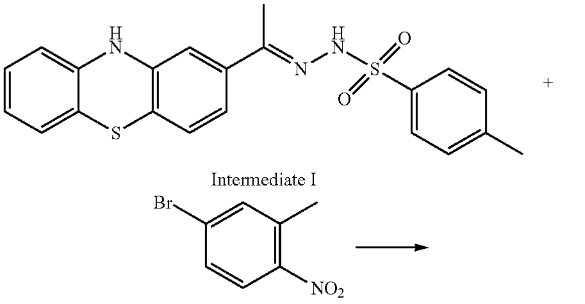

-continued

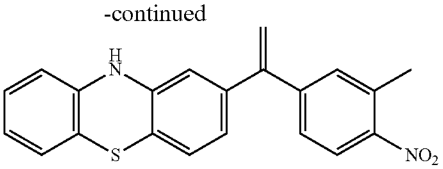

38

$^1$H NMR and HRMS data of compound 38 are as follows:

$^1$H NMR (400 MHz, DMSO-$d_6$) δ 8.57 (s, 1H), 8.00 (d, J=8.4 Hz, 1H), 7.45 (s, 1H), 7.35 (dd, J=8.4, 1.5 Hz, 1H), 6.95 (ddd, J=20.0, 13.2, 5.4 Hz, 3H), 6.76 (d, J=8.0 Hz, 2H), 6.62 (dd, J=7.9, 0.8 Hz, 1H), 6.54 (d, J=1.7 Hz, 1H), 5.61 (s, 1H), 5.54 (s, 1H), 2.54 (s, 3H).

HRMS m/z (ESI) calcd for $C_{21}H_{16}N_2O_2S$ $[M+H]^+$ 361.1011 found: 361.1015.

The detailed preparative method is same as that of compound 1, with a yield of 73.7%.

Compound 39: 2-(1-(3,4-dimethoxylphenyl)ethenyl)-10H-phenothiazine

The synthetic route is as follows:

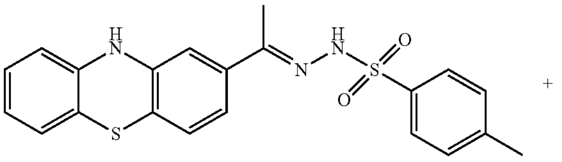

Intermediate I

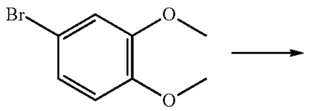

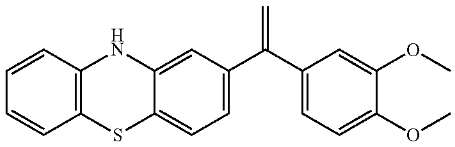

39

$^1$H NMR and HRMS data of compound 39 are as follows:

$^1$H NMR (400 MHz, DMSO-$d_6$) δ 8.56 (s, 1H), 6.93 (ddd, J=20.3, 8.4, 3.1 Hz, 5H), 6.78 (ddd, J=13.3, 8.1, 1.9 Hz, 3H), 6.62 (t, J=5.3 Hz, 2H), 5.35 (d, J=5.9 Hz, 2H), 3.76 (d, J=13.3 Hz, 6H).

HRMS m/z (ESI) calcd for $C_{22}H_{19}NO_2S$ $[M+H]^+$ 362.1215 found: 361.1218.

The detailed preparative method is same as that of compound 1, with a yield of 54.4%.

Compound 40: 4-(1-(10H-phenothiazin-2-yl)ethenyl)-2-fluorobenzonitrile

The synthetic route is as follows:

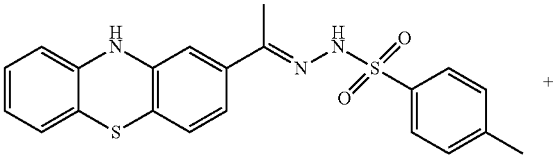

Intermediate I

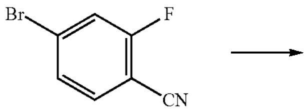

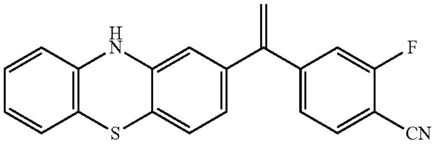

40

$^1$H NMR and HRMS data of compound 40 are as follows:

$^1$H NMR (400 MHz, DMSO-$d_6$) δ 8.58 (s, 1H), 7.93 (t, J=7.5 Hz, 1H), 7.49 (d, J=10.6 Hz, 1H), 7.32 (d, J=8.0 Hz, 1H), 6.95 (dt, J=17.1, 8.2 Hz, 3H), 6.75 (dd, J=15.3, 7.7 Hz, 2H), 6.63 (d, J=7.8 Hz, 1H), 6.55 (s, 1H), 5.65 (d, J=1.9 Hz, 2H).

HRMS m/z (ESI) calcd for $C_{21}H_{13}FN_2S$ $[M+H]^+$ 345.0862 found: 345.0866.

The detailed preparative method is same as that of compound 1, with a yield of 76.5%.

Compound 41: 2-(1-(3,5-di-t-butylphenyl)ethenyl)-10H-phenothiazine

The synthetic route is as follows:

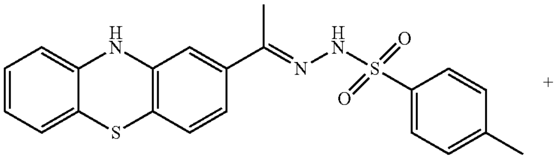

Intermediate I

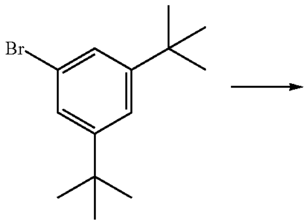

-continued

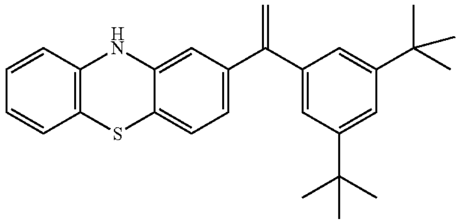

41

$^1$H NMR and HRMS data of compound 41 are as follows:

$^1$H NMR (400 MHz, DMSO-$d_6$) δ 8.58 (s, 1H), 7.40 (t, J=1.7 Hz, 1H), 7.10 (d, J=1.8 Hz, 2H), 6.96 (td, J=7.8, 1.4 Hz, 1H), 6.91 (d, J=7.9 Hz, 2H), 6.80-6.70 (m, 2H), 6.62 (dd, J=8.0, 1.2 Hz, 2H), 5.47-5.31 (m, 2H), 1.25 (d, J=22.6 Hz, 18H).

HRMS m/z (ESI) calcd for $C_{28}H_{31}NS$ $[M+H]^+$ 414.2255 found: 414.2259.

The detailed preparative method is same as that of compound 1, with a yield of 75.6%.

Compound 42: 2-(1-(3,4,5-trimethoxylphenyl)ethenyl)-10H-phenothiazine

The synthetic route is as follows:

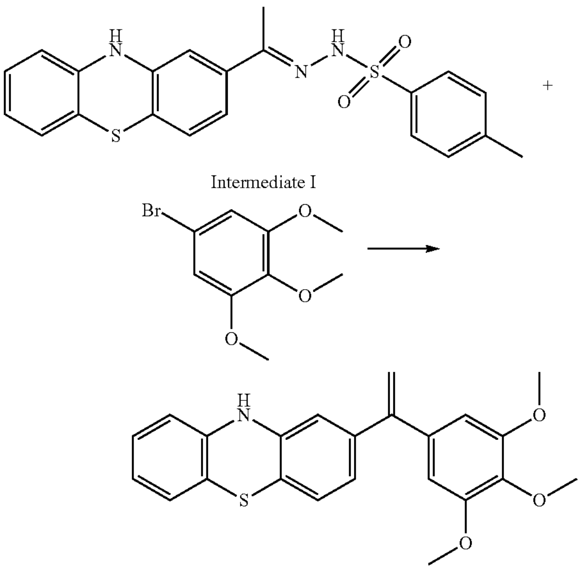

42

$^1$H NMR and HRMS data of compound 42 are as follows:

$^1$H NMR (400 MHz, DMSO-$d_6$) δ 8.57 (s, 1H), 6.97 (t, J=7.6 Hz, 1H), 6.91 (d, J=7.9 Hz, 2H), 6.85-6.71 (m, 2H), 6.63 (d, J=6.1 Hz, 2H), 6.56 (s, 2H), 5.41 (d, J=10.9 Hz, 2H), 3.72 (d, J=21.8 Hz, 9H).

HRMS m/z (ESI) calcd for $C_{23}H_{21}NO_3S$ $[M+H]^+$ 392.1320 found: 392.1321.

The detailed preparative method is same as that of compound 1, with a yield of 72.7%.

Compound 43: N-(5-(1-(10H-phenothiazin-2-yl)ethenyl)pyridin-2-yl)acetylamine

The synthetic route is as follows:

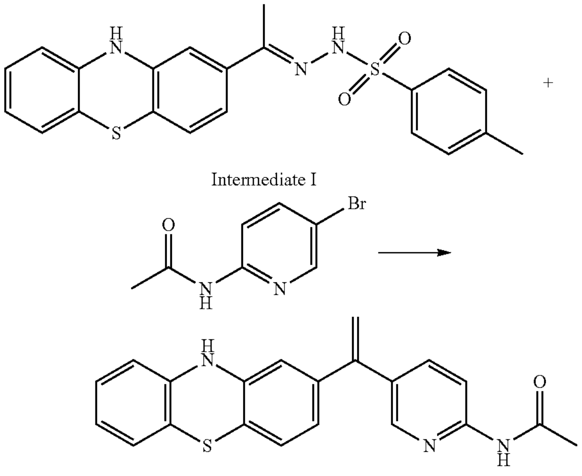

43

$^1$H NMR and HRMS data of compound 43 are as follows:

$^1$H NMR (400 MHz, DMSO-$d_6$) δ 10.59 (s, 1H), 8.57 (s, 1H), 8.24 (d, J=2.2 Hz, 1H), 8.08 (d, J=8.6 Hz, 1H), 7.69 (dd, J=8.6, 2.4 Hz, 1H), 6.96 (d, J=7.8 Hz, 1H), 6.92 (t, J=6.7 Hz, 2H), 6.82-6.70 (m, 2H), 6.65-6.60 (m, 1H), 6.58 (d, J=1.7 Hz, 1H), 5.46 (d, J=11.9 Hz, 2H), 2.11 (s, 3H).

HRMS m/z (ESI) calcd for $C_{21}H_{17}N_3OS$ $[M+H]^+$ 360.1171 found: 360.1175.

The detailed preparative method is same as that of compound 1, with a yield of 76.3%.

Compound 44: 5-(1-(10H-phenothiazin-2-yl)ethenyl)pyridin-2-amine

The synthetic route is as follows:

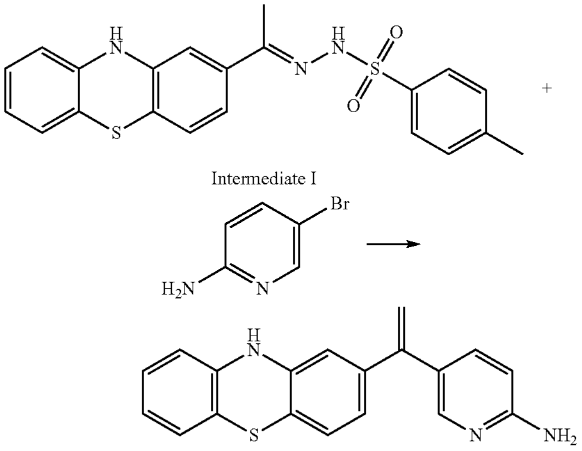

44

$^1$H NMR and HRMS data of compound 44 are as follows:

$^1$H NMR (400 MHz, DMSO-$d_6$) δ 8.56 (s, 1H), 7.86 (d, J=2.2 Hz, 1H), 7.30 (dd, J=8.6, 2.4 Hz, 1H), 6.96 (dd, J=7.6, 1.2 Hz, 1H), 6.94-6.87 (m, 2H), 6.79-6.70 (m, 2H), 6.67-6.58 (m, 2H), 6.44 (d, J=8.6 Hz, 1H), 6.08 (s, 2H), 5.42-5.14 (m, 2H).

HRMS m/z (ESI) calcd for $C_{19}H_{15}N_3S$ $[M+H]^+$ 318.1065 found: 318.1069.

The detailed preparative method is same as that of compound 1, with a yield of 68.9%.

Compound 45: 4-(5-(1-(10H-phenothiazin-2-yl)ethenyl)pyridin-2-yl)morpholine

The synthetic route is as follows:

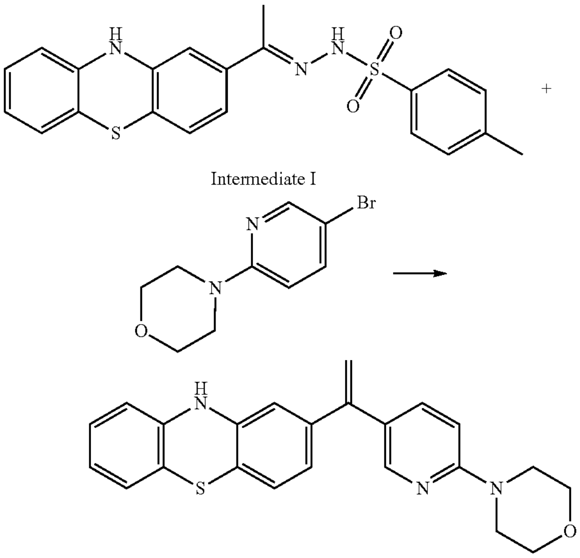
Intermediate I

45

$^1$H NMR and HRMS data of compound 45 are as follows: $^1$H NMR (400 MHz, DMSO-$d_6$) δ 8.55 (s, 1H), 8.09 (d, J=2.2 Hz, 1H), 7.46 (dd, J=8.8, 2.4 Hz, 1H), 7.03-6.95 (m, 1H), 6.91 (d, J=7.9 Hz, 2H), 6.84 (d, J=8.8 Hz, 1H), 6.75 (dd, J=12.5, 4.7 Hz, 2H), 6.62 (d, J=7.9 Hz, 1H), 6.59 (d, J=1.7 Hz, 1H), 5.33 (d, J=5.6 Hz, 2H), 3.81-3.65 (m, 4H), 3.51-3.40 (m, 4H).

HRMS m/z (ESI) calcd for $C_{23}H_{21}N_3OS$ $[M+H]^+$ 388.1484 found: 388.1487.

The detailed preparative method is same as that of compound 1, with a yield of 68.1%.

Compound 46: 4-(1-(10H-phenothiazin-2-yl)ethenyl)-3-methyl-N-(4-((4-methylpiperazin-1-yl)methyl)-3-(trifluoromethyl)phenyl)benzamide The synthetic route is as follows:

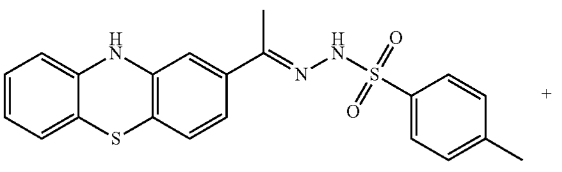
Intermediate I

-continued

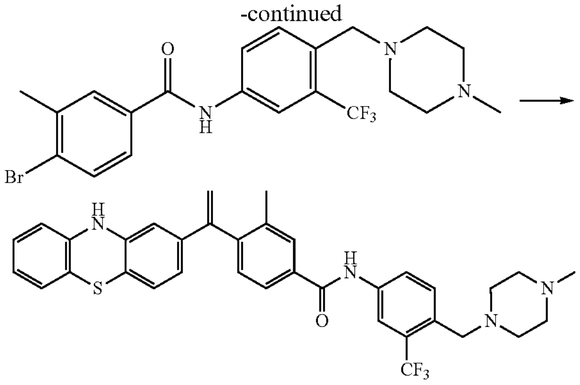

46

$^1$H NMR and HRMS data of compound 46 are as follows: $^1$H NMR (400 MHz, DMSO-$d_6$) δ 10.45 (s, 1H), 8.55 (s, 1H), 8.20 (d, J=1.9 Hz, 1H), 8.14-8.03 (m, 1H), 7.94 (dd, J=7.9, 1.8 Hz, 1H), 7.84 (d, J=1.7 Hz, 1H), 7.70 (d, J=8.5 Hz, 1H), 7.42 (d, J=8.1 Hz, 1H), 6.95 (td, J=7.9, 1.3 Hz, 1H), 6.90 (t, J=6.7 Hz, 2H), 6.79 (dd, J=8.0, 1.8 Hz, 1H), 6.73 (td, J=7.6, 1.1 Hz, 1H), 6.65-6.58 (m, 1H), 6.48 (d, J=1.7 Hz, 1H), 5.84 (s, 1H), 5.21 (s, 1H), 3.56 (s, 2H), 2.41 (d, J=15.1 Hz, 8H), 2.17 (s, 3H), 2.11 (s, 3H).

HRMS m/z (ESI) calcd for $C_{35}H_{33}F_3N_4S$ $[M+H]^+$ 615.2405 found: 615.2407.

The detailed preparative method is same as that of compound 1, with a yield of 57.1%.

Compound 47: (4-(1-(10H-phenothiazin-2-yl)ethenyl)phenyl)(morpholine)ketone

The synthetic route is as follows:

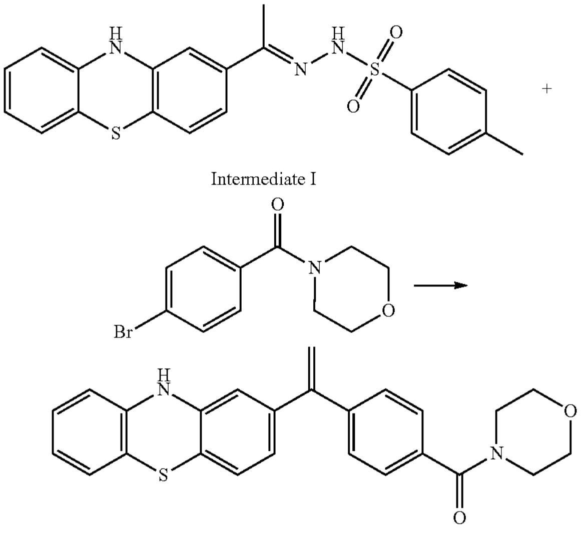
Intermediate I

47

$^1$H NMR and HRMS data of compound 47 are as follows: $^1$H NMR (400 MHz, DMSO-$d_6$) δ 8.58 (s, 1H), 7.40 (dd, J=21.0, 8.1 Hz, 4H), 6.94 (dt, J=14.2, 6.8 Hz, 3H), 6.76 (dd, J=13.0, 4.8 Hz, 2H), 6.62 (d, J=7.8 Hz, 1H), 6.57 (d, J=1.3 Hz, 1H), 5.48 (d, J=14.7 Hz, 2H), 3.61 (s, 8H).

HRMS m/z (ESI) calcd for $C_{25}H_{22}N_2O_2S$ $[M+H]^+$ 415.1480 found: 415.1486.

The detailed preparative method is same as that of compound 1, with a yield of 64.9%.

Compound 48: (4-(1-(10H-phenothiazin-2-yl)ethenyl)phenyl)(4-methylpiperazin-1-yl)ketone The synthetic route is as follows:

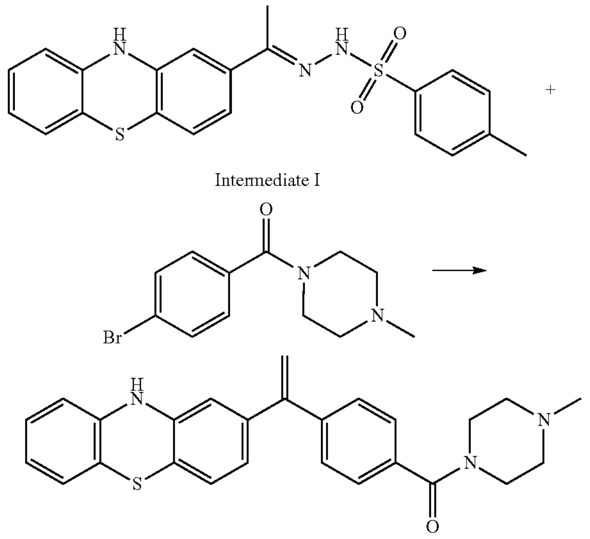

48

$^1$H NMR and HRMS data of compound 48 are as follows:

$^1$H NMR (400 MHz, DMSO-$d_6$) δ 8.58 (s, 1H), 7.46-7.31 (m, 4H), 6.96 (dd, J=7.6, 1.1 Hz, 1H), 6.92 (t, J=7.1 Hz, 2H), 6.76 (ddd, J=7.4, 3.8, 1.4 Hz, 2H), 6.68-6.60 (m, 1H), 6.57 (d, J=1.7 Hz, 1H), 5.48 (d, J=13.0 Hz, 2H), 3.48 (d, J=91.0 Hz, 4H), 2.32 (s, 4H), 2.20 (s, 3H).

HRMS m/z (ESI) calcd for $C_{26}H_{25}N_3OS$ $[M+H]^+$ 428.1797 found: 428.1795.

The detailed preparative method is same as that of compound 1, with a yield of 76.9%.

Compound 49: 2-(1-(2-(4-methylpiperazin-1-yl)pyrimidin-5-yl)ethenyl)-10H-phenothiazine The synthetic route is as follows:

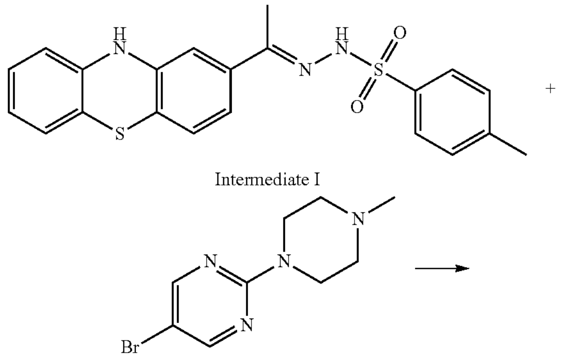

-continued

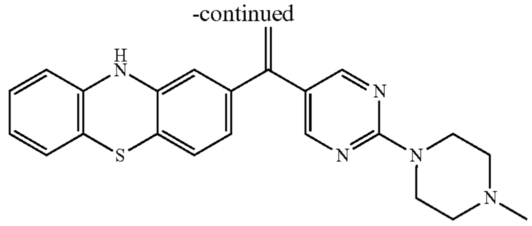

49

$^1$H NMR and HRMS data of compound 49 are as follows:

$^1$H NMR (400 MHz, DMSO-$d_6$) δ 8.56 (s, 1H), 8.30 (s, 2H), 6.98 (td, J=7.8, 1.4 Hz, 1H), 6.94-6.91 (m, 1H), 6.90 (d, J=1.9 Hz, 1H), 6.84-6.70 (m, 2H), 6.62 (dd, J=9.1, 1.3 Hz, 2H), 5.38 (d, J=2.8 Hz, 2H), 3.93-3.65 (m, 4H), 2.47-2.30 (m, 4H), 2.22 (s, 3H).

HRMS m/z (ESI) calcd for $C_{23}H_{23}N_5S$ $[M+H]^+$ 402.1752 found: 402.1756.

The detailed preparative method is same as that of compound 1, with a yield of 64.9%.

Compound 50: 2-(1-(2-(4-methyl-1,4-homopiperazin-1-yl)pyrimidin-5-yl)ethenyl)-10H-phenothiazine The synthetic route is as follows:

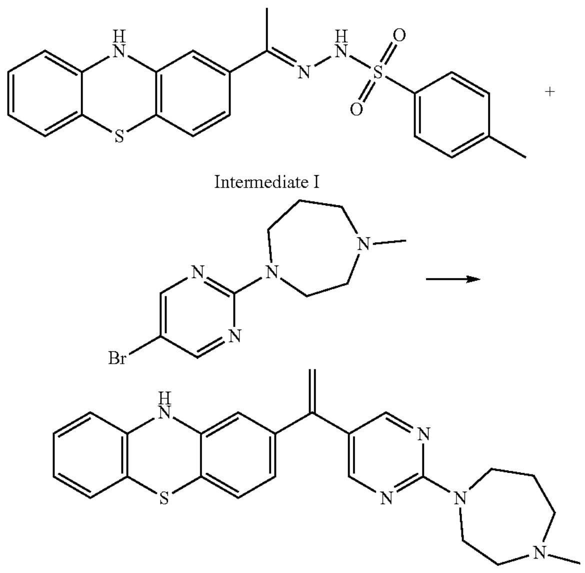

50

$^1$H NMR and HRMS data of compound 50 are as follows:

$^1$H NMR (400 MHz, DMSO-$d_6$) δ 8.58 (s, 1H), 8.28 (s, 2H), 6.98 (t, J=7.6 Hz, 1H), 6.95-6.88 (m, 2H), 6.82-6.71 (m, 2H), 6.63 (d, J=7.0 Hz, 2H), 5.35 (d, J=6.1 Hz, 2H), 3.97-3.81 (m, 2H), 3.76 (t, J=6.1 Hz, 2H), 2.75-2.57 (m, 2H), 2.28 (s, 3H), 1.97-1.80 (m, 2H).

HRMS m/z (ESI) calcd for $C_{24}H_{25}N_5S$ $[M+H]^+$ 416.1909 found: 416.1913.

The detailed preparative method is same as that of compound 1, with a yield of 69.0%.

Compound 51: 4-(5-(1-(10H-phenothiazin-2-yl) ethenyl)pyrimidin-2-yl)morpholine

The synthetic route is as follows:

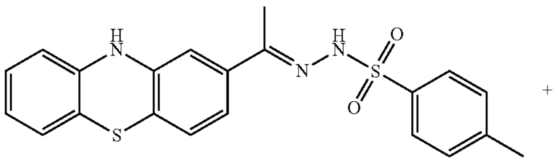

Intermediate I

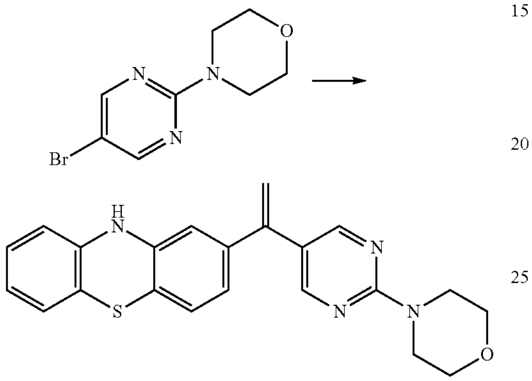

51

$^1$H NMR and HRMS data of compound 51 are as follows:

$^1$H NMR (400 MHz, DMSO-$d_6$) δ 8.56 (s, 1H), 8.33 (s, 2H), 6.98 (t, J=7.6 Hz, 1H), 6.92 (dd, J=7.5, 3.2 Hz, 2H), 6.85-6.71 (m, 2H), 6.62 (d, J=8.6 Hz, 2H), 5.39 (d, J=5.6 Hz, 2H), 3.84-3.71 (m, 4H), 3.71-3.60 (m, 4H).

HRMS m/z (ESI) calcd for $C_{22}H_{20}N_4OS$ [M+H]$^+$ 389.1436 found: 389.14367.

The detailed preparative method is same as that of compound 1, with a yield of 64.8%.

Compound 52: 4-(1-(10H-phenothiazin-2-yl)ethenyl)-N-(tetrahydro-2H-pyran-4-yl)benzenesulfonamide The synthetic route is as follows:

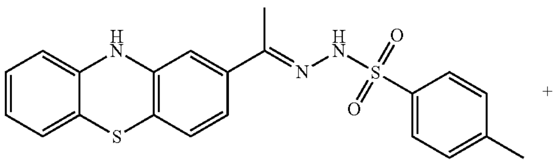

Intermediate I

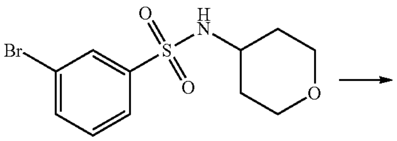

-continued

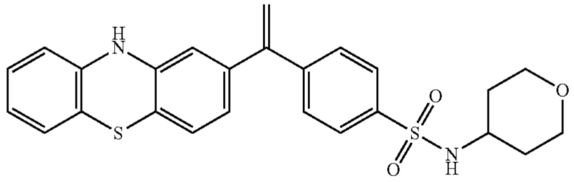

52

$^1$H NMR and HRMS data of compound 52 are as follows:

$^1$H NMR (400 MHz, DMSO-$d_6$) δ 8.58 (s, 1H), 7.94-7.76 (m, 3H), 7.51 (d, J=8.4 Hz, 2H), 7.03-6.88 (m, 3H), 6.81-6.70 (m, 2H), 6.62 (d, J=7.9 Hz, 1H), 6.55 (d, J=1.6 Hz, 1H), 5.55 (d, J=7.7 Hz, 2H), 3.86-3.62 (m, 2H), 3.24 (dd, J=11.2, 9.7 Hz, 3H), 1.53 (t, J=18.7 Hz, 2H), 1.48-1.32 (m, 2H).

HRMS m/z (ESI) calcd for $C_{25}H_{24}N_2O_3S_2$ [M+H]$^+$ 465.1307 found: 465.1309.

The detailed preparative method is same as that of compound 1, with a yield of 78.8%.

Compound 53: 3-(1-(10H-phenothiazin-2-yl)ethenyl)-N-(t-butyl)Benzenesulfonamide

The synthetic route is as follows:

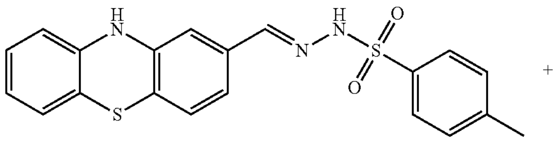

Intermediate I

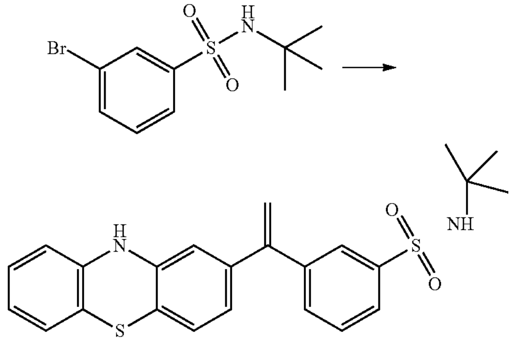

53

$^1$H NMR and HRMS data of compound 53 are as follows:

$^1$H NMR (400 MHz, DMSO-$d_6$) δ 8.59 (s, 1H), 7.89-7.77 (m, 1H), 7.70 (s, 1H), 7.58 (dd, J=14.3, 8.0 Hz, 3H), 7.06-6.86 (m, 3H), 6.75 (t, J=7.5 Hz, 1H), 6.70 (dd, J=7.9, 1.5 Hz, 1H), 6.63 (d, J=7.9 Hz, 1H), 6.58 (d, J=1.4 Hz, 1H), 5.51 (d, J=23.4 Hz, 2H), 1.08 (s, 9H).

HRMS m/z (ESI) calcd for $C_{24}H_{24}N_2O_2S_2$ [M+H]$^+$ 437.1357 found: 437.1356.

The detailed preparative method is same as that of compound 1, with a yield of 75.3%.

Compound 54: 2-(1-(4-(pyrrolin-1-ylsulfonyl)phenyl)ethenyl)-10H-phenothiazine

The synthetic route is as follows:

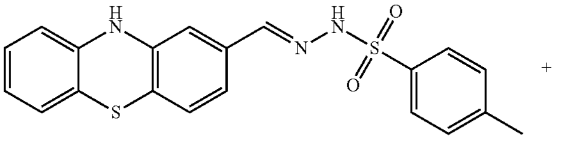

Intermediate I

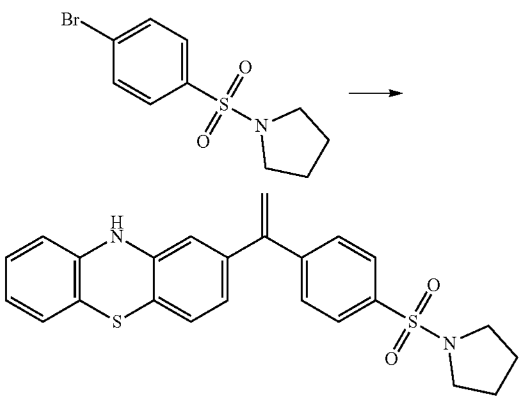

54

$^1$H NMR and HRMS data of compound 54 are as follows:

$^1$H NMR (400 MHz, DMSO-$d_6$) δ 8.58 (s, 1H), 7.81 (d, J=8.4 Hz, 2H), 7.55 (d, J=8.4 Hz, 2H), 7.07-6.88 (m, 3H), 6.83-6.71 (m, 2H), 6.62 (d, J=7.9 Hz, 1H), 6.55 (d, J=1.7 Hz, 1H), 5.57 (d, J=11.8 Hz, 2H), 3.17 (s, 4H), 1.68 (d, J=2.8 Hz, 4H).

HRMS m/z (ESI) calcd for $C_{24}H_{22}N_2O_2S_2$ $[M+H]^+$ 435.1201 found: 435.1205.

The detailed preparative method is same as that of compound 1, with a yield of 67.2%.

Compound 55: 3-(1-(10H-phenothiazin-2-yl)ethenyl)-N-(tetrahydro-2H-pyran-4-yl)benzenesulfonamide The synthetic route is as follows:

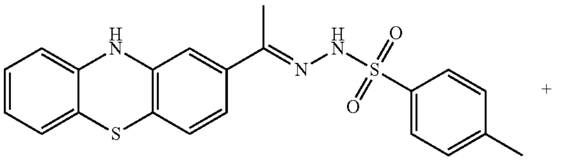

Intermediate I

-continued

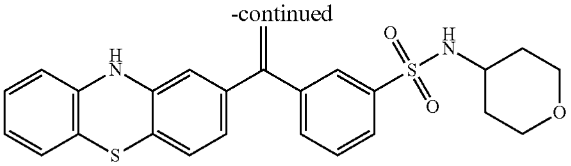

55

$^1$H NMR and HRMS data of compound 55 are as follows:

$^1$H NMR (400 MHz, DMSO-$d_6$) δ 8.57 (s, 1H), 7.81 (ddd, J=6.3, 5.6, 4.5 Hz, 2H), 7.68 (s, 1H), 7.66-7.54 (m, 2H), 6.96 (ddd, J=19.4, 11.9, 4.1 Hz, 3H), 6.81-6.67 (m, 2H), 6.67-6.60 (m, 1H), 6.56 (d, J=1.7 Hz, 1H), 5.51 (d, J=26.3 Hz, 2H), 3.71 (dd, J=8.3, 3.3 Hz, 2H), 3.22 (td, J=11.5, 2.2 Hz, 3H), 1.50 (d, J=10.4 Hz, 2H), 1.43-1.27 (m, 2H).

HRMS m/z (ESI) calcd for $C_{25}H_{24}N_2O_3S_2$ $[M+H]^+$ 465.1307 found: 465.1303.

The detailed preparative method is same as that of compound 1, with a yield of 81.8%.

Compound 56: 4-(1-(10H-phenothiazin-2-yl)ethenyl)-N-((tetrahydro-2H-pyran-4-yl)methyl)Benzenesulfonamide The synthetic route is as follows:

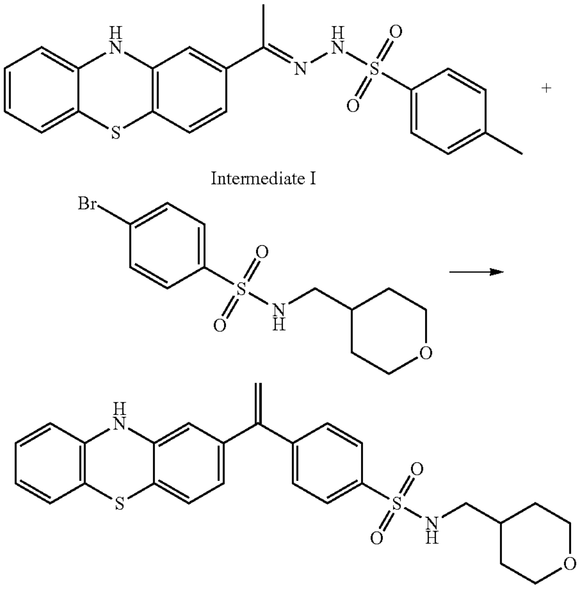

Intermediate I

56

$^1$H NMR and HRMS data of compound 56 are as follows:

$^1$H NMR (400 MHz, DMSO-$d_6$) δ 8.58 (s, 1H), 7.79 (d, J=8.3 Hz, 2H), 7.70 (t, J=6.1 Hz, 1H), 7.52 (d, J=8.3 Hz, 2H), 6.96 (ddd, J=18.9, 12.3, 4.6 Hz, 3H), 6.75 (t, J=7.3 Hz, 2H), 6.62 (d, J=7.8 Hz, 1H), 6.55 (d, J=1.6 Hz, 1H), 5.54 (d, J=19.5 Hz, 2H), 3.81 (dd, J=11.2, 3.1 Hz, 2H), 3.21 (t, J=10.9 Hz, 2H), 2.66 (t, J=6.3 Hz, 2H), 1.55 (d, J=13.3 Hz, 3H), 1.09 (dd, J=11.9, 3.7 Hz, 2H).

HRMS m/z (ESI) calcd for $C_{26}H_{26}N_2O_3S_2$ $[M+H]^+$ 479.1463 found: 479.1466.

The detailed preparative method is same as that of compound 1, with a yield of 79.8%.

Compound 57: 4-((4-(1-(10H-phenothiazin-2-yl) ethenyl)phenyl)sulfonyl)morpholine The synthetic route is as follows:

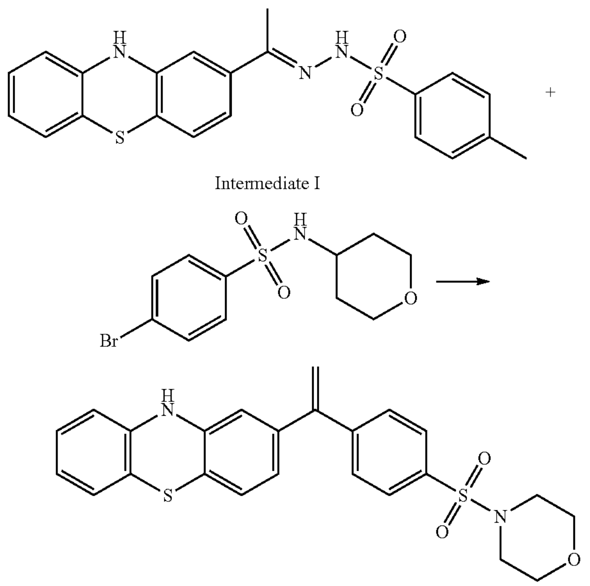

57

$^1$H NMR and HRMS data of compound 57 are as follows:

$^1$H NMR (400 MHz, DMSO-$d_6$) δ 8.58 (s, 1H), 7.75 (d, J=8.4 Hz, 2H), 7.59 (d, J=8.4 Hz, 2H), 7.09-6.87 (m, 3H), 6.76 (d, J=8.1 Hz, 2H), 6.69-6.60 (m, 1H), 6.55 (d, J=1.7 Hz, 1H), 5.59 (d, J=15.1 Hz, 2H), 3.79-3.54 (m, 4H), 3.03-2.83 (m, 4H).

HRMS m/z (ESI) calcd for $C_{24}H_{22}N_2O_3S_2$ $[M+H]^+$ 451.1150 found: 451.1154.

The detailed preparative method is same as that of compound 1, with a yield of 69.8%.

Compound 58: 4-(1-(10H-phenothiazin-2-yl)ethenyl)-N-cyclobutylbenzenesulfonamide The synthetic route is as follows:

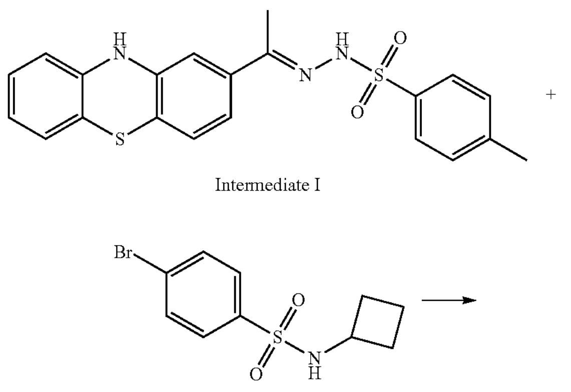

-continued

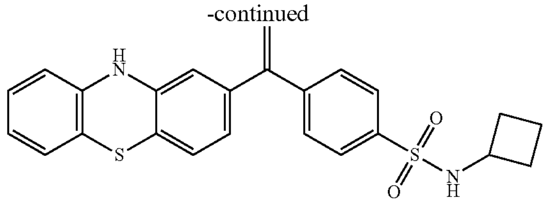

58

$^1$H NMR and HRMS data of compound 58 are as follows:

$^1$H NMR (400 MHz, DMSO-$d_6$) δ 8.58 (s, 1H), 8.00 (d, J=8.5 Hz, 1H), 7.78 (d, J=8.4 Hz, 2H), 7.50 (d, J=8.4 Hz, 2H), 7.06-6.86 (m, 3H), 6.74 (ddd, J=9.7, 7.8, 1.4 Hz, 2H), 6.69-6.57 (m, 1H), 6.55 (d, J=1.7 Hz, 1H), 5.54 (d, J=12.7 Hz, 2H), 3.72-3.53 (m, 1H), 2.02-1.87 (m, 2H), 1.77 (dd, J=15.4, 6.3 Hz, 2H), 1.50 (td, J=10.3, 5.8 Hz, 2H).

HRMS m/z (ESI) calcd for $C_{24}H_{22}N_2O_2S_2$ $[M+H]^+$ 435.1201 found: 435.1203.

The detailed preparative method is same as that of compound 1, with a yield of 67.4%.

Compound 59: 4-(1-(10H-phenothiazin-2-yl)ethenyl)-N-(1-methylpiperidin-4-yl)Benzenesulfonamide The synthetic route is as follows:

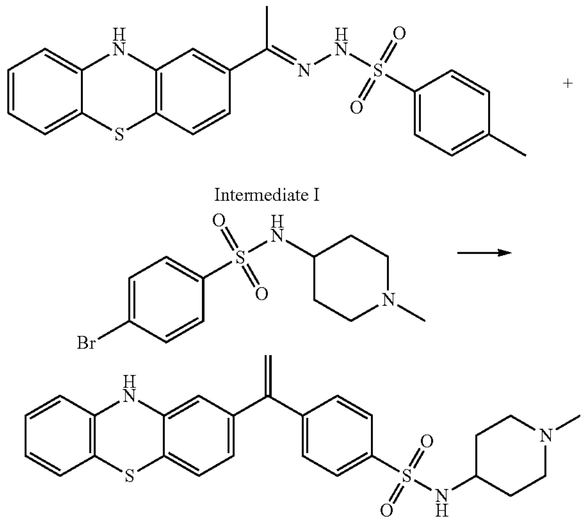

59

$^1$H NMR and HRMS data of compound 59 are as follows:

$^1$H NMR (400 MHz, DMSO-$d_6$) δ 8.58 (s, 1H), 7.81 (d, J=8.4 Hz, 2H), 7.74 (d, J=7.1 Hz, 1H), 7.51 (d, J=8.4 Hz, 2H), 6.96 (ddd, J=18.8, 12.4, 4.7 Hz, 3H), 6.84-6.70 (m, 2H), 6.62 (d, J=7.9 Hz, 1H), 6.55 (d, J=1.6 Hz, 1H), 5.55 (d, J=7.4 Hz, 2H), 2.94 (dd, J=10.6, 4.1 Hz, 1H), 2.61 (d, J=11.7 Hz, 2H), 2.08 (s, 3H), 1.83 (t, J=10.7 Hz, 2H), 1.56 (d, J=10.0 Hz, 2H), 1.42 (dd, J=17.2, 6.5 Hz, 2H).

HRMS m/z (ESI) calcd for $C_{26}H_{27}N_3O_2S_2$ $[M+H]^+$ 478.1623 found: 478.1624.

The detailed preparative method is same as that of compound 1, with a yield of 79.8%.

Example 4 Synthesis of Compounds C1-C59 of the Present Invention

Compounds 1-59 in Example 4 were also named compounds C1-C59.

Using the intermediate I prepared in Example 1 and secondary amine as starting materials, to prepare compounds 1-59, namely compounds C1-C59. Among them, the method for preparation of compounds 2-59 is the same as that of compound 1 in Example 4.

Compound 1: 4-((1-(10H-phenothiazin-2-yl)ethyl) sulfonyl)morpholine

The synthetic route was as follows:

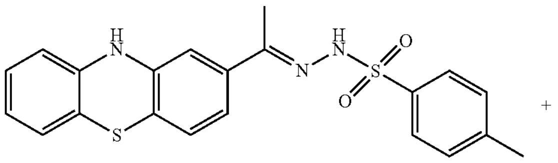

Intermediate I

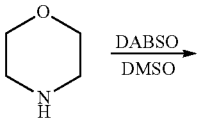

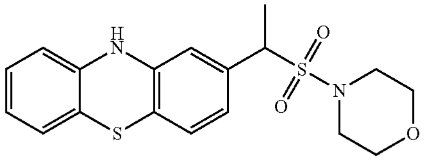

1

Intermediate I (100 mg, 0.244 mmol, 1.0 eq), morpholine (42 mg, 0.488 mmol, 2.0 eq), and DABSO (32 mg, 0.134 mmol, 0.55 eq) were dissolved in 10 mL DMSO, and argon was purged and exchanged 3 times. The resultant mixture was warmed to 100° C. for reaction, and the reaction was monitored by TLC. After about 12 h, the reaction was completed, and cooled to room temperature, then directly extracted with saturated aqueous solution/EA(1:1). The organic layer was concentrated and separated by column chromatography to obtain the target product compound 1 (47 mg), with a yield of 76.8%.

$^1$H NMR and HRMS data of compound 1 are as follows:

$^1$H NMR (400 MHz, DMSO-$d_6$) δ 8.70 (s, 1H), 6.98 (t, J=7.6 Hz, 1H), 6.91 (t, J=8.1 Hz, 2H), 6.86-6.81 (m, 1H), 6.78 (s, 1H), 6.74 (dd, J=11.5, 7.6 Hz, 1H), 6.68 (d, J=7.9 Hz, 1H), 4.46 (d, J=7.1 Hz, 1H), 3.60-3.42 (m, 4H), 3.09 (ddd, J=12.0, 5.7, 3.2 Hz, 2H), 3.02-2.87 (m, 2H), 1.54 (d, J=7.0 Hz, 3H).

HRMS m/z (ESI) calcd for $C_{18}H_{20}N_2O_3S_2$ $[M+H]^+$ 377.0994 found: 377.0998.

Compound 2: 2-(1-((4-methylpiperazin-1-yl)sulfonyl)ethyl)-10H-phenothiazine

The synthetic route is as follows:

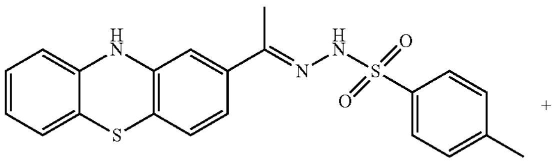

Intermediate I

-continued

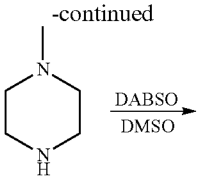

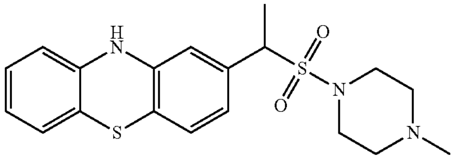

2

$^1$H NMR and HRMS data of compound 2 are as follows:

$^1$H NMR (400 MHz, DMSO-$d_6$) δ 8.71 (s, 1H), 6.98 (td, J=7.8, 1.4 Hz, 1H), 6.95-6.87 (m, 2H), 6.82 (dd, J=8.0, 1.6 Hz, 1H), 6.79-6.72 (m, 2H), 6.68 (dd, J=7.9, 1.0 Hz, 1H), 4.42 (q, J=7.0 Hz, 1H), 3.18-3.00 (m, 2H), 3.00-2.86 (m, 2H), 2.22 (d, J=2.9 Hz, 4H), 2.12 (s, 3H), 1.53 (d, J=7.0 Hz, 3H).

HRMS m/z (ESI) calcd for $C_{19}H_{23}N_3O_2S_2$ $[M+H]^+$ 390.1310 found: 390.1312.

The detailed preparative method is same as that of compound 1, with a yield of 74.1%.

Compound 3: 2-(1-((4-methyl-1,4-homopiperazin-1-yl)sulfonyl)ethyl)-10H-phenothiazine The synthetic route is as follows:

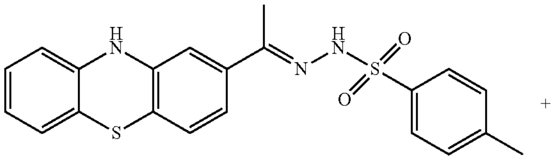

Intermediate I

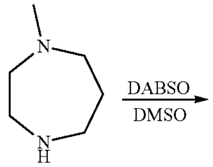

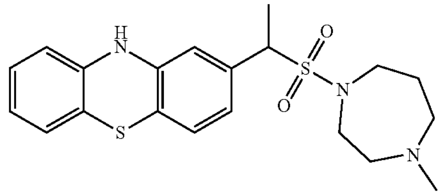

3

$^1$H NMR and HRMS data of compound 3 are as follows:

$^1$H NMR (400 MHz, DMSO-$d_6$) δ 8.69 (s, 1H), 6.99 (td, J=7.8, 1.3 Hz, 1H), 6.90 (d, J=7.8 Hz, 2H), 6.84-6.71 (m, 3H), 6.68 (d, J=7.9 Hz, 1H), 4.44 (q, J=7.0 Hz, 1H), 3.12 (dd, J=13.6, 6.4 Hz, 2H), 2.48-2.40 (m, 4H), 2.21 (s, 3H), 1.75-1.62 (m, 2H), 1.52 (d, J=7.0 Hz, 3H).

HRMS m/z (ESI) calcd for $C_{20}H_{25}N_3O_2S_2$ $[M+H]^+$ 404.1466 found: 404.1467.

The detailed preparative method is same as that of compound 1, with a yield of 80.1%.

Compound 4: 2-(1-((4-isopropylpiperazin-1-yl) sulfonyl)ethyl)-10H-phenothiazine The synthetic route is as follows:

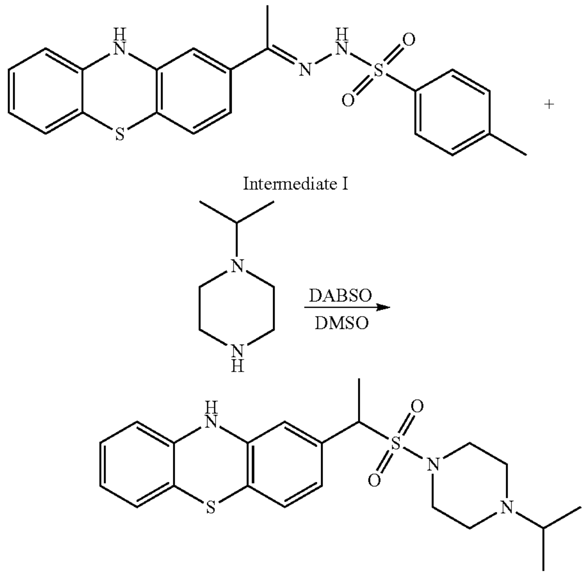

4

$^1$H NMR and HRMS data of compound 4 are as follows: $^1$H NMR (400 MHz, DMSO-$d_6$) δ 8.70 (s, 1H), 6.98 (t, J=7.2 Hz, 1H), 6.95-6.87 (m, 2H), 6.82 (d, J=7.9 Hz, 1H), 6.80-6.71 (m, 2H), 6.67 (d, J=7.7 Hz, 1H), 4.40 (dd, J=13.7, 6.7 Hz, 1H), 3.07 (s, 2H), 2.93 (s, 2H), 2.62 (s, 1H), 2.33 (s, 4H), 1.52 (d, J=7.0 Hz, 3H), 0.90 (d, J=3.9 Hz, 6H).

HRMS m/z (ESI) calcd for $C_{21}H_{27}N_3O_2S_2$ $[M+H]^+$ 418.1623 found: 418.1619.

The detailed preparative method is same as that of compound 1, with a yield of 67.8%.

Compound 5 2-(1-((4-(benzo[d][1,3]dioxa-5-ylmethyl)piperazin-1-yl)sulfonyl)ethyl)-10H-phenothiazine The synthetic route is as follows:

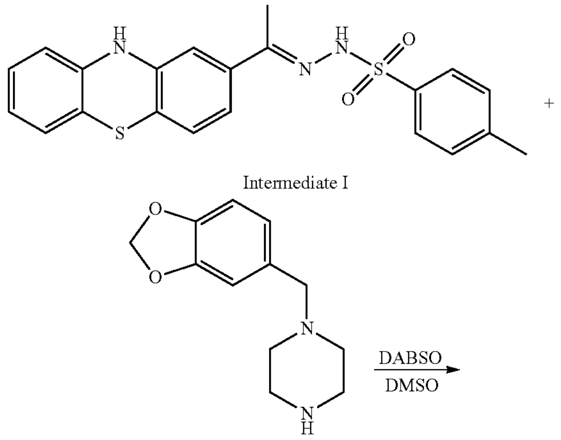

-continued

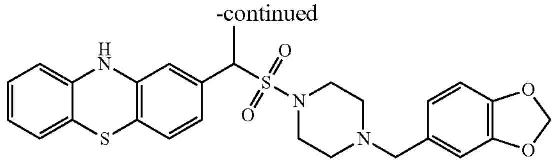

5

$^1$H NMR and HRMS data of compound 5 are as follows:

$^1$H NMR (400 MHz, DMSO-$d_6$) δ 8.70 (s, 1H), 6.99 (t, J=7.2 Hz, 1H), 6.91 (d, J=7.8 Hz, 2H), 6.86-6.72 (m, 6H), 6.69 (d, J=7.6 Hz, 2H), 5.98 (d, J=6.7 Hz, 2H), 4.39 (q, J=6.7 Hz, 1H), 3.34 (d, J=10.1 Hz, 2H), 3.07 (s, 2H), 2.97 (s, 2H), 2.26 (s, 4H), 1.51 (t, J=11.9 Hz, 3H).

HRMS m/z (ESI) calcd for $C_{26}H_{27}N_3O_4S_2$ $[M+H]^+$ 510.1521 found: 510.1523.

The detailed preparative method is same as that of compound 1, with a yield of 59.4%.

Compound 6 2-(4-((1-(10H-phenothiazin-2-yl)ethyl) sulfonyl)piperazin-1-yl)-1-(pyrrolin-1-yl)-1-ethanone The synthetic route is as follows:

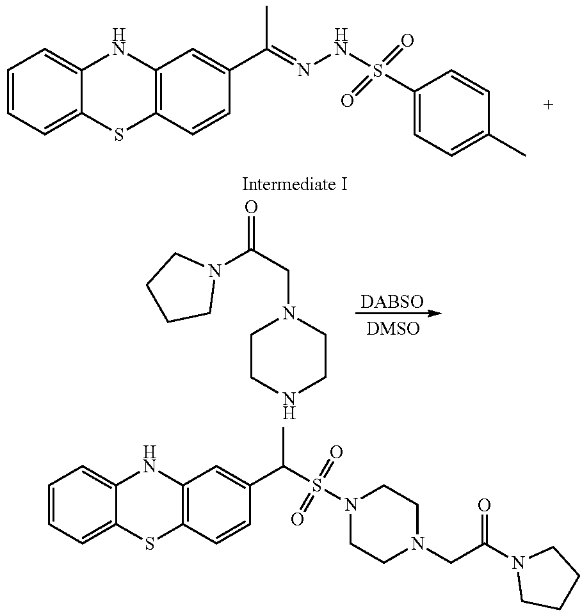

6

$^1$H NMR and HRMS data of compound 6 are as follows:

$^1$H NMR (400 MHz, DMSO-$d_6$) δ 8.69 (s, 1H), 6.98 (t, J=7.4 Hz, 1H), 6.96-6.86 (m, 2H), 6.83 (d, J=7.9 Hz, 1H), 6.80-6.72 (m, 2H), 6.68 (d, J=7.8 Hz, 1H), 4.41 (d, J=7.0 Hz, 1H), 3.37 (t, J=6.6 Hz, 2H), 3.25 (t, J=6.8 Hz, 2H), 3.09 (s, 4H), 2.94 (s, 2H), 2.42 (s, 4H), 1.87-1.78 (m, 2H), 1.76-1.67 (m, 2H), 1.53 (d, J=6.9 Hz, 3H).

HRMS m/z (ESI) calcd for $C_{24}H_{30}N_4O_3S_2$ $[M+H]^+$ 487.1838 found: 487.1839.

The detailed preparative method is same as that of compound 1, with a yield of 73.5%.

Compound 7 3-(4-((1-(10H-phenothiazin-2-yl)ethyl) sulfonyl)piperazin-1-yl)-N,N-dimethylpropan-1-amine The synthetic route is as follows:

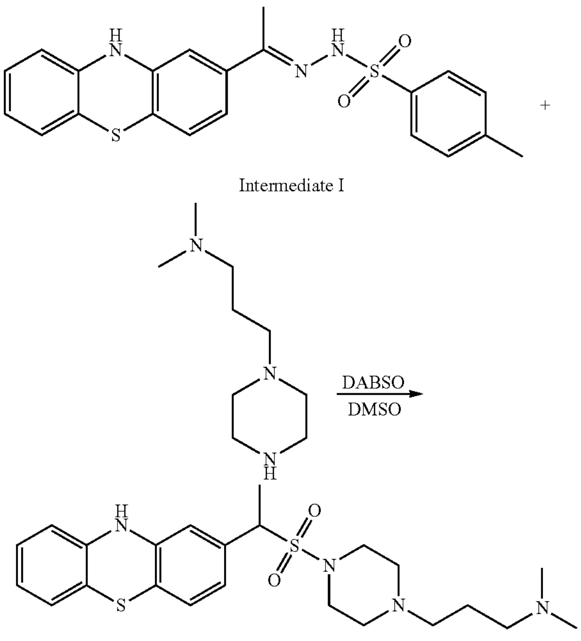

7

$^1$H NMR and HRMS data of compound 7 are as follows:

$^1$H NMR (400 MHz, DMSO-$d_6$) δ 8.69 (s, 1H), 6.98 (td, J=7.7, 1.4 Hz, 1H), 6.90 (dd, J=7.1, 4.3 Hz, 2H), 6.82 (dd, J=8.0, 1.6 Hz, 1H), 6.80-6.72 (m, 2H), 6.68 (d, J=7.9 Hz, 1H), 4.40 (q, J=7.0 Hz, 1H), 3.12-3.01 (m, 2H), 2.94 (d, J=5.5 Hz, 2H), 2.30-2.17 (m, 8H), 2.11 (d, J=7.2 Hz, 6H), 1.53 (d, J=7.1 Hz, 3H), 1.49 (s, 2H).

HRMS m/z (ESI) calcd for $C_{23}H_{32}N_4O_2S_2$ $[M+H]^+$ 461.2045 found: 461.2041.

The detailed preparative method is same as that of compound 1, with a yield of 73.5%.

Compound 8: 8-((1-(10H-phenothiazin-2-yl)ethyl) sulfonyl)-8-azabicyclo[3.2.1]-3-octanol The synthetic route is as follows:

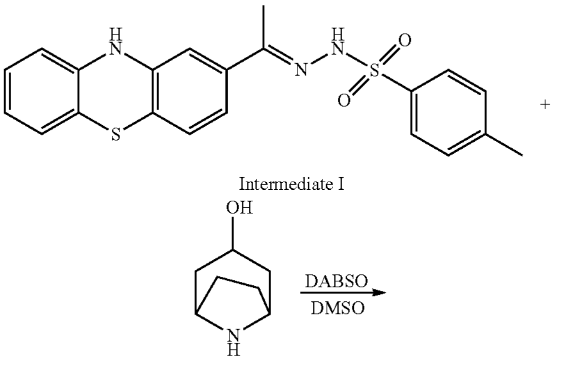

-continued

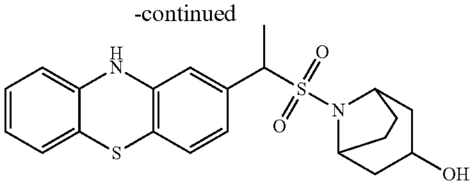

8

$^1$H NMR and HRMS data of compound 8 are as follows:

$^1$H NMR (400 MHz, DMSO-$d_6$) δ 8.66 (s, 1H), 6.98 (td, J=7.7, 1.4 Hz, 1H), 6.90 (dd, J=10.8, 4.5 Hz, 2H), 6.83-6.73 (m, 3H), 6.73-6.63 (m, 1H), 4.29 (d, J=7.1 Hz, 1H), 4.10 (s, 1H), 3.90-3.75 (m, 2H), 2.08 (t, J=6.4 Hz, 2H), 1.94-1.83 (m, 2H), 1.74 (d, J=8.1 Hz, 2H), 1.63 (d, J=10.2 Hz, 2H), 1.53 (d, J=7.0 Hz, 3H).

HRMS m/z (ESI) calcd for $C_{21}H_{24}N_2O_3S_2$ $[M+H]^+$ 417.1307 found: 417.1309.

The detailed preparative method is same as that of compound 1, with a yield of 86.2%.

Compound 9: 2-(1-((4-phenethylpiperazin-1-yl) sulfonyl)ethyl)-10H-phenothiazine The synthetic route is as follows:

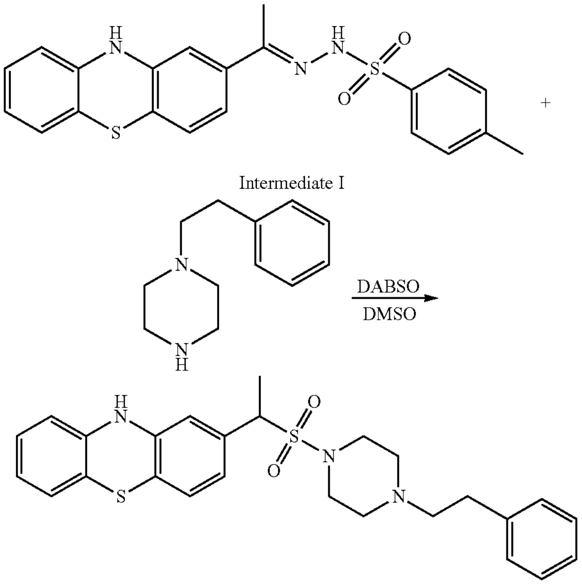

9

$^1$H NMR and HRMS data of compound 9 are as follows:

$^1$H NMR (400 MHz, DMSO-$d_6$) δ 8.70 (s, 1H), 7.29-7.22 (m, 2H), 7.17 (dd, J=7.6, 3.5 Hz, 3H), 6.98 (td, J=7.6, 1.4 Hz, 1H), 6.94-6.87 (m, 2H), 6.83 (dd, J=7.9, 1.7 Hz, 1H), 6.77 (dd, J=3.3, 1.5 Hz, 1H), 6.76-6.72 (m, 1H), 6.68 (d, J=7.9 Hz, 1H), 4.41 (q, J=7.0 Hz, 1H), 3.21-3.02 (m, 2H), 2.92 (dd, J=22.3, 15.4 Hz, 2H), 2.77-2.62 (m, 2H), 2.46-2.27 (m, 4H), 1.52 (t, J=10.6 Hz, 3H).

HRMS m/z (ESI) calcd for $C_{26}H_{29}N_3O_2S_2$ $[M+H]^+$ 480.1799 found: 480.1795.

The detailed preparative method is same as that of compound 1, with a yield of 62.7%.

Compound 10: 2-(1-((4-ethylpiperazin-1-yl)sulfonyl)ethyl)-10H-phenothiazine

The synthetic route is as follows:

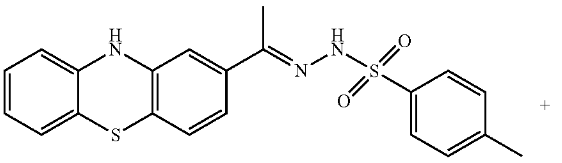

Intermediate I

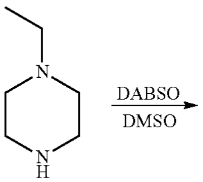

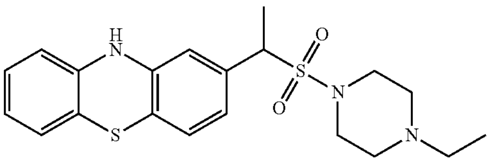

10

$^1$H NMR and HRMS data of compound 10 are as follows:

$^1$H NMR (400 MHz, DMSO-$d_6$) δ 8.69 (s, 1H), 6.98 (t, J=7.1 Hz, 1H), 6.94-6.86 (m, 2H), 6.82 (d, J=7.8 Hz, 1H), 6.76 (d, J=7.9 Hz, 2H), 6.68 (d, J=7.6 Hz, 1H), 4.40 (d, J=6.7 Hz, 1H), 3.07 (s, 2H), 2.94 (s, 2H), 2.29 (d, J=6.9 Hz, 6H), 1.53 (d, J=6.6 Hz, 3H), 0.94 (t, J=6.8 Hz, 3H).

HRMS m/z (ESI) calcd for $C_{20}H_{25}N_3O_2S_2$ $[M+H]^+$ 404.1466 found: 404.1467.

The detailed preparative method is same as that of compound 1, with a yield of 76.8%.

Compound 11: (4-((1-(10H-phenothiazin-2-yl)ethyl)sulfonyl)piperazin-1-yl)(tetrahydrofuran-2-yl)ketone The synthetic route is as follows:

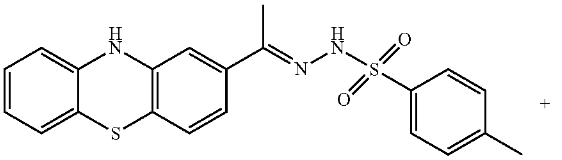

Intermediate I

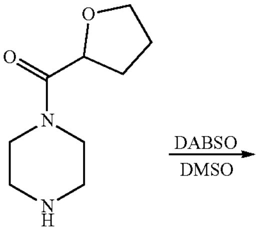

-continued

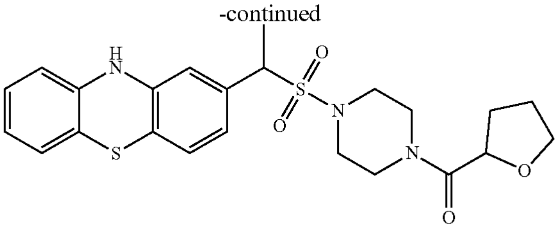

11

$^1$H NMR and HRMS data of compound 11 are as follows:

$^1$H NMR (400 MHz, DMSO-$d_6$) δ 8.69 (s, 1H), 6.98 (td, J=7.7, 1.4 Hz, 1H), 6.94-6.87 (m, 2H), 6.82 (dd, J=8.0, 1.6 Hz, 1H), 6.79-6.71 (m, 2H), 6.67 (dd, J=7.9, 1.0 Hz, 1H), 4.59 (dd, J=7.4, 5.7 Hz, 1H), 4.45 (dd, J=7.0, 3.0 Hz, 1H), 3.80-3.63 (m, 2H), 3.60-3.35 (m, 4H), 3.18-3.01 (m, 2H), 2.89 (dd, J=48.8, 20.8 Hz, 2H), 2.00-1.87 (m, 2H), 1.86-1.71 (m, 2H), 1.54 (d, J=7.0 Hz, 3H).

HRMS m/z (ESI) calcd for $C_{23}H_{27}N_3O_4S_2$ $[M+H]^+$ 474.1521 found: 474.1523.

The detailed preparative method is same as that of compound 1, with a yield of 79.8%.

Compound 12: 4-(2-(4-((1-(10H-phenothiazin-2-yl)ethyl)sulfonyl)piperazin-1-yl)ethyl)morpholine The synthetic route is as follows:

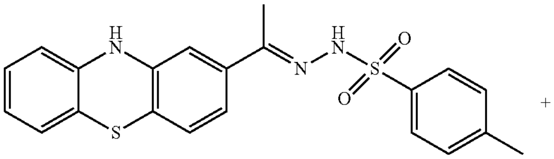

Intermediate I

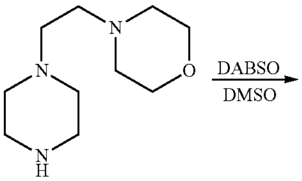

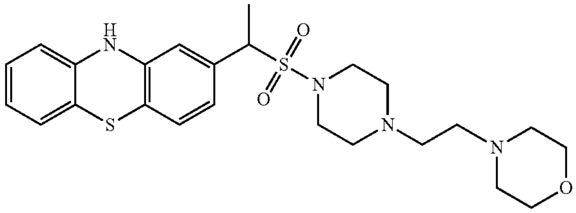

12

$^1$H NMR and HRMS data of compound 12 are as follows:

$^1$H NMR (400 MHz, DMSO-$d_6$) δ 8.69 (s, 1H), 6.97 (dd, J=7.6, 1.2 Hz, 1H), 6.94-6.88 (m, 2H), 6.82 (dd, J=8.0, 1.6 Hz, 1H), 6.76 (dd, J=7.4, 1.1 Hz, 2H), 6.68 (dd, J=7.9, 1.0 Hz, 1H), 4.40 (q, J=6.9 Hz, 1H), 3.55-3.49 (m, 4H), 3.15-3.01 (m, 2H), 2.92 (d, J=4.3 Hz, 2H), 2.44-2.23 (m, 12H), 1.52 (d, J=7.0 Hz, 3H).

HRMS m/z (ESI) calcd for $C_{24}H_{32}N_4O_3S_2$ $[M+H]^+$ 489.1994 found: 489.1996.

The detailed preparative method is same as that of compound 1, with a yield of 76.4%.

Compound 13: 2-(4-((1-(10H-phenothiazin-2-yl) ethyl)sulfonyl)piperazin-1-yl)-1-ethanol The synthetic route is as follows:

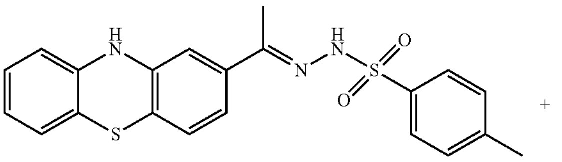

Intermediate I

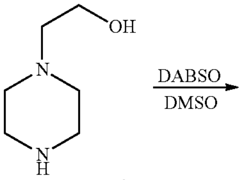

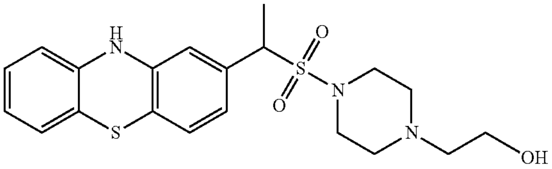

13

$^1$H NMR and HRMS data of compound 13 are as follows:

$^1$H NMR (400 MHz, DMSO-$d_6$) δ 8.69 (s, 1H), 6.98 (td, J=7.7, 1.4 Hz, 1H), 6.95-6.88 (m, 2H), 6.82 (dd, J=7.9, 1.7 Hz, 1H), 6.80-6.71 (m, 2H), 6.68 (dd, J=7.9, 1.0 Hz, 1H), 4.46-4.33 (m, 2H), 3.54-3.41 (m, 2H), 3.14-3.02 (m, 2H), 3.00-2.88 (m, 2H), 2.42-2.27 (m, 6H), 1.53 (d, J=7.0 Hz, 3H).

HRMS m/z (ESI) calcd for $C_{20}H_{25}N_3O_3S_2$ $[M+H]^+$ 420.1416 found: 420.1419.

The detailed preparative method is same as that of compound 1, with a yield of 77.8%.

Compound 14: (3R)-1-((1-(10H-phenothiazin-2-yl) ethyl)sulfonyl)pyrrolin-3-ol

The synthetic route is as follows:

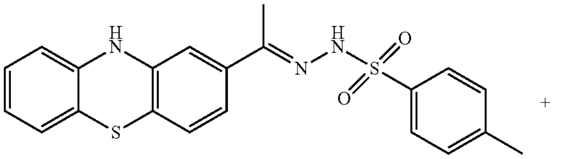

Intermediate I

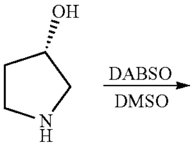

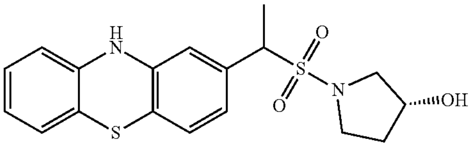

14

$^1$H NMR and HRMS data of compound 14 are as follows:

$^1$H NMR (400 MHz, DMSO-$d_6$) δ 8.67 (s, 1H), 6.98 (td, J=7.8, 1.3 Hz, 1H), 6.90 (dd, J=10.0, 3.6 Hz, 2H), 6.82 (d, J=7.9 Hz, 1H), 6.78 (s, 1H), 6.75 (td, J=7.6, 1.0 Hz, 1H), 6.68 (d, J=7.9 Hz, 1H), 5.00 (d, J=3.3 Hz, 1H), 4.56-4.41 (m, 1H), 4.20 (dd, J=29.5, 2.9 Hz, 1H), 3.32-3.13 (m, 2H), 2.99 (dddd, J=17.2, 12.5, 9.2, 2.8 Hz, 2H), 1.91-1.62 (m, 2H), 1.55 (d, J=7.0 Hz, 3H).

HRMS m/z (ESI) calcd for $C_{18}H_{20}N_2O_3S_2$ $[M+H]^+$ 377.0994 found: 377.0996.

The detailed preparative method is same as that of compound 1, with a yield of 80.2%.

Compound 15: 1-(4-((1-(10H-phenothiazin-2-yl) ethyl)sulfonyl)piperazin-1-yl)-1-ethanone The synthetic route is as follows:

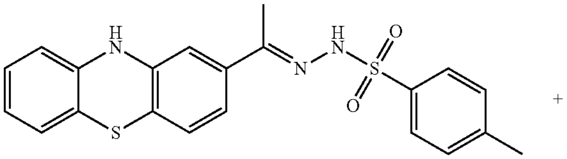

Intermediate I

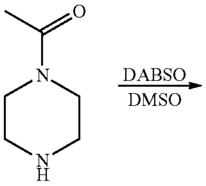

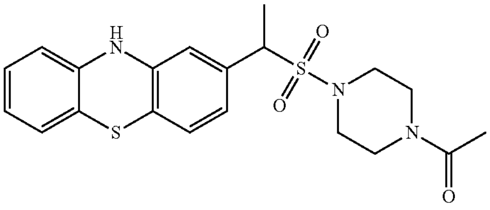

15

$^1$H NMR and HRMS data of compound 15 are as follows:

$^1$H NMR (400 MHz, DMSO-$d_6$) δ 8.68 (s, 1H), 7.05-6.95 (m, 1H), 6.90 (dd, J=7.7, 3.1 Hz, 2H), 6.81 (dd, J=8.0, 1.4 Hz, 1H), 6.75 (dd, J=12.0, 4.4 Hz, 2H), 6.67 (d, J=7.9 Hz, 1H), 4.44 (q, J=7.0 Hz, 1H), 3.39 (d, J=22.5 Hz, 4H), 3.15-3.02 (m, 2H), 3.02-2.88 (m, 2H), 1.97 (d, J=11.4 Hz, 3H), 1.54 (d, J=7.0 Hz, 3H).

HRMS m/z (ESI) calcd for $C_{20}H_{23}N_3O_3S_2$ $[M+H]^+$ 418.1259 found: 418.1255.

The detailed preparative method is same as that of compound 1, with a yield of 57.8%.

Compound 16: 2-(1-((4-(methylsulfonyl)piperazin-1-yl)sulfonyl)ethyl)-10H-phenothiazine The synthetic route is as follows:

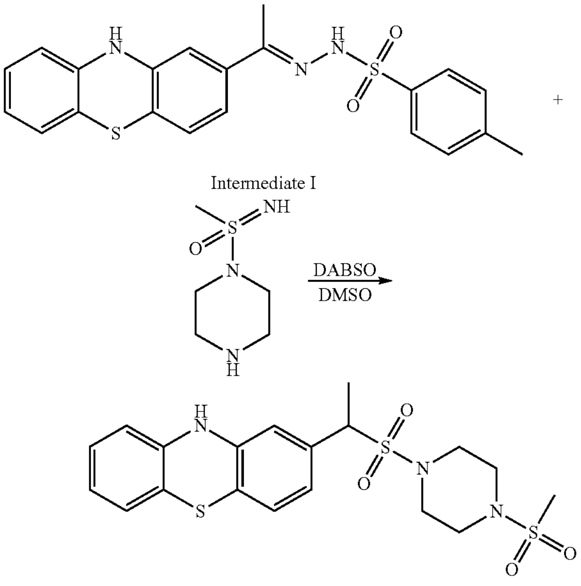

16

$^1H$ NMR and HRMS data of compound 16 are as follows:

$^1H$ NMR (400 MHz, DMSO-$d_6$) δ 8.71 (s, 1H), 6.98 (dd, J=10.8, 4.4 Hz, 1H), 6.95-6.87 (m, 2H), 6.84 (dd, J=7.9, 1.6 Hz, 1H), 6.80-6.72 (m, 2H), 6.67 (d, J=7.8 Hz, 1H), 4.46 (q, J=7.0 Hz, 1H), 3.21 (dd, J=9.4, 6.8 Hz, 2H), 3.06 (dt, J=14.7, 6.5 Hz, 6H), 2.84 (d, J=6.5 Hz, 3H), 1.55 (d, J=7.0 Hz, 3H).

HRMS m/z (ESI) calcd for $C_{19}H_{23}N_3O_4S_3$ $[M+H]^+$ 454.0929 found: 454.0928.

The detailed preparative method is same as that of compound 1, with a yield of 80.9%.

Compound 17: 2-(1-((4-(pyridin-4-yl)piperazin-1-yl)sulfonyl)ethyl)-10H-phenothiazine The synthetic route is as follows:

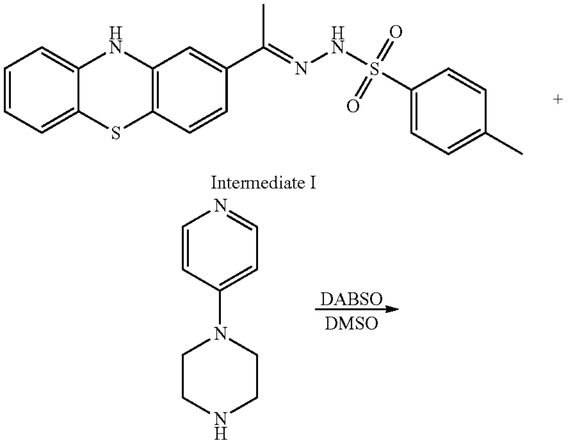

-continued

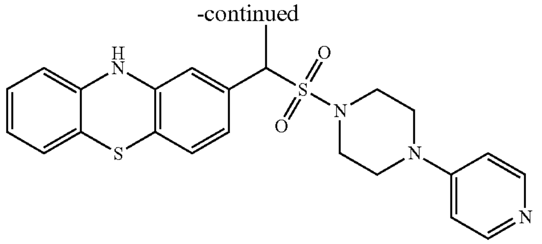

17

$^1H$ NMR and HRMS data of compound 17 are as follows:

$^1H$ NMR (400 MHz, DMSO-$d_6$) δ 8.70 (s, 1H), 8.15 (t, J=6.6 Hz, 2H), 6.98 (td, J=7.8, 1.4 Hz, 1H), 6.93-6.87 (m, 2H), 6.83 (dd, J=8.0, 1.6 Hz, 1H), 6.79 (d, J=6.0 Hz, 3H), 6.77-6.72 (m, 1H), 6.66 (d, J=7.8 Hz, 1H), 4.49 (q, J=7.0 Hz, 1H), 3.32-3.25 (m, 4H), 3.25-3.17 (m, 2H), 3.06 (dd, J=11.9, 6.4 Hz, 2H), 1.56 (d, J=7.0 Hz, 3H).

HRMS m/z (ESI) calcd for $C_{23}H_{24}N_4O_2S_2$ $[M+H]^+$ 453.1419 found: 453.1423.

The detailed preparative method is same as that of compound 1, with a yield of 78.4%.

Compound 18: 1-((1-(10H-phenothiazin-2-yl)ethyl)sulfonyl)-4-piperidinol

The synthetic route is as follows:

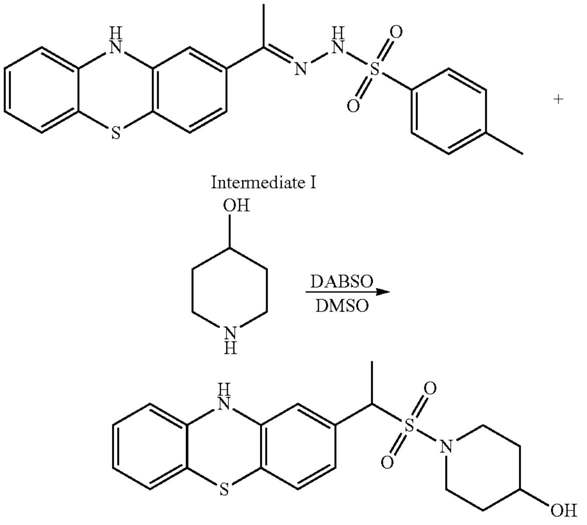

18

$^1H$ NMR and HRMS data of compound 18 are as follows:

$^1H$ NMR (400 MHz, DMSO-$d_6$) δ 8.68 (s, 1H), 6.98 (t, J=7.2 Hz, 1H), 6.89 (d, J=7.8 Hz, 2H), 6.83-6.71 (m, 3H), 6.68 (d, J=7.8 Hz, 1H), 4.68 (d, J=3.9 Hz, 1H), 4.37 (d, J=7.0 Hz, 1H), 3.61-3.48 (m, 1H), 3.34-3.19 (m, 2H), 2.91 (t, J=9.3 Hz, 1H), 2.73 (t, J=9.4 Hz, 1H), 1.63 (d, J=13.0 Hz, 2H), 1.52 (d, J=7.0 Hz, 3H), 1.29 (ddd, J=19.8, 14.0, 9.7 Hz, 2H).

HRMS m/z (ESI) calcd for $C_{19}H_{22}N_2O_3S_2$ $[M+H]^+$ 391.1150 found: 391.1152.

The detailed preparative method is same as that of compound 1, with a yield of 61.4%.

Compound 19 (4-((1-(10H-phenothiazin-2-yl)ethyl) sulfonyl)piperazin-1-yl)(2,3-dihydrobenzo[b][1,4] dioxane-6-yl)ketone The synthetic route is as follows:

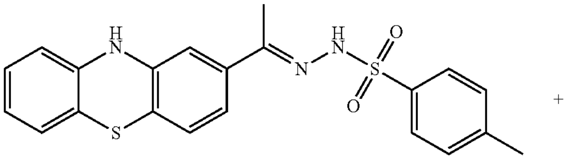

Intermediate I

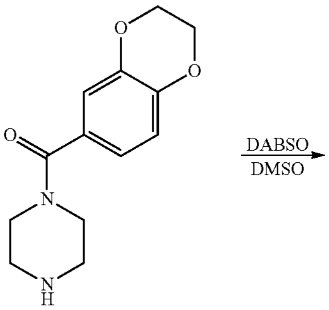

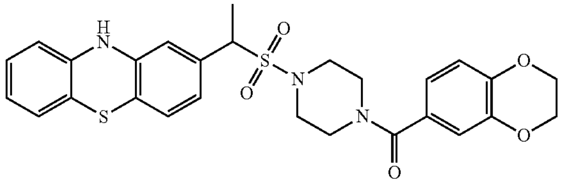

19

$^1$H NMR and HRMS data of compound 19 are as follows: $^1$H NMR (400 MHz, DMSO-$d_6$) δ 8.70 (d, J=7.2 Hz, 1H), 7.02-6.95 (m, 1H), 6.95-6.87 (m, 3H), 6.87-6.81 (m, 4H), 6.81-6.78 (m, 1H), 6.74 (dd, J=10.8, 4.1 Hz, 1H), 6.68 (d, J=7.8 Hz, 1H), 5.16 (ddd, J=16.0, 6.5, 2.5 Hz, 1H), 4.53-4.41 (m, 1H), 4.34 (ddd, J=11.4, 8.6, 2.5 Hz, 1H), 4.22-4.04 (m, 2H), 3.59 (s, 2H), 3.46 (s, 2H), 3.28-3.02 (m, 4H), 1.55 (d, J=7.0 Hz, 3H).

HRMS m/z (ESI) calcd for $C_{27}H_{27}N_3O_5S_2$ $[M+H]^+$ 538.1470 found: 538.1473.

The detailed preparative method is same as that of compound 1, with a yield of 78.1%.

Compound 20: 2-(1-(thiomorpholinesulfonyl)ethyl)-10H-phenothiazine

The synthetic route is as follows:

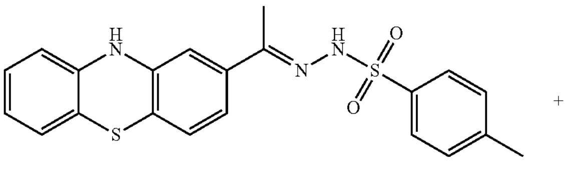

Intermediate I

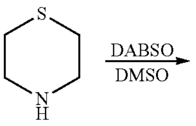

-continued

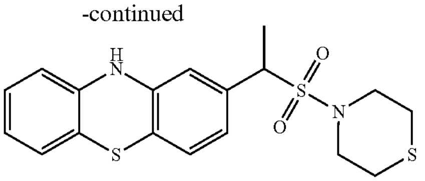

20

$^1$H NMR and HRMS data of compound 20 are as follows:

$^1$H NMR (400 MHz, DMSO-$d_6$) δ 8.69 (s, 1H), 7.02-6.95 (m, 1H), 6.91 (t, J=8.4 Hz, 2H), 6.82 (dd, J=8.0, 1.5 Hz, 1H), 6.78-6.72 (m, 2H), 6.68 (d, J=7.9 Hz, 1H), 4.40 (q, J=7.0 Hz, 1H), 3.39-3.31 (m, 2H), 3.26-3.12 (m, 2H), 2.58-2.52 (m, 2H), 2.50-2.44 (m, 2H), 1.52 (d, J=7.0 Hz, 3H).

HRMS m/z (ESI) calcd for $C_{18}H_{20}N_2O_2S_3$ $[M+H]^+$ 393.0765 found: 393.0767.

The detailed preparative method is same as that of compound 1, with a yield of 64.5%.

Compound 21: 2-(1-(pyrrolin-1-ylsulfonyl)ethyl)-10H-phenothiazine

The synthetic route is as follows:

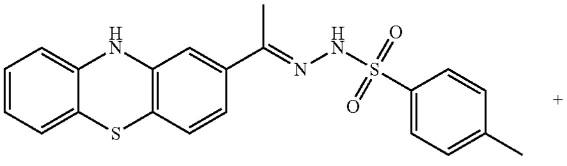

Intermediate I

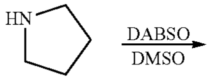

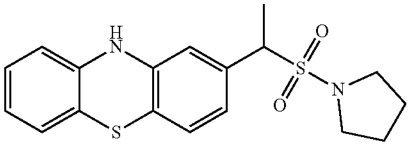

21

$^1$H NMR and HRMS data of compound 21 are as follows:

$^1$H NMR (400 MHz, DMSO-$d_6$) δ 8.69 (s, 1H), 6.98 (td, J=7.8, 1.3 Hz, 1H), 6.90 (d, J=7.8 Hz, 2H), 6.86-6.72 (m, 3H), 6.68 (d, J=7.9 Hz, 1H), 4.49 (q, J=7.0 Hz, 1H), 3.28-3.13 (m, 2H), 3.01-2.84 (m, 2H), 1.72 (dd, J=12.7, 6.1 Hz, 4H), 1.54 (d, J=7.1 Hz, 3H).

HRMS m/z (ESI) calcd for $C_{18}H_{20}N_2O_2S_2$ $[M+H]^+$ 361.1004 found: 361.1007.

The detailed preparative method is same as that of compound 1, with a yield of 74.8%.

Compound 22: 2-(1-((4-(2-methoxylphenyl)piperazin-1-yl)sulfonyl)ethyl)-10H-phenothiazine The synthetic route is as follows:

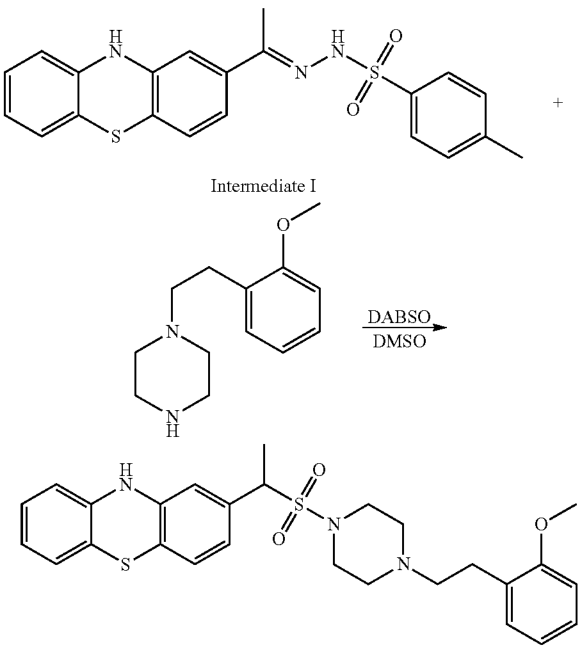

22

$^1$H NMR and HRMS data of compound 22 are as follows: $^1$H NMR (400 MHz, DMSO-$d_6$) δ 8.69 (s, 1H), 7.41-7.30 (m, 2H), 7.26 (t, J=6.1 Hz, 3H), 6.98 (t, J=7.6 Hz, 1H), 6.91 (dd, J=7.7, 2.7 Hz, 2H), 6.82 (d, J=8.0 Hz, 1H), 6.80-6.72 (m, 2H), 6.68 (d, J=7.8 Hz, 1H), 4.40 (q, J=6.9 Hz, 1H), 4.32 (dd, J=7.8, 3.7 Hz, 1H), 3.08 (s, 3H), 3.05 (d, J=6.4 Hz, 2H), 2.92 (d, J=5.3 Hz, 2H), 2.61 (d, J=8.0 Hz, 1H), 2.50-2.28 (m, 6H), 1.53 (d, J=7.0 Hz, 3H).

HRMS m/z (ESI) calcd for $C_{27}H_{31}N_3O_3S_2$ $[M+H]^+$ 510.1885 found: 510.1886.

The detailed preparative method is same as that of compound 1, with a yield of 68.8%.

Compound 23: ethyl 1-((1-(10H-phenothiazin-2-yl)ethyl)sulfonyl)piperazin-4-formic acid The synthetic route is as follows:

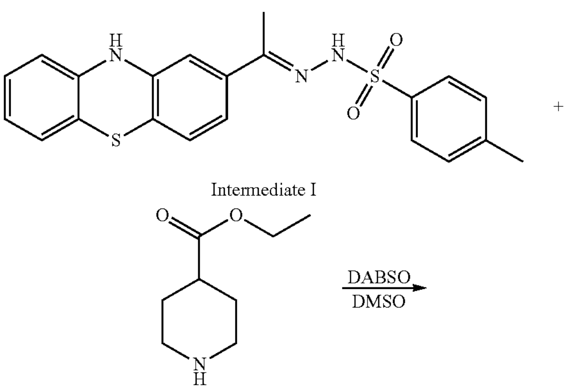

-continued

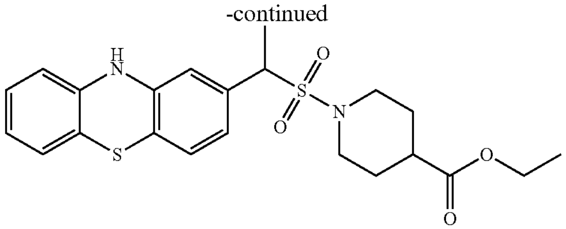

23

$^1$H NMR and HRMS data of compound 23 are as follows: $^1$H NMR (400 MHz, DMSO-$d_6$) δ 8.67 (s, 1H), 7.06-6.94 (m, 1H), 6.89 (dd, J=7.3, 3.9 Hz, 2H), 6.85-6.70 (m, 3H), 6.68 (d, J=7.9 Hz, 1H), 4.39 (q, J=7.0 Hz, 1H), 4.04 (q, J=7.1 Hz, 2H), 3.38 (dd, J=12.4, 4.6 Hz, 2H), 2.88 (t, J=10.6 Hz, 1H), 2.63 (t, J=10.7 Hz, 1H), 2.48-2.36 (m, 1H), 1.77 (t, J=10.7 Hz, 2H), 1.52 (d, J=7.0 Hz, 3H), 1.48-1.32 (m, 2H), 1.16 (dd, J=9.1, 5.1 Hz, 3H).

HRMS m/z (ESI) calcd for $C_{22}H_{26}N_2O_4S_2$ $[M+H]^+$ 447.1412 found: 447.1415.

The detailed preparative method is same as that of compound 1, with a yield of 79.2%.

Compound 24: 2-(1-((4-phenylpiperazin-1-yl)sulfonyl)ethyl)-10H-phenothiazine

The synthetic route is as follows:

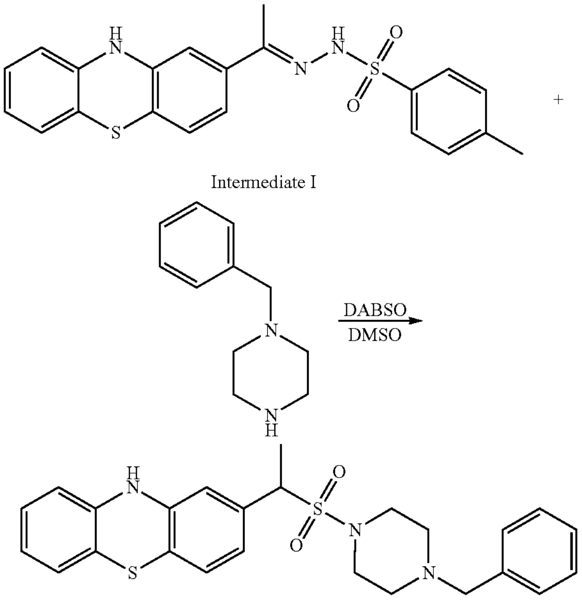

24

$^1$H NMR and HRMS data of compound 24 are as follows: $^1$H NMR (400 MHz, DMSO-$d_6$) δ 8.70 (s, 1H), 7.36-7.27 (m, 2H), 7.27-7.17 (m, 3H), 7.05-6.95 (m, 1H), 6.91 (d, J=7.8 Hz, 2H), 6.82 (dd, J=8.0, 1.5 Hz, 1H), 6.80-6.73 (m, 2H), 6.69 (d, J=7.9 Hz, 1H), 4.40 (d, J=7.1 Hz, 1H), 3.44 (q, J=13.2 Hz, 2H), 3.10 (dd, J=8.1, 4.5 Hz, 2H), 2.97 (d, J=5.9 Hz, 2H), 2.28 (dq, J=14.5, 8.1 Hz, 4H), 1.53 (d, J=7.0 Hz, 3H).

HRMS m/z (ESI) calcd for $C_{25}H_{27}N_3O_2S_2$ $[M+H]^+$ 466.1623 found: 466.1627.

The detailed preparative method is same as that of compound 1, with a yield of 69.8%.

Compound 25: 1-(4-((1-(10H-phenothiazin-2-yl)ethyl)sulfonyl)-1,4-homopiperazin-1-yl)-1-ethanone The synthetic route is as follows:

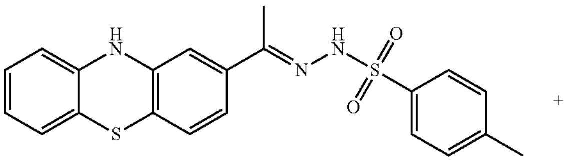

Intermediate I

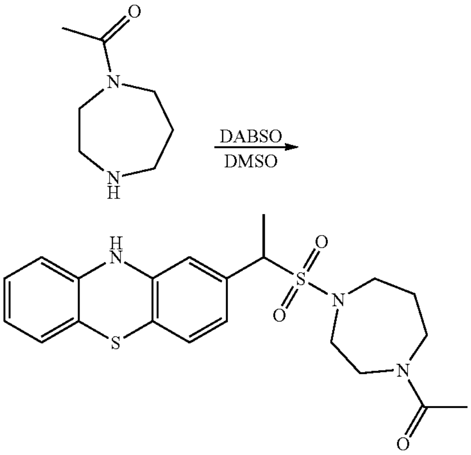

25

$^1$H NMR and HRMS data of compound 25 are as follows:

$^1$H NMR (400 MHz, DMSO-$d_6$) δ 8.66 (s, 1H), 6.98 (t, J=7.6 Hz, 1H), 6.90 (d, J=7.7 Hz, 2H), 6.82-6.71 (m, 3H), 6.67 (d, J=7.9 Hz, 1H), 4.47 (dd, J=7.0, 3.7 Hz, 1H), 3.52-3.36 (m, 4H), 3.11 (dd, J=30.1, 25.6 Hz, 4H), 1.97 (t, J=11.3 Hz, 3H), 1.73-1.65 (m, 1H), 1.64-1.56 (m, 1H), 1.53 (dd, J=7.0, 3.2 Hz, 3H).

HRMS m/z (ESI) calcd for $C_{21}H_{25}N_3O_3S_2$ $[M+H]^+$ 432.1416 found: 432.1419.

The detailed preparative method is same as that of compound 1, with a yield of 81.5%.

Compound 26: 2-(1-((4-diphenylmethylpiperazin-1-yl)sulfonyl)ethyl)-10H-phenothiazine The synthetic route is as follows:

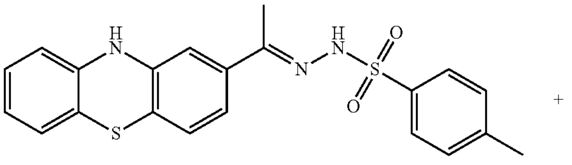

Intermediate I

-continued

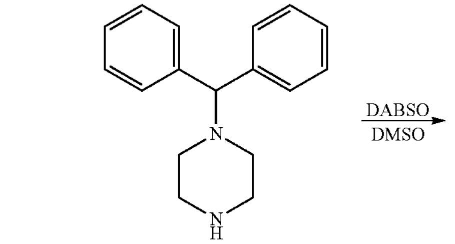

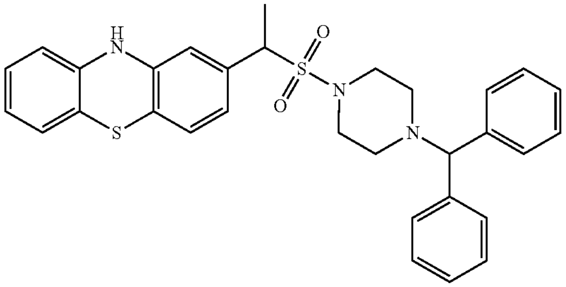

26

$^1$H NMR and HRMS data of compound 26 are as follows: $^1$H NMR (400 MHz, DMSO-$d_6$) δ 8.75 (s, 1H), 7.41-7.29 (m, 4H), 7.26 (t, J=7.5 Hz, 4H), 7.16 (dd, J=7.9, 6.0 Hz, 2H), 7.01 (td, J=7.8, 1.3 Hz, 1H), 6.93 (d, J=7.8 Hz, 2H), 6.83 (dd, J=8.0, 1.4 Hz, 1H), 6.82-6.71 (m, 3H), 4.40 (q, J=6.9 Hz, 1H), 4.27 (s, 1H), 3.21-3.07 (m, 2H), 2.99 (d, J=6.8 Hz, 2H), 2.30-2.07 (m, 4H), 1.53 (d, J=7.0 Hz, 3H).

HRMS m/z (ESI) calcd for $C_{31}H_{31}N_3O_2S_2$ $[M+H]^+$ 542.1936 found: 542.1938.

The detailed preparative method is same as that of compound 1, with a yield of 81.4%.

Compound 27: t-butyl 4-((1-(10H-phenothiazin-2-yl)ethyl)sulfonyl)piperazin-1-carbamate The synthetic route is as follows:

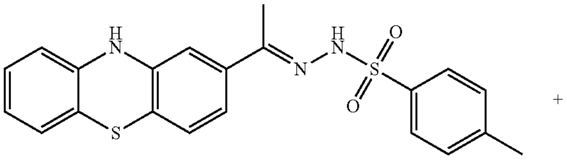

Intermediate I

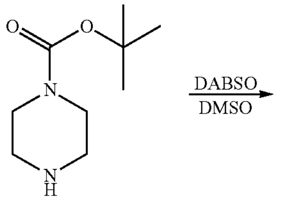

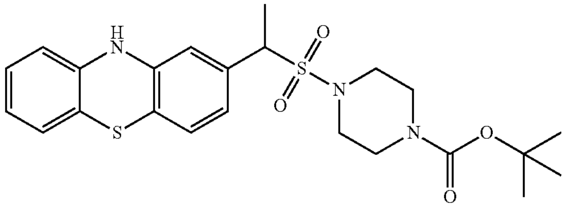

27

$^{1}H$ NMR and HRMS data of compound 27 are as follows:

$^{1}H$ NMR (400 MHz, DMSO-$d_6$) δ 8.68 (s, 1H), 6.98 (t, J=7.6 Hz, 1H), 6.90 (d, J=7.7 Hz, 2H), 6.82 (d, J=8.0 Hz, 1H), 6.79-6.70 (m, 2H), 6.67 (d, J=7.8 Hz, 1H), 4.43 (q, J=6.9 Hz, 1H), 3.25 (d, J=5.6 Hz, 4H), 3.07 (dd, J=12.1, 4.9 Hz, 2H), 2.92 (s, 2H), 1.53 (d, J=7.0 Hz, 3H), 1.39 (d, J=16.1 Hz, 10H).

HRMS m/z (ESI) calcd for $C_{23}H_{29}N_3O_4S_2$ $[M+H]^+$ 476.1678 found: 476.1679.

The detailed preparative method is same as that of compound 1, with a yield of 71.5%.

Compound 28: 2-(1-((4-phenylpiperazin-1-yl)sulfonyl)ethyl)-10H-phenothiazine

The synthetic route is as follows:

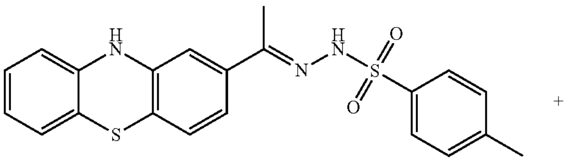

Intermediate I

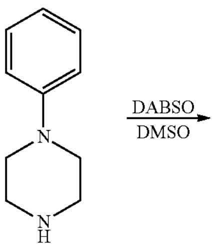

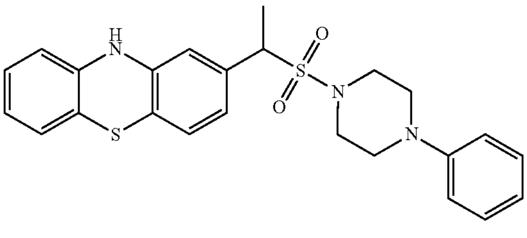

28

$^{1}H$ NMR and HRMS data of compound 28 are as follows:

$^{1}H$ NMR (400 MHz, DMSO-$d_6$) δ 8.70 (s, 1H), 7.20 (t, J=7.9 Hz, 2H), 6.97 (dd, J=10.9, 4.3 Hz, 1H), 6.91 (d, J=7.9 Hz, 4H), 6.87-6.71 (m, 4H), 6.67 (d, J=7.6 Hz, 1H), 4.48 (q, J=7.0 Hz, 1H), 3.29-3.18 (m, 2H), 3.08 (t, J=9.6 Hz, 6H), 1.56 (d, J=7.0 Hz, 3H).

HRMS m/z (ESI) calcd for $C_{24}H_{25}N_3O_2S_2$ $[M+H]^+$ 452.1466 found: 452.1469.

The detailed preparative method is same as that of compound 1, with a yield of 73.8%.

Compound 29: t-butyl ((3S)-1-((1-(10H-phenothiazin-2-yl)ethyl)sulfonyl)piperidin-3-yl) carbamate The synthetic route is as follows:

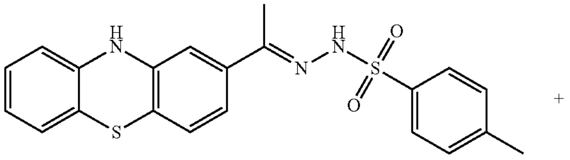

Intermediate I

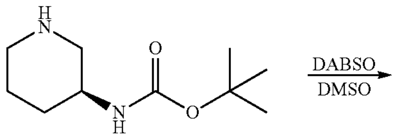

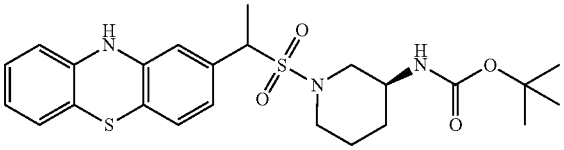

29

$^{1}H$ NMR and HRMS data of compound 29 are as follows:

$^{1}H$ NMR (400 MHz, DMSO-$d_6$) δ 8.67 (s, 1H), 6.98 (t, J=7.6 Hz, 1H), 6.89 (d, J=7.5 Hz, 2H), 6.86-6.71 (m, 4H), 6.67 (d, J=7.8 Hz, 1H), 4.46-4.28 (m, 1H), 3.59-3.34 (m, 2H), 3.30-3.15 (m, 2H), 2.71 (t, J=10.9 Hz, 1H), 2.41-2.17 (m, 1H), 1.75-1.57 (m, 2H), 1.51 (d, J=7.0 Hz, 3H), 1.36 (d, J=13.0 Hz, 9H).

HRMS m/z (ESI) calcd for $C_{24}H_{31}N_3O_4S_2$ $[M+H]^+$ 490.1834 found: 490.1835.

The detailed preparative method is same as that of compound 1, with a yield of 82.8%.

Compound 30: 1-((1-(10H-phenothiazin-2-yl)ethyl)sulfonyl)-4-(4-chlorophenyl)-4-piperidinol The synthetic route is as follows:

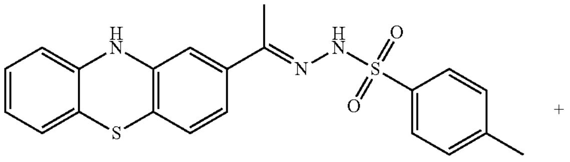

Intermediate I

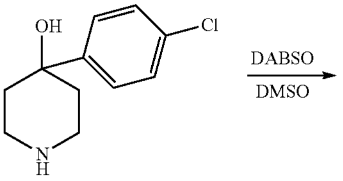

-continued

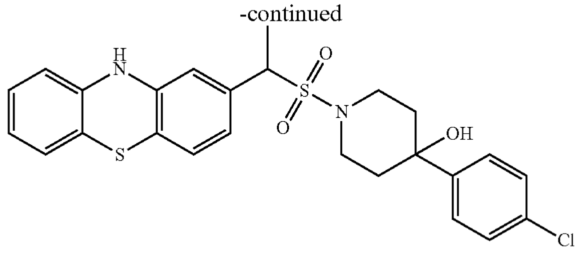

30

$^1$H NMR and HRMS data of compound 30 are as follows:

$^1$H NMR (400 MHz, DMSO-$d_6$) δ 8.70 (s, 1H), 7.43 (d, J=8.6 Hz, 2H), 7.32 (d, J=8.6 Hz, 2H), 7.04-6.96 (m, 1H), 6.89 (dt, J=9.4, 8.0 Hz, 3H), 6.81 (s, 1H), 6.78-6.71 (m, 1H), 6.68 (d, J=7.9 Hz, 1H), 5.13 (s, 1H), 4.44 (q, J=6.9 Hz, 1H), 3.45 (d, J=11.9 Hz, 1H), 3.35 (s, 1H), 3.27-3.13 (m, 1H), 2.88 (t, J=11.4 Hz, 1H), 1.76 (td, J=13.0, 4.8 Hz, 1H), 1.66 (td, J=12.7, 4.2 Hz, 1H), 1.54 (t, J=12.9 Hz, 5H).

HRMS m/z (ESI) calcd for $C_{25}H_{25}ClN_2O_3S_2$ $[M+H]^+$ 501.1073 found: 501.1075.

The detailed preparative method is same as that of compound 1, with a yield of 80.7%.

Compound 31: t-butyl ((3S)-1-((1-(10H-phenothiazin-2-yl)ethyl)sulfonyl)pyrrolin-3-yl)carbamate The synthetic route is as follows:

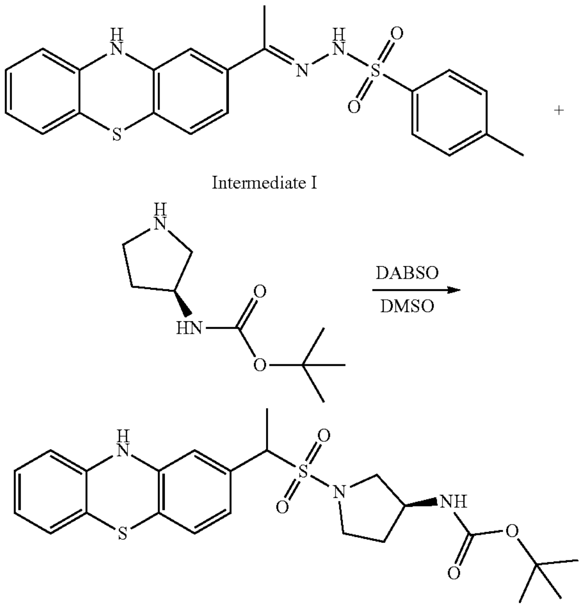

31

$^1$H NMR and HRMS data of compound 31 are as follows:

$^1$H NMR (400 MHz, DMSO-$d_6$) δ 8.68 (s, 1H), 7.09 (s, 1H), 7.03-6.95 (m, 1H), 6.94-6.85 (m, 2H), 6.82 (d, J=7.9 Hz, 1H), 6.76 (dd, J=14.6, 7.1 Hz, 2H), 6.68 (d, J=7.8 Hz, 1H), 4.47 (q, J=7.0 Hz, 1H), 3.90 (dd, J=23.0, 5.7 Hz, 1H), 3.48 (dd, J=9.5, 6.4 Hz, 1H), 3.31-3.19 (m, 1H), 3.19-3.07 (m, 1H), 3.02 (d, J=5.2 Hz, 1H), 2.88 (dd, J=16.0, 9.4 Hz, 1H), 1.93 (ddd, J=27.8, 13.0, 6.7 Hz, 1H), 1.77-1.62 (m, 1H), 1.53 (d, J=7.0 Hz, 3H), 1.36 (d, J=11.5 Hz, 9H).

HRMS m/z (ESI) calcd for $C_{23}H_{29}N_3O_4S_2$ $[M+H]^+$ 476.1678 found: 476.1672.

The detailed preparative method is same as that of compound 1, with a yield of 77.2%.

Compound 32: t-butyl ((3R)-1-((1-(10H-phenothiazin-2-yl)ethyl)sulfonyl)piperidin-3-yl)carbamate The synthetic route is as follows:

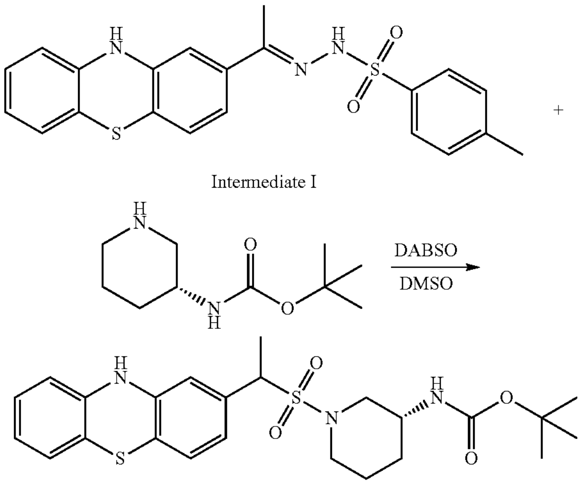

32

$^1$H NMR and HRMS data of compound 32 are as follows:

$^1$H NMR (400 MHz, DMSO-$d_6$) δ 8.68 (s, 1H), 6.98 (t, J=7.6 Hz, 1H), 6.89 (d, J=7.5 Hz, 2H), 6.86-6.70 (m, 4H), 6.67 (d, J=7.7 Hz, 1H), 4.48-4.29 (m, 1H), 3.39 (s, 1H), 3.27 (d, J=28.6 Hz, 2H), 2.31 (dd, J=39.0, 16.7 Hz, 1H), 1.68 (s, 2H), 1.51 (d, J=7.0 Hz, 3H), 1.43-1.16 (m, 11H).

HRMS m/z (ESI) calcd for $C_{24}H_{31}N_3O_4S_2$ $[M+H]^+$ 490.1834 found: 490.1836.

The detailed preparative method is same as that of compound 1, with a yield of 66.2%.

Compound 33: t-butyl (((3R)-1-((1-(10H-phenothiazin-2-yl)ethyl)sulfonyl)pyrrolin-3-yl)methyl)carbamate The synthetic route is as follows:

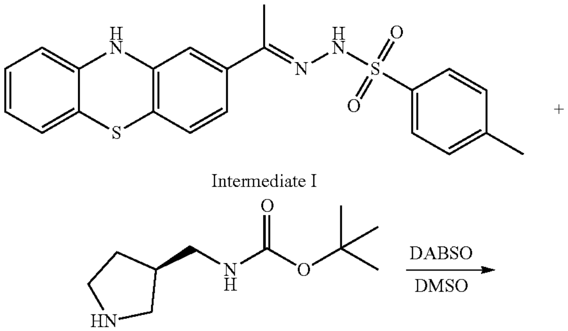

-continued

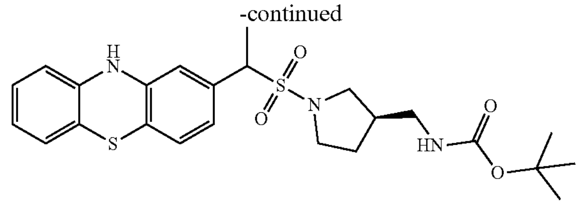

33

$^1H$ NMR and HRMS data of compound 33 are as follows: $^1H$ NMR (400 MHz, DMSO-$d_6$) δ 8.68 (s, 1H), 6.98 (t, J=7.6 Hz, 1H), 6.89 (dd, J=7.9, 3.4 Hz, 2H), 6.78 (ddd, J=16.6, 14.6, 6.7 Hz, 4H), 6.67 (d, J=7.9 Hz, 1H), 4.53-4.39 (m, 1H), 3.83 (s, 1H), 3.28 (s, 1H), 3.15 (s, 1H), 3.10-3.00 (m, 1H), 2.95-2.73 (m, 1H), 1.77 (s, 2H), 1.62 (s, 2H), 1.54 (d, J=6.9 Hz, 3H), 1.37 (t, J=11.9 Hz, 9H).

HRMS m/z (ESI) calcd for $C_{24}H_{31}N_3O_4S_2$ $[M+H]^+$ 490.1834 found: 490.1835.

The detailed preparative method is same as that of compound 1, with a yield of 76.4%.

Compound 34: 2-(1-((4-(4-fluorophenyl)piperazin-1-yl)sulfonyl)ethyl)-10H-phenothiazine The synthetic route is as follows:

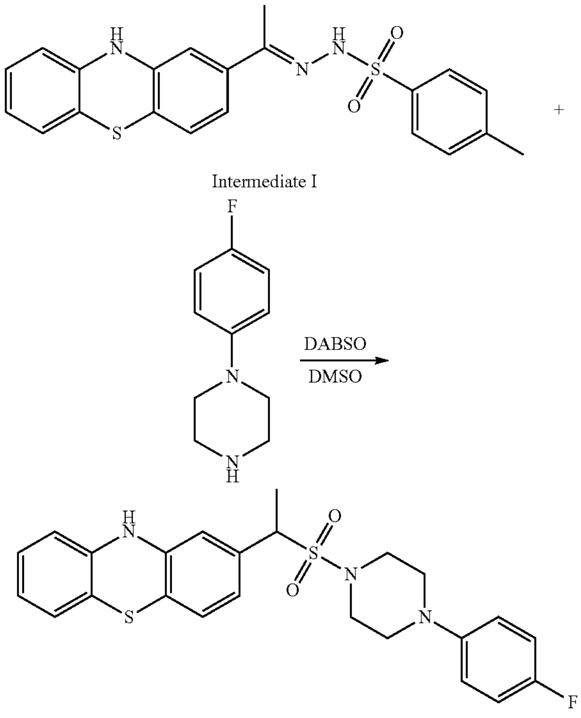

34

$^1H$ NMR and HRMS data of compound 34 are as follows: $^1H$ NMR (400 MHz, DMSO-$d_6$) δ 8.70 (s, 1H), 7.01 (dt, J=15.4, 8.1 Hz, 3H), 6.96-6.88 (m, 4H), 6.85 (d, J=8.1 Hz, 1H), 6.80 (s, 1H), 6.75 (t, J=7.5 Hz, 1H), 6.67 (d, J=7.8 Hz, 1H), 4.48 (q, J=6.9 Hz, 1H), 3.28-3.18 (m, 2H), 3.16-3.06 (m, 2H), 3.05-2.93 (m, 4H), 1.56 (d, J=7.0 Hz, 3H).

HRMS m/z (ESI) calcd for $C_{24}H_{24}FN_3O_2S_2$ $[M+H]^+$ 470.1372 found: 470.1373.

The detailed preparative method is same as that of compound 1, with a yield of 77.8%.

Compound 35: t-butyl ((1-((1-(10H-phenothiazin-2-yl)ethyl)sulfonyl)piperidin-3-yl)methyl)carbamate The synthetic route is as follows:

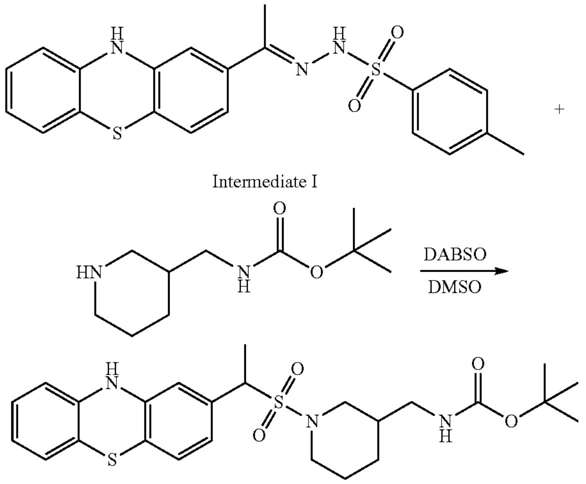

35

$^1H$ NMR and HRMS data of compound 35 are as follows: $^1H$ NMR (400 MHz, DMSO-$d_6$) δ 8.67 (d, J=9.4 Hz, 1H), 6.98 (t, J=7.6 Hz, 1H), 6.89 (t, J=6.1 Hz, 2H), 6.86-6.80 (m, 1H), 6.80-6.71 (m, 3H), 6.68 (d, J=7.9 Hz, 1H), 4.34 (dd, J=6.9, 4.5 Hz, 1H), 3.49 (dd, J=23.4, 11.7 Hz, 1H), 2.99-2.64 (m, 3H), 2.45-2.25 (m, 1H), 1.69-1.47 (m, 7H), 1.37 (d, J=4.8 Hz, 9H), 1.25 (dd, J=17.5, 5.2 Hz, 2H).

HRMS m/z (ESI) calcd for $C_{25}H_{33}N_3O_4S_2$ $[M+H]^+$ 504.1991 found: 504.1995.

The detailed preparative method is same as that of compound 1, with a yield of 74.9%.

Compound 36: 2-(1-((4-(4-chlorobenzyl)piperazin-1-yl)sulfonyl)ethyl)-10H-phenothiazine The synthetic route is as follows:

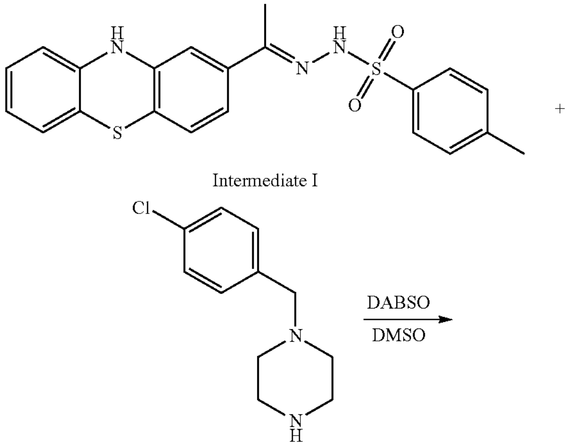

-continued

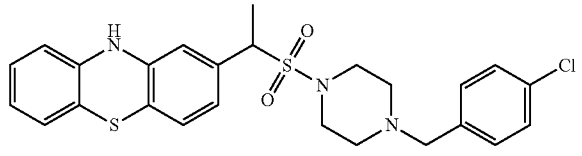

36

$^1$H NMR and HRMS data of compound 36 are as follows:

$^1$H NMR (400 MHz, DMSO-$d_6$) δ 8.70 (s, 1H), 7.35 (d, J=8.4 Hz, 2H), 7.26 (d, J=8.4 Hz, 2H), 6.99 (td, J=7.9, 1.3 Hz, 1H), 6.91 (d, J=7.9 Hz, 2H), 6.82 (dd, J=8.0, 1.5 Hz, 1H), 6.79-6.73 (m, 2H), 6.73-6.64 (m, 1H), 4.40 (q, J=7.0 Hz, 1H), 3.43 (q, J=13.4 Hz, 2H), 3.16-3.04 (m, 2H), 2.97 (d, J=5.1 Hz, 2H), 2.38-2.16 (m, 4H), 1.53 (d, J=7.0 Hz, 3H).

HRMS m/z (ESI) calcd for $C_{25}H_{26}ClN_3O_2S_2$ $[M+H]^+$ 500.1233 found: 500.1237.

The detailed preparative method is same as that of compound 1, with a yield of 63.4%.

Compound 37: t-butyl (1-((1-(10H-phenothiazin-2-yl)ethyl)sulfonyl)piperidin-4-yl)carbamate The synthetic route is as follows:

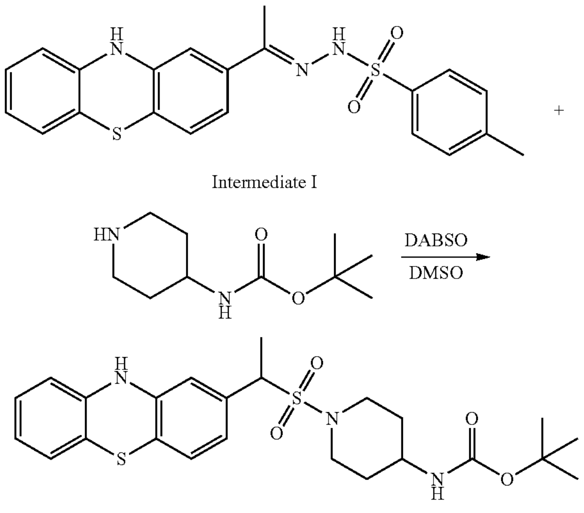

37

$^1$H NMR and HRMS data of compound 37 are as follows:

$^1$H NMR (400 MHz, DMSO-$d_6$) δ 8.67 (s, 1H), 6.98 (t, J=7.3 Hz, 1H), 6.90 (d, J=7.7 Hz, 2H), 6.81 (t, J=9.3 Hz, 2H), 6.74 (d, J=9.8 Hz, 2H), 6.68 (d, J=7.8 Hz, 1H), 4.37 (q, J=6.7 Hz, 1H), 3.50 (d, J=12.2 Hz, 1H), 3.38 (d, J=12.6 Hz, 1H), 2.86 (t, J=11.2 Hz, 1H), 1.67 (dd, J=24.3, 11.3 Hz, 2H), 1.52 (d, J=6.9 Hz, 3H), 1.38 (d, J=8.6 Hz, 10H), 1.33-1.17 (m, 3H).

HRMS m/z (ESI) calcd for $C_{24}H_{31}N_3O_4S_2$ $[M+H]^+$ 490.1834 found: 490.1838.

The detailed preparative method is same as that of compound 1, with a yield of 83.8%.

Compound 38: (1-((1-(10H-phenothiazin-2-yl)ethyl)sulfonyl)piperidin-3-yl)methanol The synthetic route is as follows:

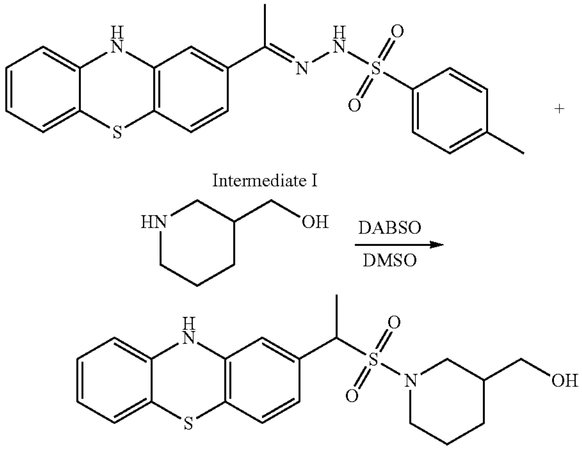

38

$^1$H NMR and HRMS data of compound 38 are as follows:

$^1$H NMR (400 MHz, DMSO-$d_6$) δ 8.67 (d, J=4.7 Hz, 1H), 6.98 (t, J=7.6 Hz, 1H), 6.90 (d, J=7.7 Hz, 2H), 6.84-6.71 (m, 3H), 6.68 (d, J=7.9 Hz, 1H), 4.60-4.45 (m, 1H), 4.43-4.27 (m, 1H), 3.64 (d, J=9.6 Hz, 1H), 3.55 (d, J=9.4 Hz, 1H), 3.41 (d, J=12.1 Hz, 1H), 3.32-3.23 (m, 2H), 3.23-3.06 (m, 1H), 2.74 (t, J=10.8 Hz, 1H), 2.43-2.22 (m, 1H), 1.69-1.56 (m, 2H), 1.50 (t, J=10.8 Hz, 4H), 1.37-1.23 (m, 1H).

HRMS m/z (ESI) calcd for $C_{20}H_{24}N_2O_3S_2$ $[M+H]^+$ 405.1307 found: 405.1302.

The detailed preparative method is same as that of compound 1, with a yield of 84.7%.

Compound 39: ethyl (3R)-1-((1-(10H-phenothiazin-2-yl)ethyl)sulfonyl)piperidin-3-formate The synthetic route is as follows:

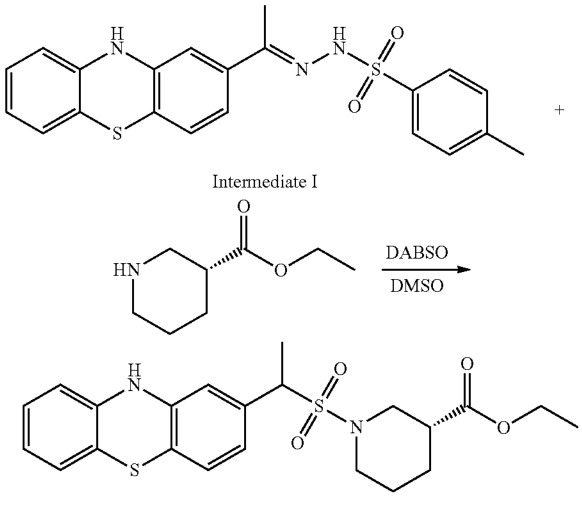

39

$^1$H NMR and HRMS data of compound 39 are as follows:

$^1$H NMR (400 MHz, DMSO-$d_6$) δ 8.68 (d, J=2.2 Hz, 1H), 6.98 (dd, J=11.1, 4.1 Hz, 1H), 6.91 (d, J=2.6 Hz, 1H), 6.89 (s, 1H), 6.85-6.71 (m, 3H), 6.68 (d, J=7.9 Hz, 1H), 4.41 (q, J=6.9 Hz, 1H), 4.15-3.92 (m, 2H), 3.50 (t, J=9.0 Hz, 1H), 3.02-2.78 (m, 1H), 2.74-2.53 (m, 1H), 2.49-2.26 (m, 2H), 1.83 (s, 1H), 1.61 (dd, J=19.6, 9.0 Hz, 1H), 1.52 (d, J=7.0 Hz, 3H), 1.40 (dd, J=23.5, 13.1 Hz, 2H), 1.17-1.06 (m, 3H).

HRMS m/z (ESI) calcd for $C_{22}H_{26}N_2O_4S_2$ $[M+H]^+$ 447.1412 found: 447.1416.

The detailed preparative method is same as that of compound 1, with a yield of 74.4%.

Compound 40: 1-((1-(10H-phenothiazin-2-yl)ethyl)sulfonyl)piperidin-3-ol

The synthetic route is as follows:

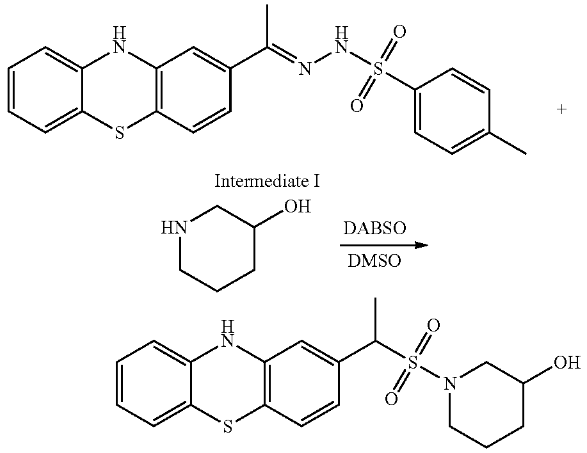

40

$^1$H NMR and HRMS data of compound 40 are as follows:

$^1$H NMR (400 MHz, DMSO-$d_6$) δ 8.67 (s, 1H), 6.98 (t, J=7.1 Hz, 1H), 6.90 (d, J=7.8 Hz, 2H), 6.81 (d, J=7.7 Hz, 1H), 6.78-6.71 (m, 2H), 6.68 (d, J=7.8 Hz, 1H), 4.91 (dd, J=22.3, 4.1 Hz, 1H), 4.37 (dd, J=7.0, 2.8 Hz, 1H), 3.40 (dd, J=36.2, 10.2 Hz, 2H), 2.80-2.53 (m, 1H), 2.31 (dt, J=23.1, 10.6 Hz, 1H), 1.77 (d, J=9.3 Hz, 1H), 1.61 (dd, J=24.0, 13.7 Hz, 1H), 1.52 (d, J=7.0 Hz, 3H), 1.28 (dd, J=21.9, 11.2 Hz, 1H), 1.16 (dd, J=17.2, 9.9 Hz, 1H).

HRMS m/z (ESI) calcd for $C_{19}H_{22}N_2O_3S_2$ $[M+H]^+$ 391.1150 found: 391.1155.

The detailed preparative method is same as that of compound 1, with a yield of 82.5%.

Compound 41: (3S)-1-((1-(10H-phenothiazin-2-yl)ethyl)sulfonyl)pyrrolin-3-ol

The synthetic route is as follows:

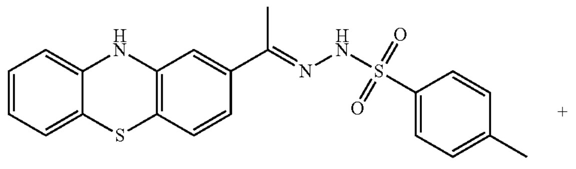

Intermediate I

-continued

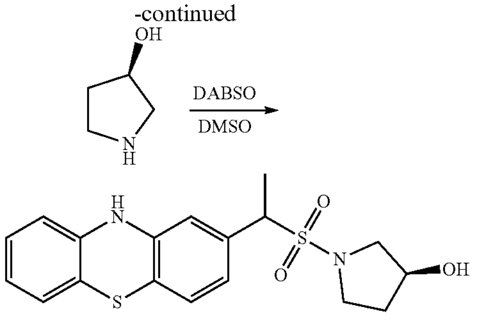

41

$^1$H NMR and HRMS data of compound 41 are as follows:

$^1$H NMR (400 MHz, DMSO-$d_6$) δ 8.66 (s, 1H), 6.99 (td, J=7.9, 1.2 Hz, 1H), 6.94-6.86 (m, 2H), 6.86-6.72 (m, 3H), 6.68 (d, J=7.9 Hz, 1H), 5.00 (d, J=2.9 Hz, 1H), 4.45 (tt, J=6.9, 3.4 Hz, 1H), 4.20 (dd, J=29.5, 2.5 Hz, 1H), 3.31-3.14 (m, 2H), 3.11-2.87 (m, 2H), 1.92-1.63 (m, 2H), 1.55 (d, J=7.0 Hz, 3H).

HRMS m/z (ESI) calcd for $C_{18}H_{20}N_2O_3S_2$ $[M+H]^+$ 377.0994 found: 377.0997.

The detailed preparative method is same as that of compound 1, with a yield of 75.6%.

Compound 42: 2-(1-(((S)-2-methylpyrrolin-1-yl)sulfonyl)ethyl)-10H-phenothiazine

The synthetic route is as follows:

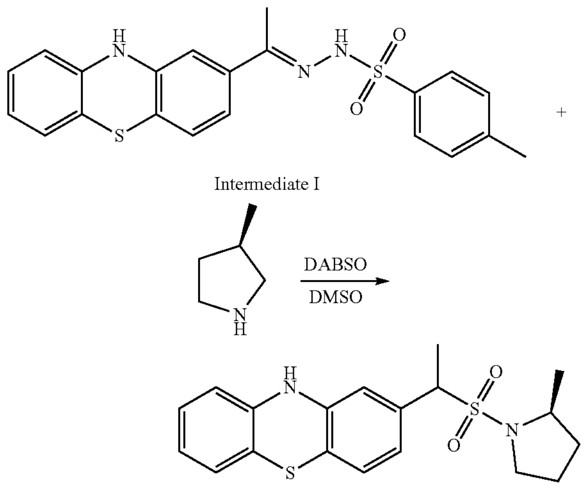

42

$^1$H NMR and HRMS data of compound 42 are as follows:

$^1$H NMR (400 MHz, DMSO-$d_6$) δ 8.69 (d, J=8.2 Hz, 1H), 6.98 (t, J=7.6 Hz, 1H), 6.89 (dd, J=7.7, 3.9 Hz, 2H), 6.81 (dd, J=13.7, 5.9 Hz, 2H), 6.75 (t, J=7.5 Hz, 1H), 6.68 (d, J=7.9 Hz, 1H), 4.44 (dq, J=20.5, 6.9 Hz, 1H), 3.91 (dd, J=10.2, 6.9 Hz, 1H), 3.24-2.99 (m, 1H), 2.96-2.76 (m, 1H), 1.96 (dd, J=12.1, 8.8 Hz, 1H), 1.90-1.66 (m, 2H), 1.69-1.29 (m, 5H), 1.05 (dd, J=9.1, 6.4 Hz, 3H).

HRMS m/z (ESI) calcd for $C_{19}H_{22}N_2O_2S_2$ $[M+H]^+$ 375.1201 found: 375.1205.

The detailed preparative method is same as that of compound 1, with a yield of 80.7%.

Compound 43: 2-(1-([1,4'-dipiperidin]-1'-ylsulfonyl)ethyl)-10H-phenothiazine

The synthetic route is as follows:

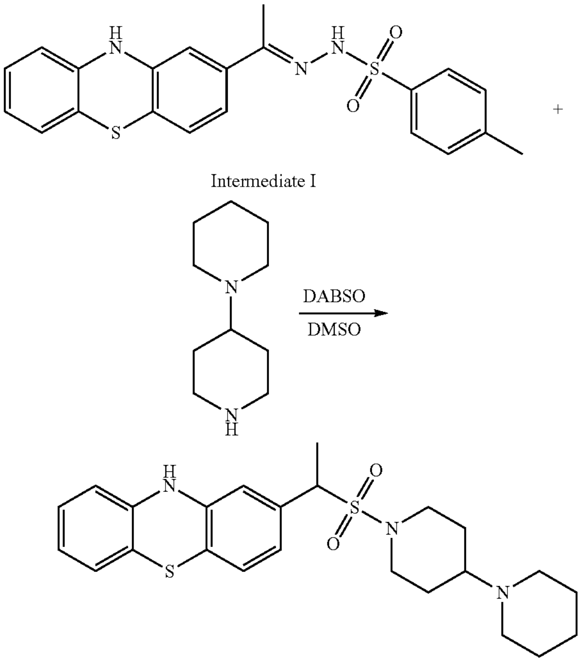

43

$^1$H NMR and HRMS data of compound 43 are as follows:

$^1$H NMR (400 MHz, DMSO-$d_6$) δ 8.68 (s, 1H), 6.98 (td, J=7.9, 1.3 Hz, 1H), 6.89 (d, J=7.9 Hz, 2H), 6.80 (dd, J=8.0, 1.5 Hz, 1H), 6.78-6.71 (m, 2H), 6.71-6.62 (m, 1H), 4.37 (q, J=7.0 Hz, 1H), 3.51 (dd, J=33.0, 12.5 Hz, 2H), 2.77 (t, J=11.2 Hz, 1H), 2.49-2.18 (m, 6H), 1.63 (s, 2H), 1.52 (d, J=7.0 Hz, 3H), 1.42 (d, J=19.7 Hz, 4H), 1.39-1.22 (m, 4H).

HRMS m/z (ESI) calcd for $C_{24}H_{31}N_3O_2S_2$ $[M+H]^+$ 458.1936 found: 458.1939.

The detailed preparative method is same as that of compound 1, with a yield of 74.3%.

Compound 44: (2S,6R)-4-((1-(10H-phenothiazin-2-yl)ethyl)sulfonyl)-2,6-dimethylmorpholine The synthetic route is as follows:

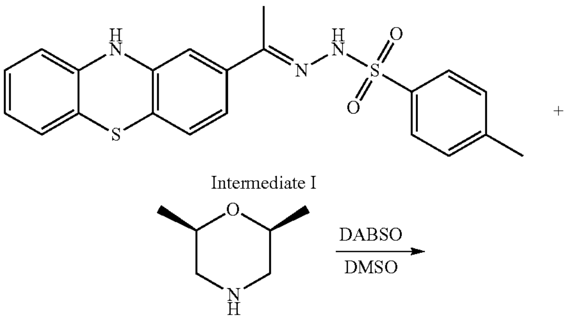

-continued

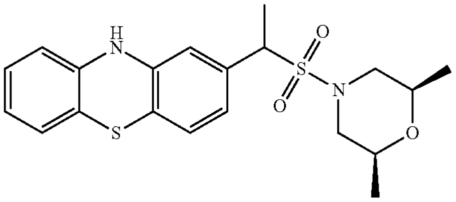

44

$^1$H NMR and HRMS data of compound 44 are as follows:

$^1$H NMR (400 MHz, DMSO-$d_6$) δ 8.69 (s, 1H), 6.98 (dd, J=11.0, 4.2 Hz, 1H), 6.91 (t, J=6.6 Hz, 2H), 6.82 (d, J=7.9 Hz, 1H), 6.79-6.72 (m, 2H), 6.69 (d, J=7.8 Hz, 1H), 4.44 (q, J=6.9 Hz, 1H), 3.54-3.42 (m, 1H), 3.38 (d, J=11.6 Hz, 2H), 3.29 (d, J=15.7 Hz, 2H), 2.24-2.09 (m, 1H), 1.53 (d, J=7.0 Hz, 3H), 1.02 (d, J=6.1 Hz, 3H), 0.98 (d, J=6.2 Hz, 3H).

HRMS m/z (ESI) calcd for $C_{20}H_{24}N_2O_3S_2$ $[M+H]^+$ 405.1307 found: 405.1303.

The detailed preparative method is same as that of compound 1, with a yield of 83.9%.

Compound 45: 2-(1-((4-methylpiperidin-1-yl)sulfonyl)ethyl)-10H-phenothiazine

The synthetic route is as follows:

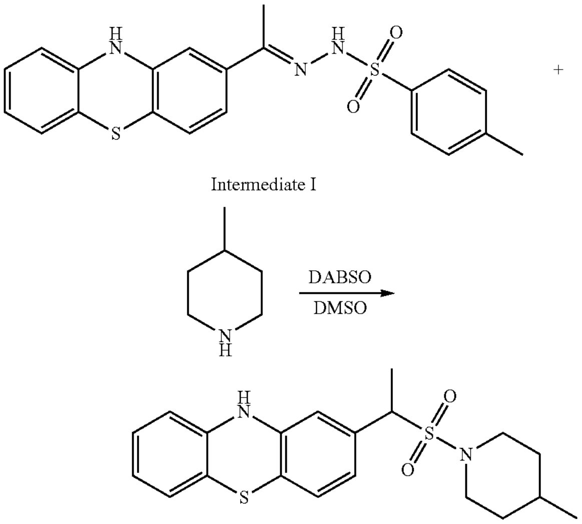

45

$^1$H NMR and HRMS data of compound 45 are as follows:

$^1$H NMR (400 MHz, DMSO-$d_6$) δ 8.69 (s, 1H), 6.94 (d, J=33.6 Hz, 3H), 6.72 (d, J=33.3 Hz, 4H), 4.37 (s, 1H), 3.51 (s, 1H), 3.39 (s, 1H), 2.76 (s, 1H), 2.40 (s, 1H), 1.52 (s, 4H), 1.35 (s, 1H), 1.24 (s, 1H), 0.96 (s, 2H), 0.85 (s, 3H).

HRMS m/z (ESI) calcd for $C_{20}H_{24}N_2O_2S_2$ $[M+H]^+$ 389.1357 found: 389.1359.

The detailed preparative method is same as that of compound 1, with a yield of 76.1%.

Compound 46: 2-(1-((3-methylpiperidin-1-yl)sulfonyl)ethyl)-10H-phenothiazine

The synthetic route is as follows:

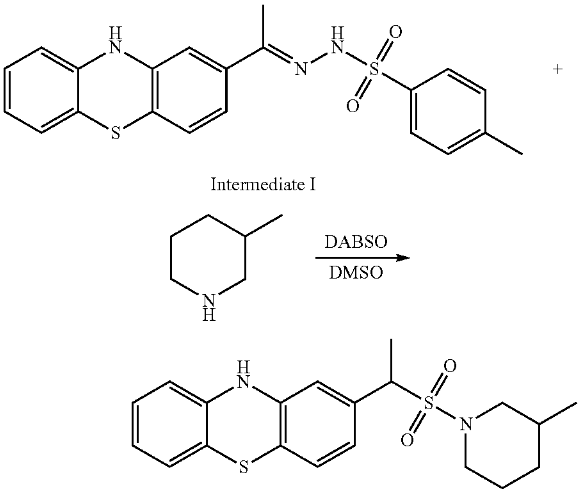

46

$^1$H NMR and HRMS data of compound 46 are as follows:

$^1$H NMR (400 MHz, DMSO-$d_6$) δ 8.70 (s, 1H), 7.12-6.87 (m, 3H), 6.85-6.63 (m, 4H), 4.38 (s, 1H), 3.40 (s, 1H), 2.74 (d, J=9.5 Hz, 1H), 2.41 (s, 1H), 2.30-2.10 (m, 1H), 1.65 (s, 2H), 1.52 (s, 3H), 1.25 (s, 2H), 0.94 (s, 1H), 0.79 (d, J=19.6 Hz, 3H).

HRMS m/z (ESI) calcd for $C_{20}H_{24}N_3O_2S_2$ $[M+H]^+$ 389.1357 found: 389.1353.

The detailed preparative method is same as that of compound 1, with a yield of 75.1%.

Compound 47: 1-((1-(10H-phenothiazin-2-yl)ethyl)sulfonyl)piperidin-4-formamide

The synthetic route is as follows:

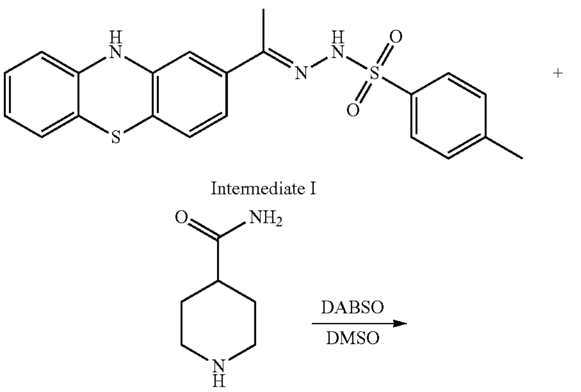

-continued

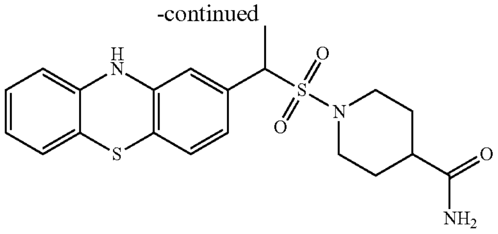

47

$^1$H NMR and HRMS data of compound 47 are as follows:

$^1$H NMR (400 MHz, DMSO-$d_6$) δ 8.69 (s, 1H), 7.23 (s, 1H), 6.94 (d, J=37.3 Hz, 3H), 6.76 (t, J=25.7 Hz, 5H), 4.40 (s, 1H), 3.55 (s, 1H), 3.42 (d, J=10.5 Hz, 1H), 2.78 (s, 1H), 2.41 (s, 2H), 1.65 (d, J=15.4 Hz, 2H), 1.53 (s, 3H), 1.40 (s, 2H).

HRMS m/z (ESI) calcd for $C_{20}H_{23}N_3O_3S_2$ $[M+H]^+$ 418.1259 found: 418.1254.

The detailed preparative method is same as that of compound 1, with a yield of 63.8%.

Compound 48: 2-(1-((3,5-dimethylpiperazin-1-yl)sulfonyl)ethyl)-10H-phenothiazine The synthetic route is as follows:

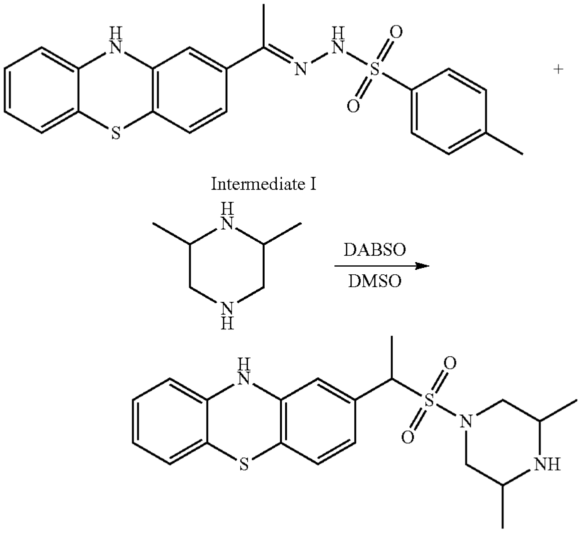

48

$^1$H NMR and HRMS data of compound 48 are as follows:

H NMR (400 MHz, DMSO-$d_6$) δ 8.67 (s, 1H), 7.05-6.94 (m, 1H), 6.90 (d, J=7.8 Hz, 2H), 6.77 (dt, J=11.3, 4.6 Hz, 3H), 6.68 (d, J=7.8 Hz, 1H), 4.38 (q, J=6.9 Hz, 1H), 3.37 (d, J=11.1 Hz, 1H), 3.24 (d, J=11.0 Hz, 1H), 2.69-2.51 (m, 2H), 2.29 (t, J=11.0 Hz, 1H), 2.07-1.90 (m, 1H), 1.51 (d, J=7.0 Hz, 3H), 0.90 (d, J=6.2 Hz, 3H), 0.84 (d, J=6.2 Hz, 4H).

HRMS m/z (ESI) calcd for $C_{20}H_{25}N_3O_2S_2$ $[M+H]^+$ 404.1466 found: 404.1469.

The detailed preparative method is same as that of compound 1, with a yield of 68.9%.

Compound 49: 2-(1-((4-(2-methoxylphenyl)piperazin-1-yl)sulfonyl)ethyl)-10H-phenothiazine The synthetic route is as follows:

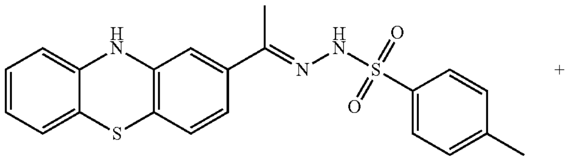

Intermediate I

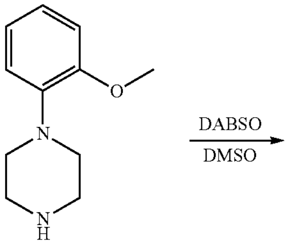

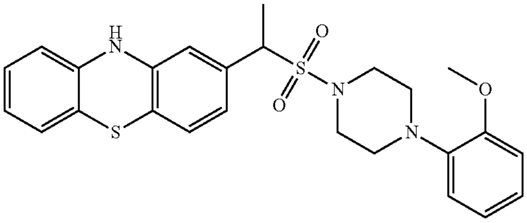

49

$^1H$ NMR and HRMS data of compound 49 are as follows:

$^1H$ NMR (400 MHz, DMSO-$d_6$) δ 8.71 (s, 1H), 7.03-6.80 (m, 9H), 6.75 (t, J=7.3 Hz, 1H), 6.69 (d, J=7.7 Hz, 1H), 4.46 (d, J=6.9 Hz, 1H), 3.74 (s, 3H), 3.22 (s, 2H), 3.12 (s, 2H), 2.87 (s, 4H), 1.57 (d, J=6.8 Hz, 3H).

HRMS m/z (ESI) calcd for $C_{25}H_{27}N_3O_3S_2$ $[M+H]^+$ 482.1572 found: 482.1576.

The detailed preparative method is same as that of compound 1, with a yield of 80.8%.

Compound 50: 2-(1-(2-(4-methyl-1,4-homopiperazin-1-yl)pyrimidin-5-yl)ethenyl)-10H-phenothiazine The synthetic route is as follows:

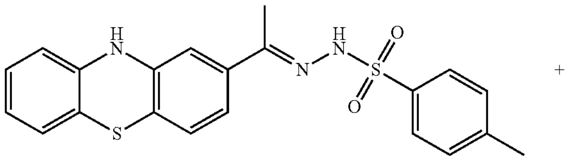

Intermediate I

-continued

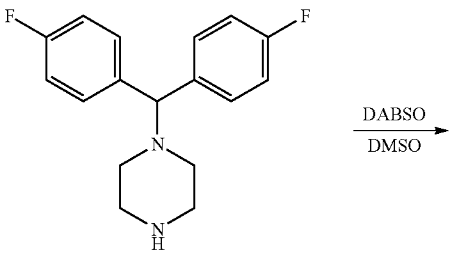

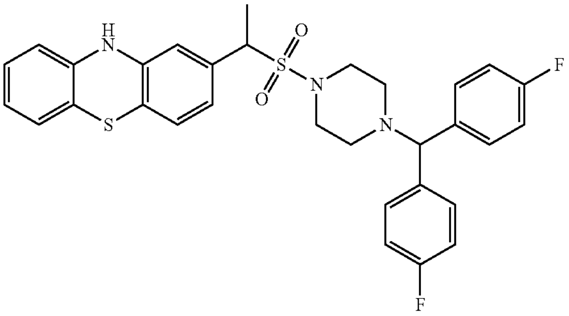

50

$^1H$ NMR and HRMS data of compound 50 are as follows:

$^1H$ NMR (400 MHz, DMSO-$d_6$) δ 8.77 (s, 1H), 7.33 (s, 4H), 7.19-6.47 (m, 11H), 4.38 (d, J=26.0 Hz, 2H), 3.11 (s, 2H), 2.97 (s, 2H), 2.17 (d, J=26.3 Hz, 4H), 1.52 (s, 3H).

HRMS m/z (ESI) calcd for $C_{31}H_{29}F_2N_3O_2S_2$ $[M+H]^+$ 578.1748 found: 578.1745.

The detailed preparative method is same as that of compound 1, with a yield of 82.8%.

Compound 51: 4-(5-(1-(10H-phenothiazin-2-yl)ethenyl)pyrimidin-2-yl)morpholine

The synthetic route is as follows:

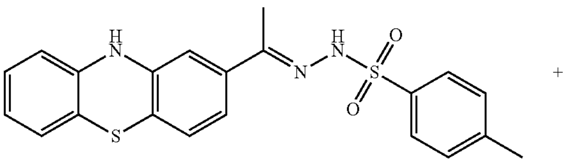

Intermediate I

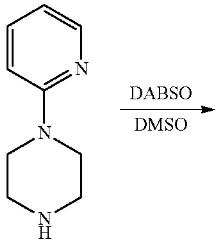

-continued

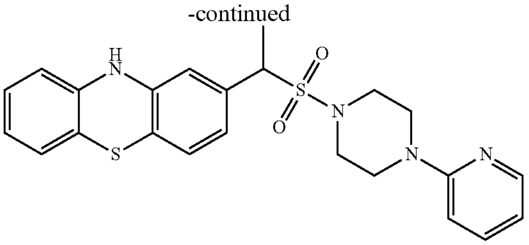

51

$^1$H NMR and HRMS data of compound 51 are as follows:

$^1$H NMR (400 MHz, DMSO-$d_6$) δ 8.70 (s, 1H), 8.09 (s, 1H), 7.52 (s, 1H), 6.73 (d, J=53.8 Hz, 9H), 4.47 (s, 1H), 3.43 (s, 4H), 3.18 (s, 2H), 3.04 (s, 2H), 1.55 (s, 3H).

HRMS m/z (ESI) calcd for $C_{23}H_{24}N_4O_2S_2$ $[M+H]^+$ 453.1419 found: 453.1415.

The detailed preparative method is same as that of compound 1, with a yield of 74.8%.

Compound 52: 2-(1-((4-(pyrimidin-2-yl)piperazin-1-yl)sulfonyl)ethyl)-10H-phenothiazine The synthetic route is as follows:

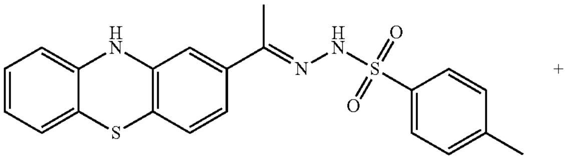

Intermediate I

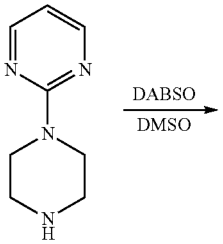

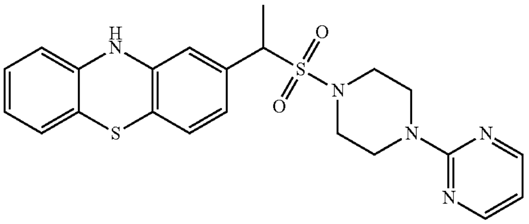

52

$^1$H NMR and HRMS data of compound 52 are as follows:

$^1$H NMR (400 MHz, DMSO-$d_6$) δ 8.68 (s, 1H), 8.36 (s, 2H), 6.82 (dd, J=85.3, 42.4 Hz, 8H), 4.47 (s, 1H), 3.69 (s, 4H), 3.11 (d, J=52.2 Hz, 4H), 1.55 (s, 3H).

HRMS m/z (ESI) calcd for $C_{22}H_{23}N_5O_2S_2$ $[M+H]^+$ 454.1371 found: 454.1375.

The detailed preparative method is same as that of compound 1, with a yield of 64.1%.

Compound 53: 4-(4-((1-(10H-phenothiazin-2-yl)ethyl)sulfonyl)piperazin-1-yl)benzonitrile The synthetic route is as follows:

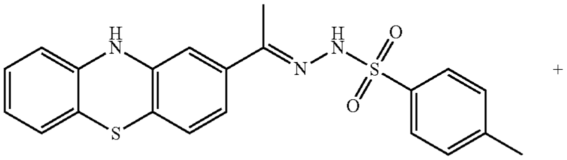

Intermediate I

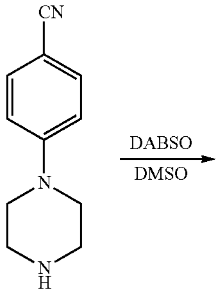

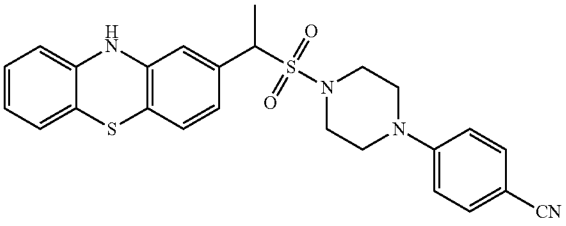

53

$^1$H NMR and HRMS data of compound 53 are as follows:

$^1$H NMR (400 MHz, DMSO-$d_6$) δ 8.70 (s, 1H), 7.58 (s, 2H), 6.99 (d, J=5.4 Hz, 3H), 6.89 (s, 2H), 6.82 (d, J=16.9 Hz, 2H), 6.75 (s, 1H), 6.67 (s, 1H), 4.49 (s, 1H), 3.30 (s, 4H), 3.26-2.99 (m, 4H), 1.56 (s, 3H).

HRMS m/z (ESI) calcd for $C_{25}H_{24}N_4O_2S_2$ $[M+H]^+$ 477.1419 found: 477.1412.

The detailed preparative method is same as that of compound 1, with a yield of 81.2%.

Compound 54: 2-(1-((4-(3-methoxylphenyl)piperazin-1-yl)sulfonyl)ethyl)-10H-phenothiazine The synthetic route is as follows:

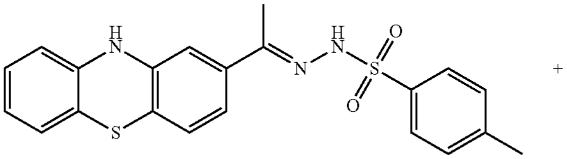

Intermediate I

-continued

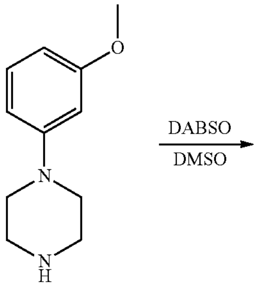

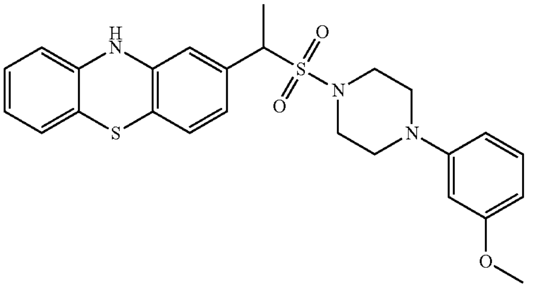

54

$^1H$ NMR and HRMS data of compound 54 are as follows:

$^1H$ NMR (400 MHz, DMSO-$d_6$) δ 8.71 (s, 1H), 7.23-6.60 (m, 8H), 6.45 (d, J=21.4 Hz, 3H), 4.47 (s, 1H), 3.69 (s, 3H), 3.26 (d, J=42.1 Hz, 4H), 1.55 (s, 3H), 1.29 (d, J=46.2 Hz, 4H).

HRMS m/z (ESI) calcd for $C_{25}H_{27}N_3O_3S_2$ $[M+H]^+$ 482.1572 found: 4482.1565.

The detailed preparative method is same as that of compound 1, with a yield of 86.4%.

Compound 55: 2-(1-((4-(4-nitrophenyl)piperazin-1-yl)sulfonyl)ethyl)-10H-phenothiazine The synthetic route is as follows:

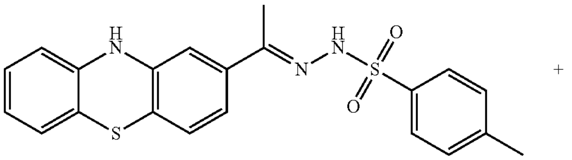

Intermediate I

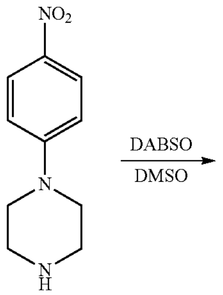

-continued

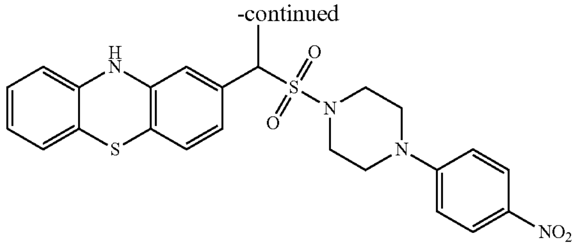

55

$^1H$ NMR and HRMS data of compound 55 are as follows: $^1H$ NMR (400 MHz, DMSO-$d_6$) δ 8.69 (s, 1H), 8.03 (s, 2H), 6.99 (s, 3H), 6.86 (d, J=15.1 Hz, 3H), 6.80-6.69 (m, 2H), 6.65 (d, J=7.1 Hz, 1H), 4.50 (s, 1H), 3.42 (s, 4H), 3.22 (s, 2H), 3.09 (s, 2H), 1.55 (s, 3H).

HRMS m/z (ESI) calcd for $C_{24}H_{24}N_4O_4S_2$ $[M+H]^+$ 497.1317 found: 497.1313.

The detailed preparative method is same as that of compound 1, with a yield of 74.6%.

Compound 56: 2-(1-((4-(4-(trifluoromethyl)phenyl)piperazin-1-yl)sulfonyl)ethyl)-10H-phenothiazine The synthetic route is as follows:

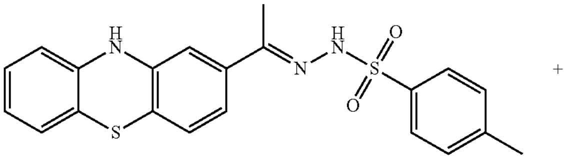

Intermediate I

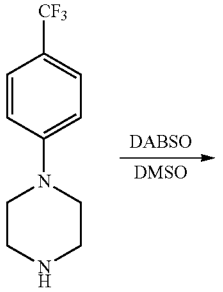

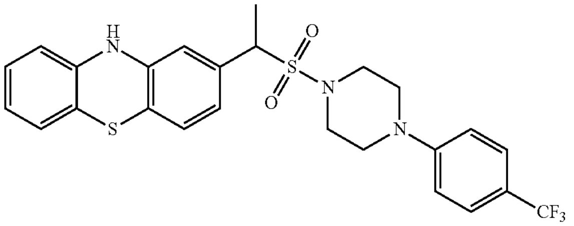

56

$^1H$ NMR and HRMS data of compound 56 are as follows: $^1H$ NMR (400 MHz, DMSO-$d_6$) δ 8.69 (s, 1H), 7.50 (d, J=8.7 Hz, 2H), 7.04 (d, J=8.6 Hz, 2H), 7.02-6.94 (m, 1H), 6.89 (d, J=8.0 Hz, 2H), 6.86-6.79 (m, 2H), 6.74 (dd, J=10.8, 4.2 Hz, 1H), 6.66 (d, J=7.9 Hz, 1H), 4.49 (q, J=6.9 Hz, 1H), 3.22 (d, J=5.6 Hz, 6H), 3.11 (d, J=8.3 Hz, 2H), 1.56 (d, J=7.0 Hz, 3H).

HRMS m/z (ESI) calcd for $C_{25}H_{24}F_3N_3O_2S_2$ $[M+H]^+$ 520.1340 found: 520.1342.

The detailed preparative method is same as that of compound 1, with a yield of 79.9%.

Compound 57: 2-(1-((4-(pyrazin-2-yl)piperazin-1-yl)sulfonyl)ethyl)-10H-phenothiazine The synthetic route is as follows:

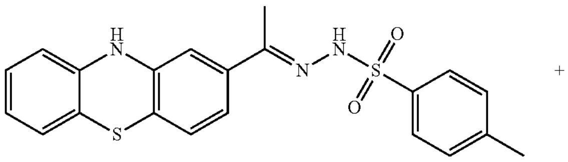

Intermediate I

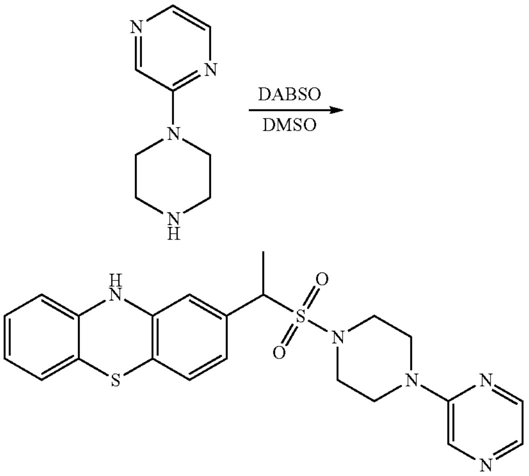

57

$^1$H NMR and HRMS data of compound 57 are as follows:

$^1$H NMR (400 MHz, DMSO-$d_6$) δ 8.70 (s, 1H), 8.30 (s, 1H), 8.07 (s, 1H), 7.86 (s, 1H), 7.20-6.38 (m, 7H), 4.49 (s, 1H), 3.52 (s, 4H), 3.13 (d, J=51.3 Hz, 4H), 1.55 (s, 3H).

HRMS m/z (ESI) calcd for $C_{22}H_{23}N_5O_2S_2$ $[M+H]^+$ 454.1371 found: 454.1375.

HRMS m/z (ESI) calcd for $C_{24}H_{22}N_2O_2S_2$ $[M+H]^+$ 435.1201 found: 435.1203.

The detailed preparative method is same as that of compound 1, with a yield of 67.4%.

Compound 58: 2-(1-((4-butylpiperazin-1-yl)sulfonyl)ethyl)-10H-phenothiazine

The synthetic route is as follows:

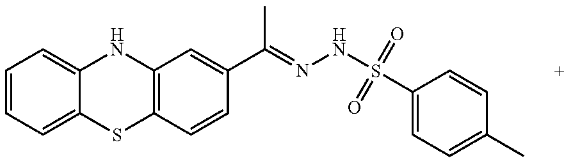

Intermediate I

-continued

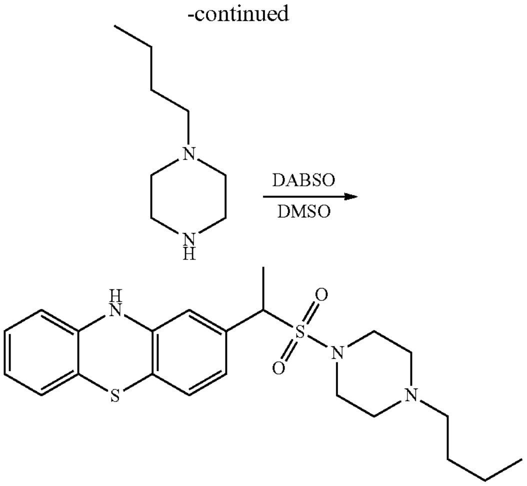

58

$^1$H NMR and HRMS data of compound 58 are as follows:

$^1$H NMR (400 MHz, DMSO-$d_6$) δ 8.70 (s, 1H), 6.83 (d, J=45.7 Hz, 7H), 4.39 (s, 1H), 2.99 (d, J=55.5 Hz, 4H), 2.23 (s, 6H), 1.51 (s, 3H), 1.27 (d, J=38.9 Hz, 4H), 0.82 (s, 3H).

HRMS m/z (ESI) calcd for $C_{22}H_{29}N_3O_2S_2$ $[M+H]^+$ 432.1779 found: 432.1775.

The detailed preparative method is same as that of compound 1, with a yield of 73.4%.

Compound 59: 2-(1-((4-(p-methylphenyl)piperazin-1-yl)sulfonyl)ethyl)-10H-phenothiazine The synthetic route is as follows:

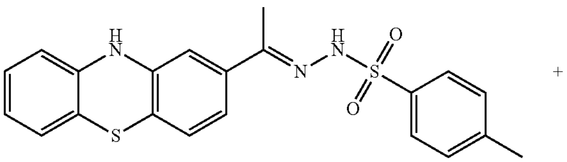

Intermediate I

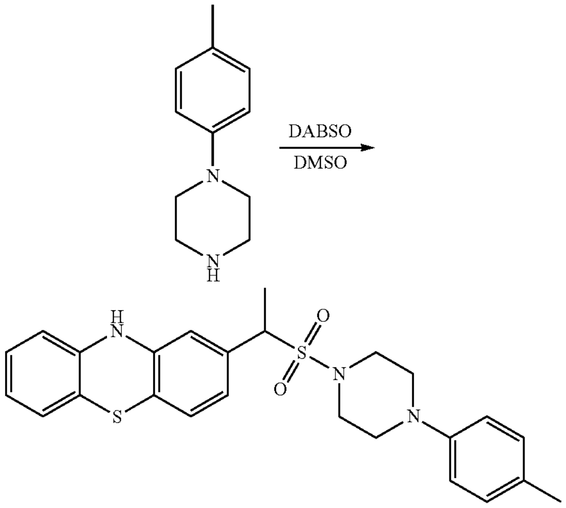

59

$^1$H NMR and HRMS data of compound 59 are as follows:

$^1$H NMR (400 MHz, DMSO-$d_6$) δ 8.71 (s, 1H), 6.84 (dd, J=83.0, 44.9 Hz, 11H), 4.48 (s, 1H), 3.29-2.83 (m, 8H), 2.19 (s, 3H), 1.56 (s, 3H).

HRMS m/z (ESI) calcd for $C_{25}H_{27}N_3O_2S_2$ $[M+H]^+$ 466.1623 found: 466.1625.

The detailed preparative method is same as that of compound 1, with a yield of 63.8%.

Example 5 Study on the Inhibition Rate of Compounds of the Present Invention Against Ferroptosis In this example, in order to study the inhibitors of ferroptosis, a screening model for ferroptosis was independently constructed, and the detailed was as follows:

The screening model for ferroptosis mainly used MTT method. First, the fibrosarcoma cell line HT1080 was cultured in a dish, and the cells in the logarithmic growth phase were inoculated into a 96-well plate in a certain number (3000-10000 cells/well), 100 μL per well, and then the plate was put in an 5% $CO_2$ incubator at 37° C., to allow the cells to adhere. After 24 h, 100 μL compound solution at a certain concentration prepared in the designated medium and ferroptosis inducer Erastin (with a final concentration of 10 M) were added, setting 3 replicate wells for each compound to ensure the accuracy of the results, and a negative control group, a positive control group (Fer-15 μM), a blank control group and a solvent control group were included. After addition of drugs, the plate was placed in an incubator and cultivated for 72 h. On the day of MTT experiment, MTT test solution (5 mg/mL MTT solution dissolved in physiological saline, and stored in the dark at 4° C.) was preprepared and 20 μL MTT solution was added to each well, then the plate was put in an incubator and continued to incubate for 2-4 h. After that, 50 μL of 20% SDS solution (dissolved in MiliiQ water, added with 1% concentrated hydrochloric acid) was added to each well and kept in an incubator overnight. On the next day, the absorbance at 570 nm was measured with a microplate reader, to calculate the inhibition rate of drugs on ferroptosis. Generally, the absorbance value of the control group should be in the range of 0.8-1.2 as a normal value. After obtaining the absorbance data, the average of 3 replicate wells was calculated, and the following formula was used to calculate the inhibition rate:

$$\text{Inhibition rate \% (IR)}=[1-(A_{experiment}-A_{blank})/(A_{solvent}-A_{blank})]*100\%$$

GraphPadPrism5 software was used to fit the change curve of inhibition rate and calculate the $EC_{50}$.

The $EC_{50}$ values of all compounds prepared in above Examples 2-4 were tested ($EC_{50}$ values being the average of three tests, with Fer-1 as the positive control group). The results are shown in the following Table:

TABLE 1

$EC_{50}$ values of compounds of the present invention

| Compound | $EC_{50}$ (μM) | Compound | $EC_{50}$ (μM) | Compound | $EC_{50}$ (μM) |
|---|---|---|---|---|---|
| Fer-1 | 0.060 | A1 | 0.003 | A2 | 0.006 |
| A3 | 0.005 | A4 | 0.005 | A5 | 0.015 |
| A6 | 0.005 | A7 | 0.001 | A8 | 0.005 |
| A9 | 0.018 | A10 | 0.012 | A11 | 0.019 |
| A12 | 0.015 | A13 | 0.025 | A14 | 0.005 |
| A15 | 0.017 | A16 | 0.049 | A17 | 0.013 |
| A18 | 0.070 | A19 | 0.006 | A20 | 0.015 |
| A21 | 0.006 | A22 | 0.006 | A23 | 0.020 |

TABLE 1-continued $EC_{50}$ values of compounds of the present invention

| Compound | $EC_{50}$ (μM) | Compound | $EC_{50}$ (μM) | Compound | $EC_{50}$ (μM) |
|---|---|---|---|---|---|
| A24 | 0.020 | A25 | 0.021 | A26 | 0.006 |
| A27 | 0.064 | A28 | 0.008 | A29 | 0.007 |
| A30 | 0.006 | A31 | 0.017 | A32 | 0.062 |
| A33 | 0.017 | A34 | 0.065 | A35 | 0.014 |
| A36 | 0.013 | A37 | 0.323 | A38 | 0.0005 |
| A39 | 0.017 | A40 | 0.005 | A41 | 0.018 |
| A42 | 0.016 | A43 | 0.017 | A44 | 0.019 |
| A45 | 0.022 | A46 | 0.021 | A47 | 0.007 |
| A48 | 0.022 | A49 | 0.019 | A50 | 0.025 |
| A51 | 0.022 | A52 | 0.013 | A53 | 0.020 |
| A54 | 0.068 | A55 | 0.059 | A56 | 0.019 |
| A57 | 0.018 | A58 | 0.019 | A59 | 0.020 |
| A60 | 0.012 | A61 | 0.034 | A62 | 0.024 |
| A63 | 0.031 | A64 | 0.064 | A65 | 0.008 |
| A66 | 0.005 | A67 | 0.016 | A68 | 0.005 |
| A69 | 0.003 | A70 | 0.018 | A71 | 0.017 |
| A72 | 0.014 | A73 | 0.005 | A74 | 0.003 |
| A75 | 0.023 | A76 | 0.005 | B1 | 0.010 |
| B2 | 0.032 | B3 | 0.011 | B4 | 0.023 |
| B5 | 0.080 | B6 | 0.045 | B7 | 0.029 |
| B8 | 0.040 | B9 | 0.003 | B10 | 0.010 |
| B11 | 0.039 | B12 | 0.040 | B13 | 0.030 |
| B14 | 0.039 | B15 | 0.680 | B16 | 0.029 |
| B17 | 0.017 | B18 | 0.040 | B19 | 0.013 |
| B20 | 0.010 | B21 | 0.011 | B22 | 0.030 |
| B23 | 0.048 | B24 | 0.031 | B25 | 0.016 |
| B26 | 0.016 | B27 | 0.038 | B28 | 0.027 |
| B29 | 0.041 | B30 | 0.045 | B31 | 0.051 |
| B32 | 0.089 | B33 | 0.111 | B34 | 0.011 |
| B35 | 0.053 | B36 | 0.030 | B37 | 0.014 |
| B38 | 0.035 | B39 | 0.023 | B40 | 0.041 |
| B41 | 0.905 | B42 | 0.045 | B43 | 0.004 |
| B44 | 0.011 | B45 | 0.013 | B46 | 0.010 |
| B47 | 0.024 | B48 | 0.013 | B49 | 0.002 |
| B50 | 0.004 | B51 | 0.010 | B52 | 0.011 |
| B53 | 0.148 | B54 | 0.032 | B55 | 0.012 |
| B56 | 0.022 | B57 | 0.034 | B58 | 0.066 |
| B59 | 0.0002 | C1 | 0.068 | C2 | 0.034 |
| C3 | 0.009 | C4 | 0.029 | C5 | 0.035 |
| C6 | 0.185 | C7 | 0.046 | C8 | 0.046 |
| C9 | 0.085 | C10 | 0.017 | C11 | 0.269 |
| C12 | 0.076 | C13 | 0.062 | C14 | 0.260 |
| C15 | 0.132 | C16 | 0.035 | C17 | 0.005 |
| C18 | 0.079 | C19 | 0.129 | C20 | 0.031 |
| C21 | 0.257 | C22 | 0.730 | C23 | 0.620 |
| C24 | 0.417 | C25 | 0.405 | C26 | 0.388 |
| C27 | 0.256 | C28 | 0.142 | C29 | 0.228 |
| C30 | 0.095 | C31 | 0.399 | C32 | 0.586 |
| C33 | 0.327 | C34 | 0.233 | C35 | 0.342 |
| C36 | 0.129 | C37 | 0.271 | C38 | 0.229 |
| C39 | 0.244 | C40 | 0.142 | C41 | 0.117 |
| C42 | 0.335 | C43 | 0.049 | C44 | 0.426 |
| C45 | 0.226 | C46 | 0.156 | C47 | 0.225 |
| C48 | 0.035 | C49 | 0.228 | C50 | 0.069 |
| C51 | 0.143 | C52 | 0.069 | C53 | 0.182 |
| C54 | 0.165 | C55 | 0.070 | C56 | 0.213 |
| C57 | 0.129 | C58 | 0.178 | C59 | 0.142 |

As shown in Table 1, the compound prepared in the present invention had good inhibitory activity against ferroptosis. Wherein, among the compounds prepared in Example 2: when the meta position of the benzene ring is substituted by an amino group, compound A38 had the highest activity, with an $EC_{50}$ value of about 1 nM, and when this position was substituted by cyano, methyl, ethyl, isopropyl, ethoxyl, isopropoxyl, formic acid tert-butyl ester, and trifluoromethoxyl, etc., the $EC_{50}$ values were about 15 nM; all of them are better than the positive control Fer-1; when the para position of the benzene ring was substituted by fluorine, chlorine, trifluoromethyl, cyano, trifluoromethoxyl, ethyl, propyl, isopropyl, isobutyl, t-butyl, methoxyl, ethoxyl, isopropoxyl, benzyloxyl and formic acid methyl ester, the $EC_{50}$ values were in the range of 6-20 nM, which was better than the positive control Fer-1; when the benzene ring was double-substituted, the resultant compounds were better than or equivalent to the positive control Fer-1; when the compound contained benzodioxane, benzodioxine, benzofuran, naphthalene, substituted naphthalene, substituted pyridine, cyclohexyl, and et. al, their activities were all better than the positive control Fer-1.

Example 6 Establishment of Rat Stroke Model of the Present Invention (1) Experimental Materials The cell lines used were human fibroma cell lines (HT1080: NRAS mutation) and human lung cancer cell lines (Calu-1: KRAS mutation), and both of them were purchased from American Type culture collection (ATCC) and cultured according to the methods of literature. The Sprague Dawley rats used in the experiment were purchased from Beijing Huafukang Biotechnology Co., Ltd. and raised in the animal room of the State Key Laboratory of Biotherapy of Sichuan University.

(2) Model Building Method 20 specific pathogen free (SPF)-grade Sprague-Dawley (SD) male rats, with a body weight of 200-300 g, were randomly raised in separated cages, and maintained at a room temperature of 20-22° C. The rats were fasted before surgery, but freely accessed to water. The thread plug with the tip diameter of 0.25 mm was soaked in heparin for use. The method of making the middle cerebral artery occlusion ischemia-reperfusion model in this experiment referred to ZeaLonga method with slight changes. The specific operation was as follows: after the rat was weighed, enflurane at the volume fraction of 4%-5% was used to induce anesthesia, while 1%-2% enflurane mixed with 70% N20 and 30% 02 was used to maintain anesthesia. The rat was supinated on the operating table, a median neck incision was cut, and the subcutaneous fat and muscle, the right common carotidartery (CCA), external carotidartery (ECA), internal carotidartery (ICA) were carefully separated; the main trunk of ECA was separated, and then the thyroid artery and occipital artery were bluntly separated and cut off by electrocautery. Ligation, electrocautery, and cutting off ECA were carried out at about 1 cm from the distal of CCA bifurcation, and CCA and ICA were temporarily clamped with an arterial clip, then an incision was cut at the ECA stump with ophthalmic scissors, through which the thread plug was inserted. The suture was ligated, and ICA arterial clamp was loosened, the thread plug was slowly pushed into ICA and then entered into the cranial artery branch. The thread plug was passed about 20 mm away from the bifurcation of ICA and ECA, and once the resistance was felt, the CCA artery clamp was released, the suture at CCA bifurcation was ligated, and the skin is sutured. After 2 h ischemia, the rats were anesthetized again, the neck incision was opened, the thread plug was pulled out, and ECA stump was electrocoagulated and the neck incision was sutured to complete the rat cerebral ischemia 2 h reperfusion injury model.

(3) Experimental Results

Figure 2:
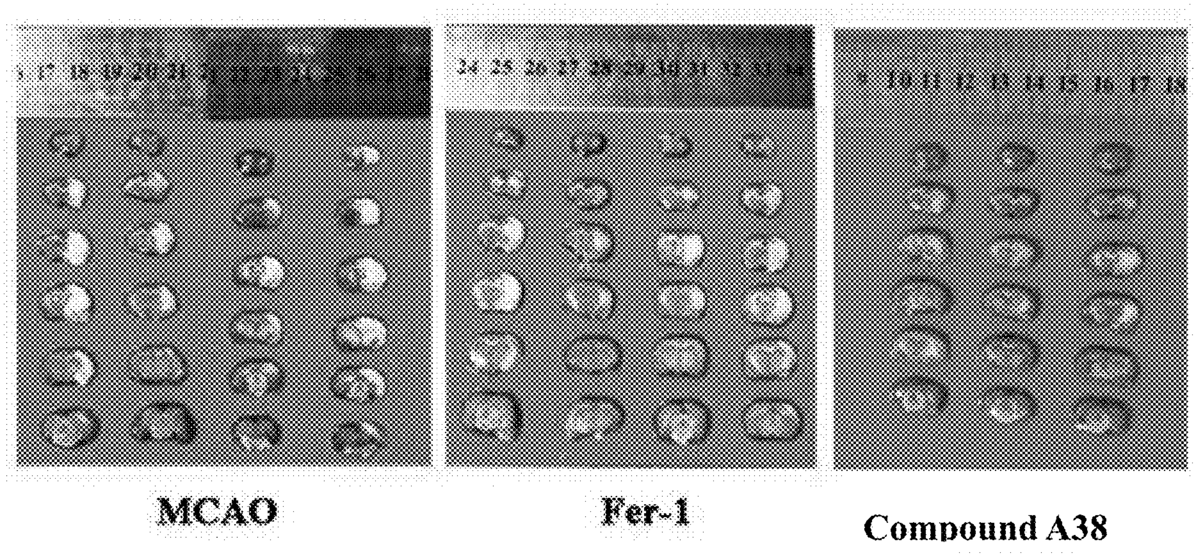
FIG. 2 shows a graph of the therapeutic effect on rat model of focal cerebral ischemia (stroke) for compound A38 according to the present invention.

The activity of compound A38 prepared in Example 2, namely 2-(1-(4-(4-methylpiperazin-1-yl)phenyl)ethyl)-10H-phenothiazine ($EC_{50}$=0.0005 μM), was about 120 times that of the active positive control Fer-1. As shown in FIG. 1, this compound was selected for further research on the therapeutic effect in ferroptosis-related disease models. A rat model of focal cerebral ischemia (stroke) was selected for investigation, and the results are shown in FIG. 2. In FIG. 2, MCAO is the rat stroke model group, Fer-1 is the positive control group, and compound A38 is the experimental group; meanwhile, in FIG. 2, the white part represents the dead brain tissue, and the others represent the normal. The less the white part of the brain tissue, the better the activity. It can be found from FIG. 2 that compared with the positive control Fer-1, compound A38 has a better therapeutic effect on the rat model of focal cerebral ischemia (stroke).

Example 7 Activity Assay of the Compound of the Present Invention in Rat MCAO Stroke Model By rat middle cerebral artery occlusion (MCAO) stroke model (also called cerebral ischemia model), the therapeutic effect of the compound of the present invention on ischemic stroke in SD rats at different doses was studied.

Male SD rats were selected and induced anesthesia by 2-3.0% isoflurane. The middle cerebral artery was blocked by the thread plug method, resulting in rat ischemia model; the ischemic rats were placed at room temperature and kept their body temperature being 37° C.

60 minutes after ischemia onset, the rats were scored by Bederson neurobehavioral scale to determine whether the model was successfully made. 90 min after ischemia onset, the thread plug was pulled out for reperfusion. The experiment included 6 groups, such as the model control group, four different dose groups of compound 38 (i.e. compound A38) of Example 2 (very low dose group 0.2 mg/kg, low dose group 0.5 mg/kg, middle dose group 1.25 mg/kg, high-dose group 2.5 mg/kg), and positive drug treatment group (butylphthalide, with administration dose of 10 mg/kg); model control group, very low dose group of compound A38, low dose group of compound A38, medium dose group of compound A38, high dose group of compound A38, and the positive drug treatment group each had 18 animals. Within 10 min of reperfusion, compound A38 and positive drug were administered via tail vein injection. After 24 h of reperfusion, the animals were scored by NSS scale to evaluate neurological deficit. And then the animals were dissected, brains were collected and subjected to TTC stain. Comprehensive analysis and evaluation of the therapeutic effect of compound A38 on ischemic stroke in rats were carried out by measuring the extent of cerebral infarction and calculating the inhibition rate.

The percentage of the weight of the infarct tissue based on the weight of the whole brain was regarded as the infarct range (%), and the inhibition rate (%) of each drug treatment group was calculated based on the infarct range. The calculation formula of the inhibition rate is as follows:

Inhibition rate (%)=(The infarct range in model group−the infarct range in treatment group)/(The infarct range in model group)×100%.

Experimental Results:

(1) Cerebral Infarction Range and Inhibition Rate of Cerebral Infarction:

The cerebral infarction ranges in very low dose group of compound A38, low dose group of compound A38, medium dose group of compound A38, high dose group of compound A38 were 12.7945.048%, 12.107±3.175%, 10.742±4.658%, and 8.644±4.779%, respectively, and compared with the model control group, there is a significant statistical difference (P=0.008, P=0.001, P<0.001, and P<0.001, respectively). The inhibition rate of cerebral infarction in very low dose group of compound A38, low dose group of compound A38, medium dose group of compound A38, high dose group of compound A38, and positive drug group were 27.307%, 31.209%, 38.968%, 50.885%, and 24.477%, respectively. Compound A38 of the present invention has the effect of significantly reducing the infarct range of ischemic stroke in rats (see Table 2 below)

(2) Neurobehavioral Score Results:

During the experiment; one day after operation, NSS score of animals in the model control group was 9.750±1.983; NSS scores of very low dose group of compound A38, low dose group of compound A38, medium dose group of compound A38, and high dose group of compound A38, were 8.412±1.278, 8.231±1.832, 7.563±1.315, and 6.667±3.039, respectively, and compared with the model control group, there is a significant statistical difference (P=0.027, P=0.043, P=0.001, and P=0.002, respectively). Compound A38 of the present invention has the effect of improving the neurological scores of cerebral ischemia in rats (see Table 3 below)

TABLE 2

Cerebral infarction range and inhibition rate of cerebral infarction of experimental animals

| Groups | Whole brain weight (g) | Infarct weight (g) | Infarct range (%) | Inhibition rate of cerebral infarction (%) |
|---|---|---|---|---|
| Model control group | 1.387 ± 0.152 | 0.242 ± 0.063 | 17.558 ± 4.600 | — |
| Very low dose group of compound A38 | 1.461 ± 0.126 | 0.187 ± 0.078 | 12.794 ± 5.048** | 27.307 |
| Low dose group of compound A38 | 1.411 ± 0.109 | 0.170 ± 0.041 | 12.107 ± 3.175** | 31.209 |
| Medium dose group of compound A38 | 1.436 ± 0.102 | 0.152 ± 0.064 | 10.742 ± 4.658*** | 38.968 |
| High dose group of compound A38 | 1.431 ± 0.118 | 0.126 ± 0.072 | 8.644 ± 4.779*** | 50.885 |
| Positive drug group | 1.446 ± 0.145 | 0.193 ± 0.075 | 13.292 ± 4.476* | 24.477 |

Note:
the data in the Table are all expressed as mean ± standard deviation (Mean ± SD);
"—" means no data for this item,
*means P ≤ 0.05 compared with animals in model control group,
**means P ≤ 0.01 compared with animals in model control group,
***means P ≤ 0.001 compared with animals in model control group.

TABLE 3

Neurological function scores of experimental animal

| Groups | Bedersonscore | NSSscore |
|---|---|---|
| Model control group | 3.000 ± 0.000 | 9.750 ± 1.983 |
| Very low dose group of compoundA38 | 2.882 ± 0.332 | 8.412 ± 1.278* |
| Low dose group of compoundA38 | 2.923 ± 0.277 | 8.231 ± 1.833* |
| Medium dose group of compoundA38 | 3.000 ± 0.000 | 7.563 ± 1.315** |
| High dose group of compoundA38 | 2.800 ± 0.414 | 6.667 ± 3.039** |
| Positive drug group | 2.929 ± 0.267 | 8.500 ± 1.401 |

Note:
the data in the Table are all expressed as mean ± standard deviation (Mean ± SD); *means P ≤ 0.05 compared with animals in model control group, **means P ≤ 0.01 compared with animals in model control group.

In summary, the present invention has synthesized a new 10H-phenothiazine derivative that can inhibit ferroptosis. By the structure optimization and structure-activity relationship study, in certain embodiments, 10H-phenothiazine derivatives were confirmed that they have a better inhibitory effect on cell death, and some compounds showed a better therapeutic effect in the rat focal cerebral ischemia model, which can be used as the main active ingredient for the preparation of ferroptosis inhibitors.

Both the compound and the inhibitors prepared by the compound have good medicinal potential and are expected to become new candidate drugs for treatment of stroke; at the same time, the preparative method of the new compound provided by the present invention is simple, and the reaction conditions are mild, that are convenient for the operation and control. Moreover, the reactions have low consumption, high yield and low cost, and are suitable for industrialized production. The prepared compound has higher biological activity, strong selectivity, and remarkable drug-like properties, and has broad market prospects.

The invention claimed is:

1. A compound of formula I, or a pharmaceutically acceptable salt, or a solvate thereof:

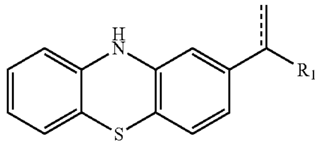

I wherein, when the dotted line is a bond, $R_1$ is selected from 3-10 membered saturated cycloalkyl, 3-10 membered unsaturated cycloalkyl, 3-10 membered saturated heterocyclic group, and 3-10 membered unsaturated heterocyclic group, all of which are substituted by m $R_2$, with m being an integer of 0-5;

$R_2$ is selected from substituted or unsubstituted $C_1$-$C_8$ linear or branched alkyl, substituted or unsubstituted $C_1$-$C_8$ alkoxy, substituted or unsubstituted 3-10 membered saturated cycloalkyl, substituted or unsubstituted 3-10 membered saturated heterocyclic group, substituted or unsubstituted 3-10 membered unsaturated cycloalkyl, carbazolyl, amino, hydroxyl, nitro, cyano, halogen, —C(O)OR$_{51}$, —N(H)C(O)R$_{51}$, —C(O)R$_{51}$, —S(O)(O)R$_{51}$, and —C(O)N(H)R$_{51}$;

$R_{51}$ is selected from H, $C_1$-$C_8$ linear or branched alkyl, amino, substituted or unsubstituted 3-10 membered unsaturated cycloalkyl, substituted or unsubstituted 3-10 membered saturated heterocyclic group, and —NR$_{52}$R$_{53}$;

$R_{52}$ and $R_{53}$ are each independently selected from H, substituted or unsubstituted 5-10 membered saturated heterocyclic groups, substituted or unsubstituted $C_1$-$C_8$ linear or branched alkyl, and substituted or unsubstituted 3-8 membered saturated cycloalkyl;

wherein, in $R_1$, $R_2$, $R_{51}$, $R_{52}$, and $R_{53}$, a substituent of the alkyl is selected from halogen and substituted or unsubstituted 4-10 membered saturated heterocyclic group;

a substituent of the alkoxyl is selected from halogen and 3-10 membered unsaturated cycloalkyl;

a substituent of the saturated cycloalkyl is $C_1$-$C_8$ alkyl;

a substituent of the unsaturated cycloalkyl is $C_1$-$C_8$ alkyl;

a substituent of the saturated heterocyclic group is $C_1$-$C_8$ alkyl;

the unsaturated heterocyclic group comprises one or two heteroatoms selected from N, O, and S;

the saturated heterocyclic group comprises one or two heteroatoms selected from N, O, and S; and wherein, when the dotted line is none, $R_1$ is selected from 3-10 membered unsaturated cycloalkyl, benzo(3-8 membered saturated)heterocyclic group, benzo(3-8 membered unsaturated)heterocyclic group, anthryl, 3-10 membered unsaturated heterocyclic group, and 3-10 membered saturated cycloalkyl, all of which are substituted by n $R_3$, n being an integer of 0-5, or $R_1$ is —S(O)(O)R$_1$', with the proviso that n is 1, 2, 3, 4, or 5 when $R_1$ is a 3-10 membered unsaturated cycloalkyl;

$R_3$ is selected from halogen, cyano, hydroxyl, amino, nitro, substituted or unsubstituted 3-10 membered unsaturated cycloalkyl, phenoxyl, substituted or unsubstituted 3-10 membered saturated heterocyclic group, substituted $C_1$-$C_8$ alkyl, substituted or unsubstituted $C_1$-$C_8$ alkoxy, —C(O)OR$_{51}$, —N(H)C(O)R$_{51}$, and —NR$_{22}$R$_{53}$;

$R_1$' is selected from 3-10 membered saturated heterocyclic group, 3-10 membered saturated cycloalkyl, 3-10 membered unsaturated cycloalkyl, and 3-10 membered unsaturated heterocyclic group, all of which are substituted by p $R_4$, with p being an integer of 0-5;

$R_4$ is selected from hydroxyl, substituted or unsubstituted $C_1$-$C_8$ alkyl, —C(O)R$_{51}$, —N(H)C(O)OR$_{51}$, —S(O)(O)R$_{51}$,_—C(O)OR$_{51}$, substituted or unsubstituted 3-10 membered unsaturated heterocyclic group, substituted or unsubstituted 3-10 membered saturated heterocyclic group, and substituted or unsubstituted 3-10 membered unsaturated cycloalkyl;

$R_{51}$ is selected from $C_1$-$C_{10}$ alkyl, amino, 3-8 membered saturated heterocyclic group, and benzo(3-8 membered saturated)heterocyclic group;

$R_{52}$ and $R_{53}$ are each independently selected from 3-10 membered unsaturated cycloalkyl, and $C_1$-$C_8$ linear or branched alkyl;

wherein, in $R_1$, $R_2$, $R_{51}$, $R_{52}$, or $R_{53}$, a substituent of the alkyl is selected from halogen, benzo(5-10 membered saturated)heterocyclic group, substituted or unsubstituted 3-10 membered unsaturated cycloalkyl, 5-10 membered saturated heterocyclic group, hydroxyl, —N(H)C(O)OR$_{51}$, —C(O)R$_{51}$, and —NR$_{52}$R$_{53}$;

a substituent of the alkoxyl is selected from 3-10 membered unsaturated cycloalkyl and halogen;

a substituent of the unsaturated cycloalkyl is selected from halogen, $C_1$-$C_6$ alkoxyl, cyano, nitro, and substituted or unsubstituted $C_1$-$C_8$ alkyl;

a substituent of the saturated heterocyclic group is $C_1$-$C_8$ alkyl;

a substituent of the unsaturated heterocyclic group is $C_1$-$C_8$ alkyl;

the saturated heterocyclic group comprises one or two heteroatoms selected from O, N, and S; and the unsaturated heterocyclic group comprises one or two heteroatoms selected from N, O, and S.

2. The compound according to claim 1, or the pharmaceutically acceptable salt, or the solvate thereof, wherein:

when the dotted line is a bond, $R_1$ is selected from 3-8 membered unsaturated cycloalkyl, and 3-8 membered unsaturated heterocyclic group, all of which are substituted by m $R_2$ and m being an integer of 0-4;

$R_2$ is selected from substituted or unsubstituted $C_1$-$C_6$ linear or branched alkyl, substituted or unsubstituted $C_1$-$C_6$ alkoxy, 3-8 membered saturated cycloalkyl, substituted or unsubstituted 3-8 membered saturated heterocyclic group, 3-8 membered unsaturated cycloalkyl, carbazolyl, amino, hydroxyl, nitro, cyano, halogen, —C(O)OR$_{51}$, —N(H)C(O)R$_{51}$, —C(O)R$_{51}$, —S(O)O)R$_{51}$, and —C(O)N(H)R$_{51}$;

$R_{51}$ is selected from H, $C_1$-$C_4$ linear or branched alkyl, amino, substituted or unsubstituted 3-8 membered unsaturated cycloalkyl, substituted or unsubstituted 5-8 membered saturated heterocyclic group, and —NR$_{52}$R$_{53}$;

$R_{52}$ and $R_{53}$ are each independently selected from H, substituted or unsubstituted 5-8 membered saturated heterocyclic group, substituted or unsubstituted $C_1$-$C_6$ linear or branched alkyl, and 3-6 membered saturated cycloalkyl;

wherein, in $R_1$, $R_2$, $R_{51}$, $R_{52}$, or $R_{53}$, the substituent of the alkyl is selected from halogen and substituted or unsubstituted 5-8 membered saturated heterocyclic group;

the substituent of the alkoxyl is selected from halogen and 3-8 membered unsaturated cycloalkyl;

the substituent of the unsaturated cycloalkyl is $C_1$-$C_4$ alkyl;

the substituent of the saturated heterocyclic group is $C_1$-$C_4$ alkyl;

the unsaturated heterocyclic group comprises one or two heteroatoms selected from N and O;

the saturated heterocyclic group comprises one or two heteroatoms selected from N and O;

where, when the dotted line is none, $R_1$ is selected from 3-8 membered unsaturated cycloalkyl, benzo(5-8 membered saturated)heterocyclic group, benzo(5-8 membered unsaturated)heterocyclic group, anthryl, 3-8 membered unsaturated heterocyclic group, and 3-8 membered saturated cycloalkyl, all of which are substituted by n $R_3$, and S(O)(O)R$_1$', with n being an integer of 1-4;

$R_3$ is selected halogen, cyano, hydroxyl, amino, nitro, 3-8 membered unsaturated cycloalkyl, phenoxyl, substituted 5-8 membered saturated heterocyclic group, substituted $C_1$-$C_6$ alkyl, substituted or unsubstituted $C_1$-$C_6$ alkoxy, —C(O)OR$_{51}$, —N(H)C(O)R$_{51}$, and —NR$_{52}$R$_{53}$;

$R_1$' is 3-8 membered saturated heterocyclic group substituted by p $R_4$, with p being an integer of 0-4;

$R_4$ is selected from hydroxyl, substituted or unsubstituted $C_1$-$C_6$ alkyl, —C(O)$R_{51}$, —N(H)C(O)O$R_{51}$, —S(O)(O)$R_{51}$, —C(O)O$R_{51}$, 3-8 membered unsaturated heterocyclic group, 3-8 membered saturated heterocyclic group, and substituted or unsubstituted 3-8 membered unsaturated cycloalkyl;

$R_{51}$ is selected from $C_1$-$C_8$ alkyl, amino, 5-8 membered saturated heterocyclic group, and benzo(5-8 membered saturated)heterocyclic group;

$R_{52}$ and $R_{53}$ are each independently selected from 3-8 membered unsaturated cycloalkyl and $C_1$-$C_4$ alkyl;

wherein, in $R_1$, $R_3$, $R_4$, $R_{51}$, $R_{52}$, or $R_{53}$, the substituent of the alkyl is selected from halogen, benzo(5-8 membered saturated)heterocyclic group, substituted or unsubstituted 3-8 membered unsaturated cycloalkyl, 5-10 membered saturated heterocyclic group, hydroxyl, —N(H)C(O)O$R_{51}$, —C(O)$R_{51}$, and —N$R_{52}R_{53}$;

the substituent of the alkoxyl is selected from 3-8 membered unsaturated cycloalkyl and halogen;

wherein the substituent of the unsaturated cycloalkyl is selected from halogen, $C_1$-$C_4$ alkoxyl, cyano, nitro, and substituted or unsubstituted $C_1$-$C_4$ alkyl;

the substituent of the saturated heterocyclic group is $C_1$-$C_4$ alkyl;

the saturated heterocyclic group comprises one or two heteroatoms selected from O, N, and S;

the unsaturated heterocyclic group comprises one or two heteroatoms selected from N and O.

3. The compound according to claim 2, or the pharmaceutically acceptable salt, or the solvate thereof, wherein said compound has a structure of formula II:

II

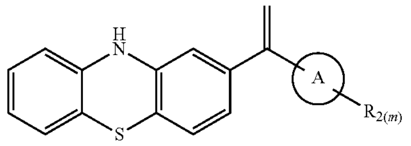

wherein, ring A is selected from aryl substituted by m $R_2$ and heteroaryl substituted by m $R_2$; said heteroaryl comprises one or two N, and m is an integer of 0-4;

$R_2$ is selected from H, substituted or unsubstituted $C_1$-$C_4$ alkyl, substituted or unsubstituted $C_1$-$C_3$ alkoxy, 6-8 membered saturated cycloalkyl, substituted or unsubstituted 6-7 membered saturated heterocyclic group, carbazolyl, amino, hydroxyl, nitro, aryl, cyano, halogen, —C(O)O$R_{51}$, —N(H)C(O)$R_{51}$, —C(O)$R_{51}$, —S(O)(O)$R_{51}$, and —C(O)N(H)$R_{51}$;

$R_{51}$ is selected from H, $C_1$-$C_2$ alkyl, amino, substituted or unsubstituted aryl, substituted or unsubstituted 5-6 membered saturated heterocyclic group, and —N$R_{52}R_{53}$;

$R_{52}$ and $R_{53}$ are each independently selected from H, substituted or unsubstituted 6-8 membered saturated heterocyclic group, substituted or unsubstituted $C_1$-$C_4$ linear or branched alkyl, and 4-5 membered saturated cycloalkyl;

wherein, in $R_2$, $R_{51}$, $R_{52}$, or $R_{53}$, the substituent of the alkyl is selected from halogen and substituted or unsubstituted 6-8 membered saturated heterocyclic group;

the substituent of the alkoxyl is selected from halogen and aryl;

the substituent of the aryl is substituted $C_1$-$C_3$ alkyl;

the substituent of the saturated heterocyclic group is $C_1$-$C_3$ alkyl;

said heterocyclic group comprises one or two heteroatoms selected from N and O, or, said compound has a structure of formula III:

III

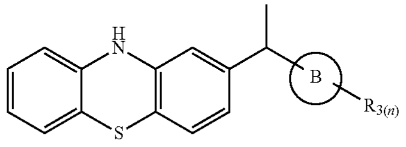

wherein, ring B is selected from aryl, benzo(5-6 membered saturated)heterocyclic group, benzo(5 membered unsaturated)heterocyclic group, anthryl, 6-8 membered unsaturated heterocyclic group, and 6-8 membered saturated cycloalkyl, all of which are substituted by n $R_3$, with n being an integer of 1-3;

$R_3$ is selected from H, halogen, cyano, hydroxyl, amino, nitro, aryl, phenoxy, substituted 6-8 membered saturated heterocyclic group, substituted $C_1$-$C_4$ alkyl, substituted or unsubstituted $C_1$-$C_3$ alkoxy, —C(O)O$R_{51}$, —N(H)C(O)$R_{51}$, and —N$R_{52}R_{53}$;

$R_{51}$ is selected from $C_1$-$C_4$ alkyl;

$R_{52}$ and $R_{53}$ are each independently selected from aryl;

wherein, in $R_3$ or $R_{51}$, the substituent of the alkyl is halogen;

the substituent of the alkoxyl is selected from aryl and halogen;

the substituent of the saturated heterocyclic group is $C_1$-$C_2$ alkyl;

the saturated heterocyclic group comprises one or two heteratoms selected from N and O;

the unsaturated heterocyclic group comprises one or two heteroatoms selected from N and O;

or, said compound has a structure of formula IV:

IV

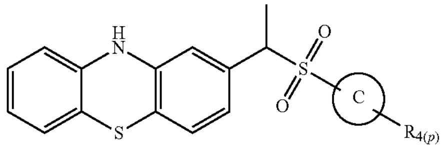

wherein, ring C is a 5-8 membered saturated heterocyclic group substituted by p $R_4$;

p is an integer of 0-4;

$R_4$ is selected from H, hydroxyl, substituted or unsubstituted $C_1$-$C_4$ alkyl, —C(O)$R_{51}$, —N(H)C(O)O$R_{51}$, —S(O)(O)$R_{51}$, —C(O)O$R_{51}$, 6-8 membered unsaturated heterocyclic group, 6-8 membered saturated heterocyclic group, and substituted or unsubstituted aryl;

$R_{51}$ is selected from $C_1$-$C_4$ alkyl, amino, 5 membered saturated heterocyclic group, and benzo(6 membered saturated)heterocyclic group;

wherein, in $R_4$ or $R_{51}$, the substituent of the alkyl is selected from halogen, benzo(5 membered saturated)

heterocyclic group, substituted or unsubstituted aryl, 6 membered saturated heterocyclic group, hydroxyl, —N(H)C(O)OR$_{51}$, —C(O)R$_{51}$, and —NR$_{52}$R$_{53}$;

the substituent of the aryl is selected from halogen, $C_1$ alkoxyl, cyano, nitro, and substituted or unsubstituted $C_1$ alkyl;

$R_{52}$ and $R_{53}$ are each $C_1$ alkyl;

the saturated heterocyclic group comprises one or two heteroatoms selected from O, N, and S; and the unsaturated heterocyclic group comprises one or two N.

4. The compound according to claim 3, or the pharmaceutically acceptable salt, or the solvate thereof, wherein said compound has a structure of formula IIA:

IIA

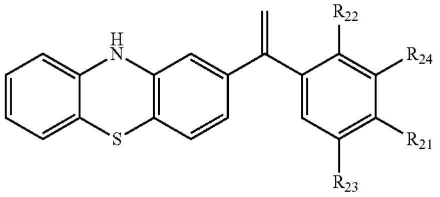

wherein, $R_{21}$, $R_{22}$, $R_{23}$, and $R_{24}$ are each independently selected from H, —C(O)OR$_{51}$, substituted or unsubstituted $C_1$-$C_4$ alkyl, substituted or unsubstituted $C_1$-$C_3$ alkoxy, —N(H)C(O)R$_{51}$, 6 membered saturated cycloalkyl, —C(O)R$_{51}$, 6-membered saturated heterocyclic group, carbazolyl, amino, hydroxyl, nitro, —S(OXO)R$_{51}$, aryl, cyano, halogen, and —C(O)N(H) R$_{51}$;

$R_{51}$ is selected from H, $C_1$-$C_2$ alkyl, amino, substituted or unsubstituted aryl, substituted or unsubstituted 5-6 membered saturated heterocyclic group, and —NR$_{52}$R$_{53}$;

$R_{52}$ and $R_{53}$ are each independently of selected from H, substituted or unsubstituted 6 membered saturated heterocyclic group, substituted or unsubstituted $C_1$-$C_4$ linear or branched chain alkyl, and 4 membered cycloalkyl;

wherein, in $R_{21}$, $R_{22}$, $R_{23}$, $R_{24}$, $R_{51}$, $R_{52}$, and $R_{53}$, the substituent of the alkyl is selected from halogen and substituted or unsubstituted 6 membered saturated heterocyclic group;

the substituent of the alkoxyl is selected from halogen and aryl;

the substituent of the aryl is substituted $C_1$ alkyl;

the substituent of the saturated heterocyclic group is $C_1$ alkyl; said saturated heterocyclic group comprises one or two heteroatoms selected from N and O;

or, said compound has a structure of formula IIB:

IIB

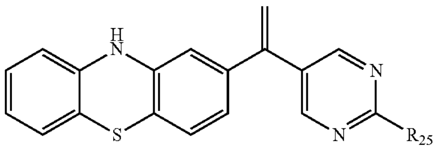

wherein, $R_{25}$ is selected from substituted or unsubstituted 6-7 membered saturated heterocyclic group and the substituent of the saturated heterocyclic group is $C_1$ alkyl;

said heterocyclic group comprises one or two heteroatoms selected from N and O;

or, said compound has a structure of formula IIC:

IIC

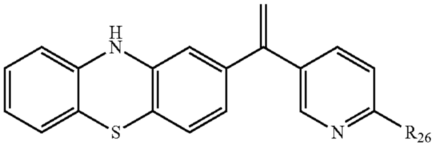

wherein, $R_{26}$ is selected from —N(H)C(O)R$_{51}$, amino, and 6 membered saturated heterocyclic group;

said saturated heterocyclic group comprises two heteroatoms selected from N and O; and $R_{51}$ is $C_1$ alkyl;

or, said compound has a structure of formula IIIA:

IIIA

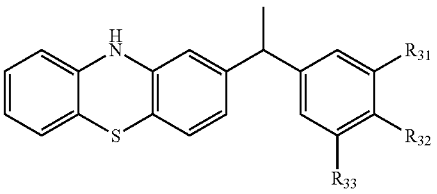

wherein, $R_{31}$, $R_{32}$, and $R_{33}$ are each independently selected from H, halogen, cyano, hydroxyl, amino, substituted or unsubstituted $C_1$-$C_3$ alkoxy, —C(O) OR$_{51}$, —N(H)C(O)R$_{51}$, aryl, phenoxy, —NR$_{52}$R$_{53}$, substituted 6 membered saturated heterocyclic group, and nitro, with the proviso that all of $R_{31}$, $R_{32}$, and $R_3$ are not simultaneously H;

$R_{51}$ is $C_1$-$C_4$ alkyl;

wherein, in $R_{31}$, $R_{32}$, and $R_{33}$, the substituent of the alkyl is halogen;

the substituent of the alkoxyl is selected from aryl and halogen;

the substituent of the saturated heterocyclic group is $C_1$ alkyl;

the saturated heterocyclic group comprise two N;

$R_{52}$ and $R_{53}$ are each independently aryl;

or, said compound has a structure of formula IIIB:

IIIB

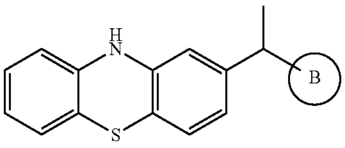

wherein, ring B is selected from benzo(5-6 membered saturated)heterocyclic group, benzo(5 membered unsaturated)heterocyclic group, anthryl, and substituted 6 membered unsaturated heterocyclic group or 6 membered saturated cycloalkyl;

the substituent of the unsaturated heterocyclic group is selected from cyano, $C_1$ alkyl, and $C_2$ alkoxyl;

the saturated heterocyclic group comprises one or two O;

the unsaturated heterocyclic group comprises one heteroatom selected from O and N;

or, said compound has a structure of formula IVA:

IVA

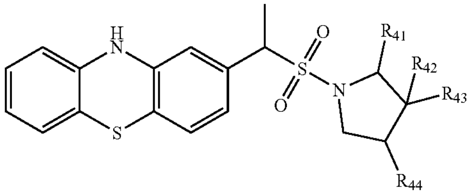

wherein, $R_{41}$, $R_{42}$, $R_{43}$, and $R_{44}$ are each independently selected from H, hydroxyl, —N(H)C(O)O$R_{51}$, and substituted or unsubstituted $C_1$ alkyl;

$R_{51}$ is $C_4$ alkyl;

the substituent of the alkyl is —N(H)C(O)O$R_{51}$;

or, said compound has a structure of formula IVB:

IVB

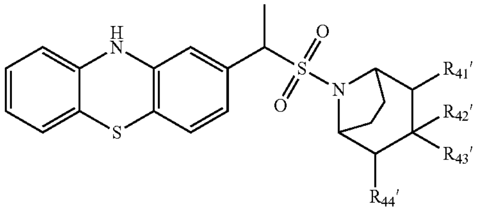

wherein, $R_{41}'$, $R_{42}'$, $R_{43}'$, and $R_{44}'$ are each independently selected from H and hydroxyl;

or, said compound has a structure of formula IVC:

IVC

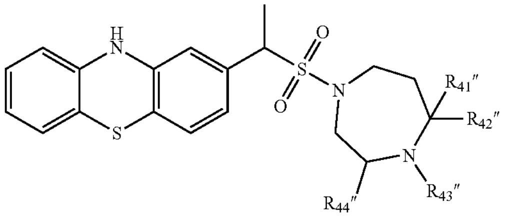

wherein, $R_{41}''$, $R_{42}''$, $R_{43}''$, and $R_{44}''$ are each independently selected from H, $C_1$ alkyl, —C(O)$R_{51}$;

$R_{51}$ is $C_1$ alkyl;

or, said compound has a structure of formula IVD:

IVD

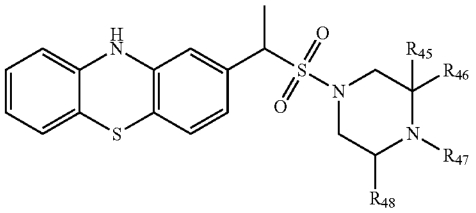

wherein, $R_{45}$, $R_{46}$, $R_{47}$, and $R_{48}$ are each independently selected from H, substituted or unsubstituted $C_1$-$C_4$ alkyl, —C(O)$R_{51}$, —S(O)(O)$R_{51}$, 6 membered unsaturated heterocyclic group, —C(O)O$R_{51}$, and substituted or unsubstituted aryl;

$R_{51}$ is selected from 5 membered saturated heterocyclic group, $C_1$-$C_4$ alkyl, and benzo(6 membered saturated) heterocyclic group;

$R_{52}$ and $R_{53}$ are each independently $C_1$ alkyl;

the substituent of the alkyl is selected from halogen, benzo(5 membered saturated)heterocyclic group, —C(O)$R_{51}$, —N$R_{52}R_{53}$, substituted or unsubstituted aryl, 6 membered saturated heterocyclic group, and hydroxyl;

the substituent of the aryl is selected from $C_1$ alkoxyl, halogen, cyano, nitro, and substituted or unsubstituted $C_1$ alkyl;

the saturated heterocyclic group comprises one or two heteroatoms selected from O and N;

the unsaturated heterocyclic group comprises one or two N;

or, said compound has a structure of formula IVE:

IVE

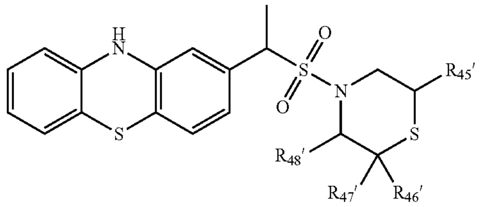

wherein, $R_{45}'$, $R_{46}'$, $R_{47}'$, and $R_{48}'$ are each independently selected from H and $C_1$ alkyl;

or, said compound has a structure of formula IVF:

IVF

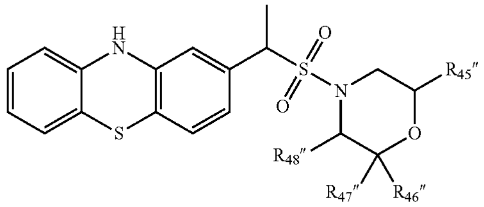

wherein, $R_{45}''$, $R_{46}''$, $R_{47}''$, and $R_{48}''$ are each independently selected from H and $C_1$ alkyl;

or, said compound has a structure of formula IVG:

IVG

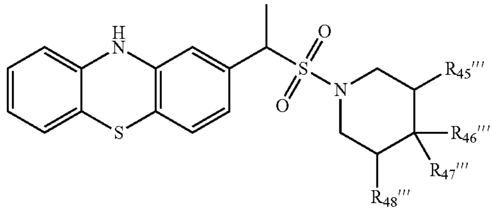

wherein, $R_{45}'''$, $R_{46}'''$, $R_{47}'''$, and $R_{48}'''$ are each independently selected from H, hydroxyl, —C(O)O$R_{51}$, —N(H)C(O)$OR_{51}$, substituted aryl, substituted or unsubstituted $C_1$ alkyl, 6 membered saturated heterocyclic group, and —C(O)$R_{51}$;

$R_{51}$ is selected from $C_2$-$C_4$ alkyl and amino;

the substituent of the aryl is halogen;

the substituent of the alkyl is selected from —N(H)C(O)$OR_{51}$ and hydroxyl;

the saturated heterocyclic group comprises one N.

5. The compound according to claim 1, or the pharmaceutically acceptable salt, or the solvate thereof, wherein said compound is selected from:

A2

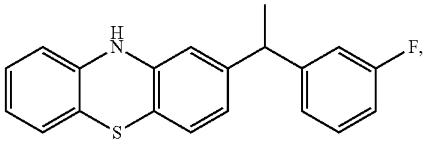

A3

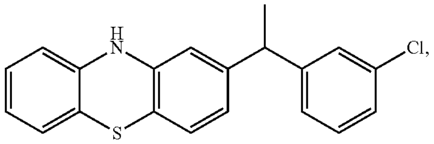

A4

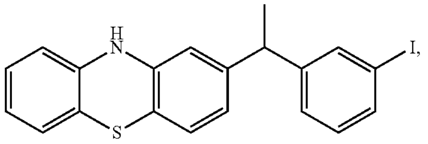

A5

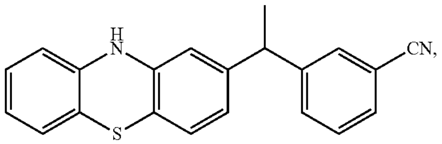

A6

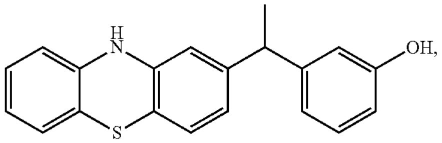

A7

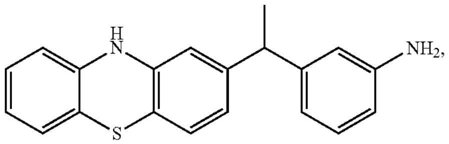

A11

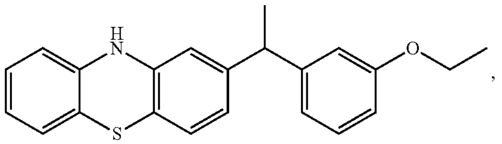

A12

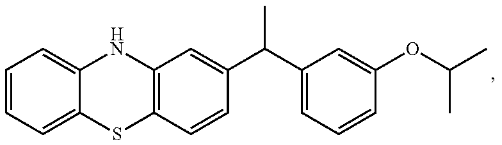

-continued

A13

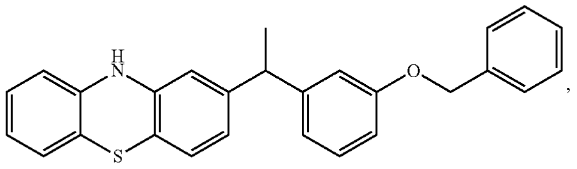

A14

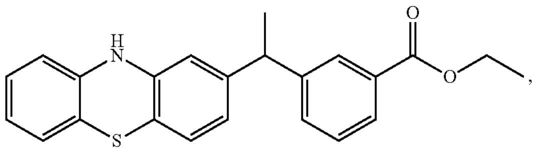

A15

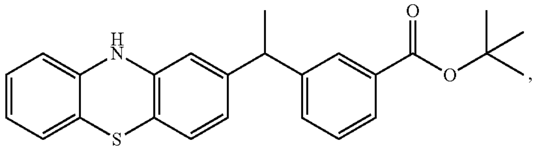

A16

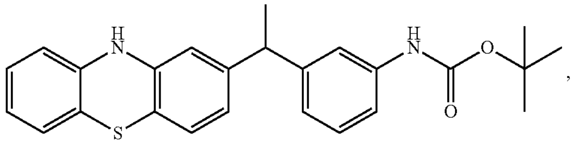

A17

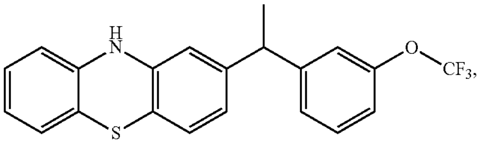

A18

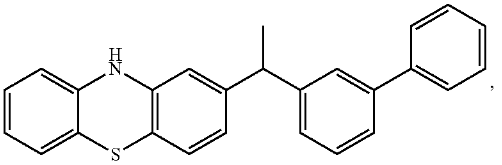

A19

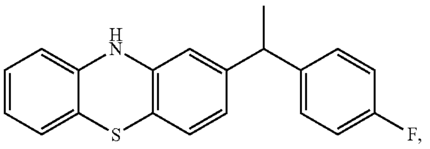

A20

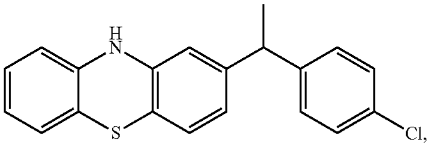

A21

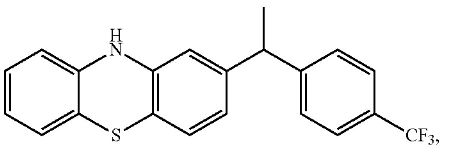

-continued
A22
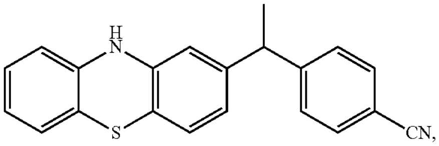
A23
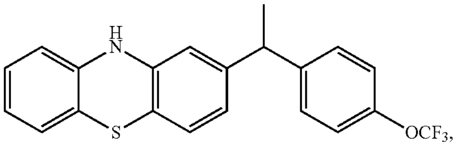
A30
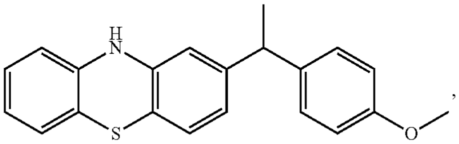
,
A31
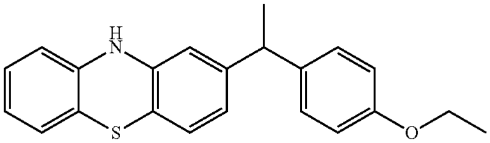
,
A32
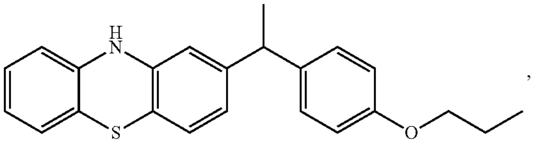
,
A33
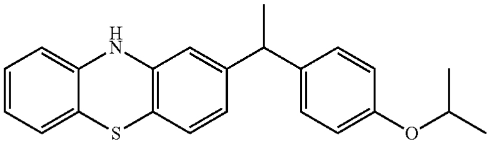
,
A34
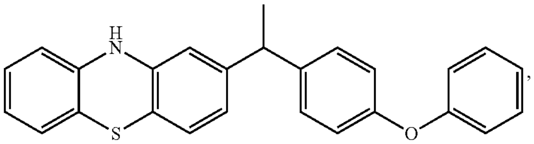
,
A35
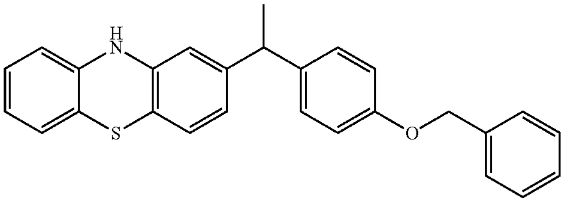
,
A36
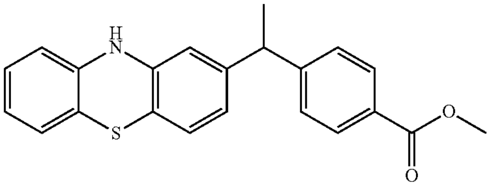
,
-continued
A37
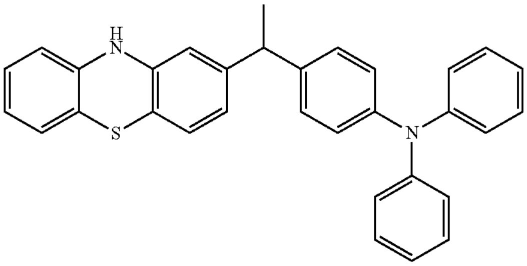
,
A38
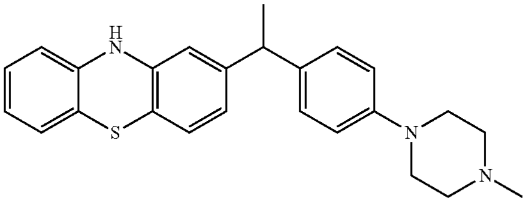
,
A39
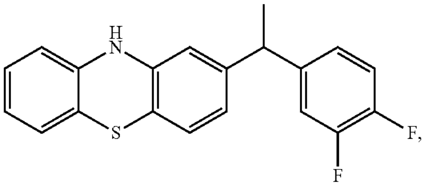
A40
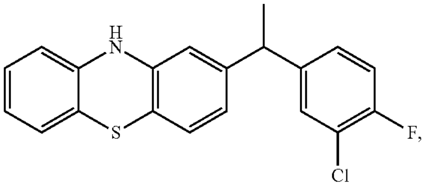
A41
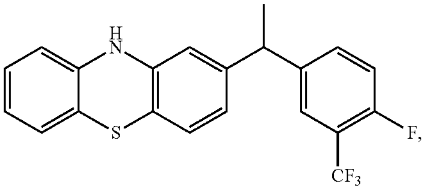
A42
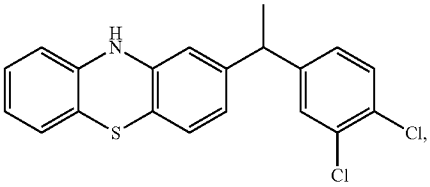
A43
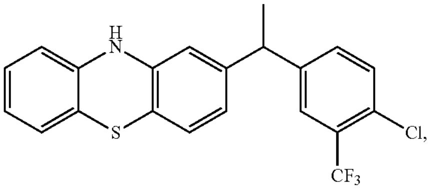

-continued
A44
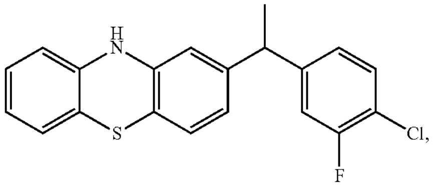
A45
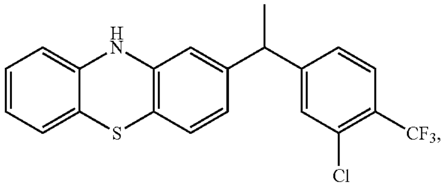
A47
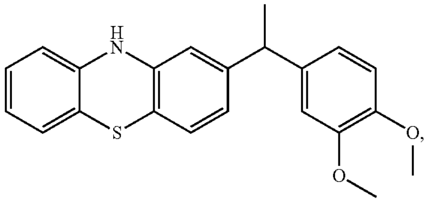
A50
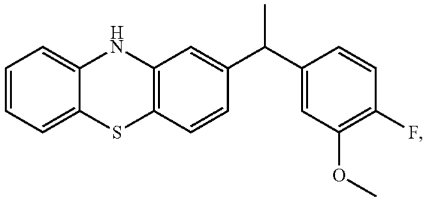
A51
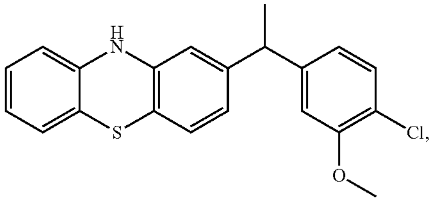
A53
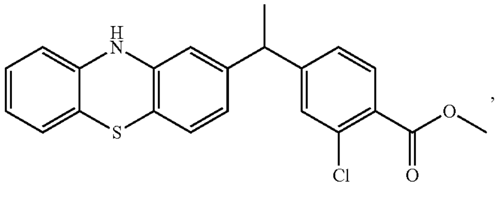
A55
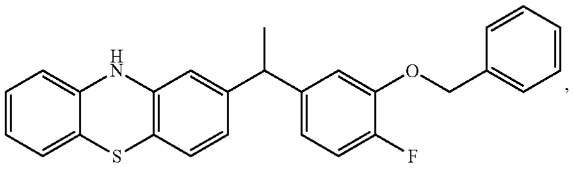
A56
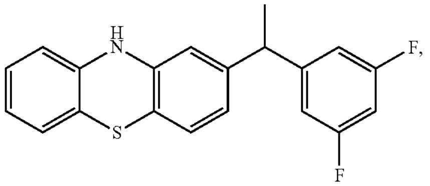
-continued
A57
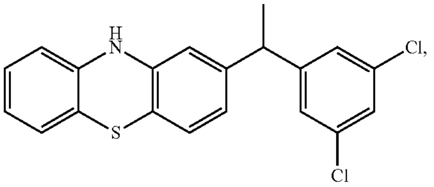
A58
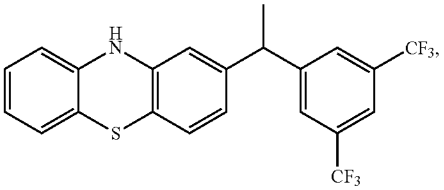
A60
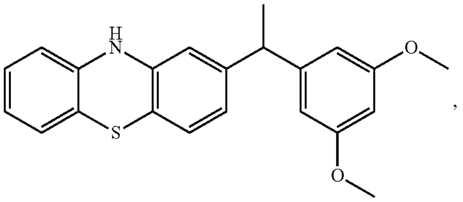
A61
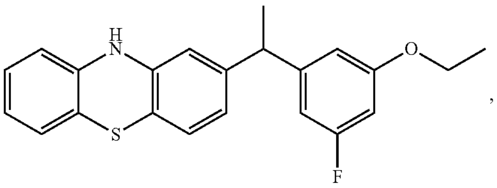
A63
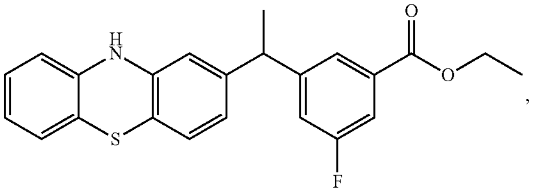
A64
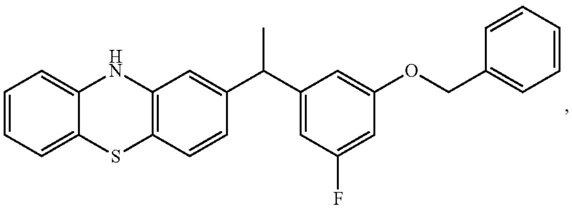
A65
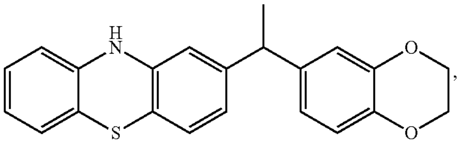
A66
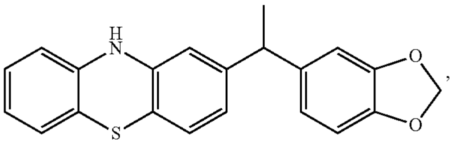

-continued
A67
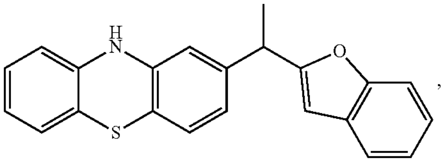
,
A69
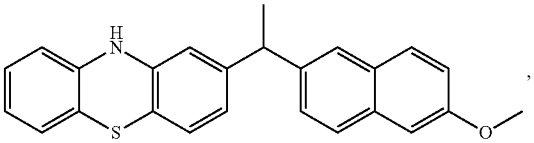
,
A70
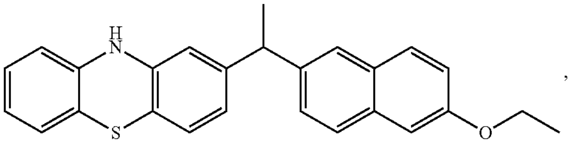
,
A71
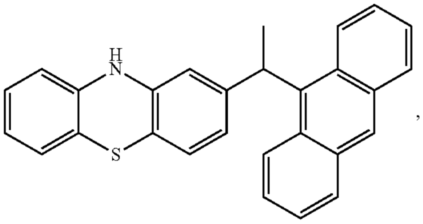
,
A72
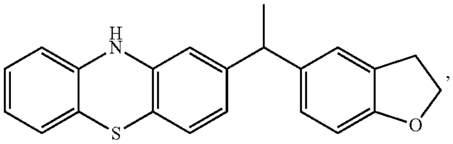
,
A73
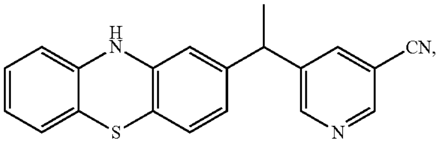
A74
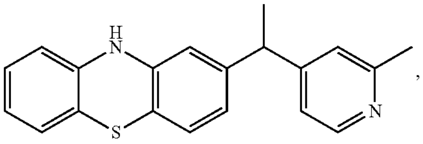
,
A75
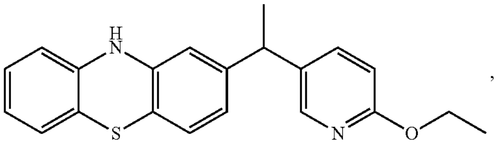
,
A76
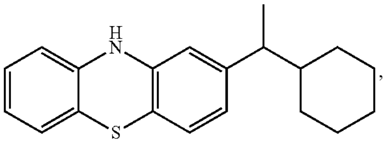
,
-continued
B1
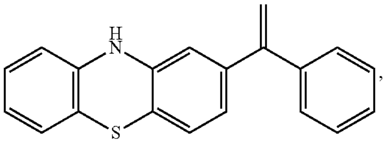
,
B2
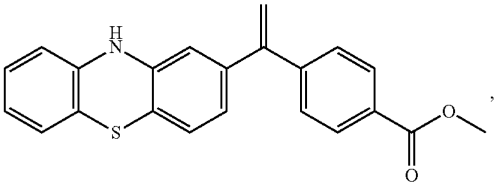
,
B3
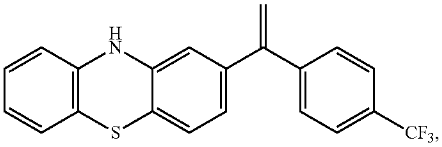
B4
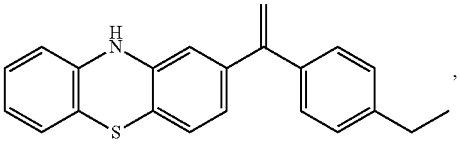
,
B5
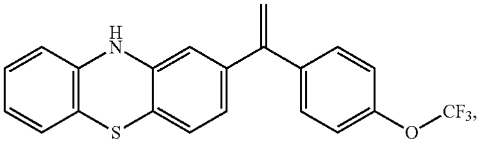
B6
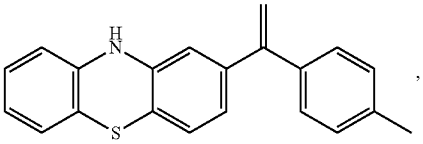
,
B7
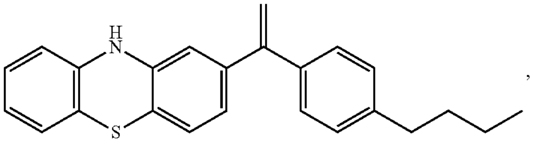
,
B8
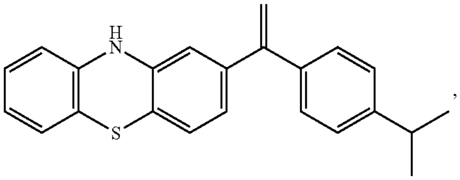
,
B9
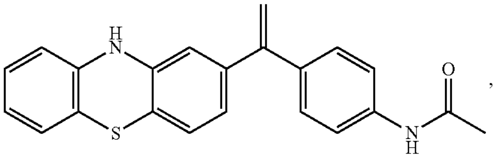
, -continued
B10
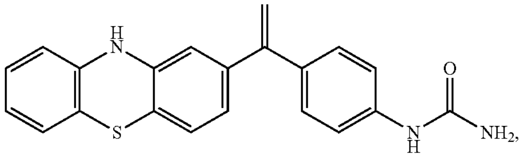
B11
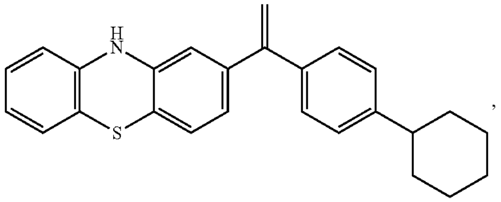
B12
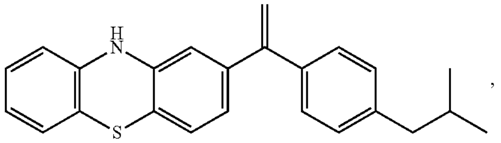
B13
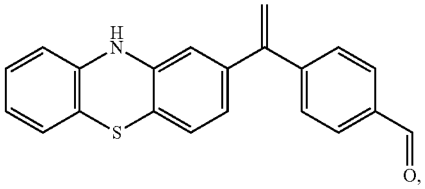
B14
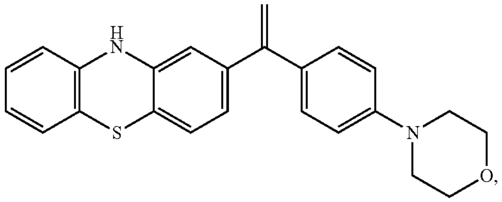
B15
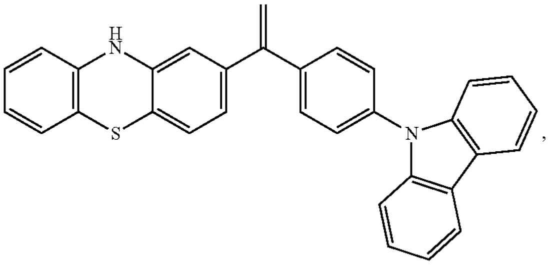
B16
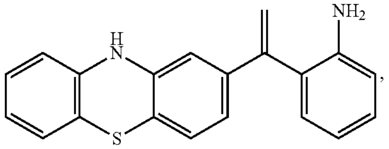
B17
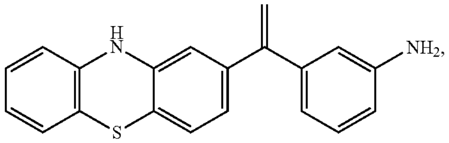
-continued
B18
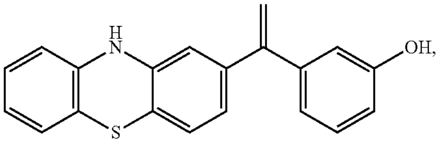
B19
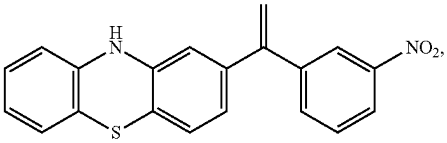
B20
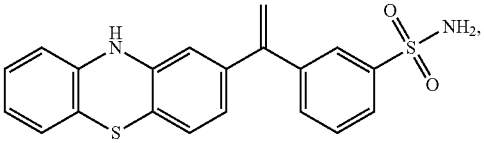
B21
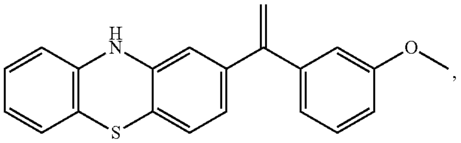
B22
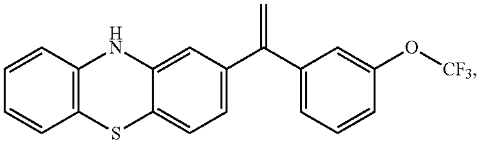
B23
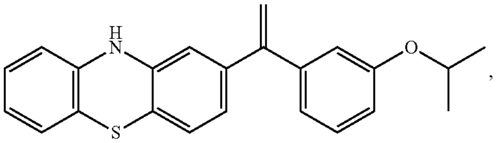
B24
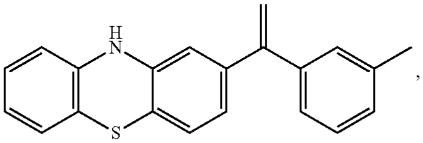
B25
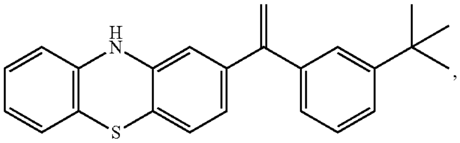
B26
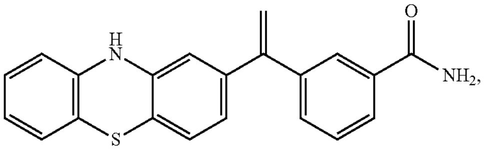
B27
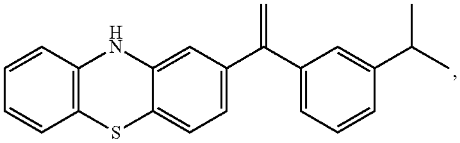

-continued
B28
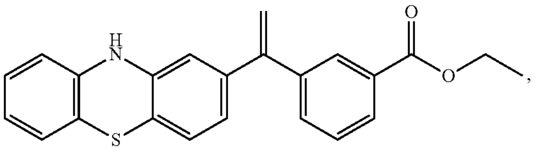
B29
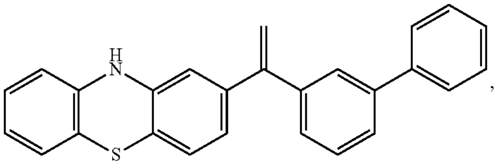
B30
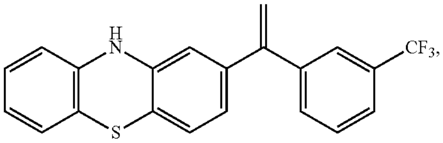
B31
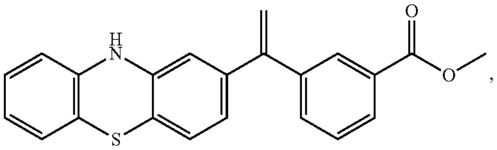
B32
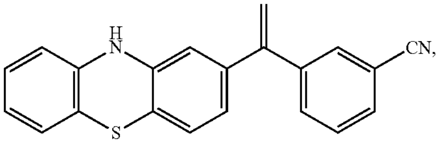
B33
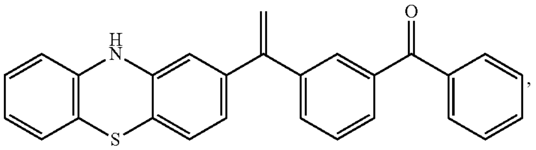
B34
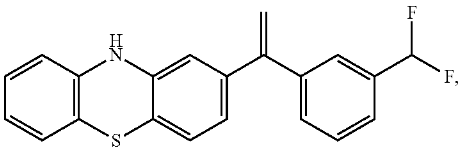
B35
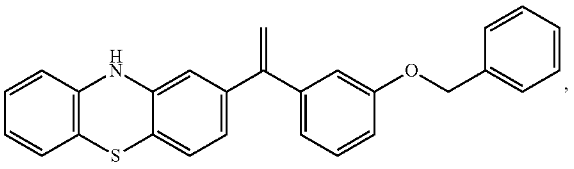
B36
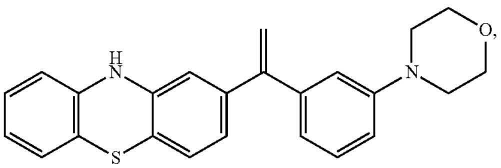
-continued
B37
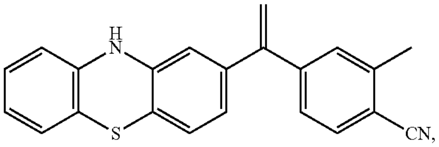
B38
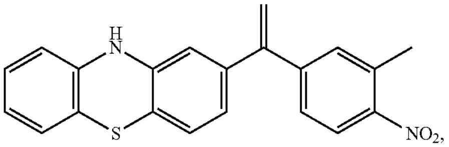
B39
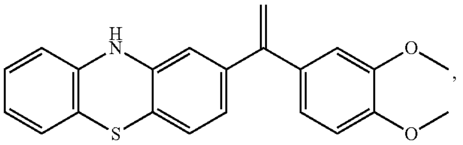
B40
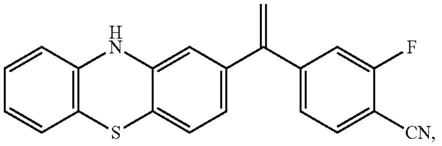
B41
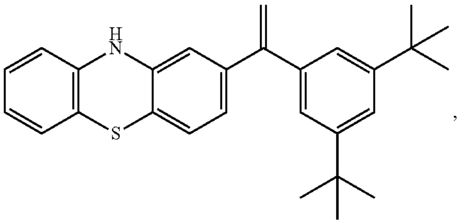
B42
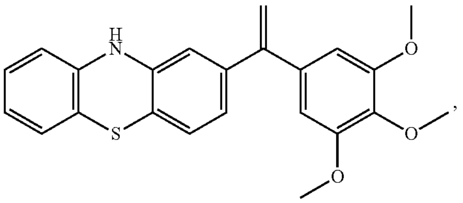
B43
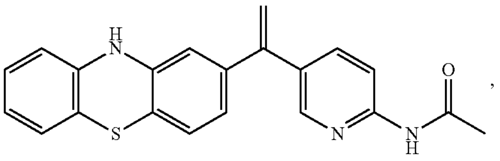
B44
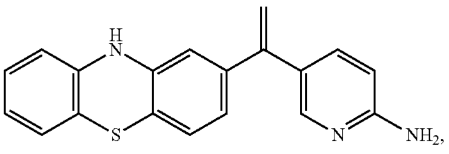

-continued
B45
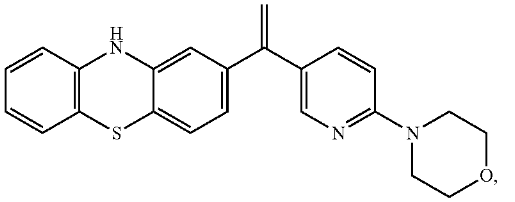
B46
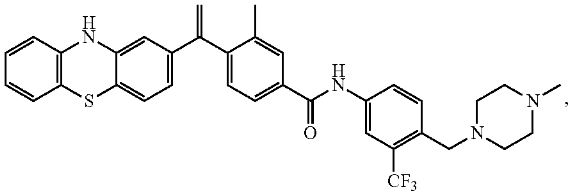
B47
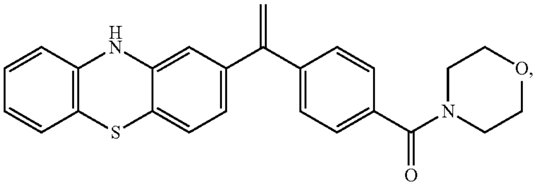
B48
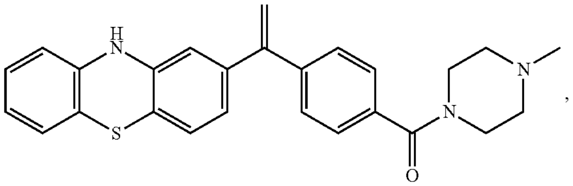
B49
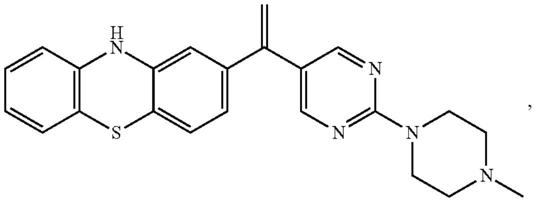
B50
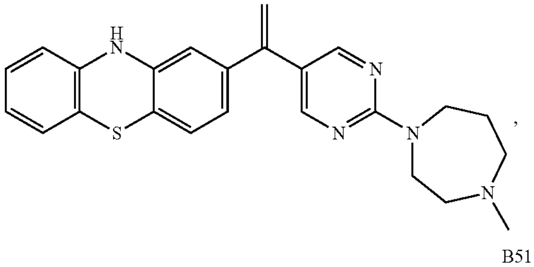
B51
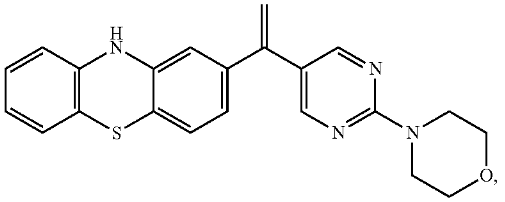
-continued
B52
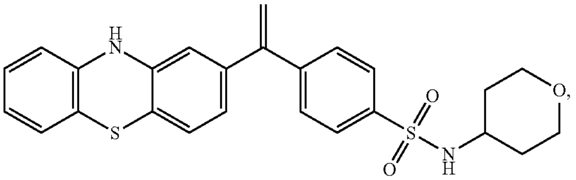
B53
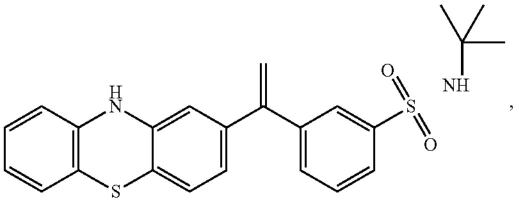
B54
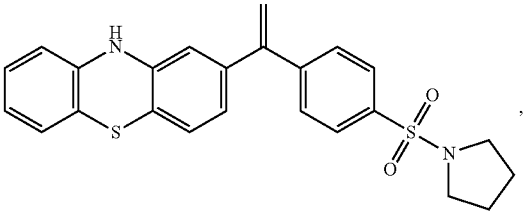
B55
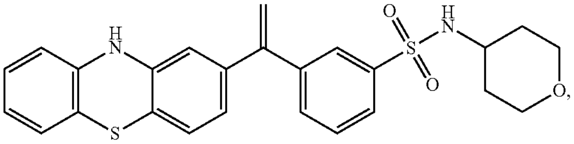
B56
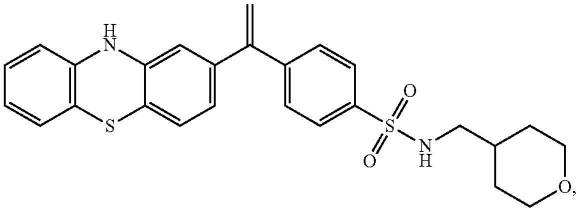
B57
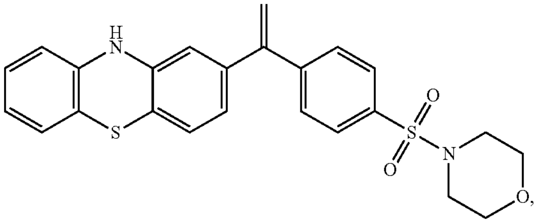
B58
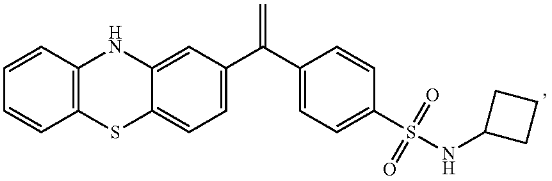

-continued
B59
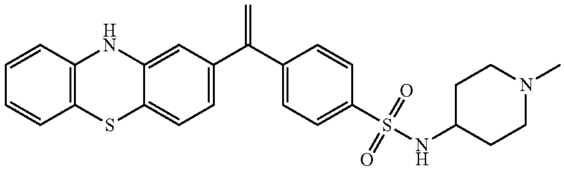
,
C1
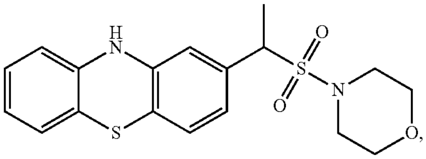
,
C2
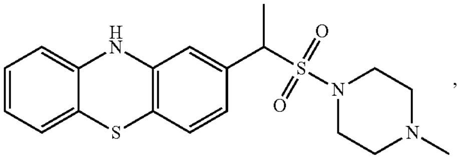
,
C3
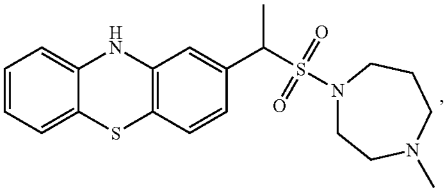
,
C4
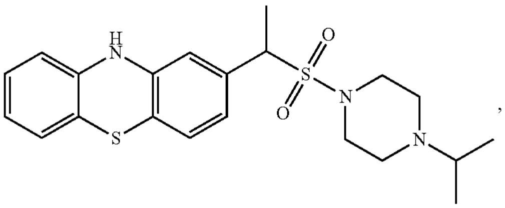
,
C5
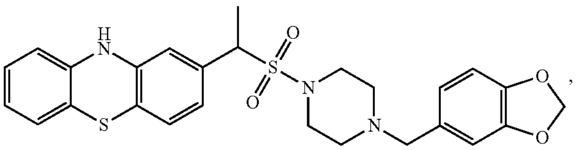
,
C6
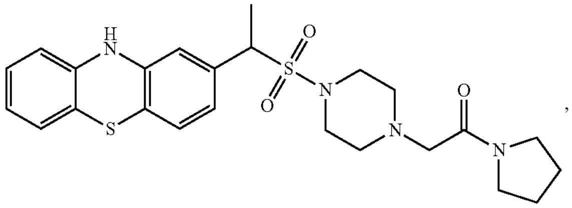
,
C7
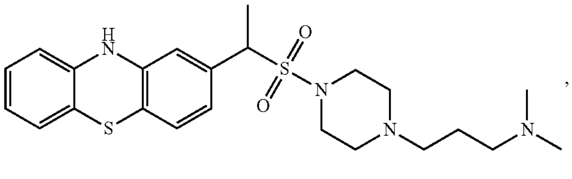
,
-continued
C8
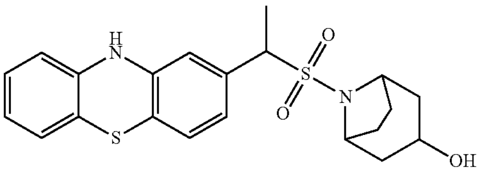
C9
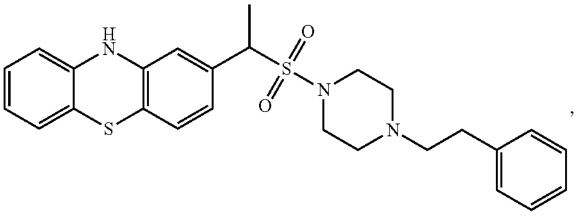
,
C10
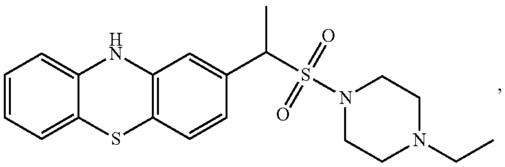
,
C11
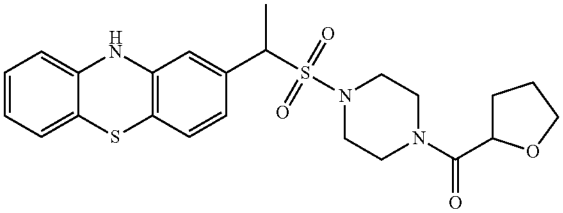
,
C12
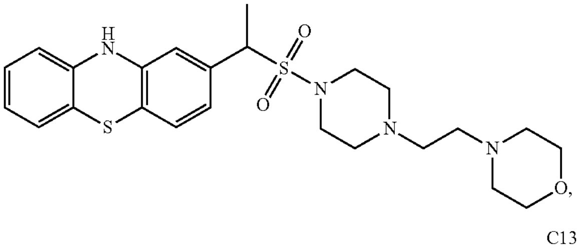
,
C13
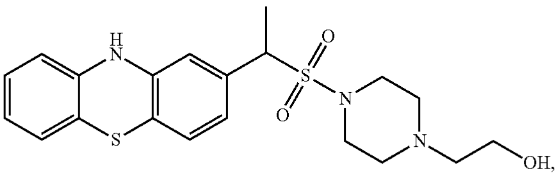
,
C14
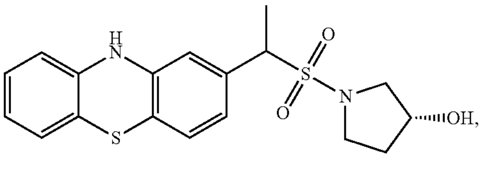
, -continued
C15
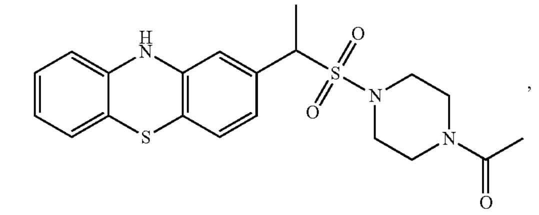
C16
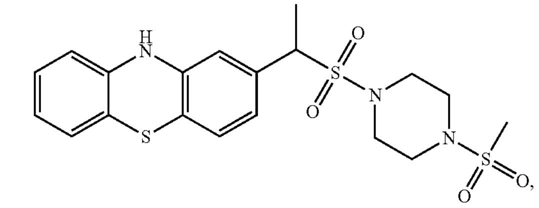
C17
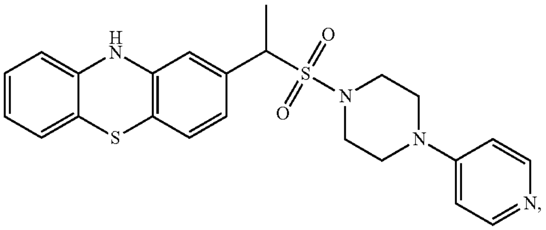
C18
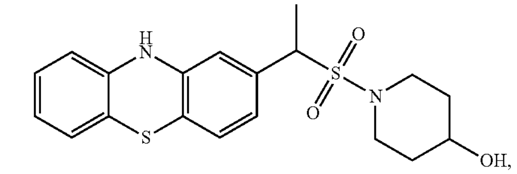
C19
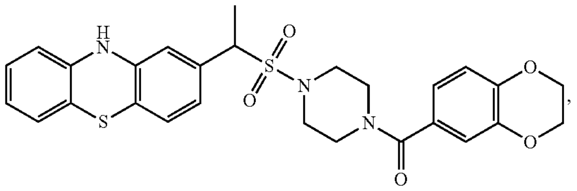
C20
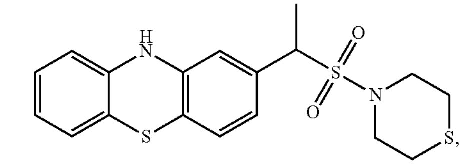
C21
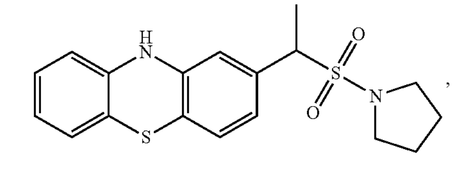
-continued
C22
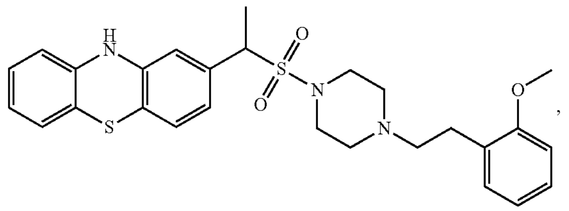
C23
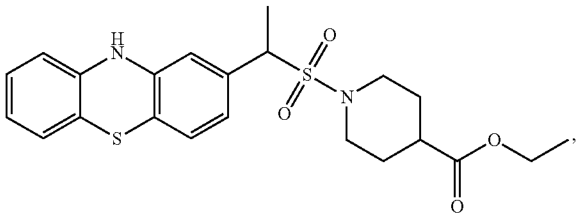
C24
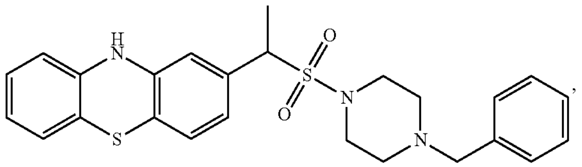
C25
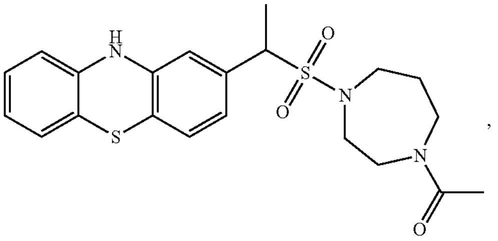
C26
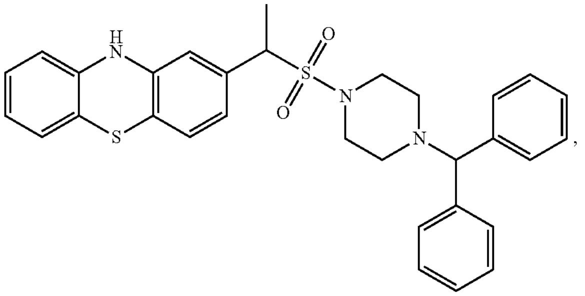
C27
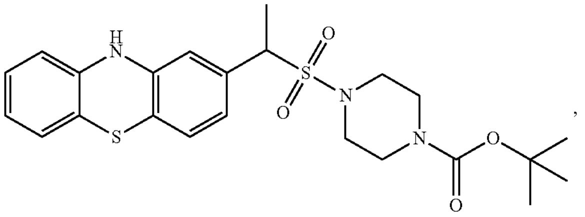

-continued
C28
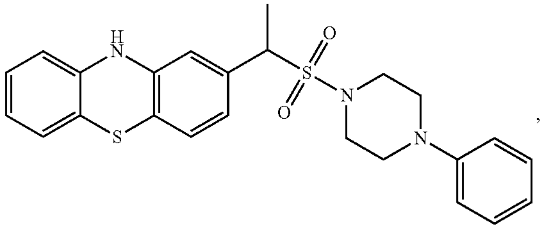
,
C29
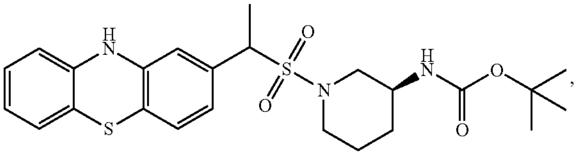
,
C30
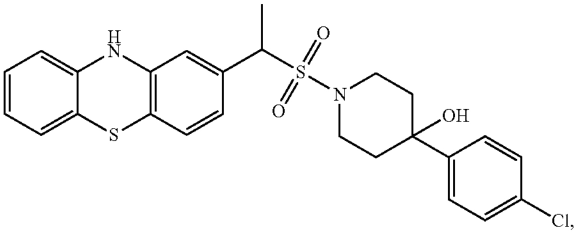
C31
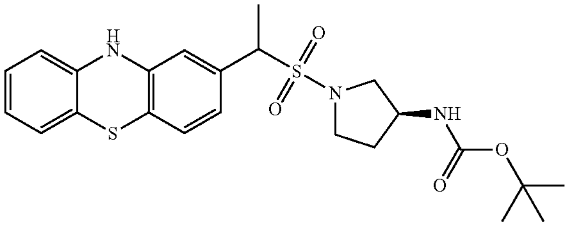
,
C32
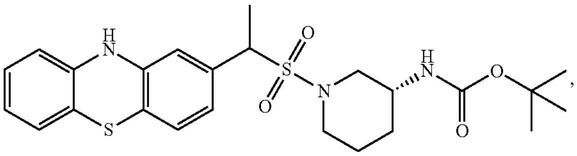
,
C33
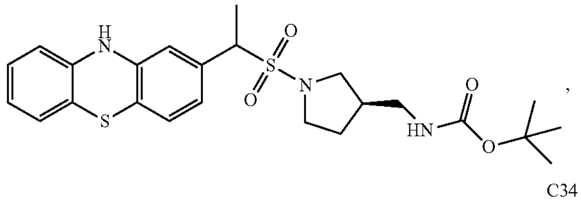
,
C34
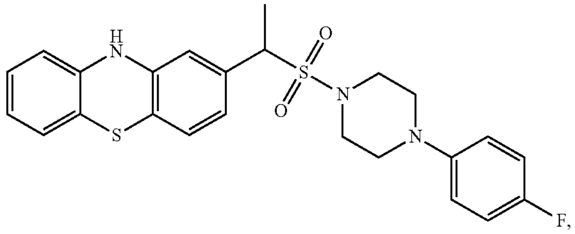
-continued
C35
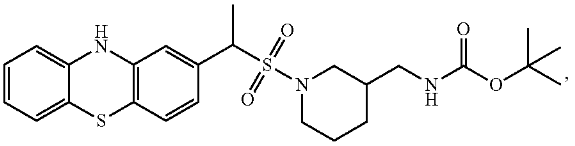
C36
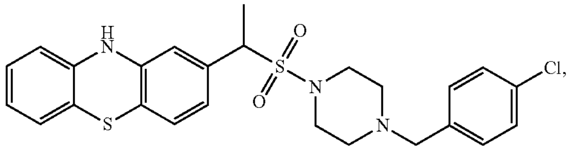
C37
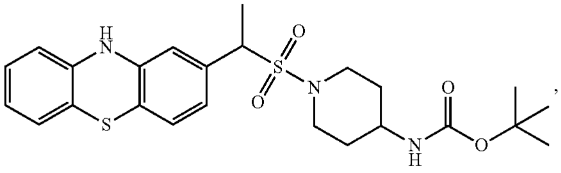
,
C38
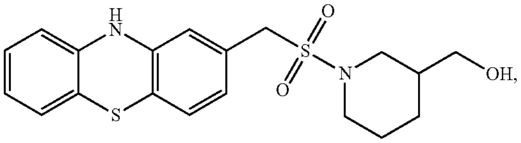
C39
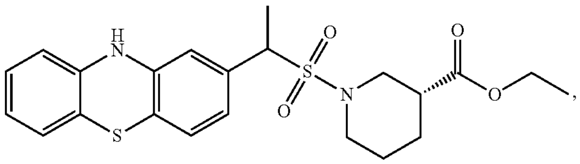
C40
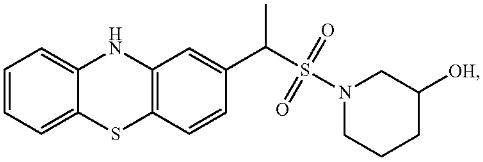
C41
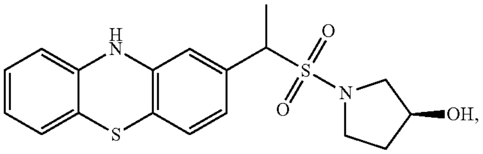
C42
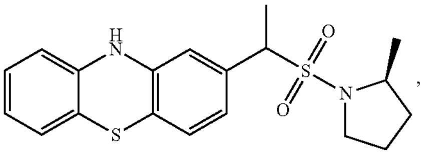
, -continued
C43
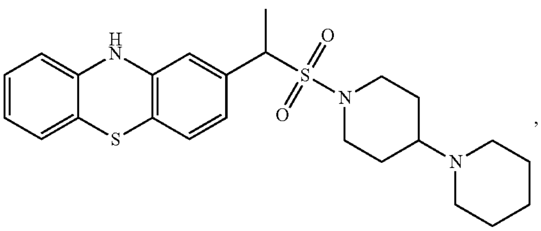
,
C44
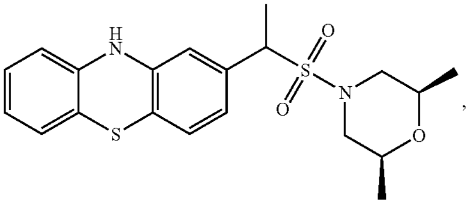
,
C45
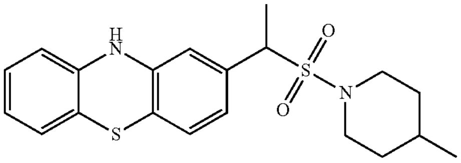
,
C46
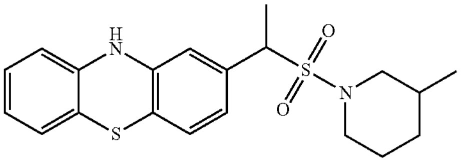
,
C47
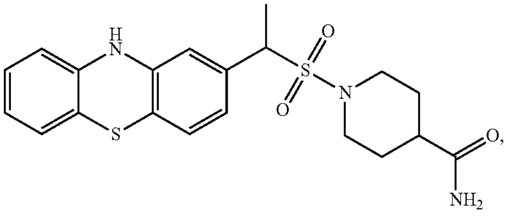
C48
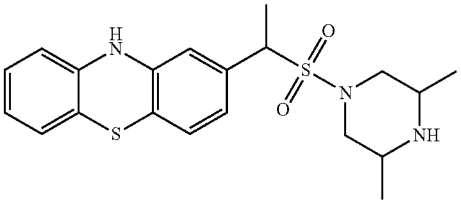
,
C49
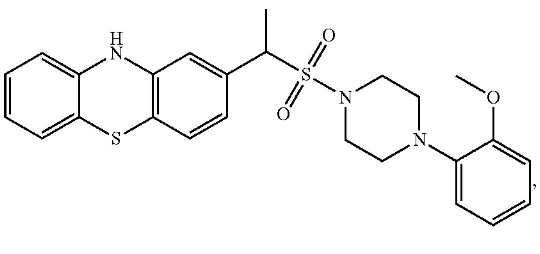
,
-continued
C50
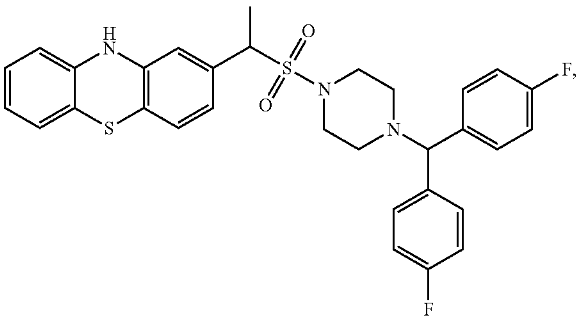
C51
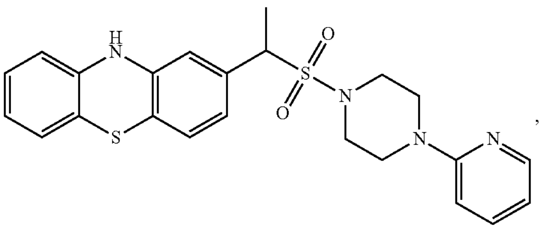
,
C52
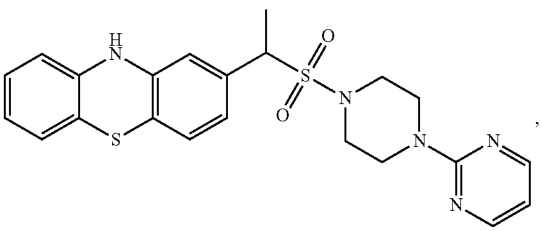
,
C53
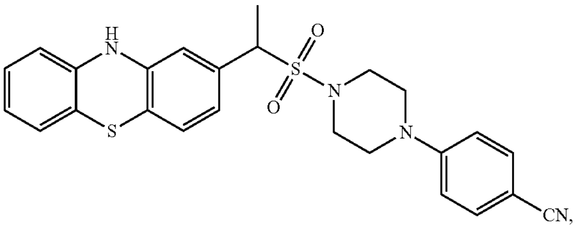
C54
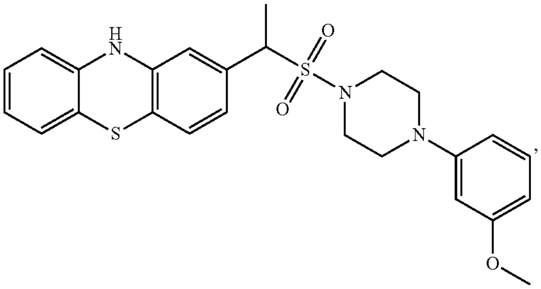
, -continued

C55

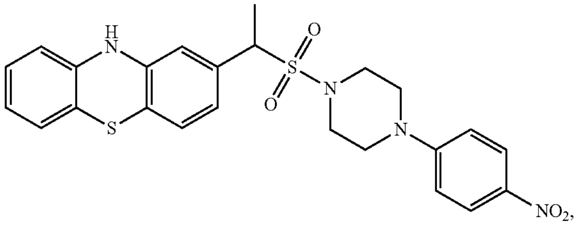

C56

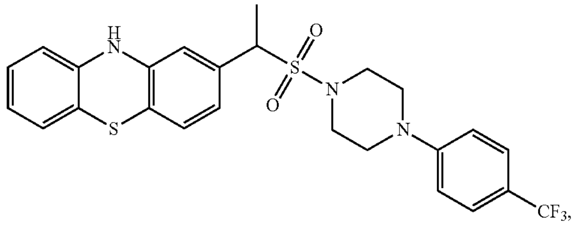

C57

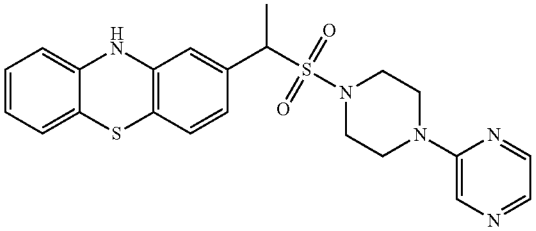

,

C58

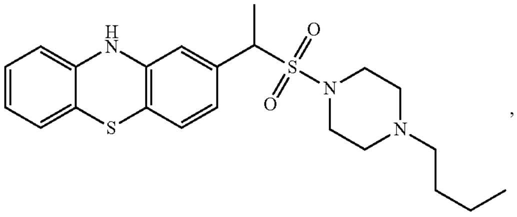

, and

C59

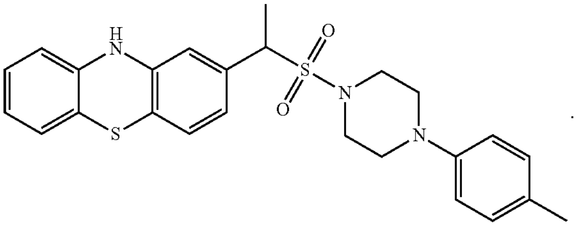

.

6. A preparative method for the compound, or the pharmaceutically acceptable salt, or the solvate thereof according to claim 1, wherein the method includes the following steps:

(1) 2-Acetylphenothiazine and 4-methylbenzenesulfonyl hydrazide are used as starting materials, and dissolved in MeOH, to which is then added the catalyst HOAc; the mixture is heated to 60° C. for reaction, and the progress of the reaction is monitored. After completion of the reaction, the reaction is cooled to room temperature, filtered under reduced pressure, and the filtrate is rinsed to be colorless, then dried in vacuo to provide intermediate 1;

(2) Intermediate I, starting material A, and anhydrous $K_2CO_3$ are dissolved in 1,4-dioxane, and then reacted at 110° C.; the progress of the reaction is monitored. And after completion of the reaction, the mixture is cooled to room temperature and concentrated under reduced pressure to remove 1, 4-dioxane; the residue is extracted, and the organic layer is concentrated and then separated by column chromatography to obtain the target product;

or, the method includes the following steps:

(1) 2-Acetylphenothiazine and 4-methylbenzenesulfonyl hydrazide are used as starting materials, that are dissolved in MeOH, to which is then added the catalyst HOAc; the mixture is heated to 60° C. for reaction, and the progress of the reaction is monitored. After completion of the reaction, the reaction is cooled to room temperature, filtered under reduced pressure, and the filtrate is rinsed to be colorless, then dried in vacuo to obtain intermediate I;

(2) Intermediate I, starting material A, tris(dibenzylideneBASE acetone)dipalladium, 2-dicyclohexylphosphino-2,4,6-triisopropylbiphenyl and anhydrous t-BuOLi are dissolved in 1,4-dioxane, to which argon is purged and exchanged for 3 times; the resultant mixture is heated to 70° C. for reaction, and the reaction is monitored by TLC. After about 4 h, the reaction is completed, cooled to room temperature, filtered, concentrated under reduced pressure, and the residue is extracted; the organic layer is concentrated and separated by column chromatography to provide the target compound;

or, the method includes the following steps:

(1) 2-Acetylphenothiazine and 4-methylbenzenesulfonyl hydrazide are used as starting materials, that are dissolved in MeOH, to which is then added the catalyst HOAc; the mixture is heated to 60° C. for reaction, and the progress of the reaction is monitored. After completion of the reaction, the reactions are cooled to room temperature, filtered under reduced pressure, and the filtrate is rinsed to be colorless, then dried in vacuo to provide intermediate I;

(2) Intermediate I, starting material A, and DABSO are dissolved in DMSO, to which argon is purged and exchanged for 3 times; the resultant mixture is heated to 100° C. for reaction, and the reaction is monitored. After about 12 h, the reaction is completed, cooled to room temperature, filtered, concentrated under reduced pressure, and the residue is extracted; the organic layer is concentrated and separated by column chromatography to provide the target compound.

7. The preparative method according to claim 6, wherein in said step (2), starting material A is selected from

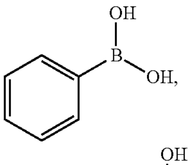

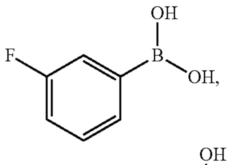

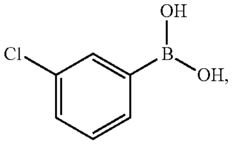

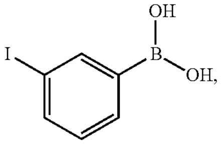

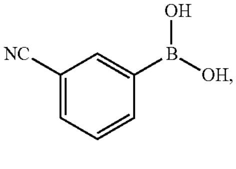

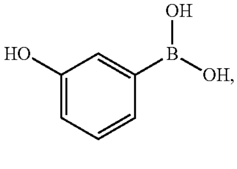

-continued
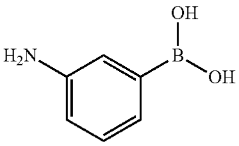
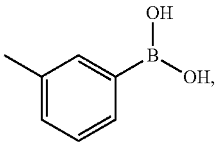
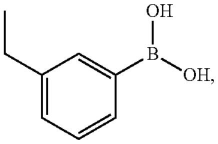
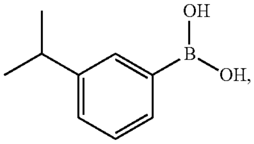
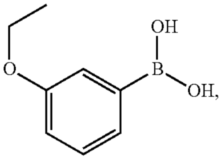
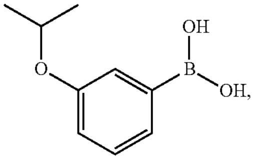
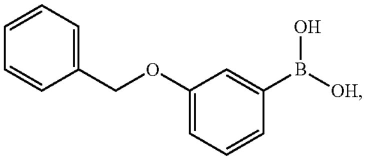
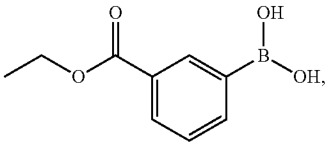
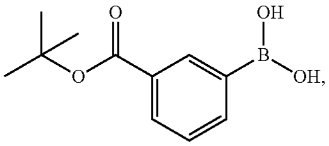
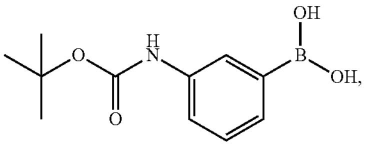
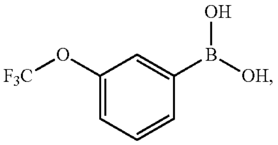
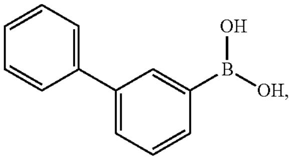
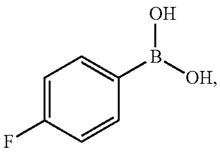
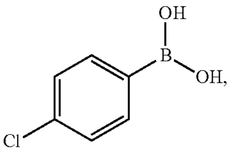
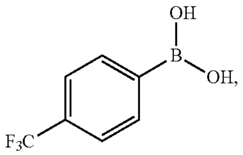
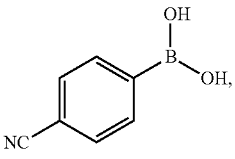
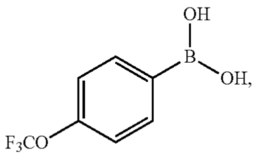
-continued
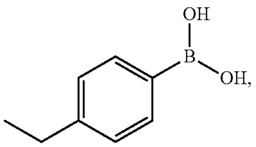
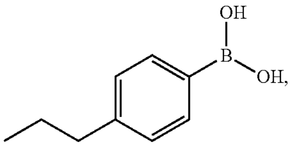
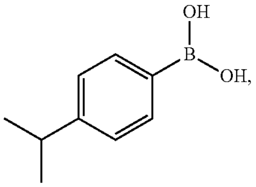
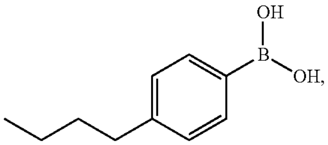
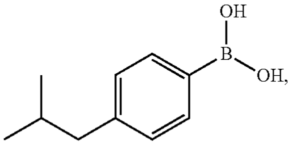
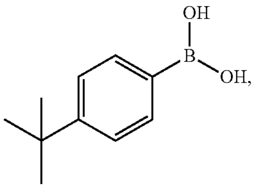
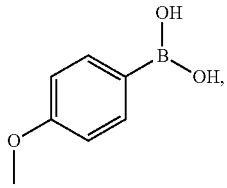
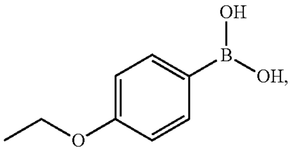
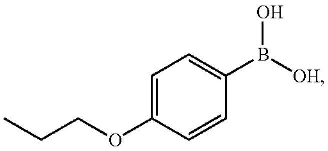
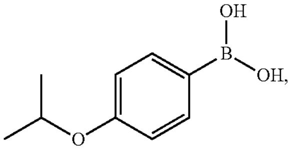
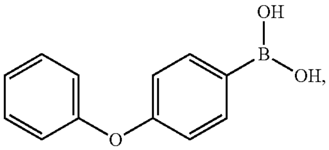

-continued
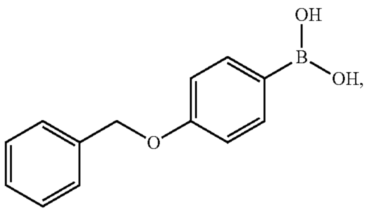
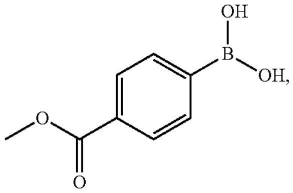
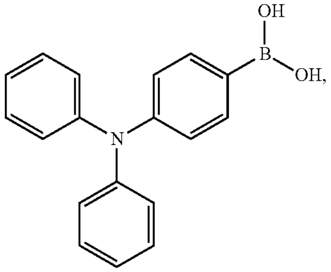
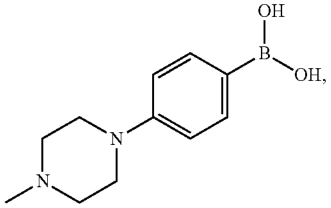
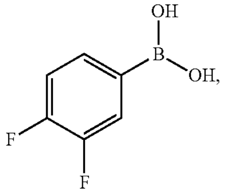 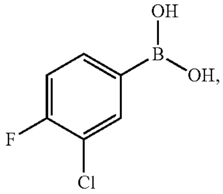
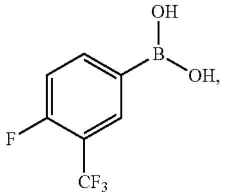 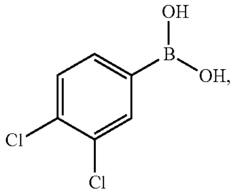
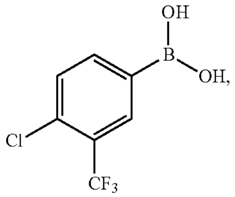 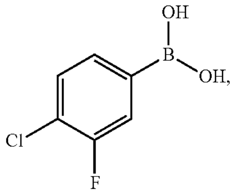
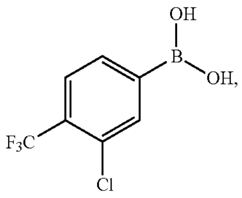 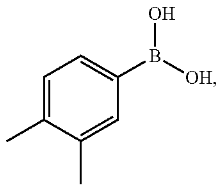
-continued
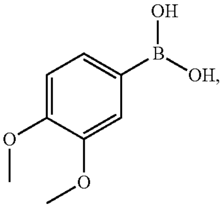 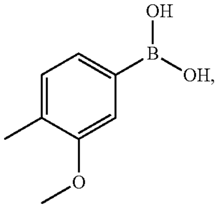
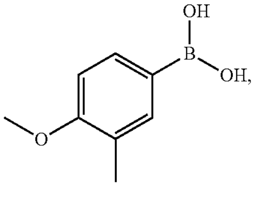 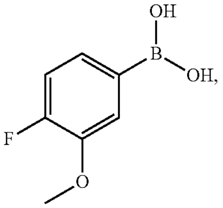
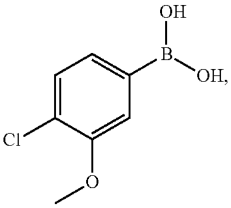 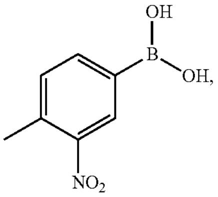
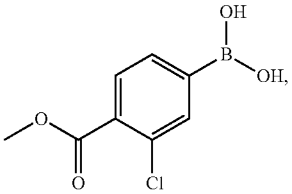
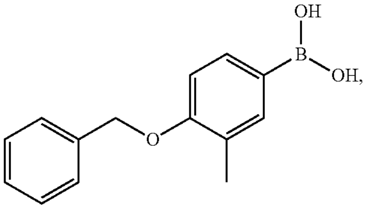
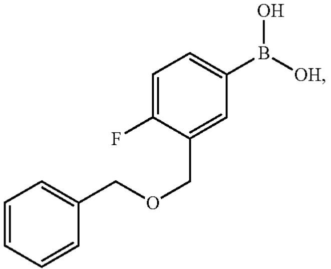
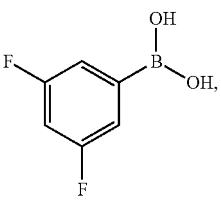 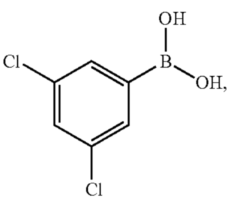
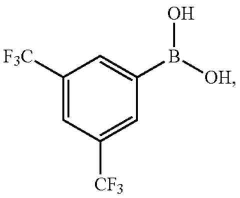 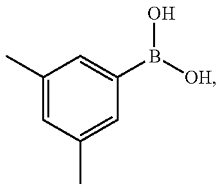

-continued
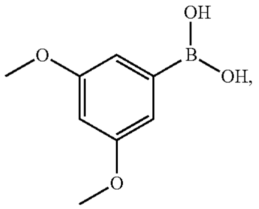
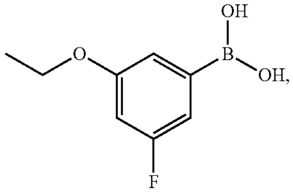
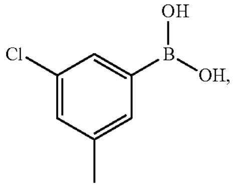
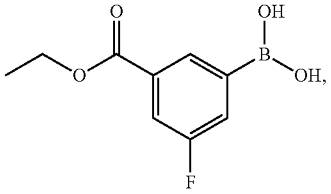
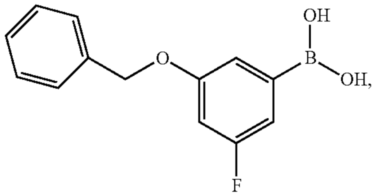
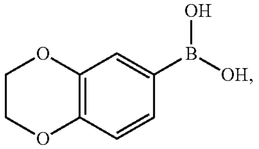 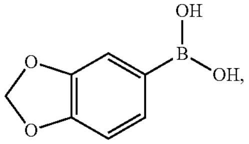
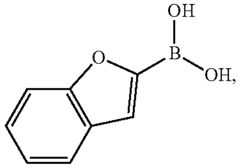 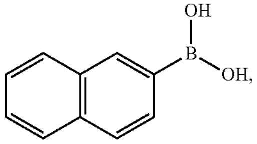
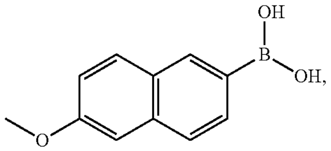
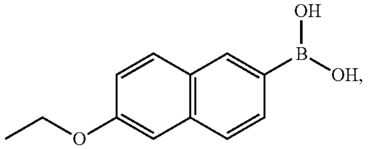
-continued
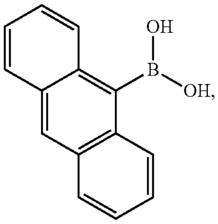 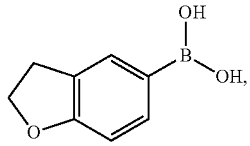
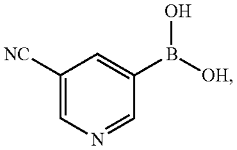 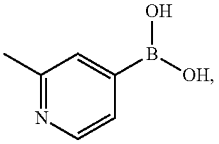
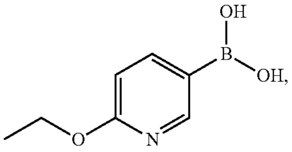 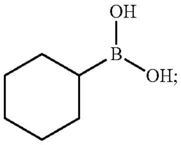
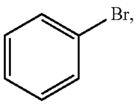 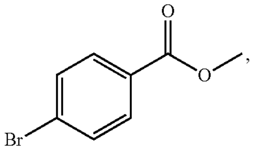
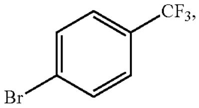 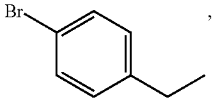 ,
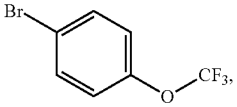 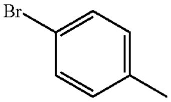 ,
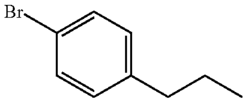 , 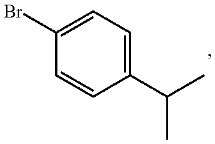 ,
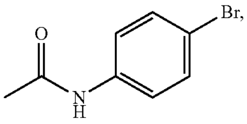 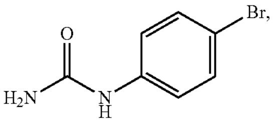
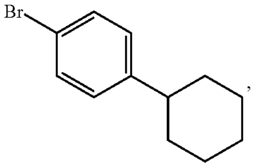 , 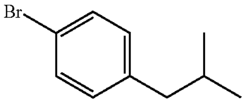 ,
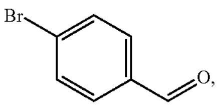 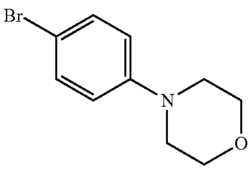 , -continued
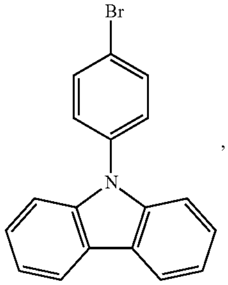,
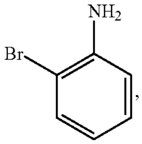,
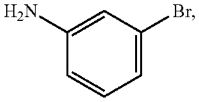
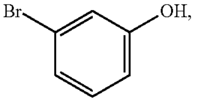
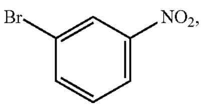
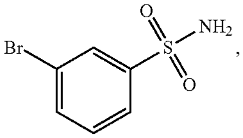,
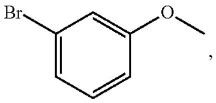,
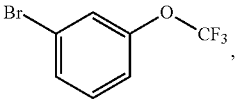,
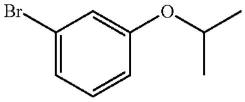,
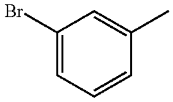,
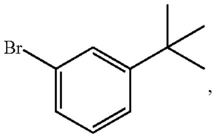,
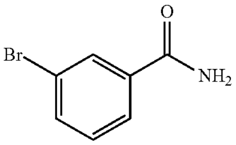,
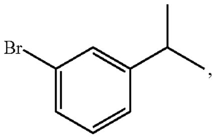,
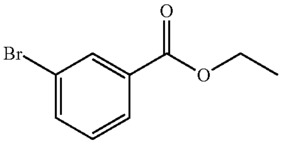,
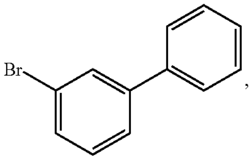,
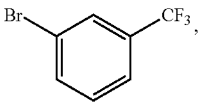
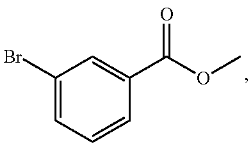,
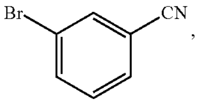,
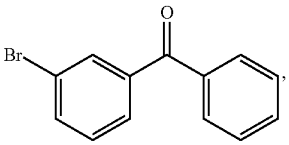,
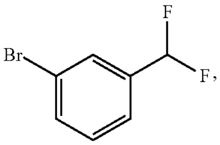
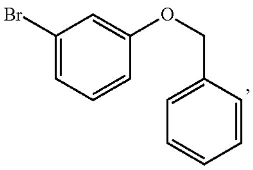,
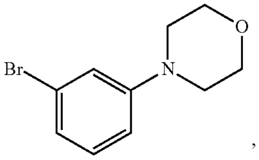,
-continued
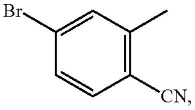
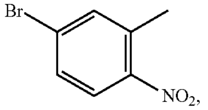
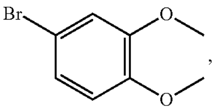,
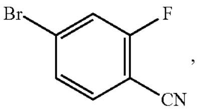,
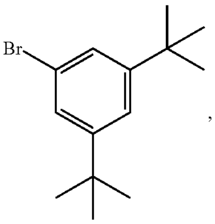,
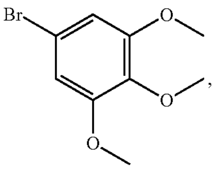
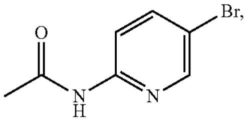
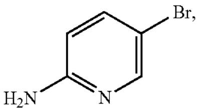
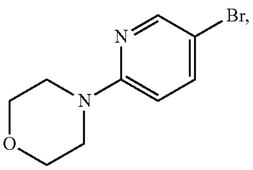
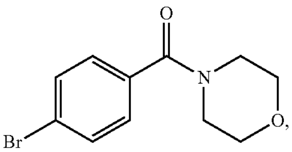
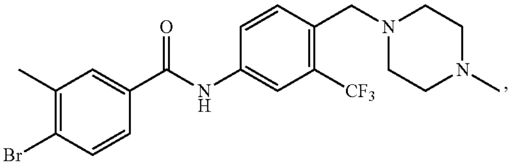
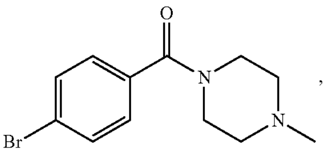,
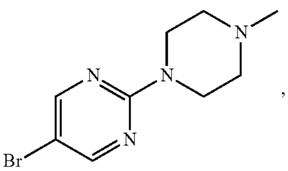,
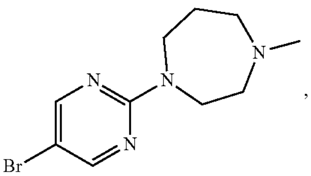,
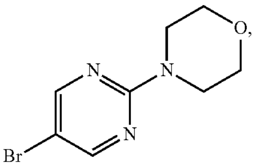

-continued
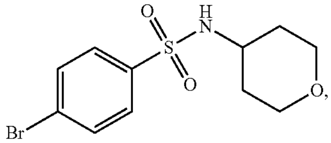,
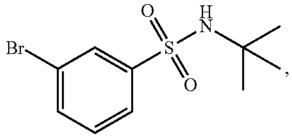,
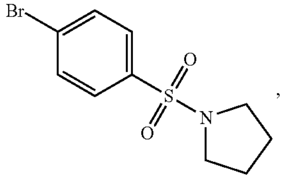,
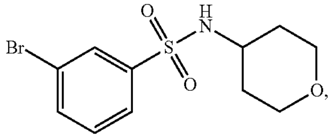,
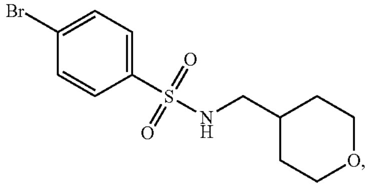,
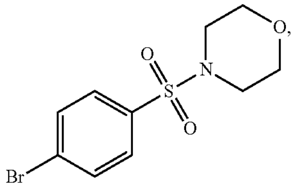,
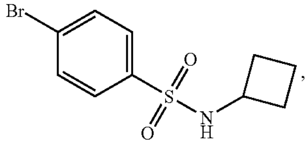,
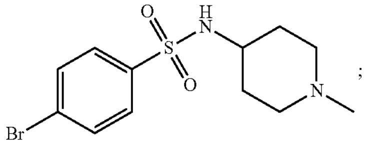;
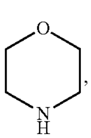, 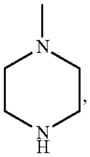, 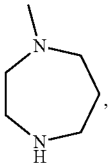, 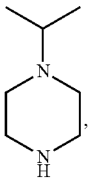,
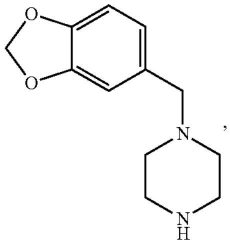, 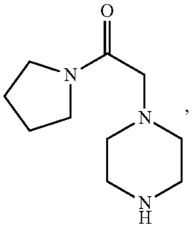,
-continued
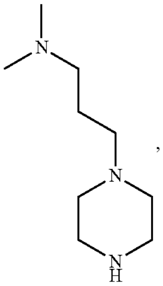, 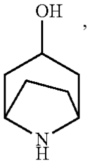, 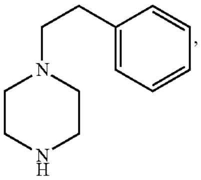,
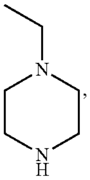, 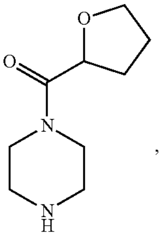, 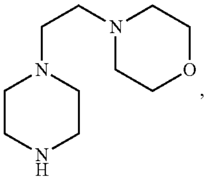,
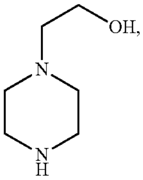, 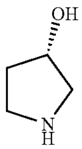, 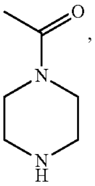, 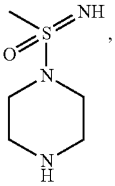,
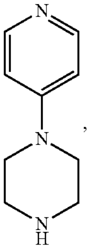, 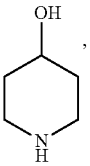, 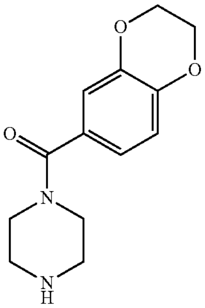, 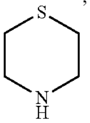,
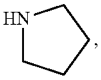, 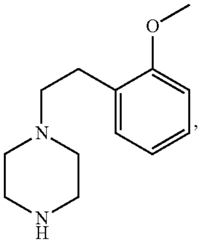, 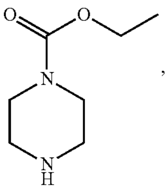,
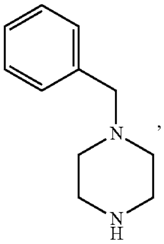, 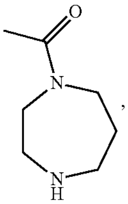, -continued

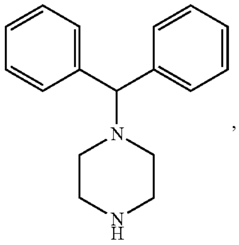,
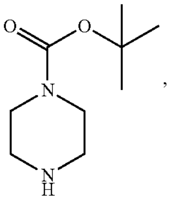,
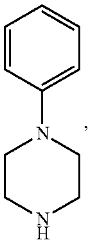,
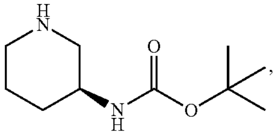,
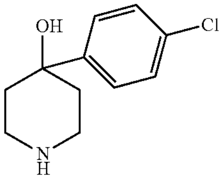,
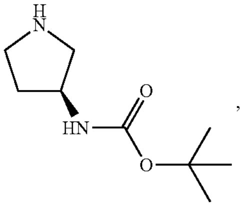,
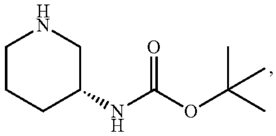,
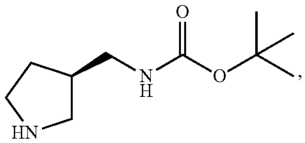,
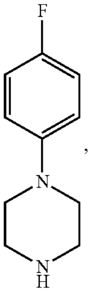,
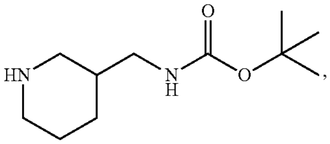,
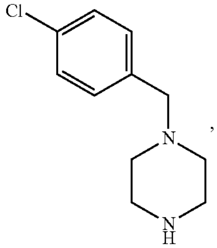,
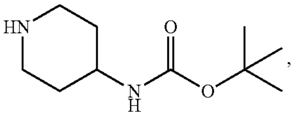,
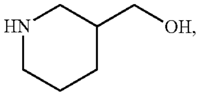,
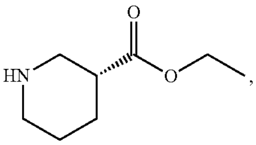,
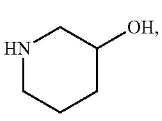,
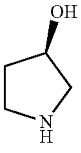,
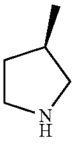,
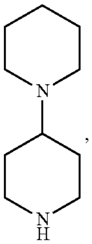, -continued

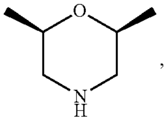,
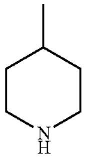,
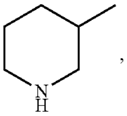,
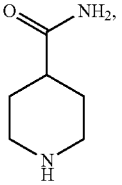
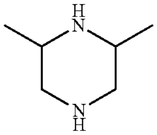,
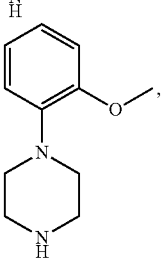,
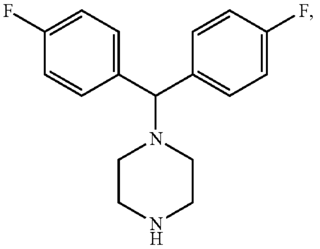
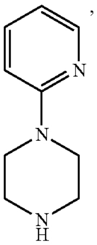,
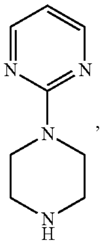,
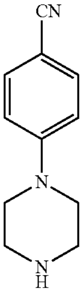,
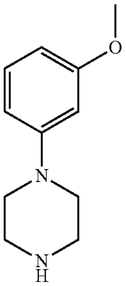,
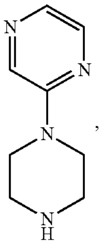,
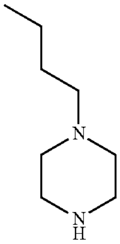,
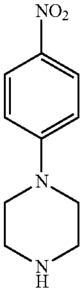,
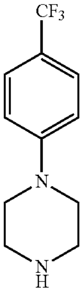, and
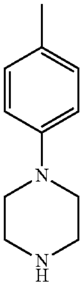.

8. The preparative method according to claim 6, wherein in said step (1), during the rinsing process after completion of the reaction, MeOH and ethyl ether are used to wash; and/or in the step (2), during the extraction process after completion of the reaction, the extraction is carried out with saturated $NaHCO_3$/DCM; and/or, the reaction process is detected all by TLC.

9. A method for inhibiting cell ferroptosis, comprising: administering a pharmaceutically acceptable amount of the compound, or the pharmaceutically acceptable salt, or the solvate thereof according to claim 1 to a subject in need thereof.

10. The method according to claim 9, wherein, in the compound according to claim 1, when the dotted line is a bond, $R_1$ is selected from 3-8 membered unsaturated cycloalkyl, and 3-8 membered unsaturated heterocyclic group, all of which are substituted by m $R_2$;

m is an integer of 0-4;

$R_2$ is selected from substituted or unsubstituted $C_1$-$C_6$ linear or branched chain alkyl, substituted or unsubstituted $C_1$-$C_6$ alkoxy, 3-8 membered saturated cycloalkyl, substituted or unsubstituted 3-8 membered saturated heterocyclic group, 3-8 membered unsaturated cycloalkyl, carbazolyl, amino, hydroxyl, nitro, cyano, halogen, —C(O)$OR_{51}$, —N(H)C(O)$R_{51}$, —C(O)$R_{51}$, —S(OXO)$R_{51}$, and —C(O)N(H)$R_{51}$;

$R_{51}$ is selected from H, $C_1$-$C_4$ alkyl, amino, substituted or unsubstituted 3-8 membered unsaturated cycloalkyl, substituted or unsubstituted 5-8 membered saturated heterocyclic group, and —$NR_{52}R_{53}$;

$R_{52}$ and $R_{53}$ are each independently selected from H, substituted or unsubstituted 5-8 membered saturated heterocyclic group, substituted or unsubstituted $C_1$-$C_6$ linear or branched chain alkyl, and 3-6 membered saturated cycloalkyl;

the substituent of the alkyl is selected from halogen and substituted or unsubstituted 5-8 membered saturated heterocyclic group;

the substituent of the alkoxyl is selected from halogen and 3-8 membered unsaturated cycloalkyl;

the substituent of the unsaturated cycloalkyl is $C_1$-$C_4$ alkyl;

the substituent of the saturated heterocyclic group is $C_1$-$C_4$ alkyl;

the unsaturated heterocyclic group comprises one or two heteroatoms selected from N and O;

the saturated heterocyclic group comprises one or two heteroatoms selected from N and O;

when the dotted line is none, $R_1$ is selected from 3-8 membered unsaturated cycloalkyl, benzo(5-8 membered saturated)heterocyclic group, benzo(5-8 membered unsaturated)heterocyclic group, anthryl, 3-8 membered unsaturated heterocyclic group, 3-8 membered saturated cycloalkyl, all of which are substituted by n $R_3$, and S(O)(O)$R_1$';

n is an integer of 1-4;

$R_3$ is selected from halogen, cyano, hydroxyl, amino, nitro, 3-8 membered unsaturated cycloalkyl, phenoxyl, substituted 5-8 membered saturated heterocyclic group, substituted $C_1$-$C_6$ alkyl, substituted or unsubstituted $C_1$-$C_6$ alkoxy, —C(O)$OR_{51}$, —N(H)C(O)$R_{51}$, and —$NR_{52}R_{53}$;

$R_1$' is selected from 3-8 membered saturated heterocyclic group substituted by p $R_4$;

p is an integer of 0-4;

$R_4$ is selected from hydroxyl, substituted or unsubstituted $C_1$-$C_6$ alkyl, —C(O)$R_{51}$, —N(H)C(O)$OR_{51}$, —S(O)(O)$R_{51}$, —C(O)$OR_{51}$, 3-8 membered unsaturated heterocyclic group, 3-8 membered saturated heterocyclic group, and substituted or unsubstituted 3-8 membered unsaturated cycloalkyl;

$R_{51}$ is selected from $C_1$-$C_8$ alkyl, amino, 5-8 membered saturated heterocyclic group, and benzo(5-8 membered saturated)heterocyclic group;

$R_{52}$ and $R_{53}$ are each independently selected from 3-8 membered unsaturated cycloalkyl and $C_1$-$C_4$ alkyl;

The substituent of the alkyl is selected from halogen, benzo(5-8 membered saturated)heterocyclic group, substituted or unsubstituted 3-8 membered unsaturated cycloalkyl, 5-10 membered saturated heterocyclic group, hydroxyl, —N(H)C(O)$OR_{51}$, —C(O)$R_{51}$, and —$NR_{52}R_{53}$;

the substituent of the alkoxyl is selected from 3-8 membered unsaturated cycloalkyl and halogen;

the substituent of the unsaturated cycloalkyl is selected from halogen, $C_1$-$C_4$ alkoxyl, cyano, nitro, and substituted or unsubstituted $C_1$-$C_4$ alkyl;

the substituent of the saturated heterocyclic group is $C_1$-$C_4$ alkyl;

the saturated heterocyclic group comprises one or two heteroatoms selected from O, N, and S;

the unsaturated heterocyclic group comprises one or two heteroatoms selected from N and O.

11. The method according to claim 9, wherein the compound according to claim 1 has a structure of formula II:

II

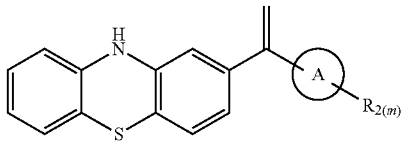

wherein, ring A is selected from aryl substituted by m $R_2$ and heteroaryl substituted by m $R_2$; said heteroaryl comprises one or two N, and m is an integer of 0-4;

$R_2$ is selected from H, substituted or unsubstituted $C_1$-$C_4$ alkyl, substituted or unsubstituted $C_1$-$C_3$ alkoxy, 6-8 membered saturated cycloalkyl, substituted or unsubstituted 6-7 membered saturated heterocyclic group, carbazolyl, amino, hydroxyl, nitro, aryl, cyano, halogen, —C(O)$OR_{51}$, —N(H)C(O)$R_{51}$, —C(O)$R_{51}$, —S(O)(O)$R_{51}$, and —C(O)N(H)$R_{51}$;

$R_{51}$ is selected from H, $C_1$-$C_2$ alkyl, amino, substituted or unsubstituted aryl, substituted or unsubstituted 5-6 membered saturated heterocyclic group, and —$NR_{52}R_{53}$;

$R_{52}$ and $R_{53}$ are each independently selected from H, substituted or unsubstituted 6-8 membered saturated heterocyclic group, substituted or unsubstituted $C_1$-$C_4$ linear or branched chain alkyl, and 4-5 membered saturated cycloalkyl;

the substituent of the alkyl is selected from halogen and substituted or unsubstituted 6-8 membered saturated heterocyclic group;

the substituent of the alkoxyl is selected from halogen and aryl;

the substituent of the aryl is substituted $C_1$-$C_3$ alkyl;

the substituent of the saturated heterocyclic group is $C_1$-$C_3$ alkyl; said heterocyclic group comprises one or more heteroatoms selected from N and O, Or, said compound has a structure of formula III:

III

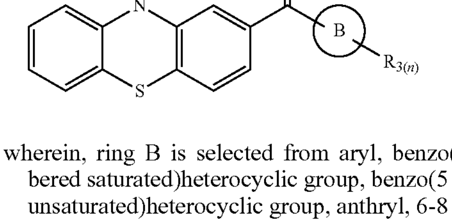

wherein, ring B is selected from aryl, benzo(5-6 membered saturated)heterocyclic group, benzo(5 membered unsaturated)heterocyclic group, anthryl, 6-8 membered unsaturated heterocyclic group, and 6-8 membered saturated cycloalkyl, all of which are substituted by n $R_3$, n is an integer of 1-3;

$R_3$ is selected from H, halogen, cyano, hydroxyl, amino, nitro, aryl, phenoxy, substituted 6-8 membered saturated heterocyclic group, substituted $C_1$-$C_4$ alkyl, substituted or unsubstituted $C_1$-$C_3$ alkoxy, —C(O)O$R_{51}$, —N(H)C(O)$R_{51}$, and —N$R_{52}R_{53}$;

$R_{51}$ is $C_1$-$C_4$ alkyl;

$R_{52}$ and $R_{53}$ are each independently aryl;

the substituent of the alkyl is halogen;

the substituent of the alkoxyl is selected from aryl and halogen;

the substituent of the saturated heterocyclic group is $C_1$-$C_2$ alkyl;

the saturated heterocyclic group comprises one or two heteroatoms selected from N and O;

the unsaturated heterocyclic group comprises one or two heteroatoms selected from N and O;

or, said compound has a structure of formula IV:

IV

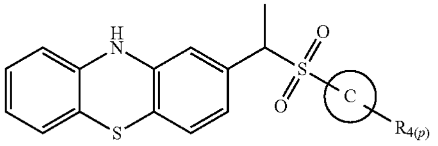

wherein, ring C is a 5-8 membered saturated heterocyclic group substituted by p $R_4$;

p is an integer of 0-4;

$R_4$ is selected from H, hydroxyl, substituted or unsubstituted $C_1$-$C_4$ alkyl, —C(O)$R_{51}$, —N(H)C(O)O$R_{51}$, —S(O)(O)$R_{51}$, —C(O)O$R_{51}$, 6-8 membered unsaturated heterocyclic group, 6-8 membered saturated heterocyclic group, and substituted or unsubstituted aryl;

$R_{51}$ is selected from $C_1$-$C_4$ alkyl, amino, 5 membered saturated heterocyclic group, and benzo(6 membered saturated)heterocyclic group;

the substituent of the alkyl is selected from halogen, benzo(5 membered saturated)heterocyclic group, substituted or unsubstituted aryl, 6 membered saturated heterocyclic group, hydroxyl, —N(H)C(O)O$R_{51}$, —C(O)$R_{51}$, and —N$R_{52}R_{53}$;

the substituent of the aryl is selected from halogen, $C_1$ alkoxyl, cyano, nitro, and substituted or unsubstituted $C_1$ alkyl;

$R_{52}$ and $R_{53}$ are each independently $C_1$-$C_1$ alkyl;

the saturated heterocyclic group comprises one or two heteroatoms selected from O, N and S;

the unsaturated heterocyclic group comprises one or two N.

12. The method according to claim 9, wherein the compound according to claim 1 has a structure of formula IIA:

IIA

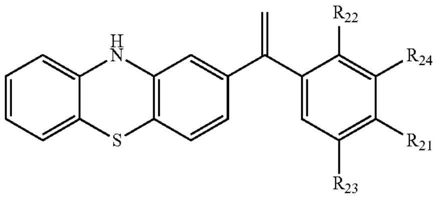

wherein, $R_{21}$, $R_{22}$, $R_{23}$, and $R_{24}$ are each independently selected from H, —C(O)O$R_{51}$, substituted or unsubstituted $C_1$-$C_4$ alkyl, substituted or unsubstituted $C_1$-$C_3$ alkoxy, —N(H)C(O)$R_{51}$, 6 membered saturated cycloalkyl, —C(O)$R_{51}$, 6-membered saturated heterocyclic group, carbazolyl, amino, hydroxyl, nitro, —S(O)(O)$R_{51}$, aryl, cyano, halogen, and —C(O)N(H)$R_{51}$;

$R_{51}$ is selected from H, $C_1$-$C_2$ alkyl, amino, substituted or unsubstituted aryl, substituted or unsubstituted 5-6 membered saturated heterocyclic group, and —N$R_{52}R_{53}$;

$R_{52}$ and $R_{53}$ are each independently of selected from H, substituted or unsubstituted 6 membered saturated heterocyclic group, substituted or unsubstituted $C_1$-$C_4$ alkyl, and 4 membered cycloalkyl;

the substituent of the alkyl is selected from halogen and substituted or unsubstituted 6 membered saturated heterocyclic group;

the substituent of the alkoxyl is selected from halogen and aryl;

the substituent of the aryl is substituted $C_1$ alkyl;

the substituent of the saturated heterocyclic group is $C_1$ alkyl; said saturated heterocyclic group comprises one or two heteroatoms selected from N and O, or, said compound has a structure of formula IIB:

IIB

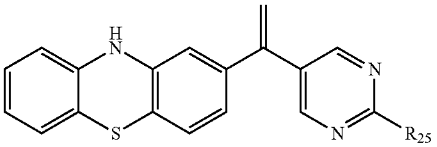

wherein, $R_{25}$ is substituted or unsubstituted 6-7 membered saturated heterocyclic group;

the substituent of the saturated heterocyclic group is $C_1$ alkyl;

said heterocyclic group comprises two heteroatoms selected from N and O;

or, said compound has a structure of formula IIC:

IIC

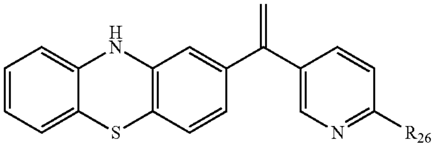

wherein, $R_{26}$ is selected from —N(H)C(O)$R_{51}$, amino, and 6 membered saturated heterocyclic group;

said saturated heterocyclic group comprises two heteroatoms selected from N and O;

$R_{51}$ is $C_1$ alkyl;

or, said compound has a structure of formula IIIA:

IIIA

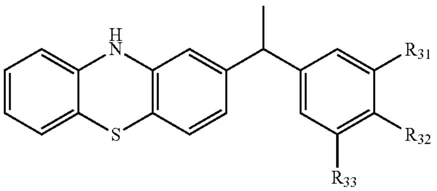

wherein, $R_{31}$, $R_{32}$, $R_{33}$ are each independently selected from H, halogen, cyano, hydroxyl, amino, substituted or unsubstituted $C_1$-$C_3$ alkoxy, —C(O)O$R_{51}$, —N(H)C(O)$R_{51}$, aryl, phenoxy, —N$R_{52}$$R_{53}$, substituted 6 membered saturated heterocyclic group, and nitro, with the proviso that all of $R_{31}$, $R_{32}$, and $R_{33}$ are not simultaneously H;

$R_{51}$ is $C_1$-$C_4$ alkyl;

the substituent of the alkyl is halogen;

the substituent of the alkoxyl is selected from aryl and halogen;

the substituent of the saturated heterocyclic group is $C_1$ alkyl;

the saturated heterocyclic group comprises two N;

$R_{52}$ and $R_{53}$ are each independently aryl;

or, said compound has a structure of formula IIIB:

IIIB

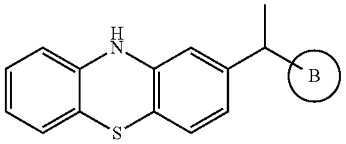

wherein, ring B is selected from benzo(5-6 membered saturated)heterocyclic group, benzo(5 membered unsaturated)heterocyclic group, anthryl, substituted 6 membered unsaturated heterocyclic group, and 6 membered saturated cycloalkyl;

the substituent of the unsaturated heterocyclic group is selected from cyano, $C_1$ alkyl, and $C_2$ alkoxyl;

the saturated heterocyclic group comprises one or two O;

the unsaturated heterocyclic group comprises one heteroatom selected from O and N;

or, said compound has a structure of formula IVA:

IVA

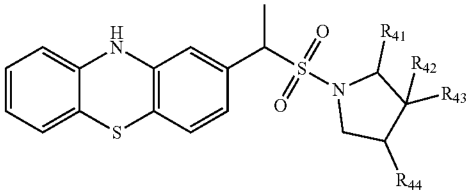

wherein, $R_{41}$, $R_{42}$, $R_{43}$, and $R_{44}$ are each independently selected from H, hydroxyl, —N(H)C(O)O$R_{51}$, and substituted or unsubstituted $C_1$ alkyl;

$R_{51}$ is $C_4$ alkyl;

the substituent of the alkyl is —N(H)C(O)O$R_{51}$;

or, said compound has a structure of formula IVB:

IVB

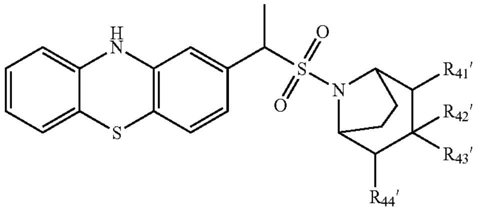

wherein, $R_{41}$', $R_{42}$', $R_{43}$', and $R_{44}$' are each independently selected from H and hydroxyl;

or, said compound has a structure of formula IVC:

IVC

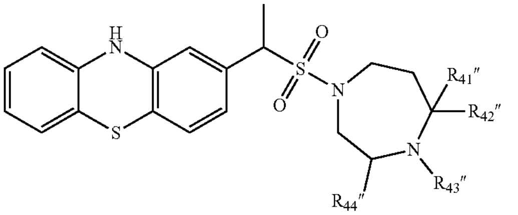

wherein, $R_{41}$", $R_{42}$", $R_{43}$", and $R_{44}$" are each independently selected from H, $C_1$ alkyl, and —C(O)$R_{51}$;

$R_{51}$ is $C_1$ alkyl;

or, said compound has a structure of formula IVD:

IVD

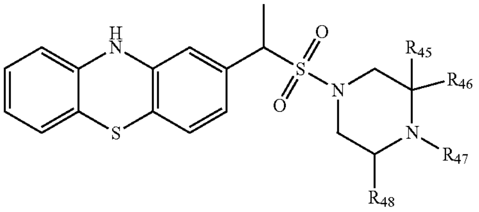

wherein, $R_{45}$, $R_{46}$, $R_{47}$, and $R_{48}$ are each independently selected from H, substituted or unsubstituted $C_1$-$C_4$ alkyl, —C(O)$R_{51}$, —S(O)(O)$R_{51}$, 6 membered unsaturated heterocyclic group, —C(O)O$R_{51}$, and substituted or unsubstituted aryl;

$R_{51}$ is selected from 5 membered saturated heterocyclic group, $C_1$-$C_4$ alkyl, and benzo(6 membered saturated) heterocyclic group;

$R_{52}$ and $R_{53}$ are each independently $C_1$ alkyl;

the substituent of the alkyl is selected from halogen, benzo(5 membered saturated)heterocyclic group, —C(O)$R_{51}$, —N$R_{52}$$R_{53}$, substituted or unsubstituted aryl, 6 membered saturated heterocyclic group, and hydroxyl;

the substituent of the aryl is selected from $C_1$ alkoxyl, halogen, cyano, nitro, and substituted or unsubstituted $C_1$ alkyl;

the saturated heterocyclic group comprises one or two heteroatoms selected from O and N;

the unsaturated heterocyclic group comprises one or two N;

or, said compound has a structure of formula IVE:

IVE

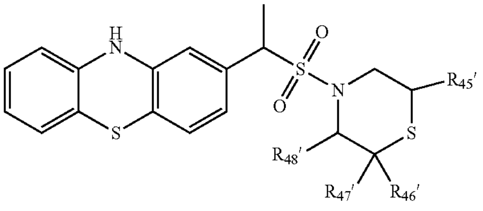

Wherein, $R_{45}'$, $R_{46}'$, $R_{47}'$, and $R_{48}'$ are each independently selected from H and $C_1$ alkyl;

or, said compound has a structure of formula IVF:

IVF

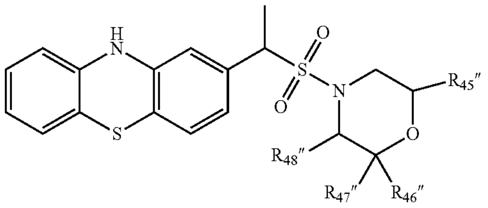

wherein, $R_{45}''$, $R_{46}''$, $R_{47}''$, and $R_{48}''$ are each independently selected from H and $C_1$ alkyl;

or, said compound has a structure of formula IVG:

IVG

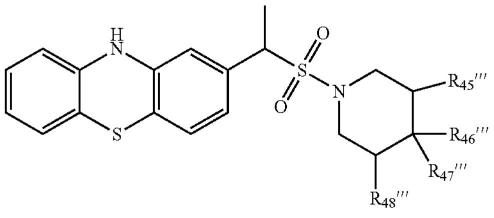

wherein, $R_{45}'''$, $R_{46}'''$, $R_{47}'''$, and $R_{48}'''$ are each independently selected from H, hydroxyl, —C(O)O$R_{51}$, —N(H)C(O)O$R_{51}$, substituted aryl, substituted or unsubstituted $C_1$ alkyl, 6 membered saturated heterocyclic group, and —C(O)$R_{51}$;

$R_{51}$ is selected from $C_2$-$C_4$ alkyl and amino;

the substituent of the aryl is halogen;

the substituent of the alkyl is selected from —N(H)C(O)O$R_{51}$ and hydroxyl;

the saturated heterocyclic group comprises one N.

13. The method according to claim 9, wherein the compound according to claim 1 is selected from:

A2

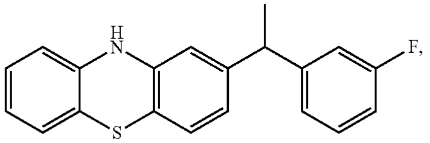

A3

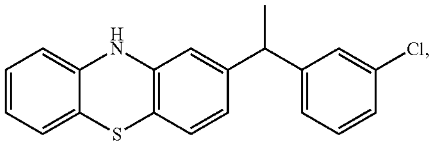

A4

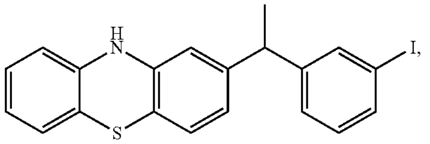

-continued

A5

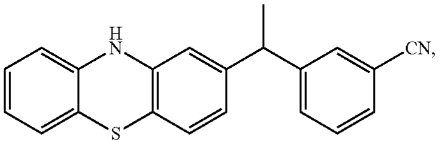

A6

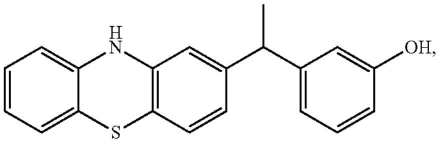

A7

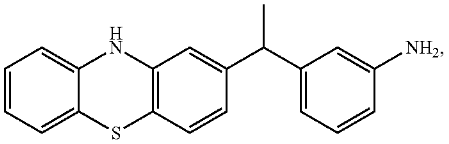

A11

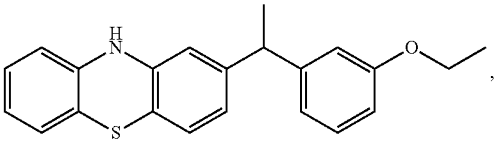

,

A12

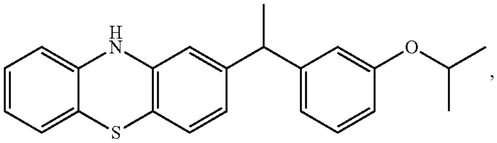

,

A13

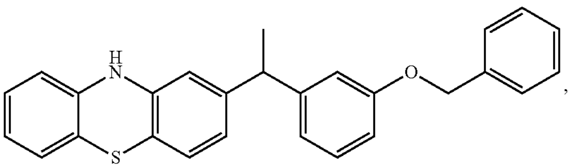

,

A14

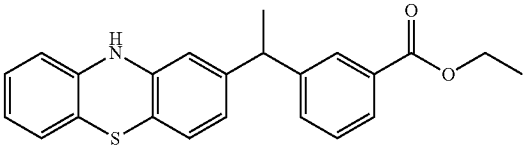

,

A15

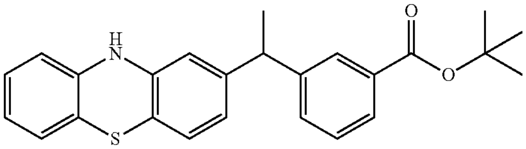

,

A16

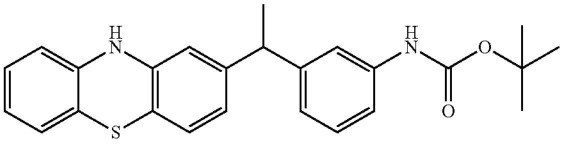

,

-continued
A17
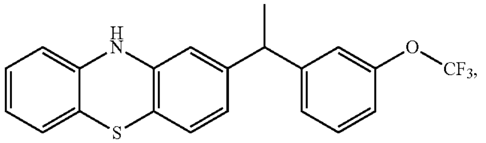
A18
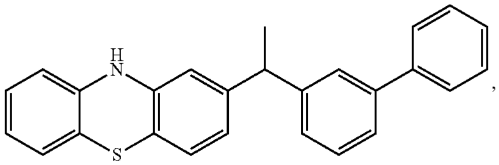
,
A19
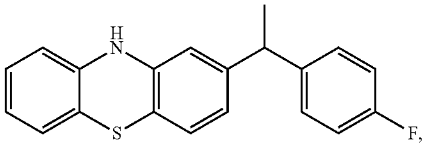
A20
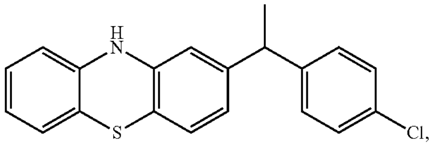
A21
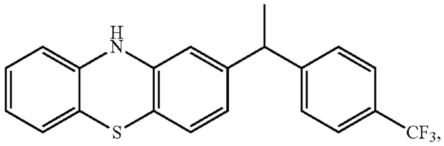
A22
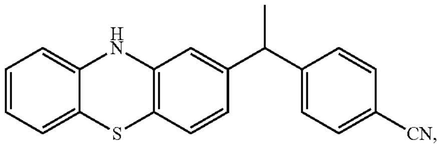
A23
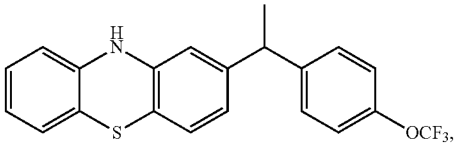
A30
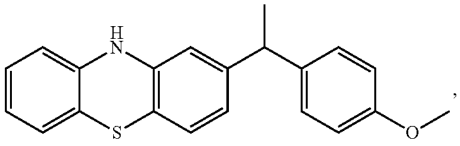
,
A31
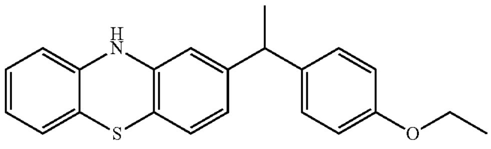
,
-continued
A32
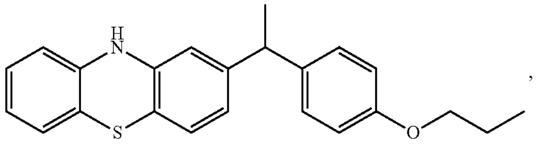
,
A33
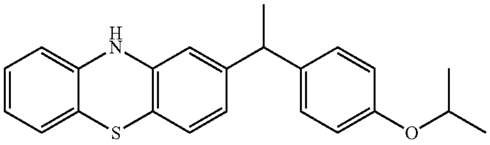
,
A34
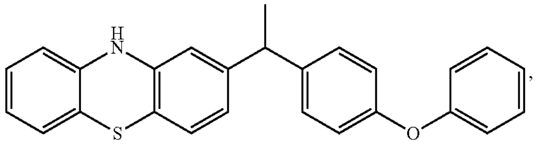
,
A35
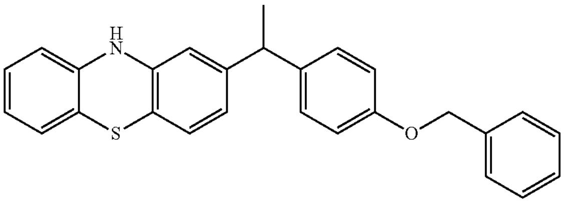
,
A36
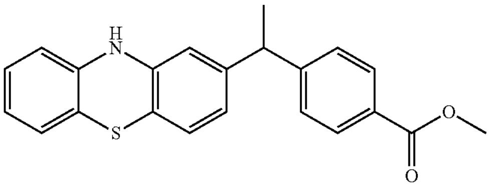
,
A37
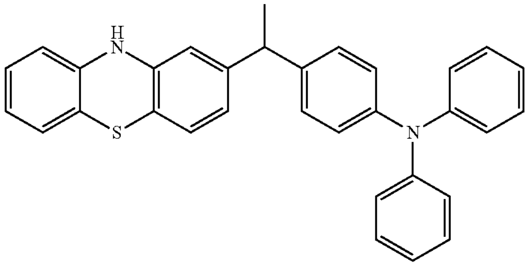
,
A38
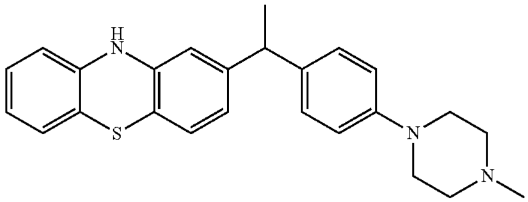
, -continued
A39
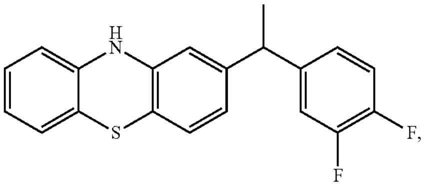
A40
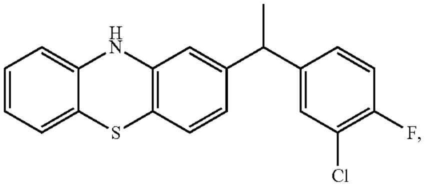
A41
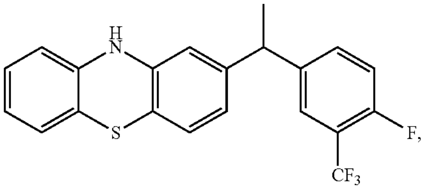
A42
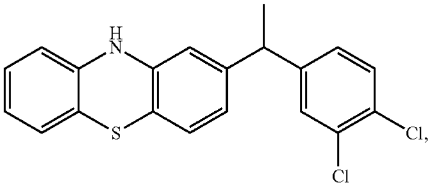
A43
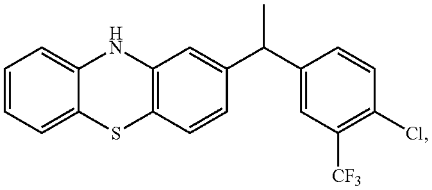
A44
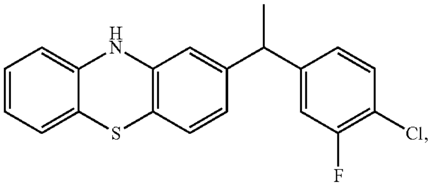
A45
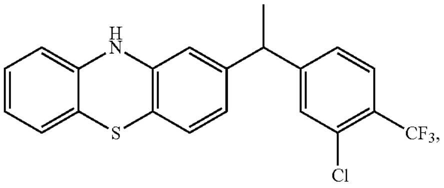
A47
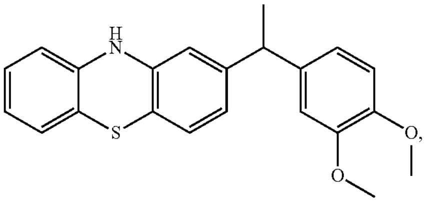
-continued
A50
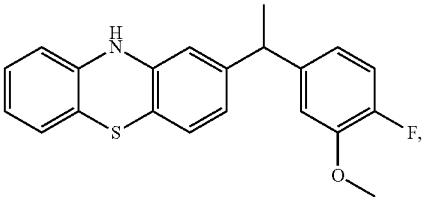
A51
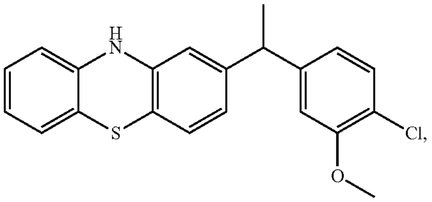
A53
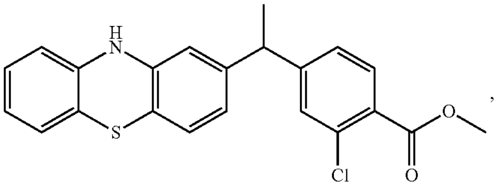
A55
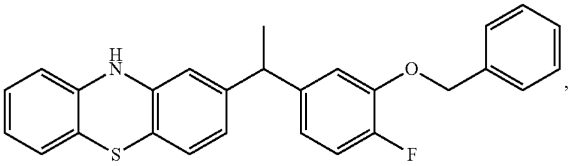
A56
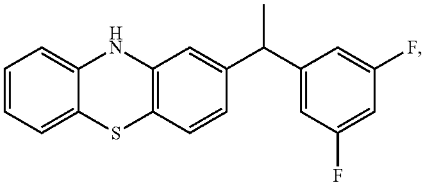
A57
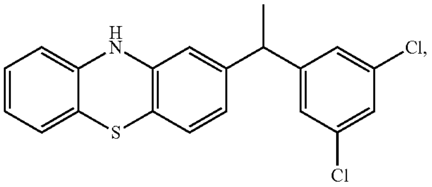
A58
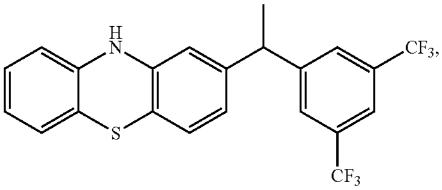
A60
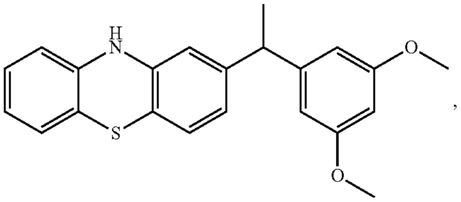

-continued
A61
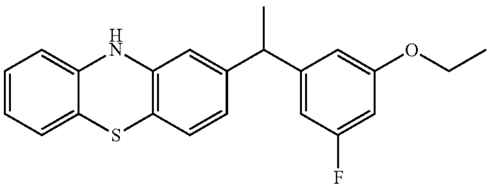
,
A63
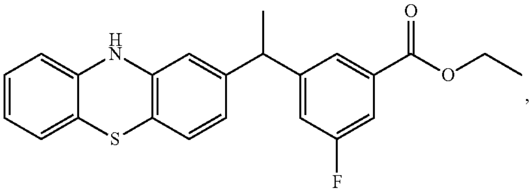
,
A64
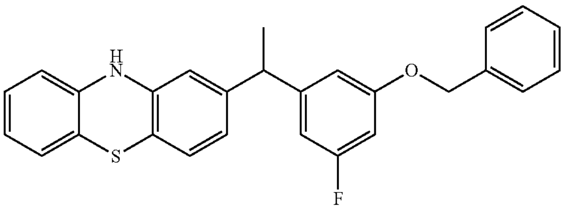
,
A65
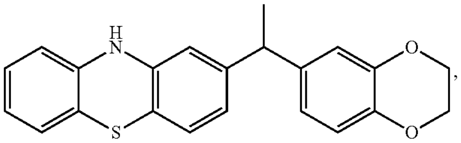
,
A66
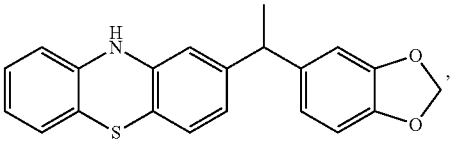
,
A67
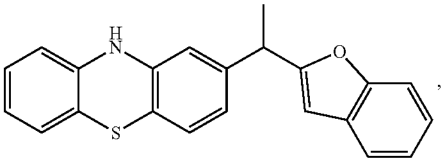
,
A69
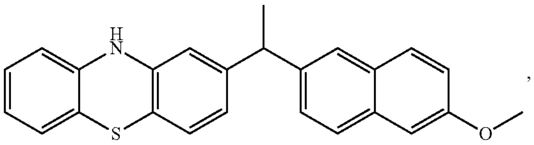
,
A70
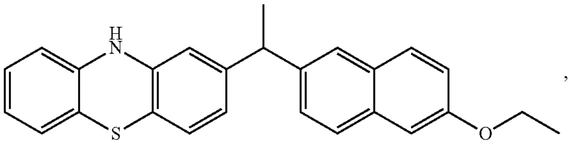
,
-continued
A71
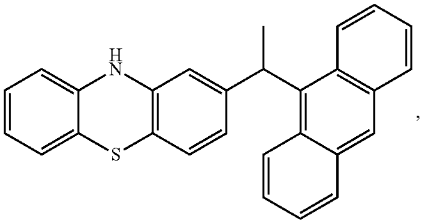
,
A72
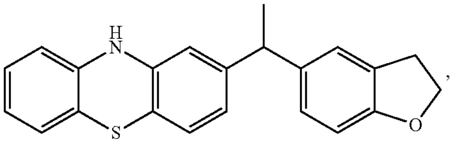
,
A73
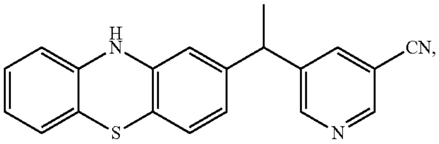
,
A74
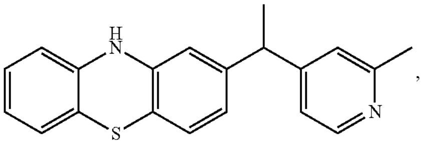
,
A75
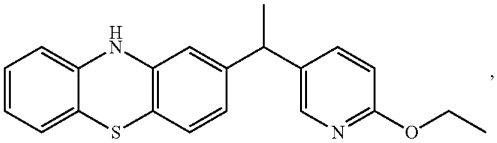
,
A76
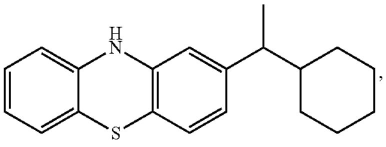
,
B1
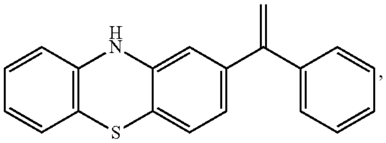
,
B2
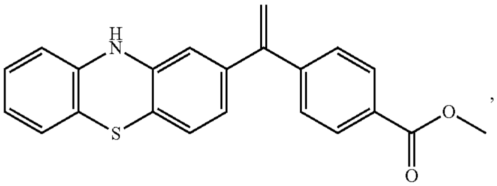
,
B3
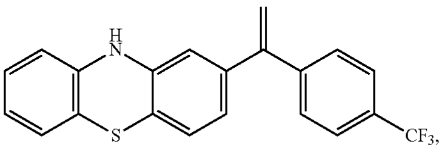
, -continued
B4
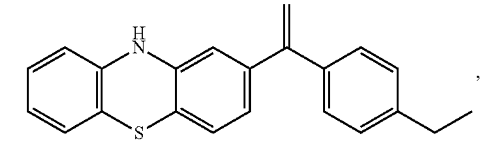
B5
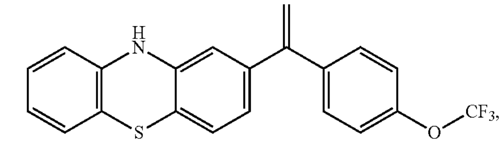
B6
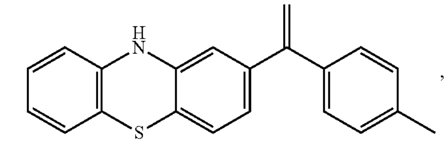
B7
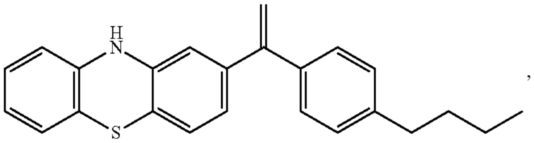
B8
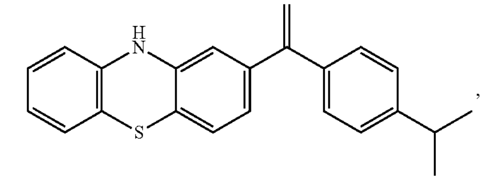
B9
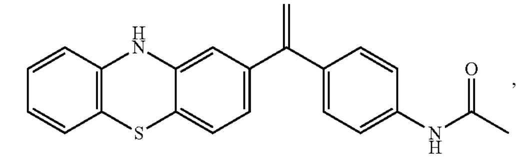
B10
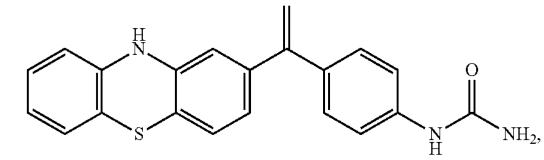
B11
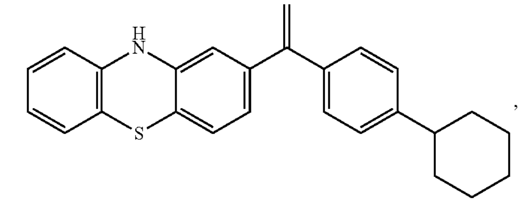
B12
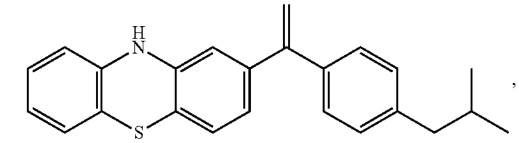
-continued
B13
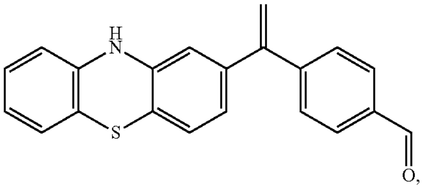
B14
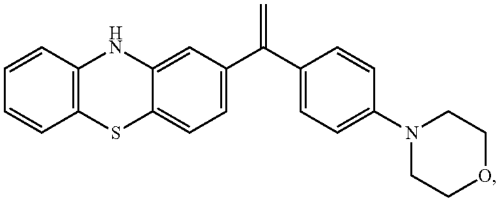
B15
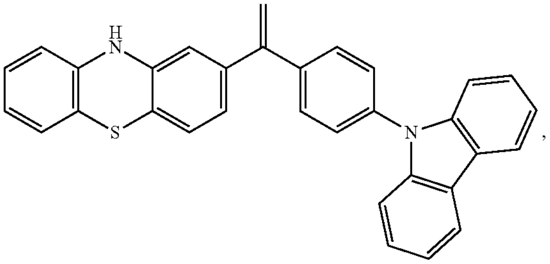
B16
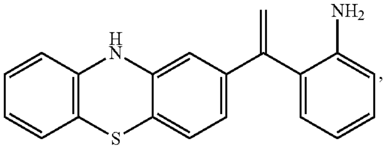
B17
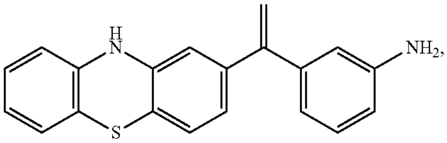
B18
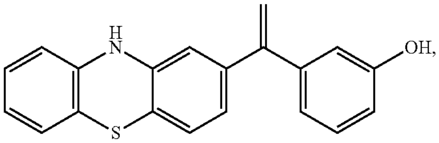
B19
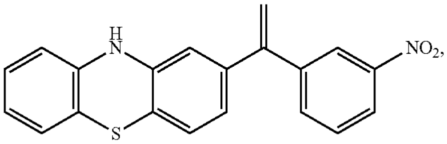
B20
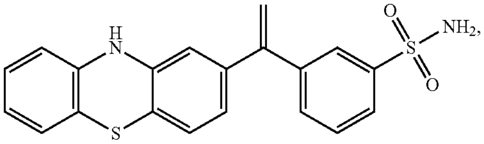

-continued
B21
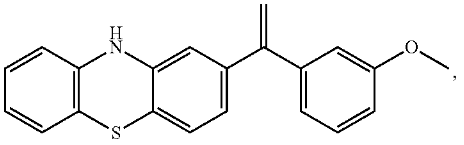
B22
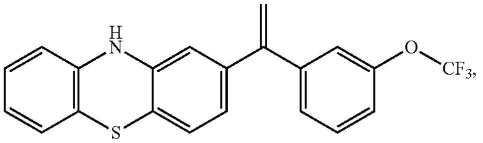
B23
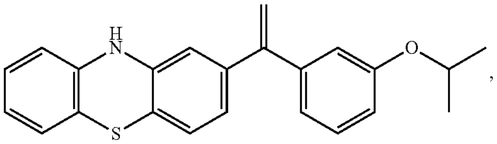
B24
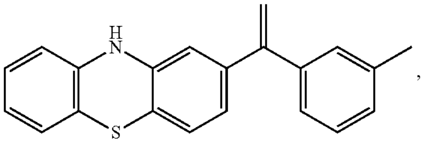
B25
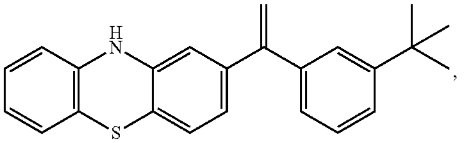
B26
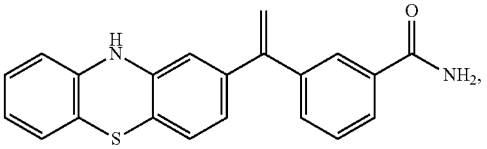
B27
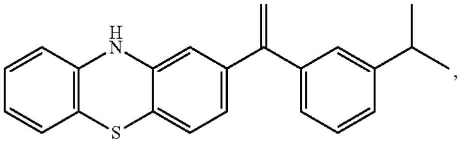
B28
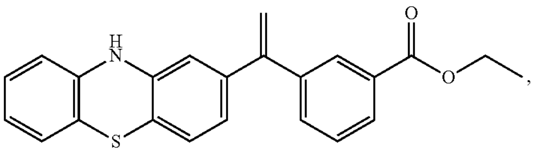
B29
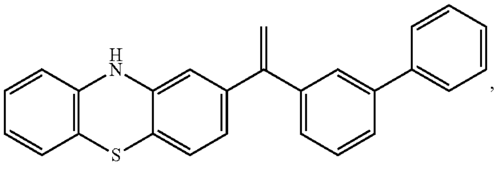
-continued
B30
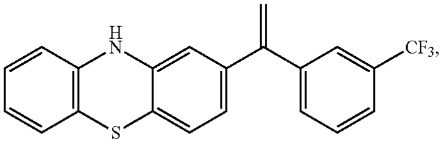
B31
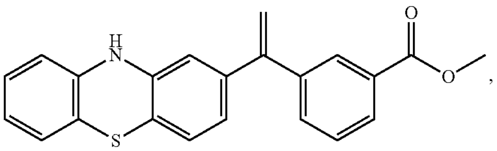
B32
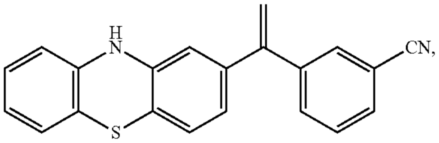
B33
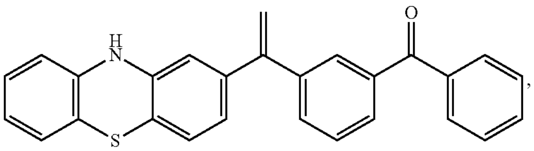
B34
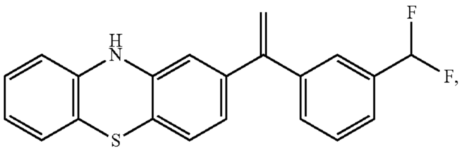
B35
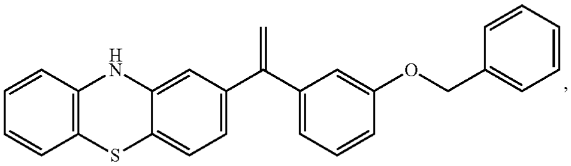
B36
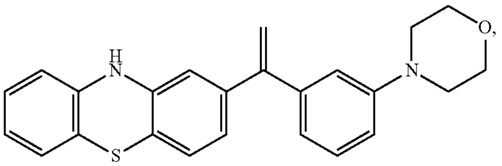
B37
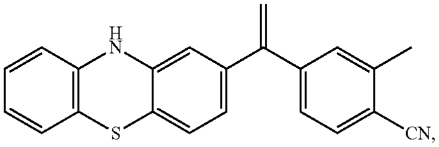
B38
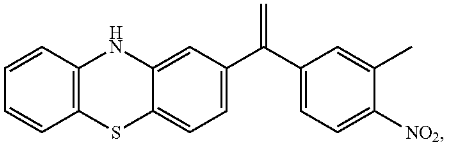

-continued
B39
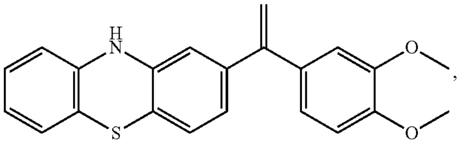
B40
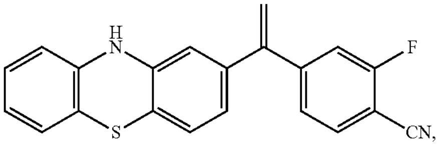
B41
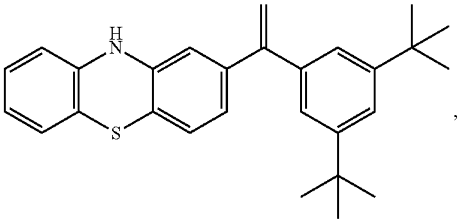
B42
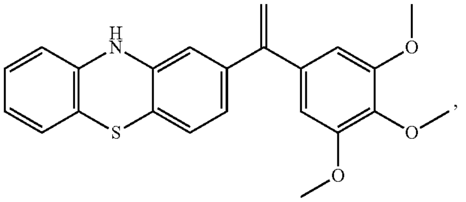
B43
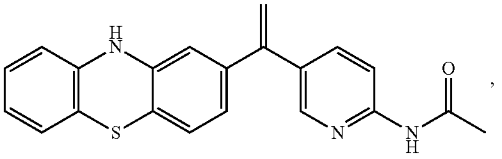
B44
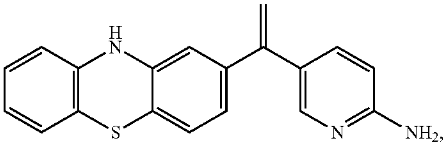
B45
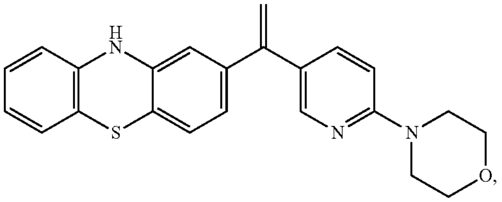
B46
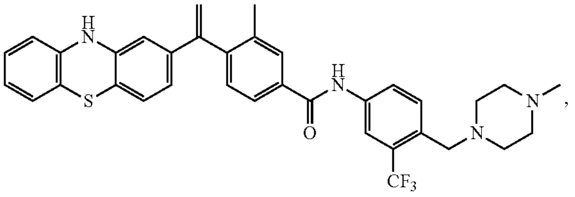
-continued
B47
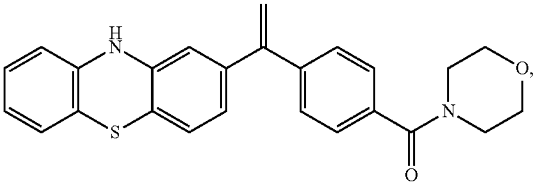
B48
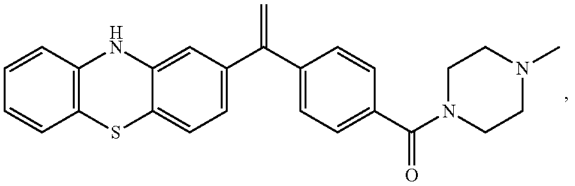
B49
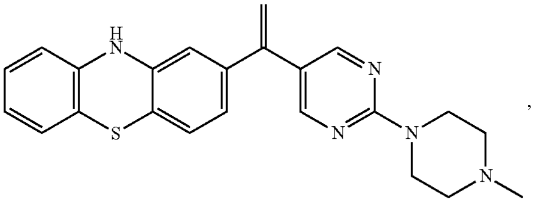
B50
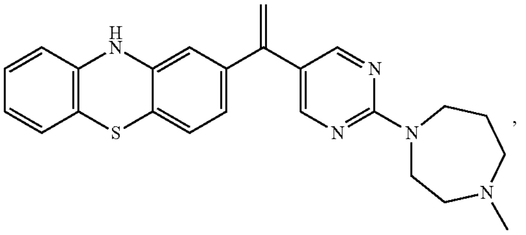
B51
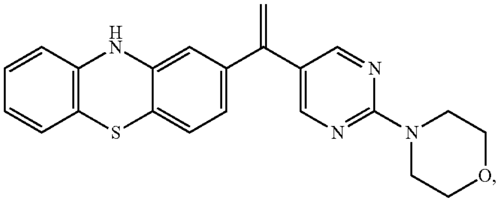
B52
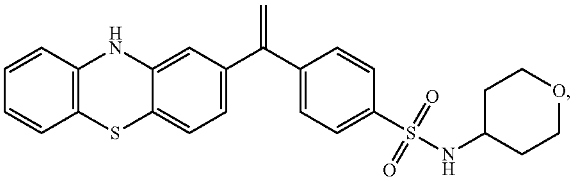
B53
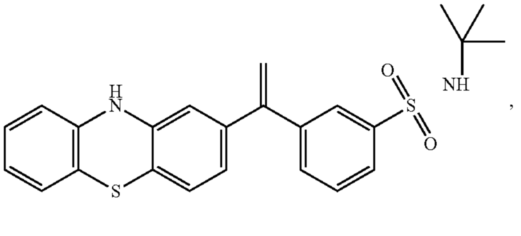

-continued
B54
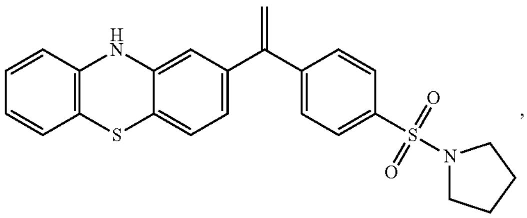
,
B55
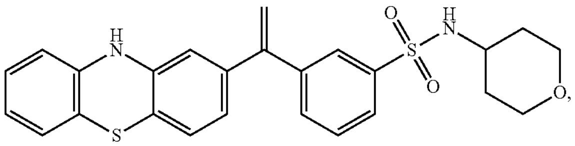
B56
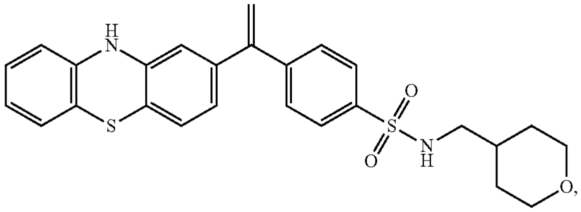
B57
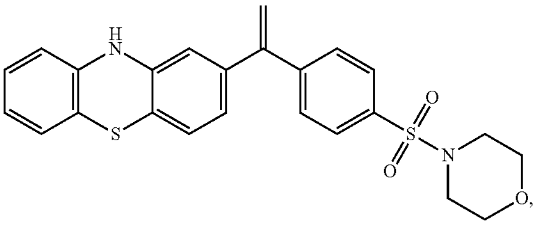
B58
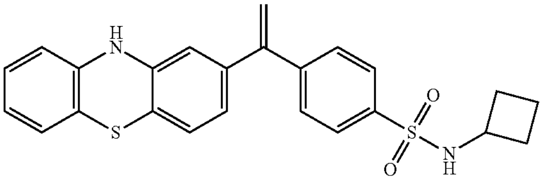
,
B59
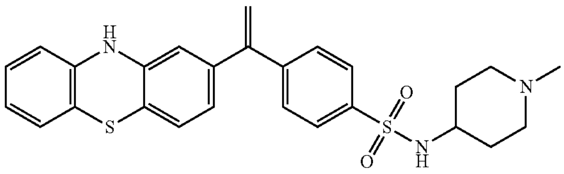
,
C1
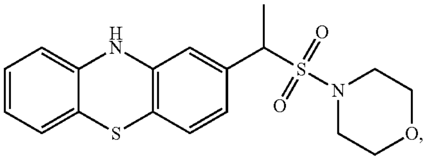
-continued
C2
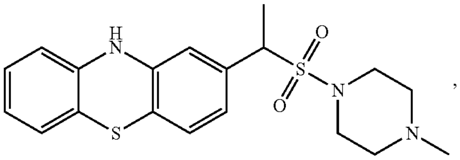
,
C3
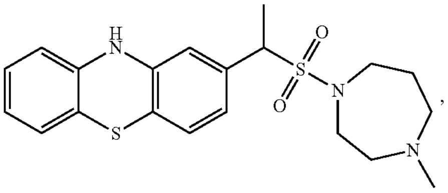
C4
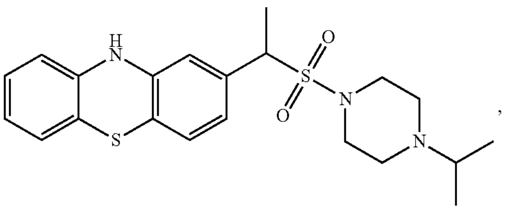
,
C5
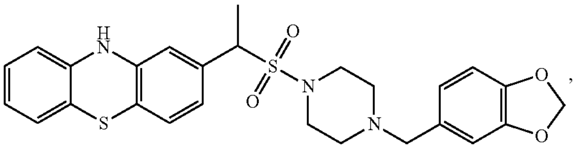
,
C6
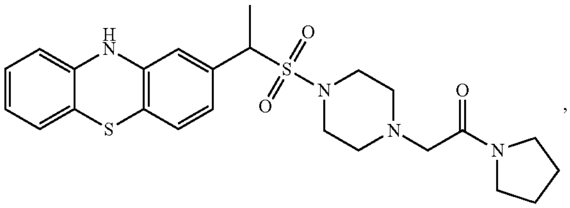
,
C7
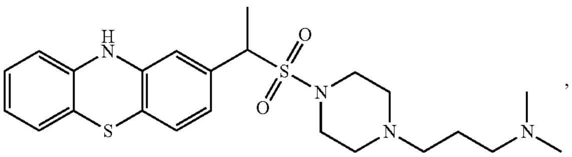
,
C8
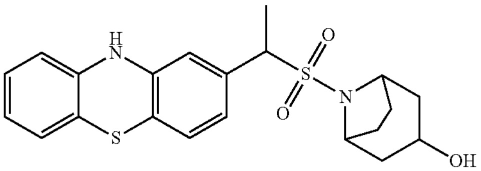
C9
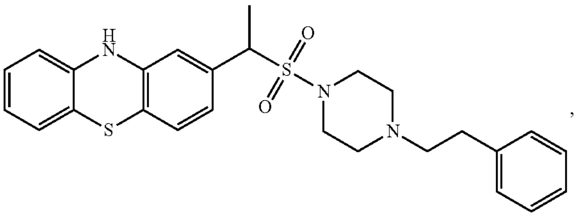
, -continued
C10
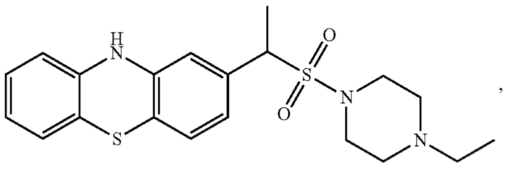
C11
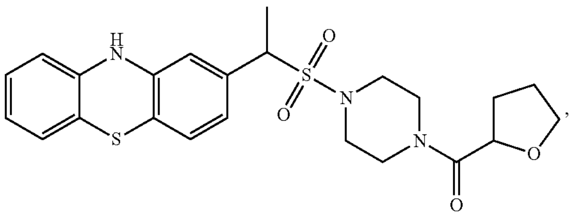
C12
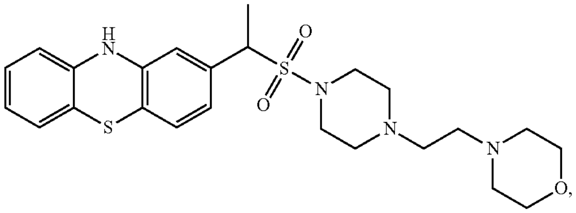
C13
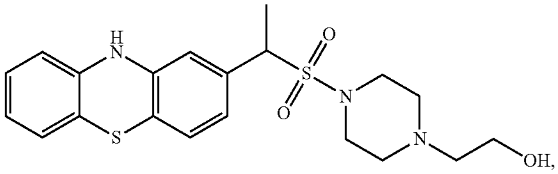
C14
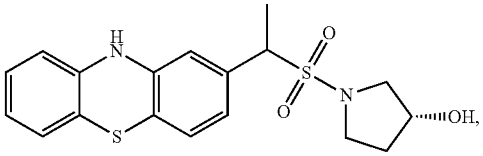
C15
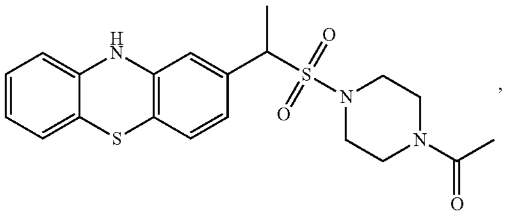
C16
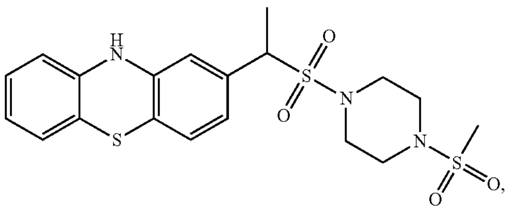
-continued
C17
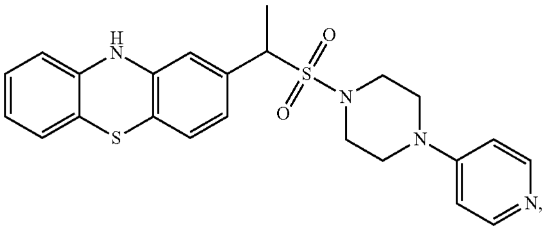
C18
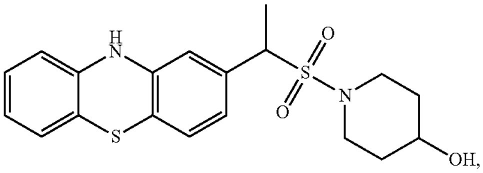
C19
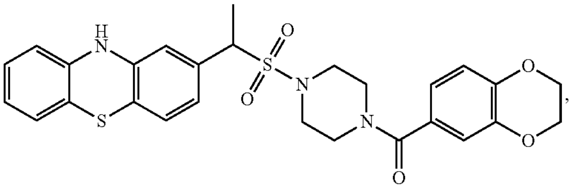
C20
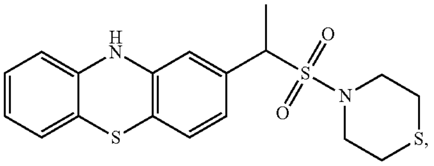
C21
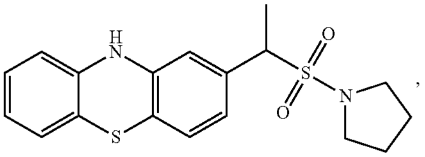
C22
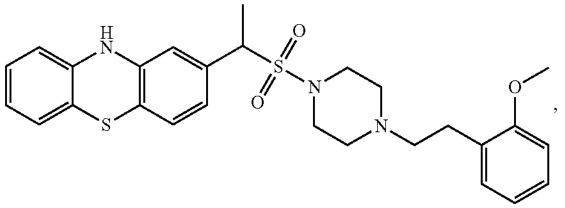
C23
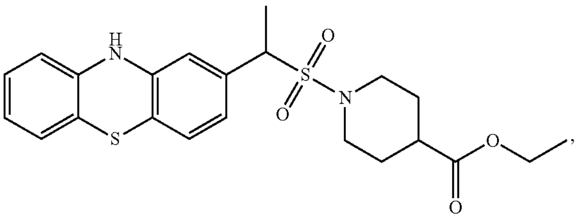

-continued
C24
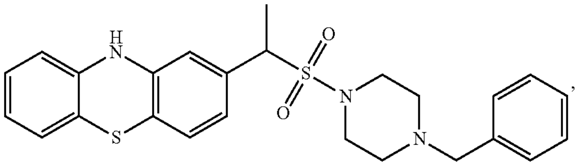
,
C25
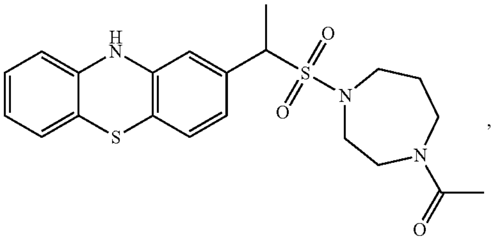
,
C26
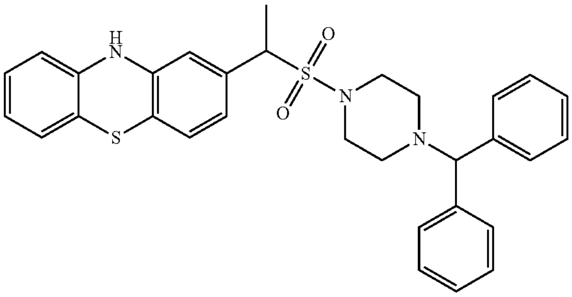
,
C27
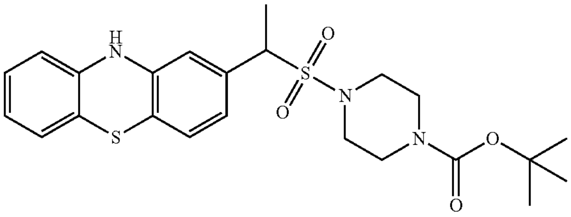
,
C28
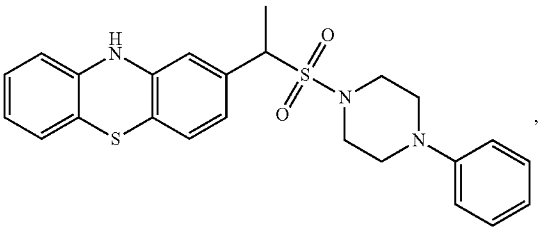
,
C29
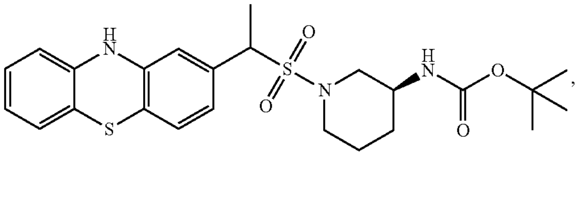
,
-continued
C30
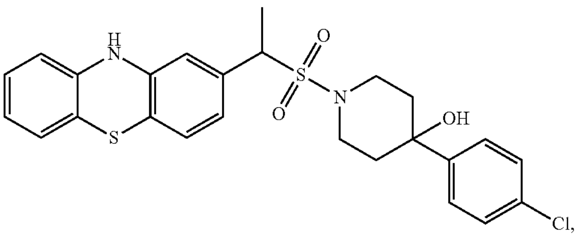
C31
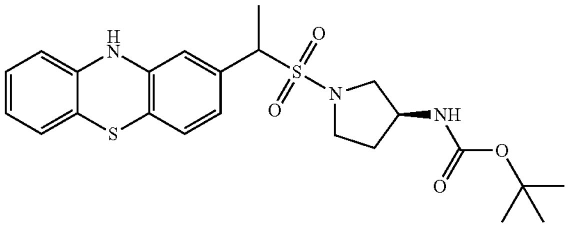
,
C32
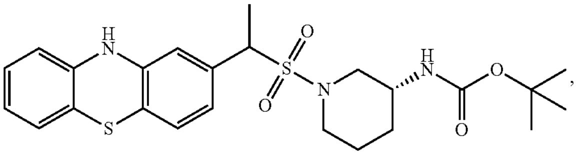
C33
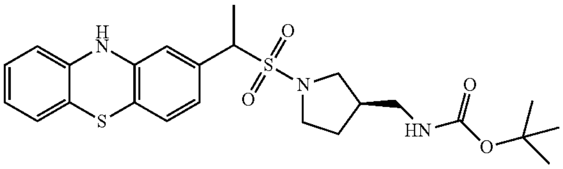
,
C34
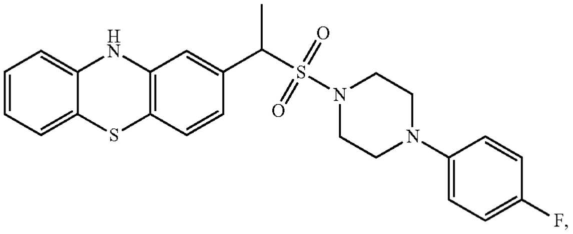
C35
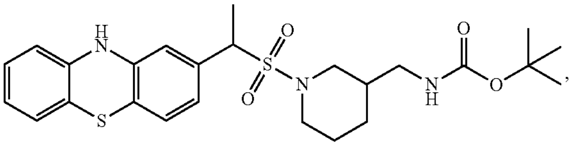
C36
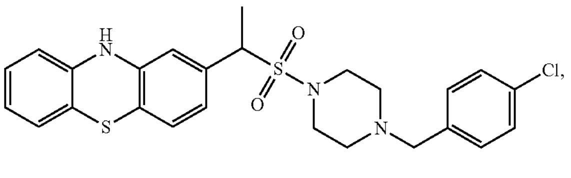

-continued
C37
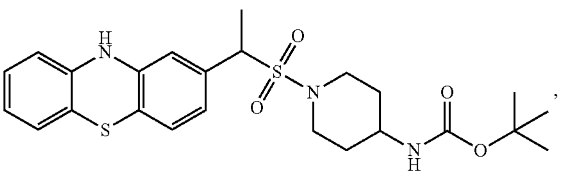
C38
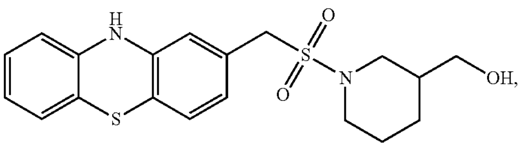
C39
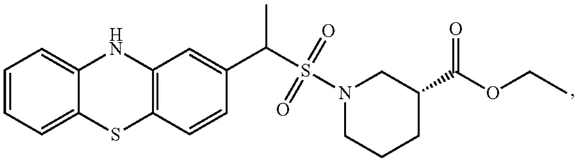
C40
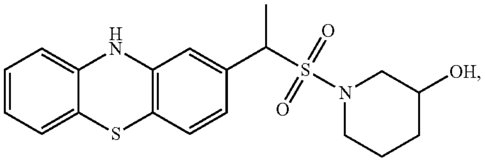
C41
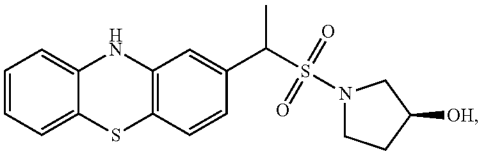
C42
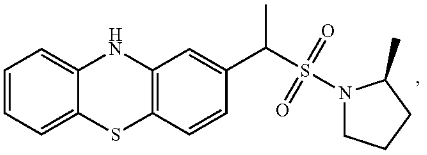
C43
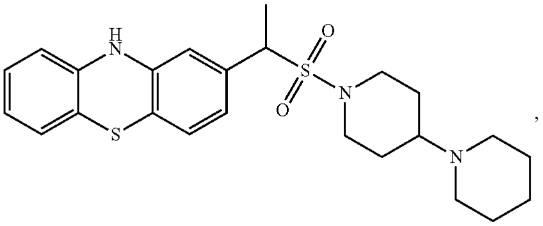
C44
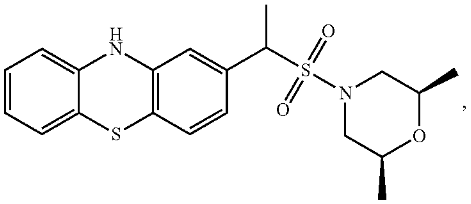
-continued
C45
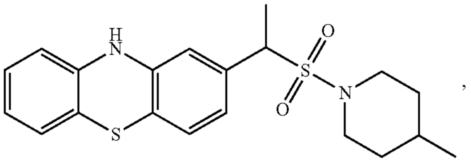
C46
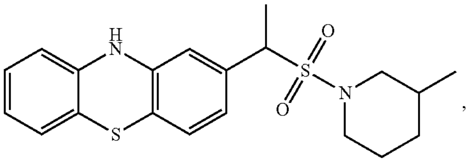
C47
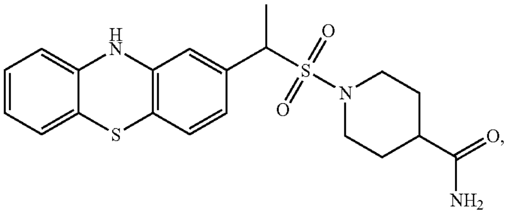
C48
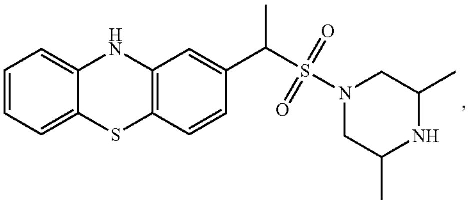
C49
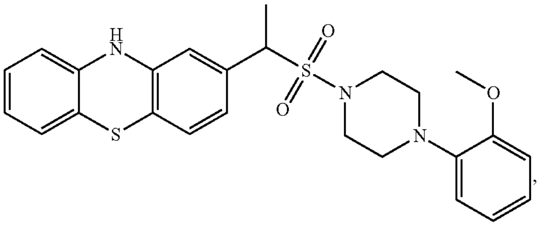
C50
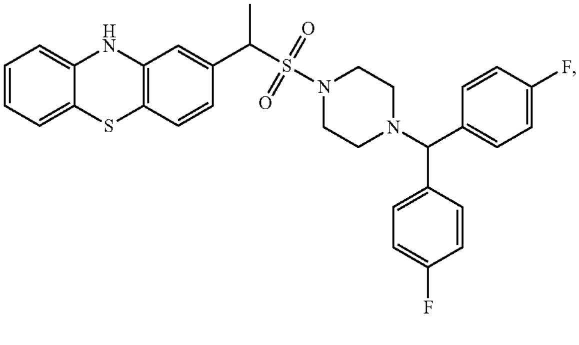

-continued

C51

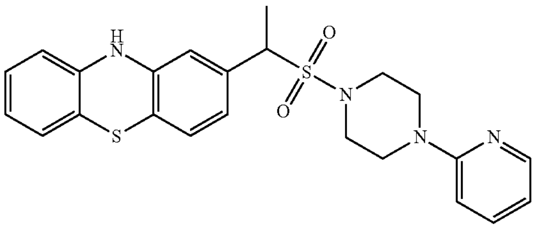

,

C52

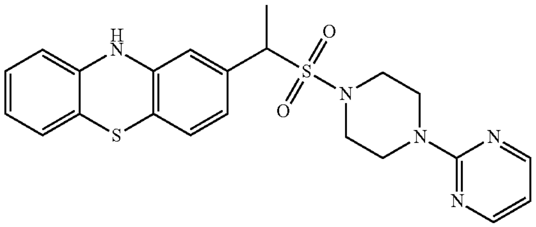

,

C53

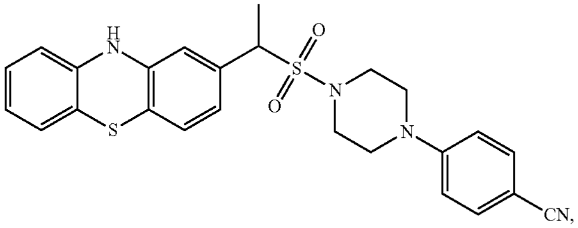

C54

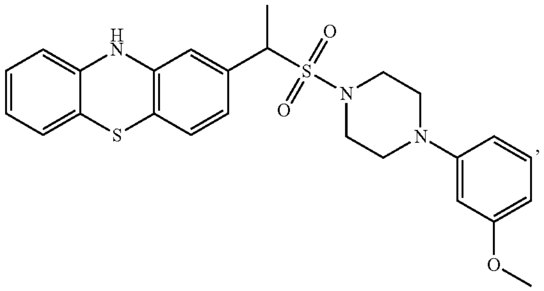

,

C55

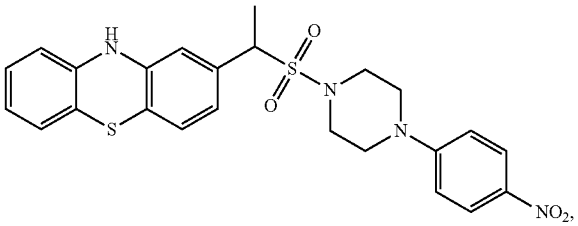

C56

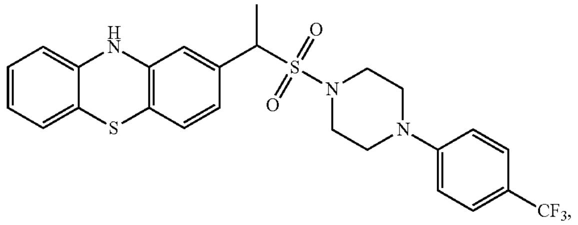

-continued

C57

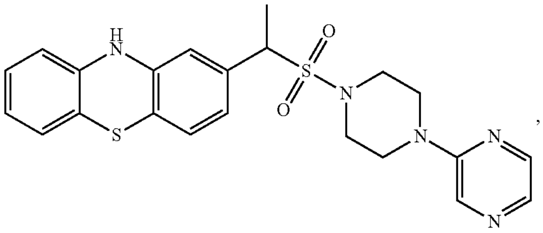

,

C58

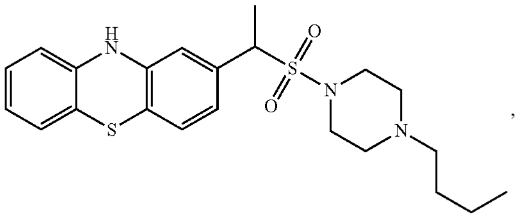

, and

C59

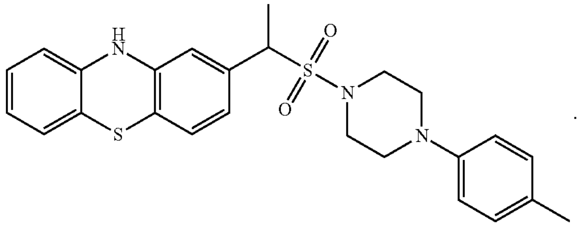

.

14. A pharmaceutical preparation, comprising the compound or the pharmaceutically acceptable salt, or the solvate thereof according to claim 1, as active ingredients, and one or more pharmaceutically acceptable excipients; wherein, said pharmaceutical preparation is an oral preparation or an intravenous injection preparation.

15. The pharmaceutical preparation according to claim 14, wherein, in the compound according to claim 1, when the dotted line is a bond, $R_1$ is selected from 3-8 membered unsaturated cycloalkyl, and 3-8 membered unsaturated heterocyclic group, all of which are substituted by m $R_2$;

m is an integer of 0-4;

$R_2$ is selected from substituted or unsubstituted $C_1$-$C_6$ linear or branched chain alkyl, substituted or unsubstituted $C_1$-$C_6$ alkoxy, 3-8 membered saturated cycloalkyl, substituted or unsubstituted 3-8 membered saturated heterocyclic group, 3-8 membered unsaturated cycloalkyl, carbazolyl, amino, hydroxyl, nitro, cyano, halogen, —C(O)O$R_{51}$, —N(H)C(O)$R_{51}$, —C(O)$R_{51}$, —S(OXO)$R_{51}$, and —C(O)N(H)$R_{51}$;

$R_{51}$ is selected from H, $C_1$-$C_4$ linear or branched chain alkyl, amino, substituted or unsubstituted 3-8 membered unsaturated cycloalkyl, substituted or unsubstituted 5-8 membered saturated heterocyclic group, and_—$NR_{52}R_{53}$;

$R_{52}$ and $R_{53}$ are each independently selected from H, substituted or unsubstituted 5-8 membered saturated heterocyclic group, substituted or unsubstituted $C_1$-$C_6$ linear or branched chain alkyl, and 3-6 membered saturated cycloalkyl;

the substituents of the alkyl are selected from halogen and substituted or unsubstituted 5-8 membered saturated heterocyclic group;

the substituents of the alkoxyl are selected from halogen and 3-8 membered unsaturated cycloalkyl;

the substituent of the unsaturated cycloalkyl is $C_1$-$C_4$ alkyl;

the substituent of the saturated heterocyclic group is $C_1$-$C_4$ alkyl;

the unsaturated heterocyclic group comprises one or two heteroatoms selected from N and O;

the saturated heterocyclic group comprises one or two heteroatoms selected from N and O;

When the dotted line is none, $R_1$ is selected from 3-8 membered unsaturated cycloalkyl, benzo(5-8 membered saturated)heterocyclic group, benzo(5-8 membered unsaturated)heterocyclic group, anthryl, 3-8 membered unsaturated heterocyclic group, 3-8 membered saturated cycloalkyl, all of which are substituted by n $R_3$, or $R_1$ is S(O)(O)$R_1$';

n is an integer of 1-4;

$R_3$ is selected from halogen, cyano, hydroxyl, amino, nitro, 3-8 membered unsaturated cycloalkyl, phenoxyl, substituted 5-8 membered saturated heterocyclic group, substituted $C_1$-$C_6$ alkyl, substituted or unsubstituted $C_1$-$C_6$ alkoxy, —C(O)O$R_{51}$, —N(H)C(O)$R_{51}$, and —N$R_{52}R_{53}$;

$R_1$' is 3-8 membered saturated heterocyclic group substituted by p $R_4$;

p is an integer of 0-4;

$R_4$ is selected from hydroxyl, substituted or unsubstituted $C_1$-$C_6$ alkyl, —C(O)$R_{51}$, —N(H)C(O)O$R_{51}$, —S(O)(O)$R_{51}$, —C(O)O$R_{51}$, 3-8 membered unsaturated heterocyclic group, 3-8 membered saturated heterocyclic group, and substituted or unsubstituted 3-8 membered unsaturated cycloalkyl;

$R_{51}$ is selected from $C_1$-$C_8$ alkyl, amino, 5-8 membered saturated heterocyclic group, and benzo(5-8 membered saturated)heterocyclic group;

$R_{52}$ and $R_{53}$ are each independently selected from 3-8 membered unsaturated cycloalkyl, and $C_1$-$C_4$ alkyl;

the substituents of the alkyl are selected from halogen, benzo(5-8 membered saturated)heterocyclic group, substituted or unsubstituted 3-8 membered unsaturated cycloalkyl, 5-10 membered saturated heterocyclic group, hydroxyl, —N(H)C(O)O$R_{51}$, —C(O)$R_{51}$, and —N$R_{52}R_{53}$;

the substituents of the alkoxyl are selected from 3-8 membered unsaturated cycloalkyl and halogen;

the substituents of the unsaturated cycloalkyl are selected from halogen, $C_1$-$C_4$ alkoxyl, cyano, nitro, and substituted or unsubstituted $C_1$-$C_4$ alkyl;

the substituent of the saturated heterocyclic group is $C_1$-$C_4$ alkyl;

the saturated heterocyclic group comprises one or two heteroatoms selected from O, N, and S;

the unsaturated heterocyclic group comprises one or two heteroatoms selected from N and O.

16. The pharmaceutical preparation according to claim 14, wherein, in the compound according to claim 1 has a structure of formula II:

II

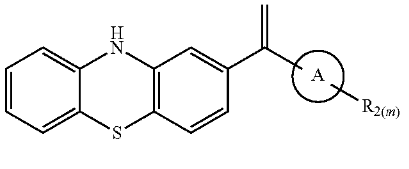

wherein, ring A is selected from aryl substituted by m $R_2$ and heteroaryl substituted by m $R_2$; said heteroaryl comprises one or two N, and m is an integer of 0-4;

$R_2$ is selected from H, substituted or unsubstituted $C_1$-$C_4$ alkyl, substituted or unsubstituted $C_1$-$C_3$ alkoxy, 6-8 membered saturated cycloalkyl, substituted or unsubstituted 6-7 membered saturated heterocyclic group, carbazolyl, amino, hydroxyl, nitro, aryl, cyano, halogen, —C(O)O$R_{51}$, —N(H)C(O)$R_{51}$, —C(O)$R_{51}$, —S(O)(O)$R_{51}$, and —C(O)N(H)$R_{51}$;

$R_{51}$ is selected from H, $C_1$-$C_2$ alkyl, amino, substituted or unsubstituted aryl, substituted or unsubstituted 5-6 membered saturated heterocyclic group, and —N$R_{52}R_{53}$;

$R_{52}$ and $R_{53}$ are each independently selected from H, substituted or unsubstituted 6-8 membered saturated heterocyclic group, substituted or unsubstituted $C_1$-$C_4$ linear or branched chain alkyl, and 4-5 membered saturated cycloalkyl;

the substituents of the alkyl are selected from halogen and substituted or unsubstituted 6-8 membered saturated heterocyclic group;

the substituents of the alkoxyl are selected from halogen and aryl;

the substituent of the aryl is substituted $C_1$-$C_3$ alkyl;

the substituent of the saturated heterocyclic group is $C_1$-$C_3$ alkyl; said heterocyclic group comprises one or two heteroatoms selected from N and O, or, said compound has a structure of formula III:

III

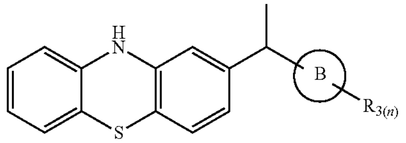

wherein, ring B is selected from aryl, benzo(5-6 membered saturated)heterocyclic group, benzo(5 membered unsaturated)heterocyclic group, anthryl, 6-8 membered unsaturated heterocyclic group or 6-8 membered saturated cycloalkyl, all of which are substituted by n $R_3$, n is an integer of 1-3;

$R_3$ is selected from H, halogen, cyano, hydroxyl, amino, nitro, aryl, phenoxy, substituted 6-8 membered saturated heterocyclic group, substituted $C_1$-$C_4$ alkyl, substituted or unsubstituted $C_1$-$C_3$ alkoxy, —C(O)O$R_{51}$, —N(H)C(O)$R_{51}$, and —N$R_{52}R_{53}$;

$R_{51}$ is $C_1$-$C_4$ alkyl, $R_{52}$ and $R_{53}$ are each independently aryl;

the substituent of the alkyl is halogen;

the substituents of the alkoxyl are aryl and halogen;

the substituent of the saturated heterocyclic group is $C_1$-$C_2$ alkyl;

the saturated heterocyclic group comprises one or two heteroatoms selected from N and O;

the unsaturated heterocyclic group comprises one or two heteroatoms selected from N and O;

or, said compound has a structure of formula IV:

IV

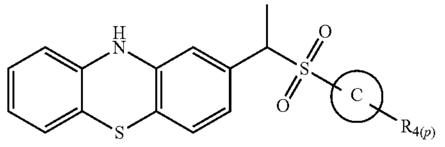

wherein, ring C is a 5-8 membered saturated heterocyclic group substituted by p $R_4$;

p is an integer of 0-4, $R_4$ is selected from H, hydroxyl, substituted or unsubstituted $C_1$-$C_4$ alkyl, —C(O)$R_{51}$, —N(H)C(O)O$R_{51}$, —S(O)(O)$R_{51}$, —C(O)O$R_{51}$, 6-8 membered unsaturated heterocyclic group, 6-8 membered saturated heterocyclic group, and substituted or unsubstituted aryl;

$R_{51}$ is selected from $C_1$-$C_4$ alkyl, amino, 5 membered saturated heterocyclic group, and benzo(6 membered saturated)heterocyclic group;

The substituents of the alkyl are selected from halogen, benzo(5 membered saturated)heterocyclic group, substituted or unsubstituted aryl, 6 membered saturated heterocyclic group, hydroxyl, —N(H)C(O)O$R_{51}$, —C(O)$R_{51}$, and —N$R_{52}R_{53}$;

the substituents of the aryl are selected from halogen, $C_1$ alkoxyl, cyano, nitro, and substituted or unsubstituted $C_1$ alkyl;

$R_{52}$ and $R_{53}$ are each independently $C_1$-$C_1$ alkyl;

the saturated heterocyclic group comprises one or two heteroatoms selected from O, N, and S; and the unsaturated heterocyclic group comprises one or two N.

17. The pharmaceutical preparation according to claim 14, wherein the compound according to claim 1 has a structure of formula IIA:

IIA

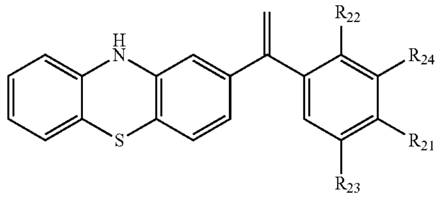

wherein, $R_{21}$, $R_{22}$, $R_{23}$, and $R_{24}$ are each independently selected from H, —C(O)O$R_{51}$, substituted or unsubstituted $C_1$-$C_4$ alkyl, substituted or unsubstituted $C_1$-$C_3$ alkoxy, —N(H)C(O)$R_{51}$, 6 membered saturated cycloalkyl, —C(O)$R_{51}$, 6-membered saturated heterocyclic group, carbazolyl, amino, hydroxyl, nitro, —S(OXO)$R_{51}$, aryl, cyano, halogen, and —C(O)N(H) $R_{51}$;

$R_{51}$ is selected from H, $C_1$-$C_2$ alkyl, amino, substituted or unsubstituted aryl, substituted or unsubstituted 5-6 membered saturated heterocyclic group, and —N$R_{52}R_{53}$;

$R_{52}$ and $R_{53}$ are each independently of selected from H, substituted or unsubstituted 6 membered saturated heterocyclic group, substituted or unsubstituted $C_1$-$C_4$ linear or branched chain alkyl, and 4 membered cycloalkyl;

the substituents of the alkyl are selected from halogen and substituted or unsubstituted 6 membered saturated heterocyclic group;

the substituents of the alkoxyl are selected from halogen and aryl;

the substituent of the aryl is substituted $C_1$ alkyl;

the substituent of the saturated heterocyclic group is $C_1$ alkyl; said saturated heterocyclic group comprises one or two heteroatoms selected from N and O, or, said compound has a structure of formula IIB:

IIB

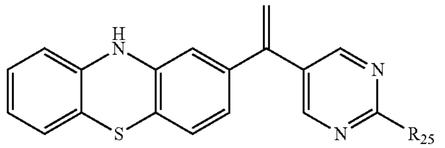

wherein, $R_{25}$ is selected from substituted or unsubstituted 6-7 membered saturated heterocyclic group;

the substituent of the saturated heterocyclic group is $C_1$ alkyl;

said heterocyclic group comprises two heteroatoms selected from N and O;

or, said compound has a structure of formula IIC:

IIC

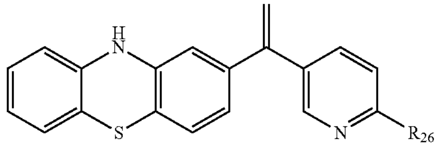

wherein, $R_{26}$ is selected from —N(H)C(O)$R_{51}$, amino, and 6 membered saturated heterocyclic group;

said saturated heterocyclic group comprises two heteroatoms selected from N and O;

$R_{51}$ is $C_1$ alkyl;

or, said compound has a structure of formula IIIA:

IIIA

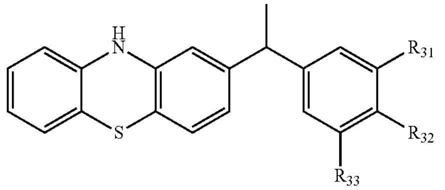

wherein, $R_{31}$, $R_{32}$, $R_{33}$ are each independently selected from H, halogen, cyano, hydroxyl, amino, substituted or unsubstituted $C_1$-$C_3$ alkoxy, —C(O)O$R_{51}$, —N(H) C(O)$R_{51}$, aryl, phenoxy, —N$R_{52}R_{53}$, substituted 6 membered saturated heterocyclic group, and nitro, with the proviso that all of R31, R32, and R33 are not simultaneously H;

$R_{51}$ is $C_1$-$C_4$ alkyl;

the substituent of the alkyl is halogen;

the substituents of the alkoxyl are selected from aryl and halogen;

the substituent of the saturated heterocyclic group is $C_1$ alkyl;

the saturated heterocyclic group comprises two N;

$R_{52}$ and $R_{53}$ are each independently aryl;

or, said compound has a structure of formula IIIB:

IIIB

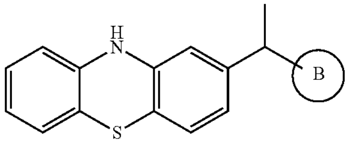

wherein, ring B is selected from benzo(5-6 membered saturated)heterocyclic group, benzo(5 membered unsaturated)heterocyclic group, anthryl, and substituted 6 membered unsaturated heterocyclic group or 6 membered saturated cycloalkyl;

the substituents of the unsaturated heterocyclic group are selected from cyano, $C_1$ alkyl, and $C_2$ alkoxyl;

the saturated heterocyclic group comprises one or two O;

the unsaturated heterocyclic group comprises one heteroatom selected from O and N;

or, said compound has a structure of formula IVA:

IVA

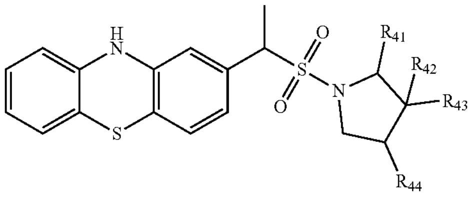

wherein, $R_{41}$, $R_{42}$, $R_{43}$, and $R_{44}$ are each independently selected from H, hydroxyl, —N(H)C(O)OR$_{51}$, and substituted or unsubstituted $C_1$ alkyl;

$R_{51}$ is $C_4$ alkyl;

the substituent of the alkyl is —N(H)C(O)OR$_{51}$;

or, said compound has a structure of formula IVB:

IVB

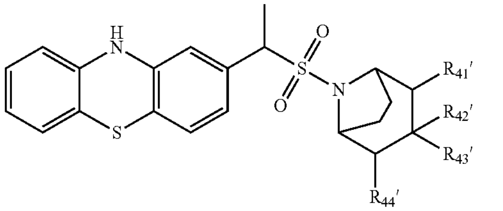

wherein, $R_{41}'$, $R_{42}'$, $R_{43}'$, and $R_{44}'$ are each independently selected from H and hydroxyl;

or, said compound has a structure of formula IVC:

IVC

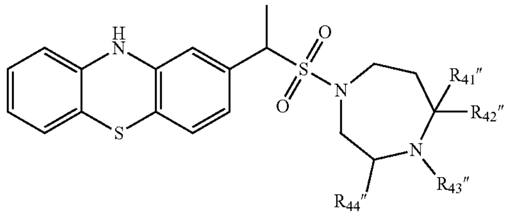

wherein, $R_{41}''$, $R_{42}''$, $R_{43}''$, and $R_{44}''$ are each independently selected from H, $C_1$ alkyl, and —C(O)R$_{51}$;

$R_{51}$ is $C_1$ alkyl;

or, said compound has a structure of formula IVD:

IVD

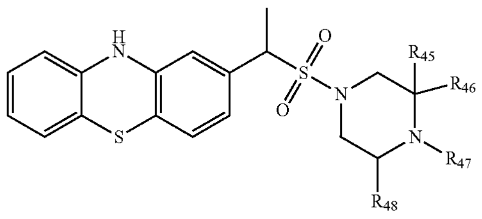

wherein, $R_{45}$, $R_{46}$, $R_{47}$, and $R_{48}$ are each independently selected from H, substituted or unsubstituted $C_1$-$C_4$ alkyl, —C(O)R$_{51}$, —S(O)(O)R$_{51}$, 6 membered unsaturated heterocyclic group, —C(O)R$_{51}$, and substituted or unsubstituted aryl;

$R_{51}$ is selected from 5 membered saturated heterocyclic group, $C_1$-$C_4$ alkyl, and benzo(6 membered saturated) heterocyclic group;

$R_{52}$ and $R_{53}$ are each independently $C_1$ alkyl;

the substituents of the alkyl are selected from halogen, benzo(5 membered saturated)heterocyclic group, —C(O)R$_{51}$, —NR$_{52}$R$_{53}$, substituted or unsubstituted aryl, 6 membered saturated heterocyclic group, and hydroxyl;

the substituents of the aryl are selected from $C_1$ alkoxyl, halogen, cyano, nitro, and substituted or unsubstituted $C_1$ alkyl;

the saturated heterocyclic group comprises one or two heteroatoms selected from O and N;

the unsaturated heterocyclic group comprises one or two N;

or, said compound has a structure of formula IVE:

IVE

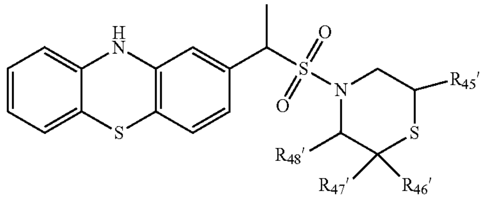

wherein, $R_{45}'$, $R_{46}'$, $R_{47}'$, and $R_{48}'$ are each independently selected from H and $C_1$ alkyl;

or, said compound has a structure of formula IVF:

IVF

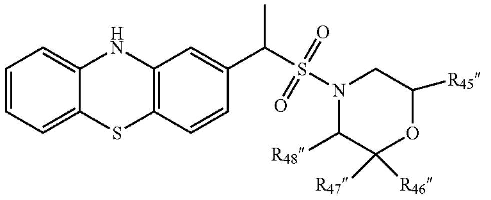

wherein, $R_{45}''$, $R_{46}''$, $R_{47}''$, and $R_{48}''$ are each independently selected from H and $C_1$ alkyl;

or, said compound has a structure of formula IVG:

IVG

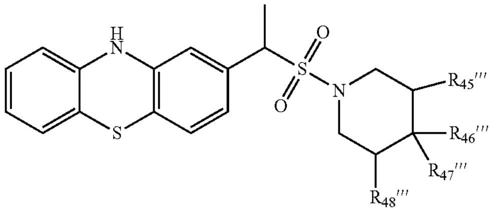

wherein, $R_{45}'''$, $R_{46}'''$, $R_{47}'''$, and $R_{48}'''$ are each independently selected from H, hydroxyl, —C(O)$OR_{51}$, —N(H)C(O)$OR_{51}$, substituted aryl, substituted or unsubstituted $C_1$ alkyl, 6 membered saturated heterocyclic group, and —C(O)$R_{51}$;

$R_{51}$ is selected from $C_2$-$C_4$ alkyl and amino;

the substituent of the aryl is halogen;

the substituents of the alkyl are selected from —N(H)C(O)$OR_{51}$ and hydroxyl; and the saturated heterocyclic group comprises one N.

18. The pharmaceutical preparation according to claim 14, wherein the compound according to claim 1 is selected from:

A2

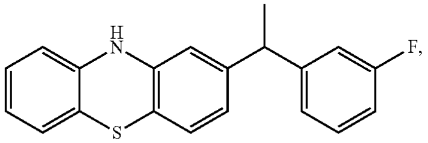

A3

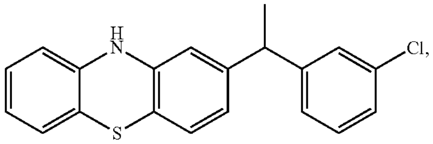

A4

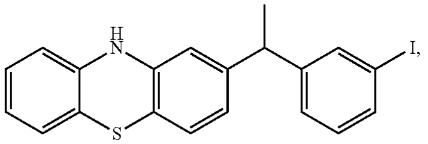

-continued

A5

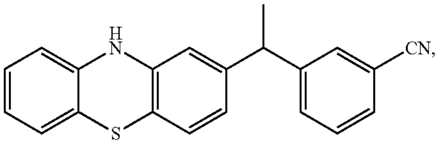

A6

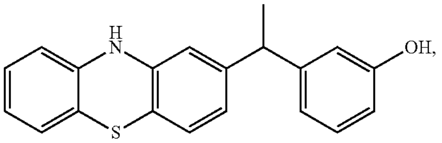

A7

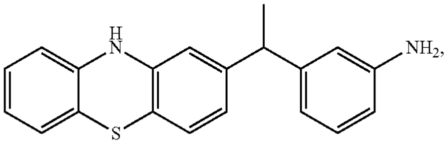

A11

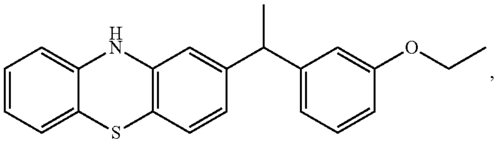

A12

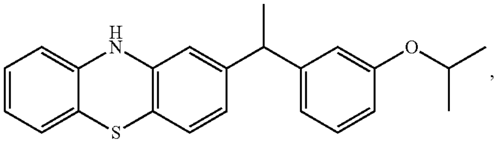

A13

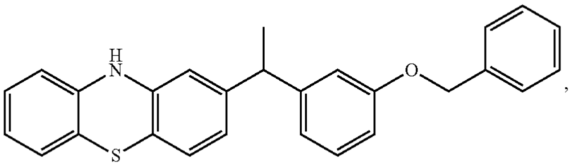

A14

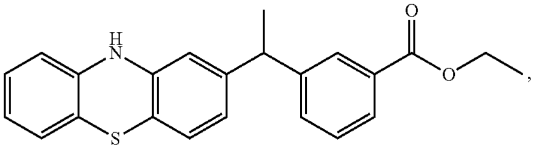

A15

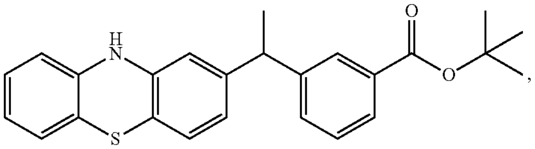

A16

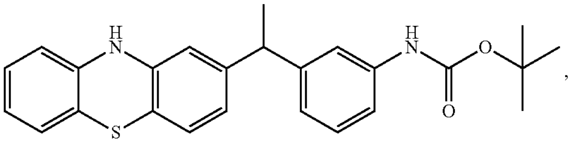

-continued
A17
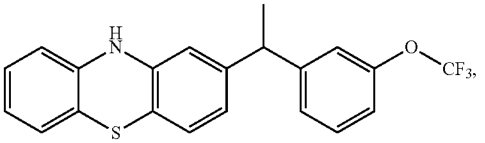,
A18
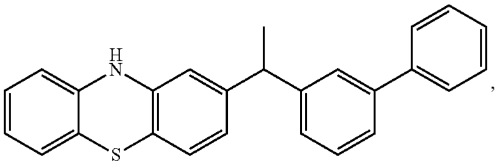,
A19
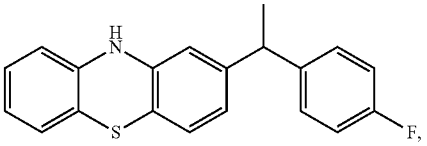,
A20
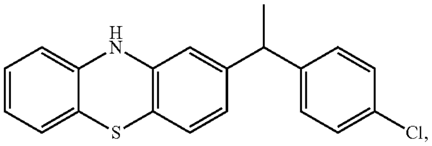,
A21
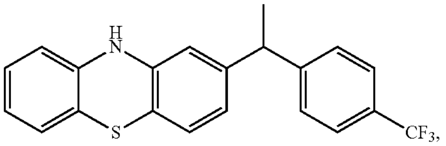,
A22
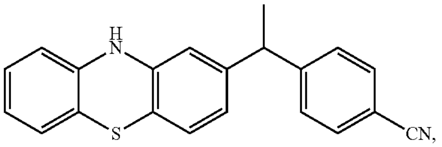,
A23
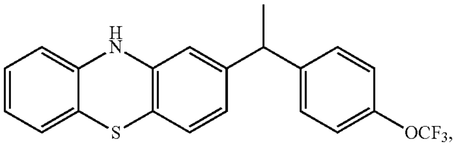,
A30
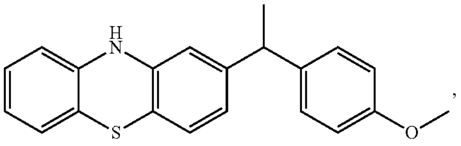,
A31
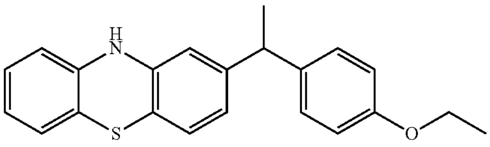,
-continued
A32
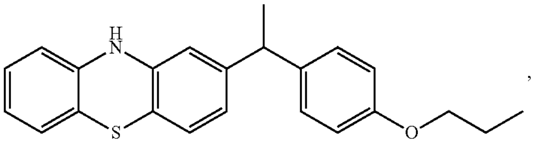,
A33
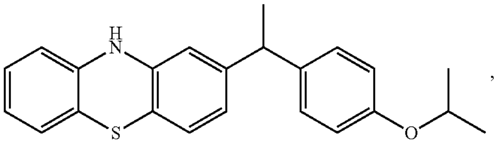,
A34
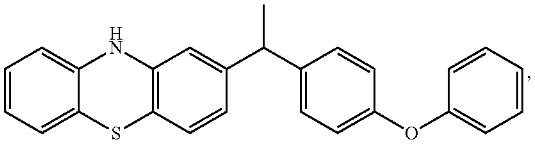,
A35
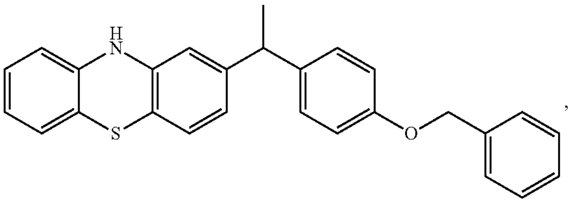,
A36
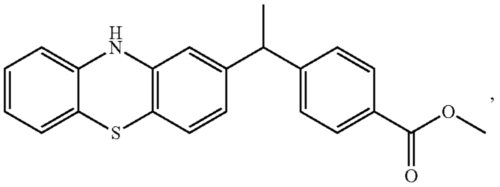,
A37
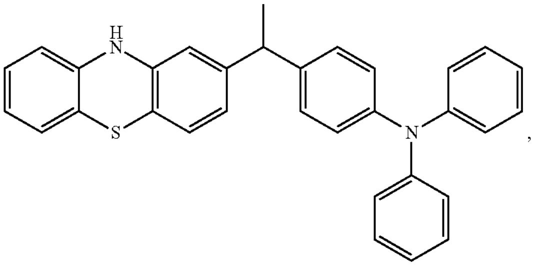,
A38
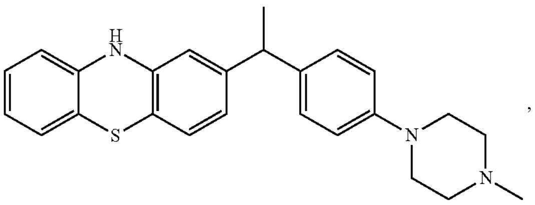, -continued
A39
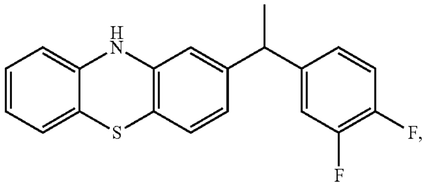
A40
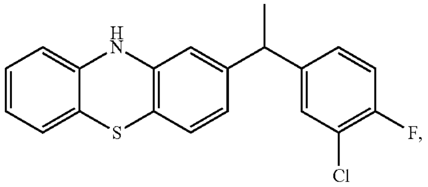
A41
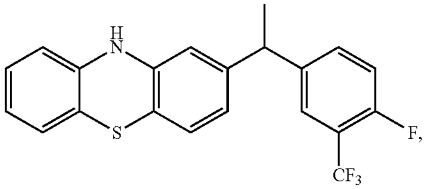
A42
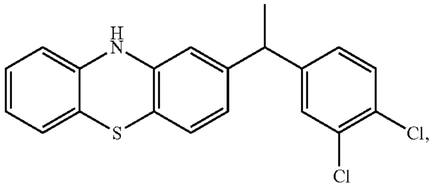
A43
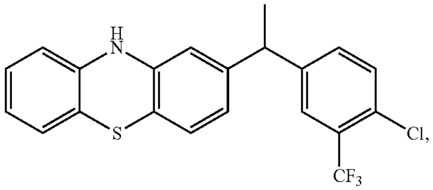
A44
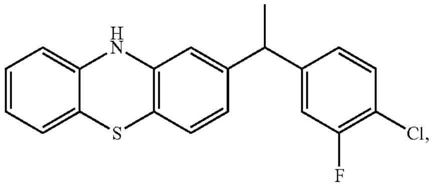
A45
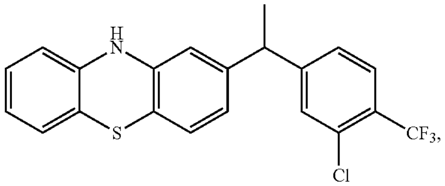
A47
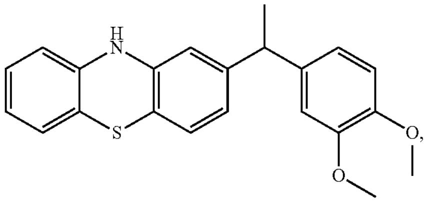
-continued
A50
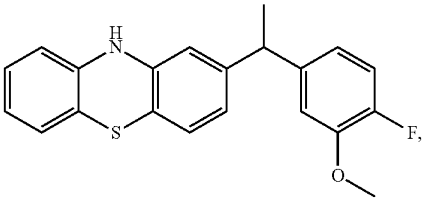
A51
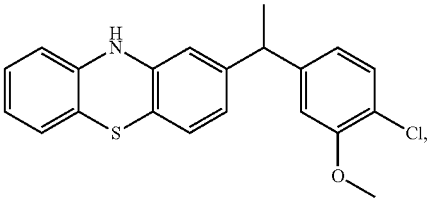
A53
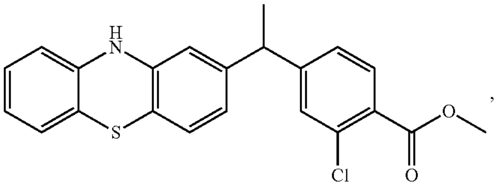
,
A55
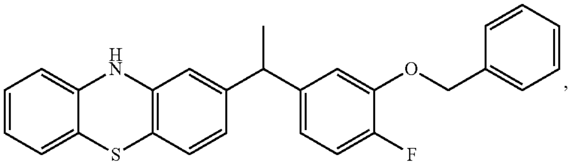
,
A56
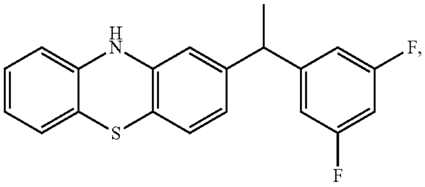
A57
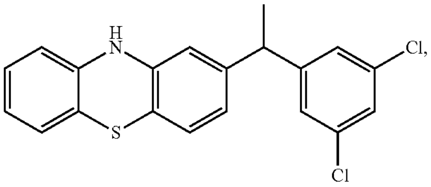
A58
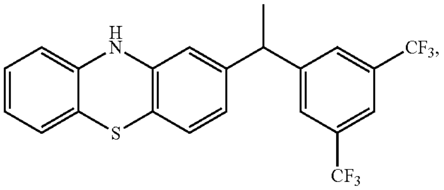
A60
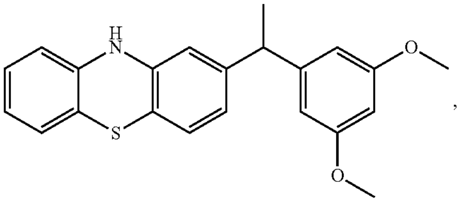
, -continued
A61
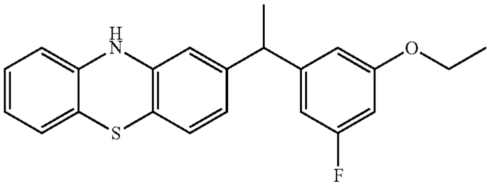
,
A63
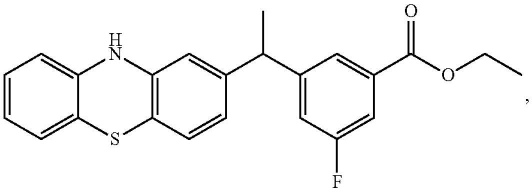
,
A64
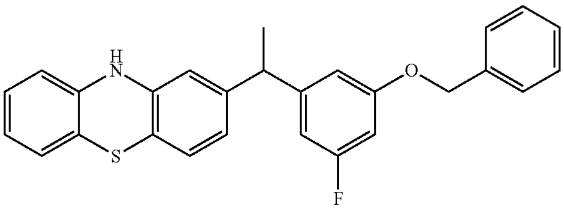
,
A65
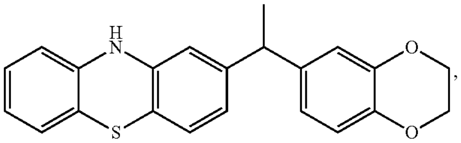
,
A66
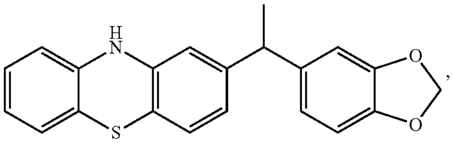
,
A67
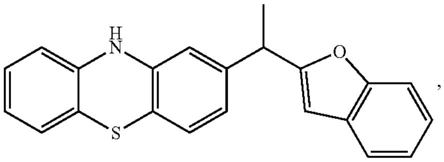
,
A69
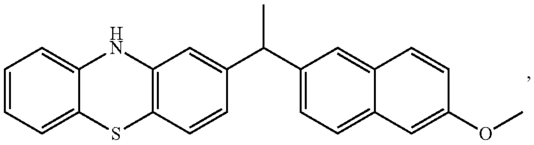
,
A70
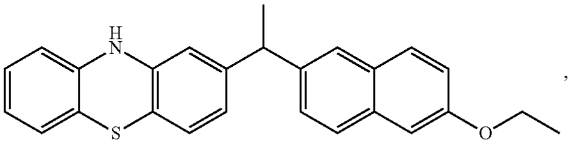
,
-continued
A71
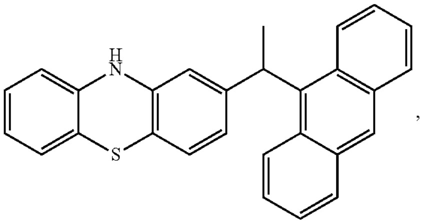
,
A72
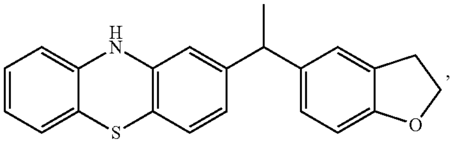
,
A73
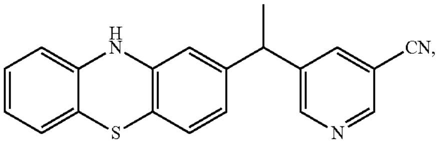
A74
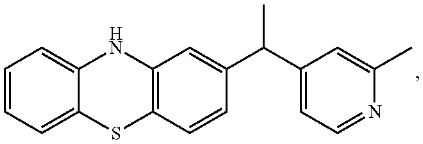
,
A75
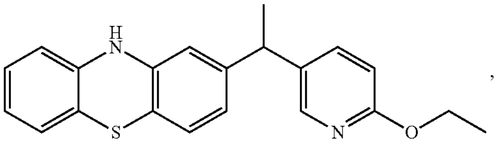
,
A76
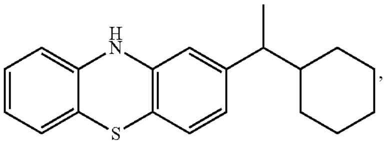
,
B1
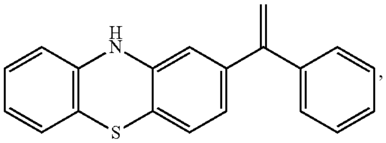
,
B2
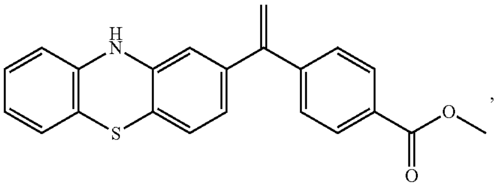
,
B3
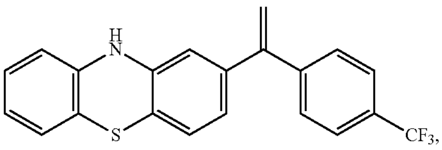

-continued
B4
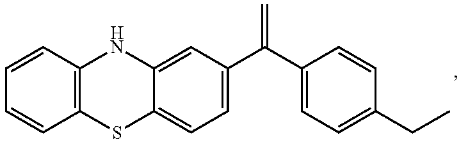
,
B5
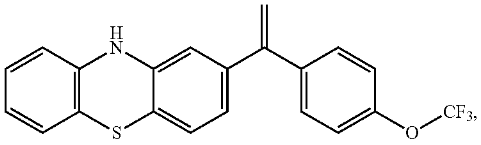
B6
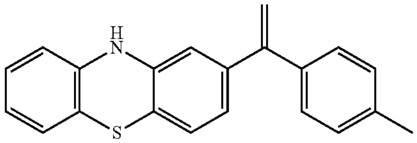
,
B7
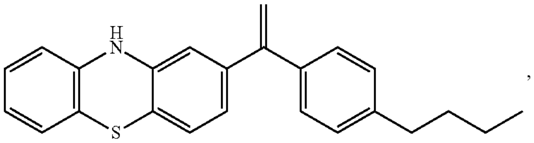
,
B8
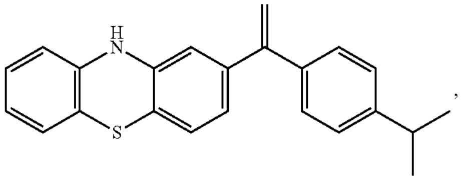
,
B9
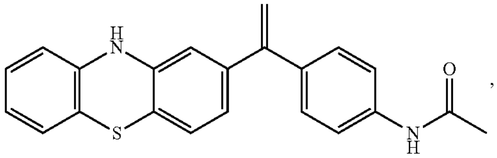
,
B10
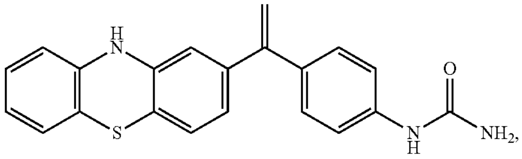
B11
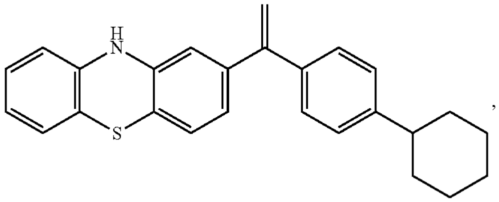
,
B12
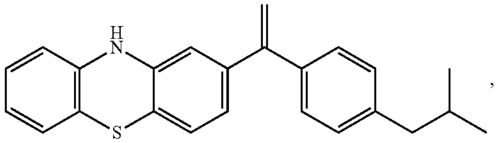
,
-continued
B13
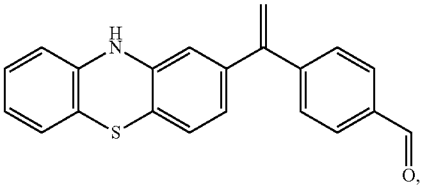
B14
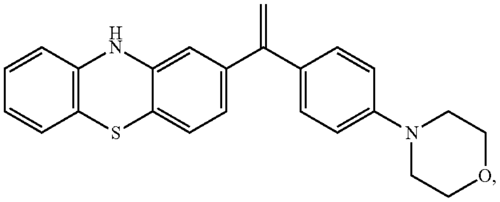
B15
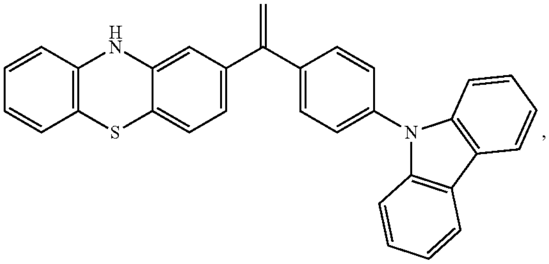
,
B16
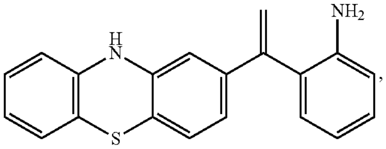
B17
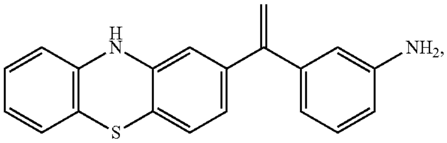
B18
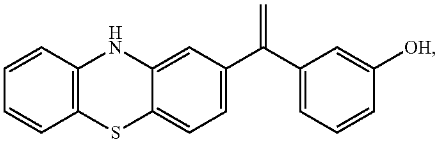
B19
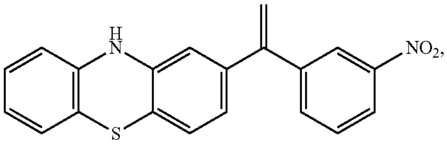
B20
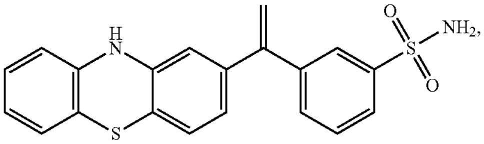

-continued
B21
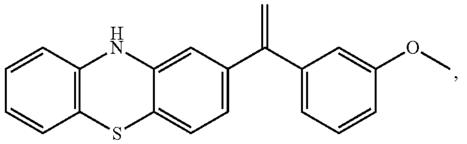
B22
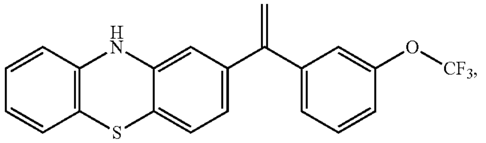
B23
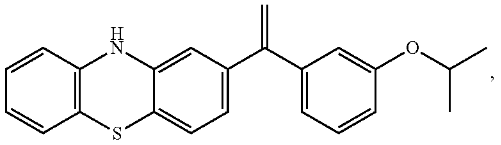
B24
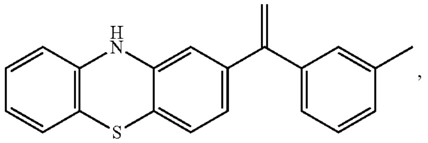
B25
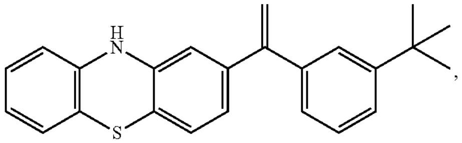
B26
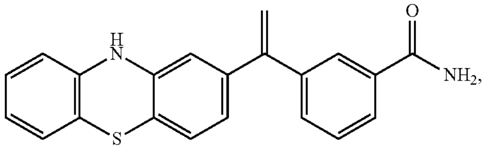
B27
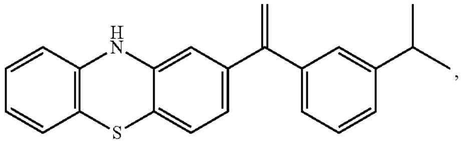
B28
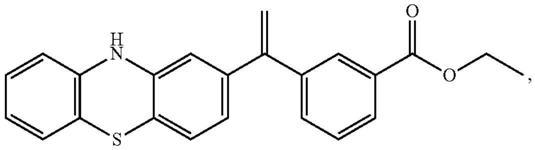
B29
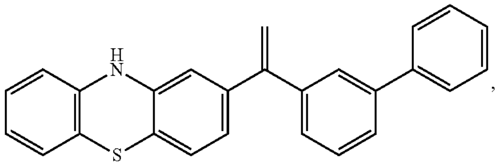
-continued
B30
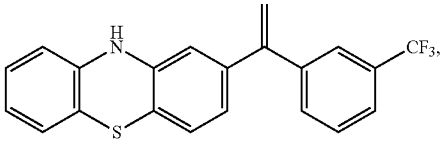
B31
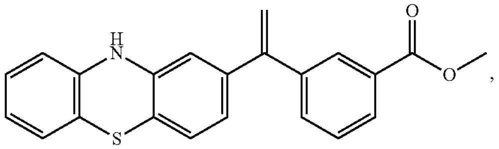
B32
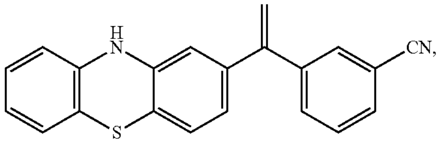
B33
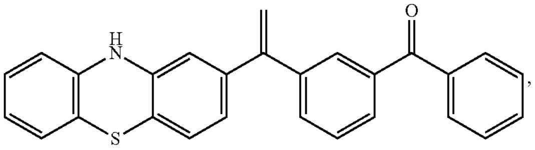
B34
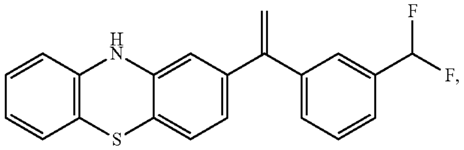
B35
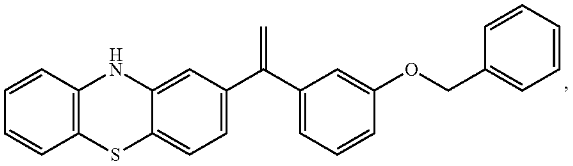
B36
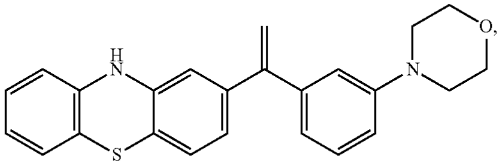
B37
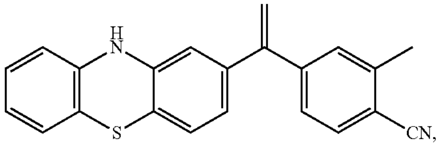
B38
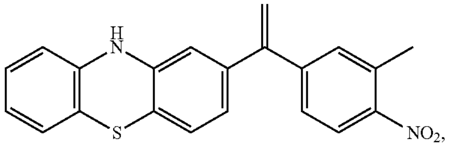

-continued
B39
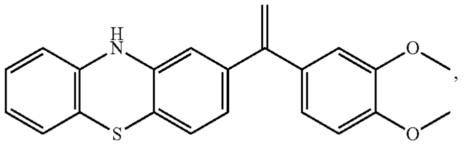
B40
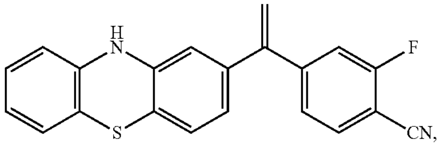
B41
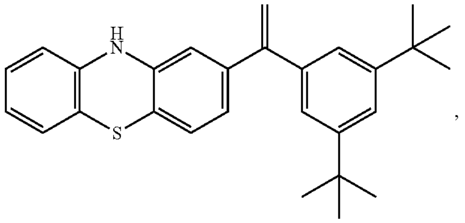
B42
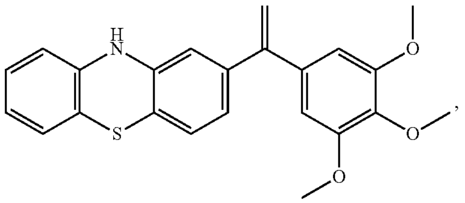
B43
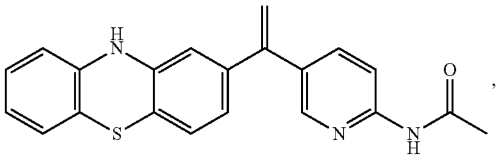
B44
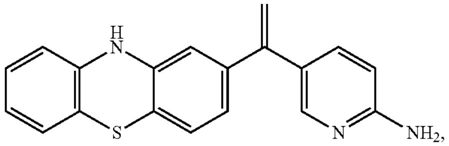
B45
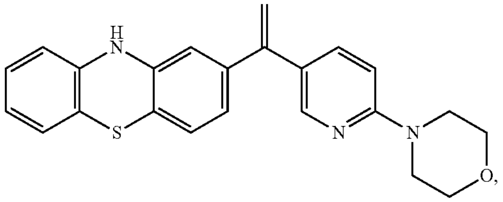
B46
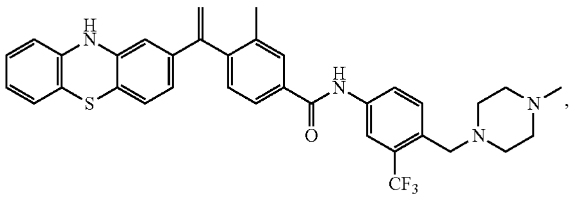
-continued
B47
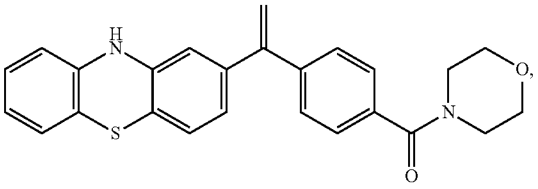
B48
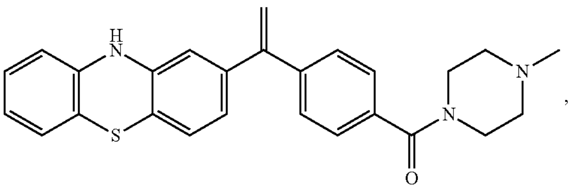
B49
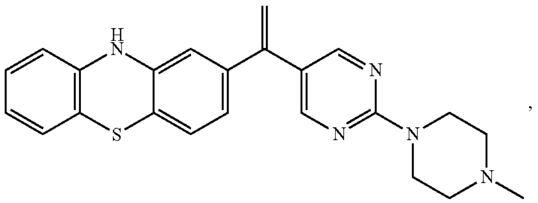
B50
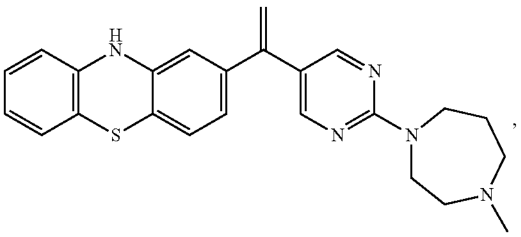
B51
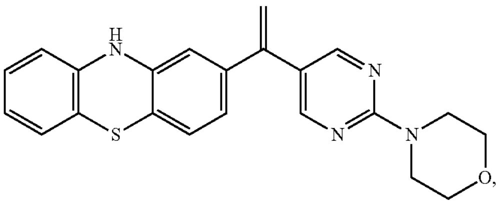
B52
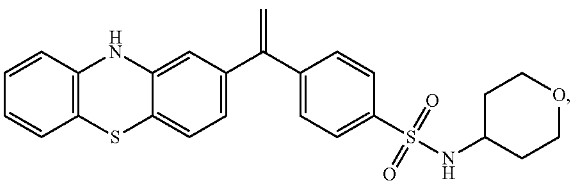
B53
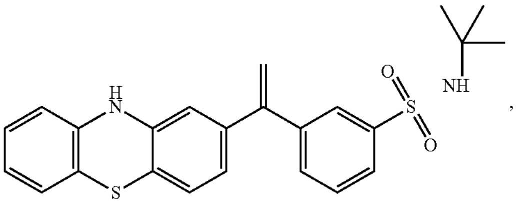

-continued
B54
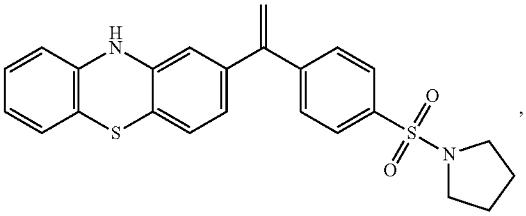
,
B55
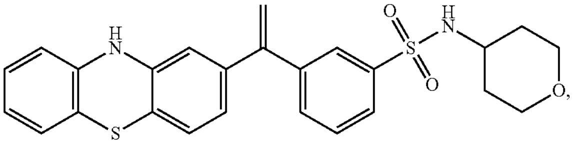
,
B56
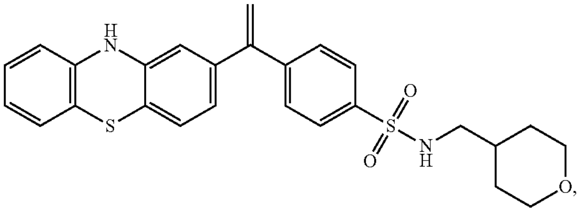
,
B57
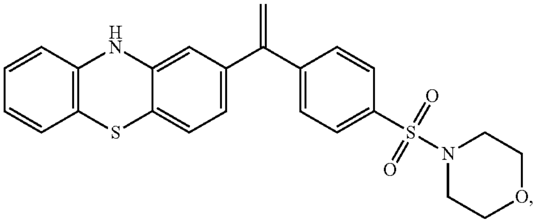
,
B58
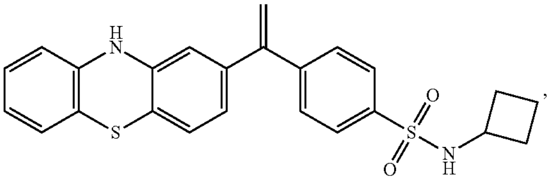
,
B59
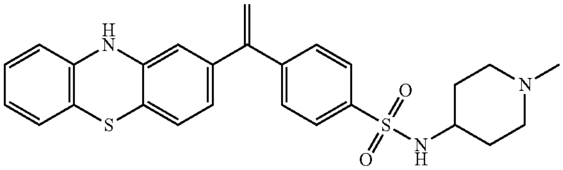
,
C1
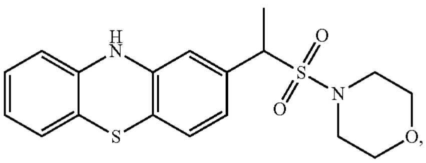
,
-continued
C2
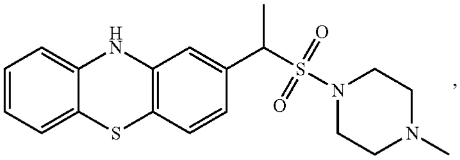
,
C3
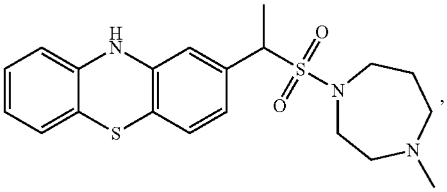
,
C4
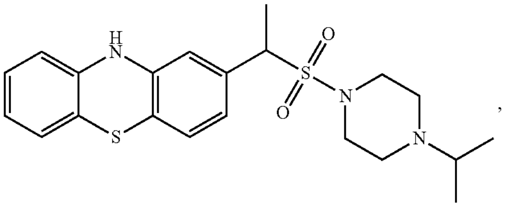
,
C5
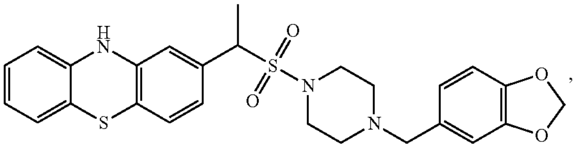
,
C6
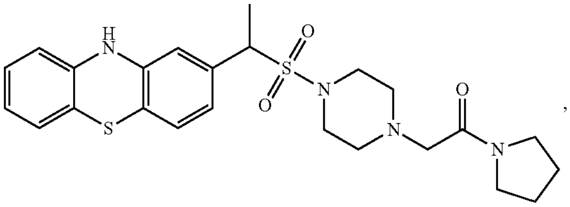
,
C7
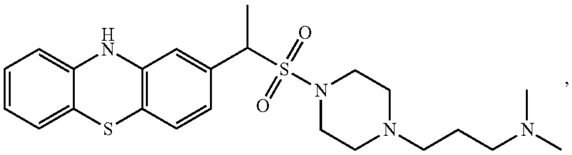
,
C8
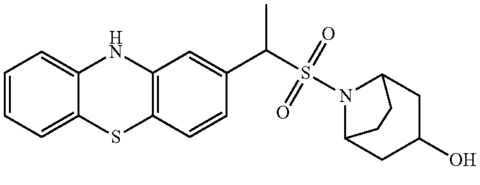
C9
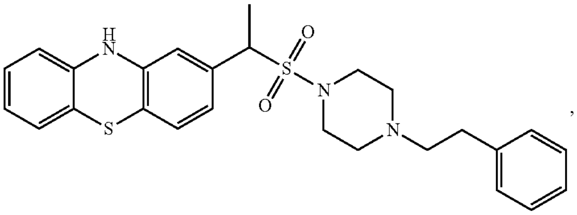
, -continued
C10
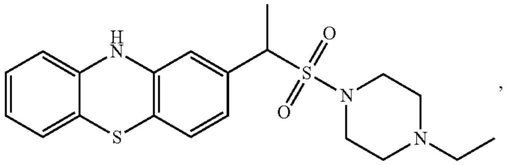
C11
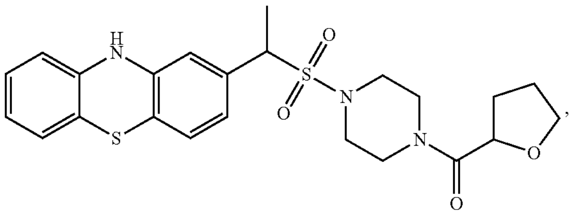
C12
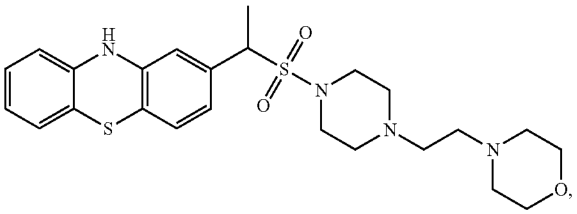
C13
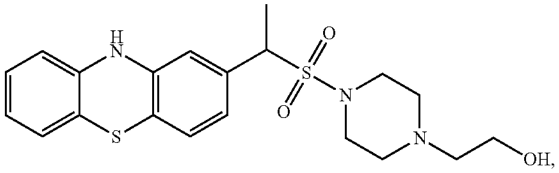
C14
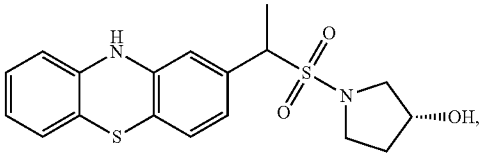
C15
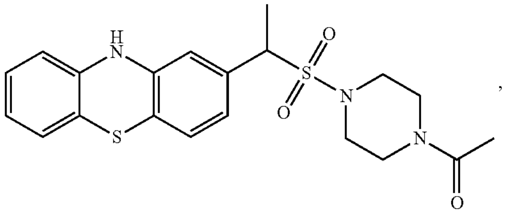
C16
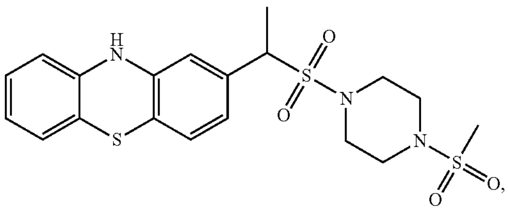
-continued
C17
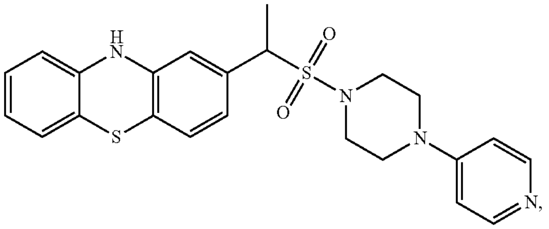
C18
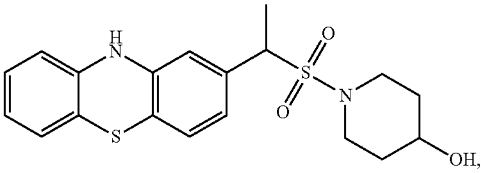
C19
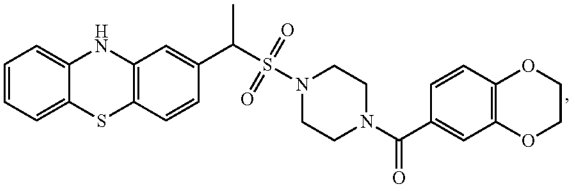
C20
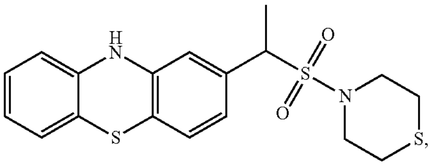
C21
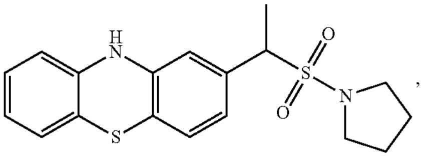
C22
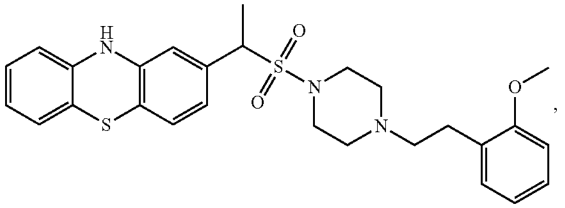
C23
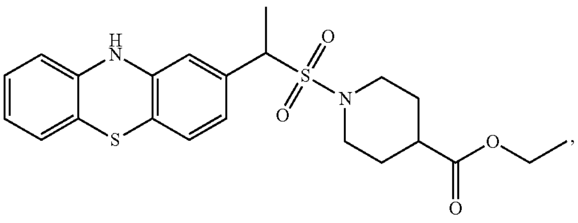

-continued
C24
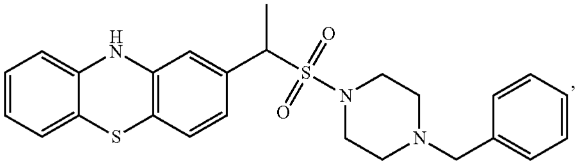
,
C25
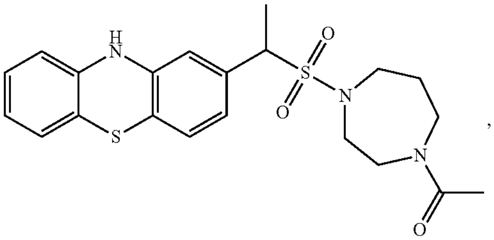
,
C26
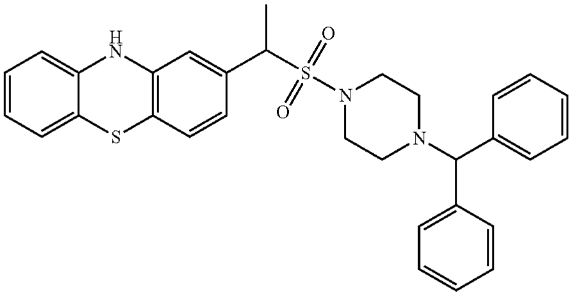
,
C27
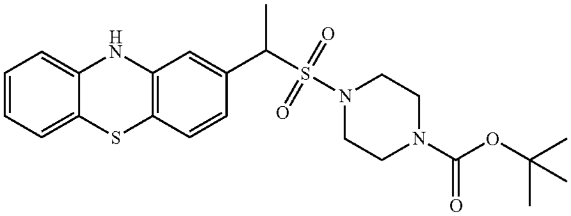
,
C28
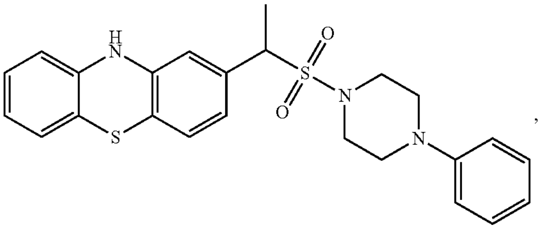
,
C29
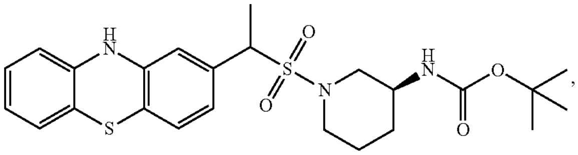
,
-continued
C30
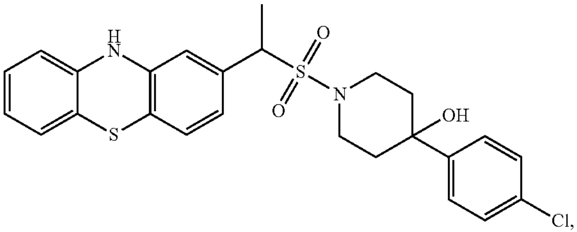
,
C31
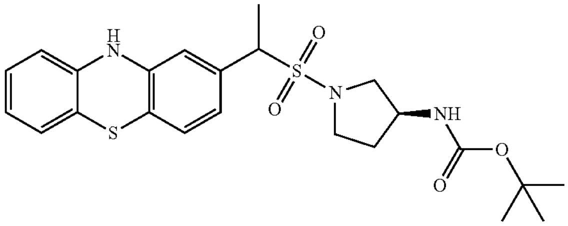
,
C32
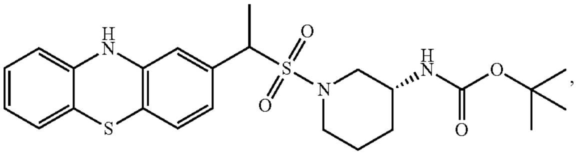
,
C33
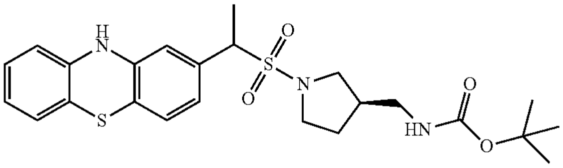
,
C34
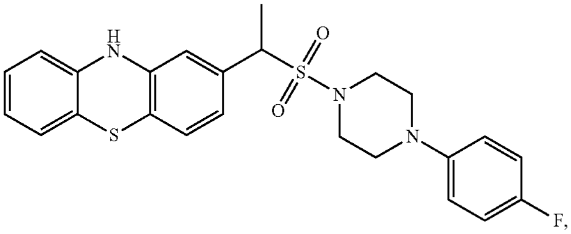
,
C35
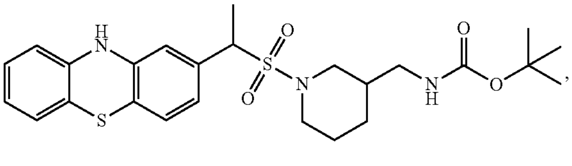
,
C36
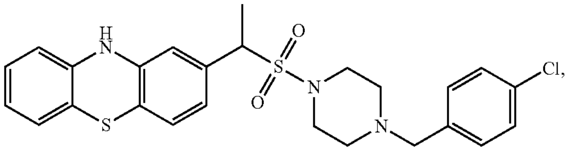
, -continued
C37
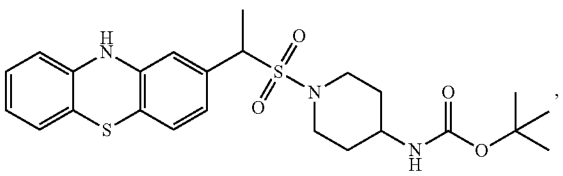
C38
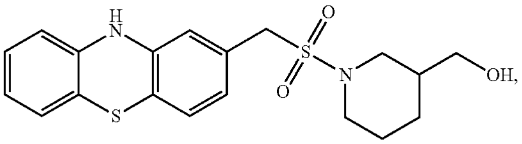
C39
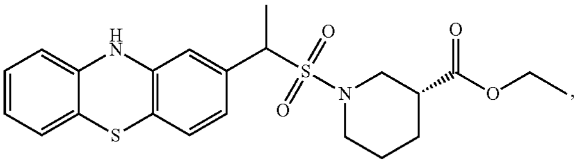
C40
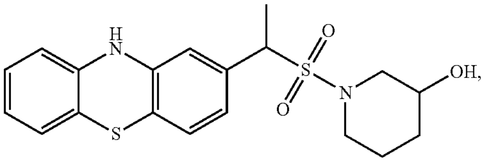
C41
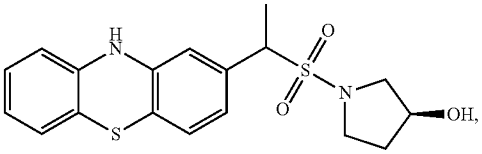
C42
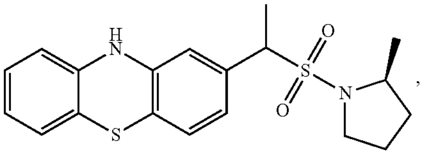
C43
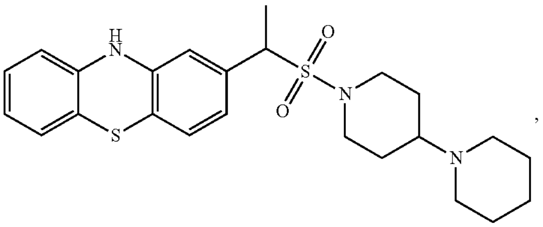
C44
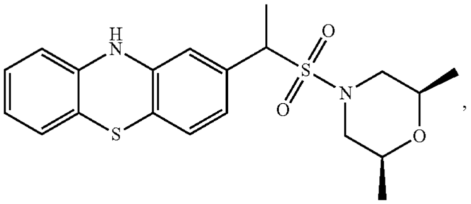
-continued
C45
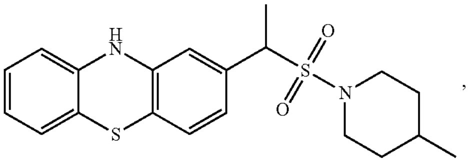
C46
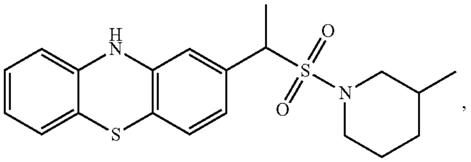
C47
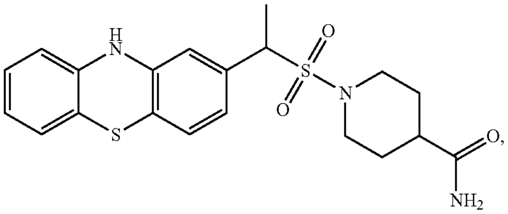
C48
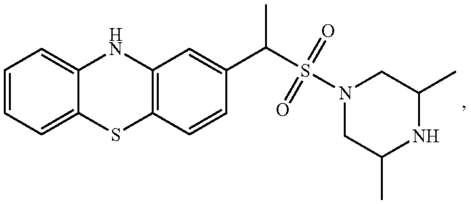
C49
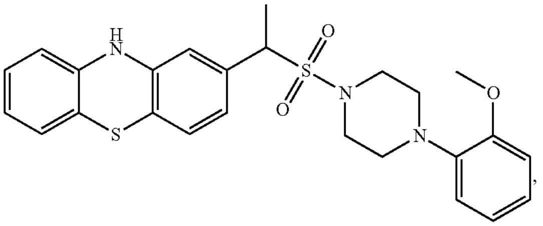
C50
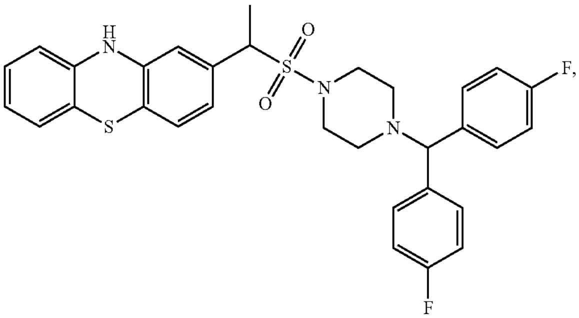

-continued
C51
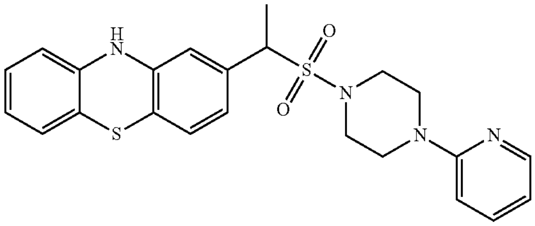
,
C52
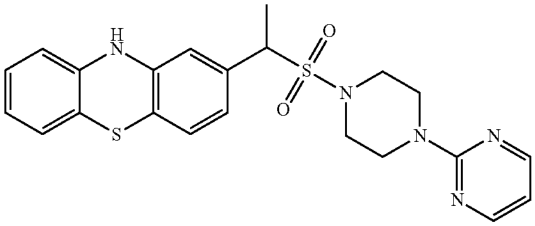
,
C53
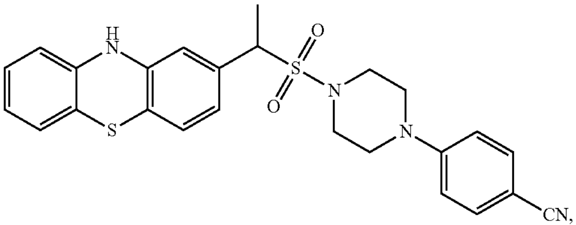
,
C54
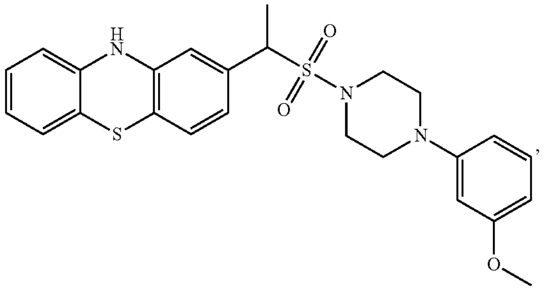
,
C55
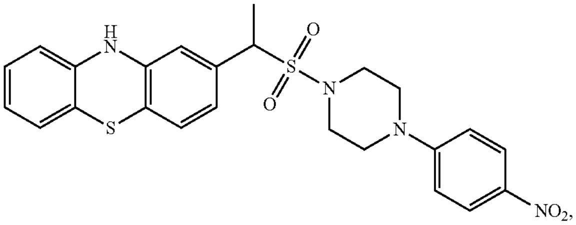
,
-continued
C56
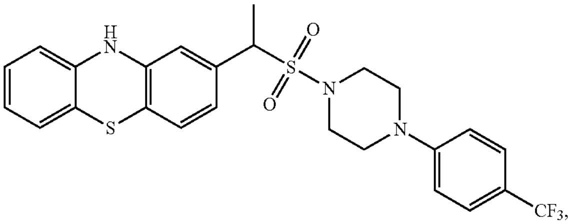
,
C57
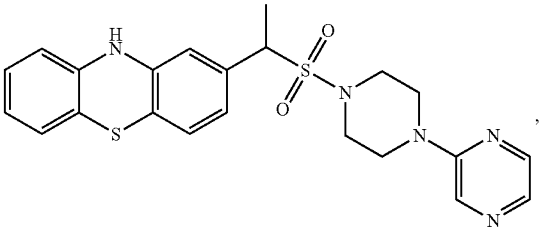
,
C58
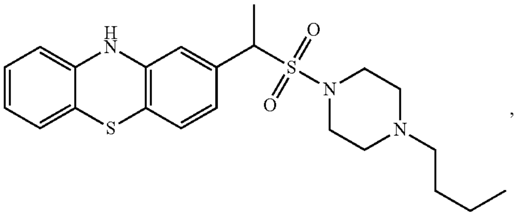
, and
C59
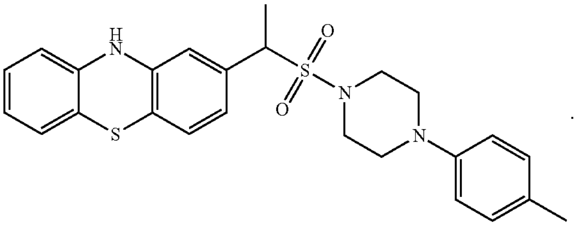
.
19. A method for treating stroke, comprising: administering a pharmaceutically acceptable amount of the compound, or the pharmaceutically acceptable salt, or the solvate thereof according to claim 1 to a subject in need thereof.
20. The method of claim 19, wherein the compound is A38:
A38
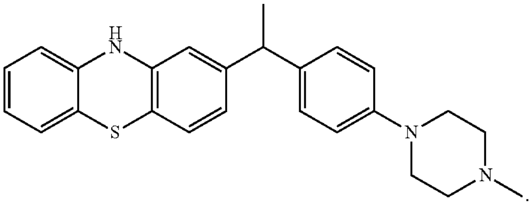
.
* * * * *